US010633672B2

(12) United States Patent
Ozias-Akins et al.

(10) Patent No.: US 10,633,672 B2
(45) Date of Patent: Apr. 28, 2020

(54) GENE FOR INDUCTION OF PARTHENOGENESIS, A COMPONENT OF APOMICTIC REPRODUCTION

(71) Applicant: UNIVERSITY OF GEORGIA RESEARCH FOUNDATION, INC., Athens, GA (US)

(72) Inventors: Peggy Ozias-Akins, Tifton, GA (US); Joann A. Conner, Tifton, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 399 days.

(21) Appl. No.: 15/031,019

(22) PCT Filed: Oct. 21, 2014

(86) PCT No.: PCT/US2014/061630
§ 371 (c)(1),
(2) Date: Apr. 21, 2016

(87) PCT Pub. No.: WO2015/061355
PCT Pub. Date: Apr. 30, 2015

(65) Prior Publication Data
US 2016/0304901 A1    Oct. 20, 2016

Related U.S. Application Data

(60) Provisional application No. 61/893,741, filed on Oct. 21, 2013, provisional application No. 62/059,842, filed on Oct. 3, 2014.

(51) Int. Cl.
*C12N 15/82* (2006.01)
(52) U.S. Cl.
CPC ................ *C12N 15/8287* (2013.01)
(58) Field of Classification Search
None
See application file for complete search history.

(56) References Cited

U.S. PATENT DOCUMENTS

| 5,811,636 A | 9/1998 | Hanna et al. |
| 6,028,185 A | 2/2000 | Ozias-Akins et al. |
| 8,420,893 B2 | 4/2013 | Gordon-Kamm et al. |

FOREIGN PATENT DOCUMENTS

| WO | 2005/075665 A2 | 8/2005 |
| WO | WO 2005/075655 A2 * | 8/2005 |

OTHER PUBLICATIONS

Kano-Murakami et al (1993, "A Rice Homeotic Genes, OSH1, Causes Unusual Phenotypes in Transgenic Tobacco" FEBS 334:365-368).*
Kano-Murakanni et al (1993, "A Rice Homeotic Genes, OSH1, Causes Unusual Phenotypes in Transgenic Tobacco". FEBS 334:365-368).*
McConnell et al, (2001, "Role of PHABULSA and PHAVOUTA in Determining Radial Patterning in Shoots". Nature 411 (6838):709-713).*
Bowie et al, (1990, "Deciphering the Message in Protein Sequences: Tolerance to Amino Acid Substitutions". Science 247:1306-1310).*
Database uniProt [Online] Oct. 16, 2013 (Oct. 16, 2013), "SubName: Full=ASGR-BBM=like 2 {ECO:0000313| EMBL:ACD80124.2};", XP002766753, retrieved from EBI accession No. UNIPROT:B3U4X0 Database accession No. B3U4X0.
J A Conner et al: "Plant Contributed Papers", In Vitro Cellular & Developmental Biology. Animal., vol. 47, No. S1, Apr. 1, 2011 (Apr. 21, 2011), pp. 34-40, XP055341947, New York. ISSN: 1071-2690, DOI: 10.1007/s11626-011-9415-6.
European Extended Search Report for European Patent Application No. 14856528.6-1410 dated Feb. 16, 2017.
Koltunow and Grossniklaus—"Apomixis: A Developmental Perspective", Annu. ev. Plant Biol. 2003, 54:547-74.
Kempel, et al. "Understanding and Engineering Parthenogenesis", The 9th Gatersleben Research Conference, 3rd International Apomixis Conference, Wernigerode, Germany, Jun. 27-Jul. 1, 2007, Scientific Programme and Abstracts, 8.1-oral.
A. Horstman, V. Willemsen, K Boutilier, R. Heidstra, Trends in Plant Science 19:146-167.
Akiyama Y. et al., J. Hered. 97:521-524 (2006).
Boutilier K. et al., Plant Cell 14:1737-1749 (2002).
Conner et al., Planta 238:51-63 (2013).
Conner J. et al., Plant Physiol. 147:1396-1411 (2008).
Crismani W. et al., J. Exp. Bot. 64:55-65 (2013).
D. Roche et al. Theor Appl Genet., 104:804-812 (2002).
E. Albertini et al., Plant Molecular Biology 56:879-894 (2004).
Eamens A. et al., Plant Physiology 147:456-568 (2008).
Elliott R. et al., PLant Cell 8:155-168 (1996).
G. Gualtieri et al., Plant Physiology 140:963-971 (2006).
G. H. Fleming, O. Olivares-Fuster, S. Del-Bosco, J. W. Grosser, In Vitro Cell Dev Biol Plant 36:450-455 (2000).
Goel S. et al., Genetics 163:1069-1082 (2003).
Goel S. et al., Genetics 173:389-400 (2006).
Grimanelli D., Cuff. Opin. Plant Biol. 15:57-62 (2012).
H. Yang et al., Plant Cell Reports, 17:693-699 (1998).
Huo H. et al., Theor. Appl. Genet. 119:199-212 (2009).
J. J. Goldman, W. W. Hanna, G. Fleming. P. Ozias-Akins, Plant Cell Rep., 21L999-1009 (2003).
Jofuku K. et al., Plant Cell 6:1211-1255 (1994).
Kim S. et al., Mol. Biol. Evol. 23:107-120 (2006).
Klucher K. et al., The Plant Cell 8:137-153 (1996).
M. Singh et al., Crop Science 50:892-902 (2010).
Malik M. eta l., Plant Physiology 144:134-154 (2007).

(Continued)

*Primary Examiner* — Stuart F Baum

(57) ABSTRACT

Methods and compositions disclosed herein generally relate to genes involved in plant reproduction and methods of using the same.

17 Claims, 38 Drawing Sheets

Specification includes a Sequence Listing.

(56) References Cited

OTHER PUBLICATIONS

N. Saitou, M. Nei, Molecular Biology and Evolution 4:406-425 (1987).
Ohme-Takagi M. and Shinshi H. Plant Cell 7:173-182 (1995).
Okamuro J. et al., Proceedings of the National Academy of Sciences 94:7076-7081 (1997).
Ossowski S. et al. Plant Journal 53:675-690 (2008).
Ozias-Akins P. et al., Proc. Natl. Acad. Sci. USA 95:5127-5132 (1998).
Passarinho P. et al., Plant Mol. Biol. 68:225-237 (2008).
Riechmann J. and Meyerowitz E., Biol. Chem. 379:633-646 (1998).
Roche D. et al., Plant J. 19:203-208 (1999).
Roche D. et al., Theor. Appl. Genet. 104:804-812 (2002).
S. El Ouakfaoui et al., Plant Mol Biol 74:313-326 (2010).
Weigel D. Plant Cell 7:388-389 (1995).
Y. Akiyama et al., BMC Evolutionary Biology, 11:289 (2011).
Zhang Z. et al., Plant Cell Reports 27:1851-1860 (2008).
Conner et al., ASGR-BABY Boom-like (AGR-BBML) from Apomictic Pennisetum squamulatum Confers Parthenogenesis to Trangenic Pearl Millet, Plant and Animal Genome XXII Meeting, Jan. 14, 2014, abstract.

\* cited by examiner

```
                         190             200             210             220             230
                         |               |               |               |               |
Consensus                NACYASSGASTGMH-QLYHHQ-SSALHFADSWMWASSA-GV--HD---GGASMLSAAA- 1. Si000593m             ---------------------------------------------------------
2. P00023058m            ---V-----------------V------------------AG-R-------------
3. Si016558m             STCYASSGASTGMH-QLYHHP-SSALHFADSWMWASSA-GV--HD---GGA-MLS-AA-
4. P00062296m            AACYASSGS-SGM---QLYHDH-PNSLQFADSWMWASSAGGV--HN---EHG-IM--
5. B2g57747              ---------------------------------FSGAGAT--------M--GSGAD-
6. B5g14960              --------------------------------------GSGC-----------Y---
7. BnBBM1 AF317904       --------------AV-------------------GAGR------------------C--
8. CcASGR BBM like1      --------------------------------------GNGD------------G--
9. AtBBM At5G17430       --------------------------------------AAGR---------------
10. Si028170m            --------------V--------------------PPHQPEAS-----------C--
11. MtBBMb AES80430      -------------SLHI-------------TSSALHFADSWMWASSAGGV--HD---GGA-MLS-AA-
12. Sb03g042810          TACYASSGATAGMHHQLYHQPTSSALHFADSWMWASSAGGV--HD---GGA-MLS-AA-
13. BBM1 Os11g19060      --------------AV-------------------GAGR------------------C--
14. PsASGR BBM like      -------------SLHI------------------PPHQPEAS---------------
15. MtBBMa AAW82334      -------------FI--------------------FSGVPM----------------
16. B3g48697             -------------MI--------------------FSGVPM----------------
17. P00052881m           -------------MI--------------------FSGVPI----------------
18. ZmBBM1 ACG27850      -------------MI--------------------FSGVPM----------------
19. Sb04g025960          -------------FI--------------------FSGVPM----------------
20. Os02g40070           -------------TDMM------------------FPAQPMSA--------G------
21. GmBBM1 gi310892427   AACYASSGSSVGM---LYPPPSSSLQFADSWMWATSS-PVVAHDGVSGGG-MV-----
22. Os01g67410           ---------------V-------------------YSGSAWG---------------
23. Os04g42570 AK287726  --------------V-----------------------AGRA---------------
24. P00061382m           TVCYASSAASTGMHHQL-YQPTSSALHFADSWMWASSA-GV--HD---GGS-MLS-AA-
25. Zm-ODP2 GRMZM2G141638 ------------------------------------GSGC-----------Y---
26. BnBBM2 AF317905      
```

```
ATGGGTTCCA CCAACAACTG GCTGCGCTTC GCCTCGTTCT CCGGCGGCGG CGGCGCCAAG    2134
|||||||||| |||||||||| |||||||||| |||||||||| |||||||||| ||||||||||
ATGGGTTCCA CCAACAACTG GCTGCGCTTC GCCTCGTTCT CCGGCGGCGG CGGCGCCAAG      60

GATGCCGCGG CCCTGCTCCC GCTGCCGCCC TCGCCCCGTG GCGATGTCGA CGAGGCCGGC    2194
|||||||||| |||||||||| |||||||||| |||||||||| |||||||||| ||||||||||
GATGCCGCGG CCCTGCTCCC GCTGCCGCCC TCGCCCCGTG GCGATGTCGA CGAGGCCGGC     120

GCAGAGCCGA AGCTCGAGGA CTTCCTCGGC CTGCAGGAGC CGAGCGCCGC CGCGGTGGGG    2254
|||||||||| |||||||||| |||||||||| |||||||||| |||||||||| ||||||||||
GCAGAGCCGA AGCTCGAGGA CTTCCTCGGC CTGCAGGAGC CGAGCGCCGC CGCGGTGGGG     180

GCTGGGCGGC CATTCGCGGT GGGTGGCGGT GCGAGCTCCA TCGGGCTGTC CATGATCAGG    2314
|||||||||| |||||||||| |||||||||| |||||||||| |||||||||| ||||||||||
GCTGGGCGGC CATTCGCGGT GGGTGGCGGT GCGAGCTCCA TCGGGCTGTC CATGATCAGG     240

AACTGGCTGC GCAGCCAGCC GGCGCCGGCC GGGCCTGCTG CGGGGGTCGA TTCGATGGTG    2374
|||||||||| |||||||||| |||||||||| |||||||||| |||||||||| ||||||||||
AACTGGCTGC GCAGCCAGCC GGCGCCGGCC GGGCCTGCTG CGGGGGTCGA TTCGATGGTG     300

CTGGCGGCTG CGGCGGCGTC GACGGAGGTG GCCGGCGATG GCGCGGAGGG CGGCGGCGCC    2434
|||||||||| |||||||||| |||||||||| |||||||||| |||||||||| ||||||||||
CTGGCGGCTG CGGCGGCGTC GACGGAGGTG GCCGGCGATG GCGCGGAGGG CGGCGGCGCC     360

GTGGCTGACG CGGTGCAGCA GAGGAAGGCG GCGGCGGTGG ACACTTTCGG GCAGCGGACC    2494
|||||||||| |||||||||| |||||||||| |||||||||| |||||||||| ||||||||||
GTGGCTGACG CGGTGCAGCA GAGGAAGGCG GCGGCGGTGG ACACTTTCGG GCAGCGGACC     420

TCCATATACC GCGGCGTCAC AAAGTAGGTT CTTGATTTTA TTTTGGTTTT GGAAAAATTC    2554
|||||||||| |||||||||| |||
TCCATATACC GCGGCGTCAC AAA.......  ..........  ..........  ..........    443

TTCTTTGTTT TTTCTGTTTT CTTCCGACTG GTATATCTTG TGTTAAGAAC TTTTTCATTA    2614
..........  ..........  ..........  ..........  ..........  ..........    443

GATGCATGTC ATACTGTTGC TTTTTCTTGT TGCTTTGAAC CTTTTGGCGT TTGCAGCTTC    2674
..........  ..........  ..........  ..........  ..........  ..........    443

GTTTGGATAT ACAGAACCTA TATTATCCCC TTTAGTAACC AGTAGATTCT TTTTTTTTCT    2734
..........  ..........  ..........  ..........  ..........  ..........    443

TTTTTTTTTT TTGCTTTCGA TGTTGTTAGT GTTCTTGCAT CACGCATGTT TTTCCTCTGA    2794
..........  ..........  ..........  ..........  ..........  ..........    443
```

Fig. 9 (continued)

```
TATTTTAATG GACGATATCA TCTCTAGTTC AAGTTTTTGC TCTTGCTCTT GTTGTAGTGG    2854
..........  ..........  ..........  ..........  ..........  ..........   443

TGCTAAGATT TTTAAAAAAA AAAATTATGA GCAGTTCTTG TGCTGTTTGA AAATGTAAGC    2914
..........  ..........  ..........  ..........  ..........  ..........   443

ATCTCACAGT TCTAAAATAT ATATATATAT ATATATATAA GTCTCTCATG TTGATTTGTG    2974
..........  ..........  ..........  ..........  ..........  ..........   443

GATGTACTGA AGCCCCGCGC GCACACATGC ACACACCGCA CGCTCACACG CCCTAAATCC    3034
..........  ..........  ..........  ..........  ..........  ..........   443

CCGGTGCAAC ACCAGGGTTG TCCCCGATGG GGATCGAACC CTGGCGGGTG GCCTAACCAC    3094
..........  ..........  ..........  ..........  ..........  ..........   443

CGTCAGCTCC CACCACCGAG CTATCAGCTC GTTTGCCCAT ATTTCGTGTG GTACCTCGAT    3154
..........  ..........  ..........  ..........  ..........  ..........   443

ATTTTTATAT TTCTAGATTG CTGTATCTAT CTTCTAGACT TATATAAGTG TTGCGCCACT    3214
..........  ..........  ..........  ..........  ..........  ..........   443

CATACTTTTT ACCGCCTGTA ATCGAGTAGA ACTGCTTCCT CTTTTGATTA TATTGTATCA    3274
..........  ..........  ..........  ..........  ..........  ..........   443

GTTAAATGAT CTTGTTGTTG ATGTGTTTAC CACTTTACCA TCACCATTGC ATGAAATCAC    3334
..........  ..........  ..........  ..........  ..........  ..........   443

TTCAAGACAT GTATTCATGA TTTGGCTGGC TAAATTTGCT AGTGGCACAT ACATGTGGTA    3394
..........  ..........  ..........  ..........  ..........  ..........   443

AAAAAATATT TTTAGTTTGT GCTTGCTATT CTTTTCGGTC ATCCCTTCGT GCCTGTTTAT    3454
..........  ..........  ..........  ..........  ..........  ..........   443
```

Fig. 9 (continued)

```
CCAGAACACC CAATCTGCTT CACATAGTTT TTGAATGCTA TCATCATATT TCTTTTTTGG    3514

.......... .......... .......... .......... .......... ..........     443

AGATATTGTT ACTAAAAGTT TGGCTTTGTC CTCAATAGGC ATAGATGGAC AGGAAGGTAT    3574
                                        ||  |||||||||| ||||||||||
.......... .......... .......... ........GC ATAGATGGAC AGGAAGGTAT     465

GAAGCCCATC TTTGGGACAA TAGCTGCAGA AGAGAAGGTC AAACTCGGAA AGGTAGACAA    3634
|||||||||| |||||||||| |||||||||| |||||||||| |||||||||| ||||||||||
GAAGCCCATC TTTGGGACAA TAGCTGCAGA AGAGAAGGTC AAACTCGGAA AGGTAGACAA     525

GGTAATGATT ATAATATAGA TATTTAAATT TGTAATTATA AGCTGCATCA TATTATTATT    3694
|
G......... .......... .......... .......... .......... ..........     526

TATTAGATCG GCTTTAAAAT TTCACTAGCT AATTTAGTGT TTTTCTTTTC TTCATCGATA    3754

.......... .......... .......... .......... .......... ..........     526

CCTGCAATCG CTTCATTCCA TTGATTCAGT GTATCTTGGT AAGTAATACT TGTTTACAAT    3814
                                | ||||||||
.......... .......... ........T GTATCTTG.. .......... ..........     535

TGCAAAATGG TATATCTCTT GTTGTTTCTC ATGTCAAGTA TATTAAATAT GTGGTTGATG    3874

.......... .......... .......... .......... .......... ..........     535

CATTGAAGGT GGATATGATA AAGAAGAAAA AGCAGCTAGA GCTTATGATT TAGCTGCTCT    3934
        || |||||||||| |||||||||| |||||||||| |||||||||| ||||||||||
........GT GGATATGATA AAGAAGAAAA AGCAGCTAGA GCTTATGATT TAGCTGCTCT     587

CAAGTACCGG GGCACCACAA CTACTACAAA TTTTCCGGTA TTACTTATTG TTAATATGTT    3994
|||||||||| |||||||||| |||||||||| |||||||
CAAGTACCGG GGCACCACAA CTACTACAAA TTTTCCG... .......... ..........     624

GGTTCTCCAG AATTGATATT TTACTTCTAA TATATAACTG CGTATATGAA TGAATGTTGT    4054

.......... .......... .......... .......... .......... ..........     624

AAGATTTTGC ATTTTATGTT CAGATGAGCA ACTATGAAAA GGAGTTAGAA GAGATGAAGC    4114
                |||||||| |||||||||| |||||||||| |||||||||| ||||||||||
.......... .......... ...ATGAGCA ACTATGAAAA GGAGTTAGAA GAGATGAAGC     661

ATATGTCACG ACAAGAATAT GTTGCATCCC TTAGAAGGTA CATGTGTTGT CAAAACTTTG    4174
|||||||||| |||||||||| |||||||||| |||||||
```

Fig. 9 (continued)

```
ATATGTCACG ACAAGAATAT GTTGCATCCC TTAGAAG...  ..........  ..........    698

TACCTTCATG GAAACTGAAC TTATATATTT CACAAATGGA TTGACATAGA ACATATATTT   4234

..........  ..........  ..........  ..........  ..........  ..........    698

GTGATACAGG AAAAGCAGTG GTTTTTCTCG TGGTGCATCA ATTTACCGAG GGGTTACCAG   4294
         |  ||||||||||  ||||||||||  ||||||||||  ||||||||||  ||||||||||
.........G AAAAGCAGTG GTTTTTCTCG TGGTGCATCA ATTTACCGAG GGGTTACCAG    749

GTACAAAATA TTCCTTTTCC TTATTATCTC TGGTTTTAGT TAGCAAGTGC ATTGTTTCTA   4354

..........  ..........  ..........  ..........  ..........  ..........    749

TGGGAATTTG TGTTGCATGT AGATGGGAAT TTGTGTTGCA TGTAGATCAT AAATAGTTGC   4414

..........  ..........  ..........  ..........  ..........  ..........    749

AACTATTAAT CTCATCGTTC TATTGCTGAA TAGTTGTGGT ACTCCTTTAC CACAGTTGAC   4474

..........  ..........  ..........  ..........  ..........  ..........    749

TATGATATTC TATTATATTA TTTTTCTTGC AAAGTTGATA TTTAATTGCT TGTCTAGCTA   4534

..........  ..........  ..........  ..........  ..........  ..........    749

ACTTTCAAGC AATCATGTAA AACAGGCACC ATCAGCATGG AAGGTGGCAA GCAAGAATAG   4594
                           |||||  ||||||||||  ||||||||||  ||||||||||
..........  ..........  .....GCACC ATCAGCATGG AAGGTGGCAA GCAAGAATAG    784

GAAGTGTGGC AGGAAACAAG GATCTTTATT TGGGCACATT CAGTAAGTCA CATTTTAATA   4654
||||||||||  ||||||||||  ||||||||||  ||||||||||  ||
GAAGTGTGGC AGGAAACAAG GATCTTTATT TGGGCACATT CA........  ..........    826

TTTTTAATGA AGCACTGATT TTTTTTTGTC AAGCAAAATG GAAGCAAGAC AGAAAAACAT   4714

..........  ..........  ..........  ..........  ..........  ..........    826

AAACCTACTG GAGCACCTTT TTCATTATTT TGTCTCTTGA ATATAATAGT ATGTGGCTGA   4774

..........  ..........  ..........  ..........  ..........  ..........    826

CCTCTCCCTG TGTAGGTACC CAGGAGGAAG CTGCAGAGGC TTACGACATT GCTGCCATCA   4834
               |||||  ||||||||||  ||||||||||  ||||||||||  ||||||||||
..........  .....GTACC CAGGAGGAAG CTGCAGAGGC TTACGACATT GCTGCCATCA    871
```

Fig. 9 (continued)

```
AATTCCGAGG CCTCAATGCT GTCACGAACT TTGACATGAG CCGGTATGAC GTCAAGAGCA    4894
|||||||||| |||||||||| |||||||||| |||||||||| |||||||||| ||||||||||
AATTCCGAGG CCTCAATGCT GTCACGAACT TTGACATGAG CCGGTATGAC GTCAAGAGCA     931

TCATTGAGAG CAGCTCCCTG CCTGTTGGCG GCACTCCAAA GCGTCTCAAG GAAGTGCCTG    4954
|||||||||| |||||||||| |||||||||| |||||||||| |||||||||| ||||||||||
TCATTGAGAG CAGCTCCCTG CCTGTTGGCG GCACTCCAAA GCGTCTCAAG GAAGTGCCTG     991

ATCAATCAGA TATGGGCATC AACATAAACG GTGACTCTGC TGGTCATATG ACTGCTATCA    5014
|||||||||| |||||||||| |||||||||| |||||||||| |||||||||| ||||||||||
ATCAATCAGA TATGGGCATC AACATAAACG GTGACTCTGC TGGTCATATG ACTGCTATCA    1051

ACCTTCTTAC TGATGGCAAT GACAGCTATG GAGCTGAGAG TTATGGTTAC AGTGGTTGGT    5074
|||||||||| |||||||||| |||||||||| |||||||||| |||||||||| ||||||||||
ACCTTCTTAC TGATGGCAAT GACAGCTATG GAGCTGAGAG TTATGGTTAC AGTGGTTGGT    1111

GTCCCACAGC CATGACGCCA ATCCCCTTTC AATTCAGCAA TGGCCATGAC CATTCCAGGC    5134
|||||||||| |||||||||| |||||||||| |||||||||| |||||||||| ||||||||||
GTCCCACAGC CATGACGCCA ATCCCCTTTC AATTCAGCAA TGGCCATGAC CATTCCAGGC    1171

TGTGGTGCAA GCCAGAGCAG GACAATGCGG TTGTTGCAGC ACTGCATAAC CTGCATCACC    5194
|||||||||| |||||||||| |||||||||| |||||||||| |||||||||| ||||||||||
TGTGGTGCAA GCCAGAGCAG GACAATGCGG TTGTTGCAGC ACTGCATAAC CTGCATCACC    1231

TCCAGCACTT GCCAGCCCCA GTTGGCACCC ATAATTTTTT CCAGCCATCG CCTGTTCAGG    5254
|||||||||| |||||||||| |||||||||| |||||||||| |||||||||| ||||||||||
TCCAGCACTT GCCAGCCCCA GTTGGCACCC ATAATTTTTT CCAGCCATCG CCTGTTCAGG    1291

ACATGACAGG TGTTGCCGAT GCTTCATCGC CACCAGTAGA ATCTAATTCA TTCCTGTACA    5314
|||||||||| |||||||||| |||||||||| |||||||||| |||||||||| ||||||||||
ACATGACAGG TGTTGCCGAT GCTTCATCGC CACCAGTAGA ATCTAATTCA TTCCTGTACA    1351

ATGGGGACGT TGGTTACCAT GGTGCCATGG GTGGCAGCTA TGCCATGCCG GTTGCCACAC    5374
|||||||||| |||||||||| |||||||||| |||||||||| |||||||||| ||||||||||
ATGGGGACGT TGGTTACCAT GGTGCCATGG GTGGCAGCTA TGCCATGCCG GTTGCCACAC    1411

TAGTTGAGGG CAACTCTGCG GGCAGTGGCT ATGGAGTTGA GGAAGGCACA GGGTCTGAAA    5434
|||||||||| |||||||||| |||||||||| |||||||||| |||||||||| ||||||||||
TAGTTGAGGG CAACTCTGCG GGCAGTGGCT ATGGAGTTGA GGAAGGCACA GGGTCTGAAA    1471

TCTTTGGTGG ACGGAACTTG TATTCTCTCT CCCAAGGTTC CTCAGGCGCC AATACTGGAA    5494
|||||||||| |||||||||| |||||||||| |||||||||| |||||||||| ||||||||||
TCTTTGGTGG ACGGAACTTG TATTCTCTCT CCCAAGGTTC CTCAGGCGCC AATACTGGAA    1531

AGGCAGATGC TTATGAAAGC TGGGATCCAT CTATGCTGGT GATATCACAG AAGTCTGCCA    5554
```

Fig. 9 (continued)

```
           ||||||||||  ||||||||||  ||||||||||  ||||||||||  ||||||||||  ||||||||||
           AGGCAGATGC  TTATGAAAGC  TGGGATCCAT  CTATGCTGGT  GATATCACAG  AAGTCTGCCA      1591

ATGTGACTGT  CTGCCATGGC  GCACCTGTAT  TTTCAGTTTG  GAAATGA                     5601
           ||||||||||  ||||||||||  ||||||||||  ||||||||||  |||||||
           ATGTGACTGT  CTGCCATGGC  GCACCTGTAT  TTTCAGTTTG  GAAATGA                     1638
```

GENE FOR INDUCTION OF PARTHENOGENESIS, A COMPONENT OF APOMICTIC REPRODUCTION

CROSS-REFERENCE TO RELATED APPLICATIONS

The present application is a U.S. National Stage entry under 35 U.S.C. § 371 of International Application No. PCT/US2014/061630, filed on Oct. 21, 2014, which claims the benefit of priority 35 U.S.C. § 119(3) to U.S. Provisional Application No. 61/893,741, filed on Oct. 21, 2013, and U.S. Provisional Application No. 62/059,842, filed on Oct. 3, 2014, each of which is hereby incorporated by reference in its entirety.

STATEMENT REGARDING FEDERALLY-SPONSORED RESEARCH

This invention was made with government support under Grant No. 2010-65116-20449 awarded by the United States Department of Agriculture, National Institute of Food and Agriculture, Agriculture and Food Research Initiative (USDA-NIFA-AFRI), and Grant No. DBI-0115911 awarded by the National Science Foundation (NSF). The government has certain rights in the invention.

FIELD OF THE INVENTION

The invention disclosed herein generally relates to genes involved in plant reproduction and methods of using the same.

BACKGROUND

Apomixis is a naturally occurring mode of asexual reproduction in flowering plants; this process results in seed formation without the involvement of meiosis or fertilization of the egg. Apomictic processes bypass meiosis and fertilization, leading directly to clonal embryo formation. Apomictic hybrids are true-breeding hybrids because seed-derived progeny of an apomictic plant are genetically identical to the maternal parent. In other words, apomictic hybrids are clonal in origin.

Apomixis is characterized by: 1) apomeiosis, which refers to the formation of unreduced embryo sacs derived from nucellar cells of the ovary, and 2) parthenogenesis, which refers to the development of the unreduced egg into an embryo. Many types of plant species feature apomictic reproduction and can be propagated asexually.

SUMMARY

Embodiments of the invention encompass methods of achieving propagation from one or more gametophytic or sporophytic cells in an ovule of a flowering plant in the absence of egg cell fertilization, the methods including: transforming a flowering plant with an ASGR-BBML gene construct capable of encoding a polypeptide having at least 75% sequence identity to the polypeptide of SEQ ID NO: 4; obtaining one or more gametophytic or sporophytic cells from an ovule from the transformed plant in the absence of egg cell fertilization; and deriving a progeny plant from the one or more gametophytic or sporophytic cells, wherein the progeny plant contains one or more sets of chromosomes from the transformed plant, thereby achieving propagation of the flowering plant in the absence of egg cell fertilization.

In some embodiments, the ASGR-BBML gene construct further includes one or more untranslated region (UTR). In some embodiments, the ASGR-BBML gene construct further including one or more UTR can have at least 70% sequence identity to SEQ ID NO: 1 or a fully complementary strand thereof. In some embodiments, the ASGR-BBML gene construct further includes a promoter. In some embodiments, the promoter is capable of regulating the expression of a polypeptide having at least 75% sequence identity to the polypeptide of SEQ ID NO: 4. In some embodiments, the promoter includes a nucleotide having at least 70% sequence identity to SEQ ID NO: 5 or a fully complementary strand thereof. In some embodiments, the ASGR-BBML gene construct further including one or more UTR and a promoter can have at least 70% sequence identity to SEQ ID NO: 3 or a fully complementary strand thereof.

In some embodiments, the embryo can be formed from an unreduced egg. In some embodiments, the embryo can be formed from a reduced egg. In some embodiments, the embryo can be formed from a somatic cell.

In some embodiments, a polyploid plant can be transformed to produce a diploid or dihaploid progeny plant. In some embodiments, a diploid plant can be transformed to produce a haploid progeny plant. In some embodiments, the haploid progeny plant can be treated to achieve chromosome doubling and production of a homozygous plant. In some embodiments, the progeny plant can be obtained via culturing.

In some embodiments, the flowering plant can be a monocot. In some embodiments, the flowering plant can be a dicot.

In some embodiments, the flowering plant can be a grass or a leguminous plant. In some embodiments, the grass can be a species of millet, rice, maize, wheat, *Sorghum*, or switchgrass.

In some embodiments, the flowering plant can be heterozygous and can be transformed to produce a clonal offspring. In some embodiments, the flowering plant can be heterozygous and can be transformed to produce a haploid offspring.

In some embodiments, the methods of the present invention can be used to propagate one or more heritable traits in the flowering plant.

The invention also encompasses plants or plant parts produced by methods of achieving propagation from one or more gametophytic or sporophytic cells in an ovule of a flowering plant in the absence of egg cell fertilization, the methods including: transforming a flowering plant with an ASGR-BBML gene construct capable of encoding a polypeptide having at least 75% sequence identity to the polypeptide of SEQ ID NO: 4; obtaining one or more gametophytic or sporophytic cells from an ovule from the transformed plant in the absence of egg cell fertilization; and deriving a progeny plant from the one or more gametophytic or sporophytic cells, wherein the progeny plant contains one or more sets of chromosomes from the transformed plant, thereby achieving propagation of the flowering plant in the absence of egg cell fertilization.

The invention also encompasses methods of obtaining a flowering plant capable of being reproduced in the absence of egg cell fertilization, the method including: transforming a flowering plant with an ASGR-BBML gene construct capable of encoding a polypeptide having at least 85% sequence identity to the polypeptide of SEQ ID NO: 4, thereby obtaining a flowering plant capable of being reproduced in the absence of egg cell fertilization.

The invention also encompasses plants or plant parts produced by methods of obtaining a flowering plant capable of being reproduced in the absence of egg cell fertilization, the method including: transforming a flowering plant with an ASGR-BBML gene construct capable of encoding a polypeptide having at least 85% sequence identity to the polypeptide of SEQ ID NO: 4, thereby obtaining a flowering plant capable of being reproduced in the absence of egg cell fertilization.

The invention also encompasses methods of producing seed of a flowering plant in the absence of egg cell fertilization, the method including: transforming a flowering plant with an ASGR-BBML gene construct; obtaining one or more embryos from the transformed plant in the absence of egg cell fertilization; and producing seed from the one or more embryos which contains one or more sets of chromosomes which are derived solely from the transformed mother plant, thereby obtaining seed propagation from the flowering plant in the absence of egg cell fertilization.

The invention also encompasses seeds produced by methods of producing seed of a flowering plant in the absence of egg cell fertilization, the method including: transforming a flowering plant with an ASGR-BBML gene construct; obtaining one or more gametophytic or sporophytic cells from an ovule from the transformed plant in the absence of egg cell fertilization; and deriving seed from the one or more gametophytic or sporophytic cells, wherein the seed contains one or more sets of chromosomes from the transformed plant, thereby producing seed of the flowering plant in the absence of egg cell fertilization.

The invention also encompasses ASGR-BBML gene constructs capable of encoding a polypeptide having at least 75% sequence identity to the polypeptide of SEQ ID NO: 4, wherein the polypeptide encoded by the ASGR-BBML gene construct, when expressed in one or more gametophytic or sporophytic cells in an ovule of a flowering plant, can allow propagation to be achieved in the absence of egg cell fertilization. In some embodiments, the ASGR-BBML gene constructs can further include one or more UTR and a promoter, wherein the ASGR-BBML gene construct has at least 70% sequence identity to SEQ ID NO: 3 or a fully complementary strand thereof.

BRIEF DESCRIPTION OF THE DRAWINGS

Those of skill in the art will understand that the drawings, described below, are for illustrative purposes only. The drawings are not intended to limit the scope of the present teachings in any way.

FIG. 1 depicts consensus sequence (SEQ ID NO: 69), Si000593m (SEQ ID NO: 41), P00023058m (SEQ ID NO: 42), Si016558m (SEQ ID NO: 43), P00062296m (SEQ ID NO: 44), B2g57747 (SEQ ID NO: 45), B5g14960 (SEQ ID NO: 46), BnBBM1_AF317904 (SEQ ID NO: 47), CcASGR_BBM_like1 (SEQ ID NO: 48), AtBBM_At5G17430 (SEQ ID NO: 49), Si028170m (SEQ ID NO: 50), MtBBMb_AES80430 (SEQ ID NO: 51), Sb03g042810 (SEQ ID NO: 52), BBM1_Os11g19060 (SEQ ID NO: 53), PsASGR_BBM_like (SEQ ID NO: 54), MtBBMa_AAW82334 (SEQ ID NO: 55), Bradi3g48697 (SEQ ID NO: 56), P00052881m (SEQ ID NO: 57), ZmBBM1_ACG27850 (SEQ ID NO: 58), Sb04g025960 (SEQ ID NO: 59), Os02g40070 (SEQ ID NO: 60), GmBBM1_gi310892427 (SEQ ID NO: 61), Os01g67410 (SEQ ID NO: 62), Os04g42570_AK287726 (SEQ ID NO: 63), P00061382m (SEQ ID NO: 64), Zm-ODP2_GRMZM2G141638 (SEQ ID NO: 65), and BnBBM2_AF317905 (SEQ ID NO: 66).

FIGS. 5A, 5B, and 5C depict results from using an antisense probe; FIG. 5D depicts results from using a control probe.

FIG. 7A depicts an aposporous embryo sac with a two-celled embryo. FIG. 7B depicts two aposporous embryo sacs, the left with a multicellular embryo and the right at a single- or bi-cellular stage.

FIGS. 8A and 8B are different planes of focus of the same ovary to show both intact synergids (S) and polar nuclei (PN). GUS expression is detected in the egg cell (E) of unfertilized sexual embryo sacs on day of anthesis. A weaker GUS signal in synergid cells can sometimes be detected (FIG. 8C). No GUS signal is detected in the polar nuclei (PN) or antipodal cells (AN) of the mature sexual embryo sac. GUS staining is detected in cells of the developing embryo (EM) three days after fertilization but not in developing endosperm (EN) (FIG. 8D). No other staining in ovary tissue is identified.

FIG. 9 depicts the alignment of the cDNA to the genomic DNA. The aligned sequence is shown at the start of ATG.

The upper lines contain the genomic DNA sequence (SEQ ID NO. 67), and the lower lines contain the cDNA sequence (SEQ ID NO. 68).

Figure 10:
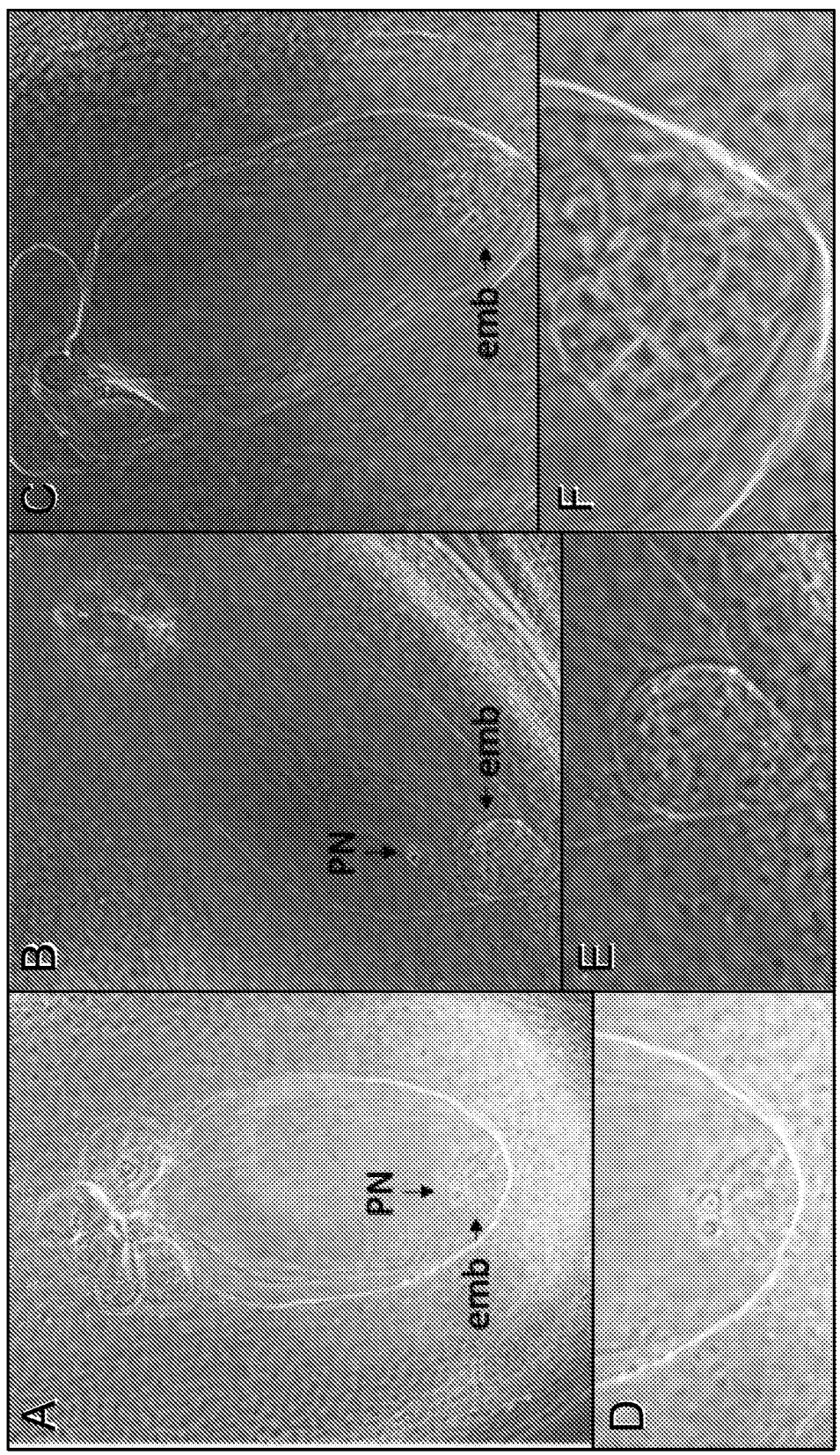

FIG. 10 depicts examples of embryo formation in embryo sacs with polar nuclei. FIGS. 10A, 10B, and 10C depict embryo sac structures typical of sexual development, i.e., all have antipodal cells which are absent from aposporous embryo sacs that develop in *Pennisetum*. Each embryo sac contains a developing embryo and unfertilized central cell, as shown by the persistent polar nuclei. FIGS. 10A, 10B, and 10C depict the full embryo sac structure. FIGS. 10D, 10E, and 10F depict a magnification of the embryo (micropylar) end of the embryo sac.

Figure 11:
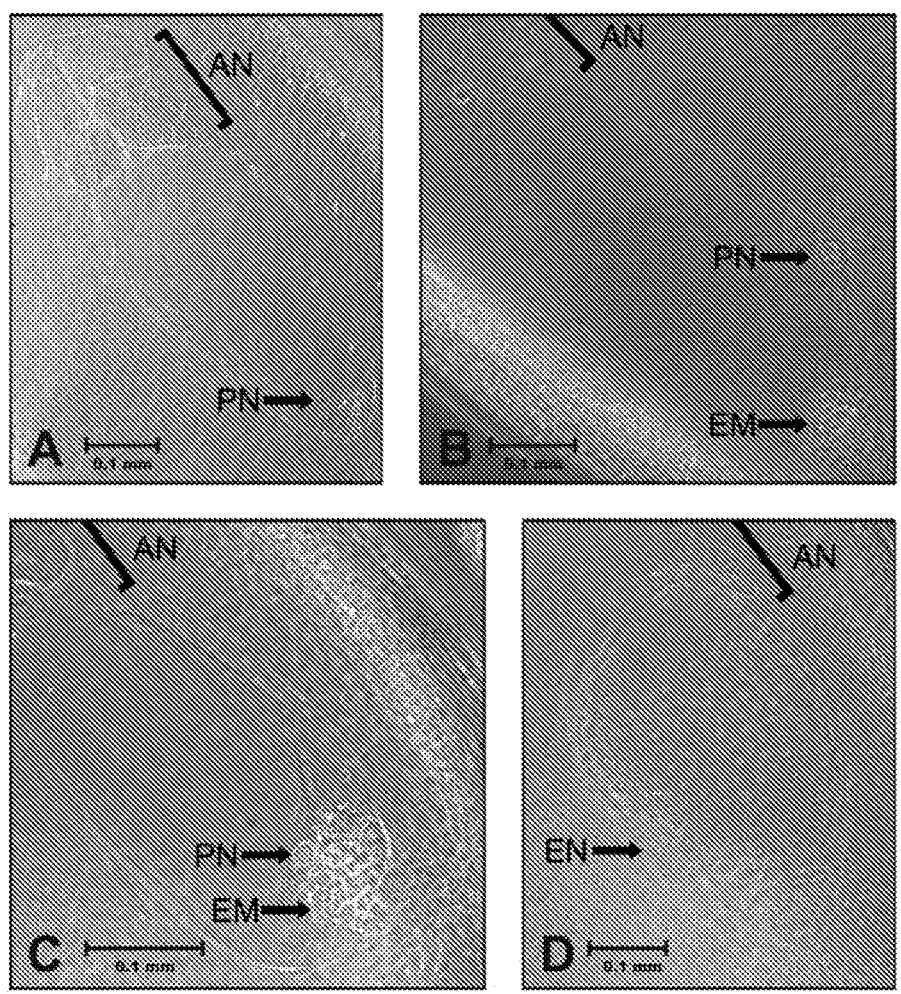

FIG. 11 depicts parthenogenetic embryo development in ovaries of sexual tetraploid pearl millet containing the gPsASGR-BBML transgene. Images are from ovaries collected and fixed 2 days after anthesis, cleared with methyl salicylate and visualized under phase contrast optics at 20×. FIG. 11A depicts a control ovary with a structurally mature embryo sac derived from an untransformed tissue culture line without fertilization. No embryo development is seen. Embryo development in unfertilized ovaries is clearly seen in sexual transgenic lines g11a (FIG. 11B) and g3f (FIG. 11C) based on the appearance of an embryo-like structure (EM) at the micropylar end of the embryo sac; polar nuclei (PN), and antipodal cells (A). FIG. 11D shows that endosperm formation (EN) at 2 days after anthesis can readily be detected when pollination is permitted as shown for line g11a.

Figure 12:
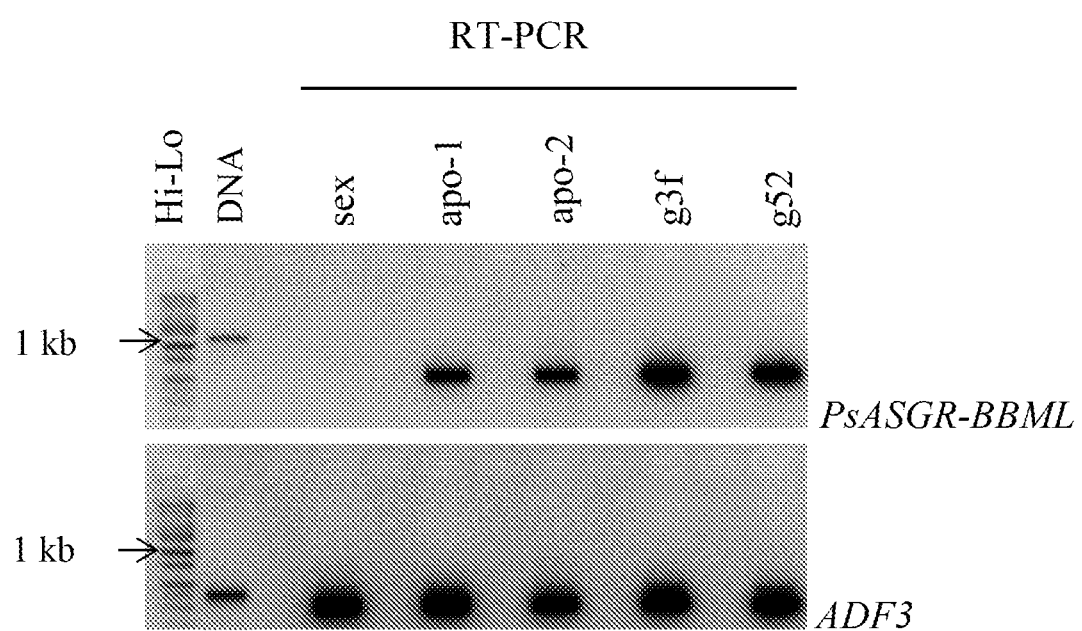

FIG. 12 depicts non-quantitative RT-PCR analysis of gPsASGR-BBML expression in ovaries. Total RNA was isolated from sexual (sex) and apomictic (apo-1, apo-2) $BC_8$ ovaries at day of anthesis and from line g3f and g52 ovaries at 2 days after anthesis. Three micrograms of total RNA was subjected to DNAse treatment, reverse transcribed and an aliquot of the first strand cDNA was amplified with PsASGR-BBML specific primers p779/80 (Y. Akiyama et al., *BMC Evolutionary Biology*, 11:289 (2011)) and ADF3 primers p1127/28. The genomic DNA sample was isolated from an apomictic $BC_8$ plant. Ladder is HI-LO DNA marker (Minnesota Molecular, Minneapolis, Minn.). The marker and DNA lanes originated from the same gel for both primers and were merged with the RT-PCR lanes to remove unnecessary lanes.

Figure 13:
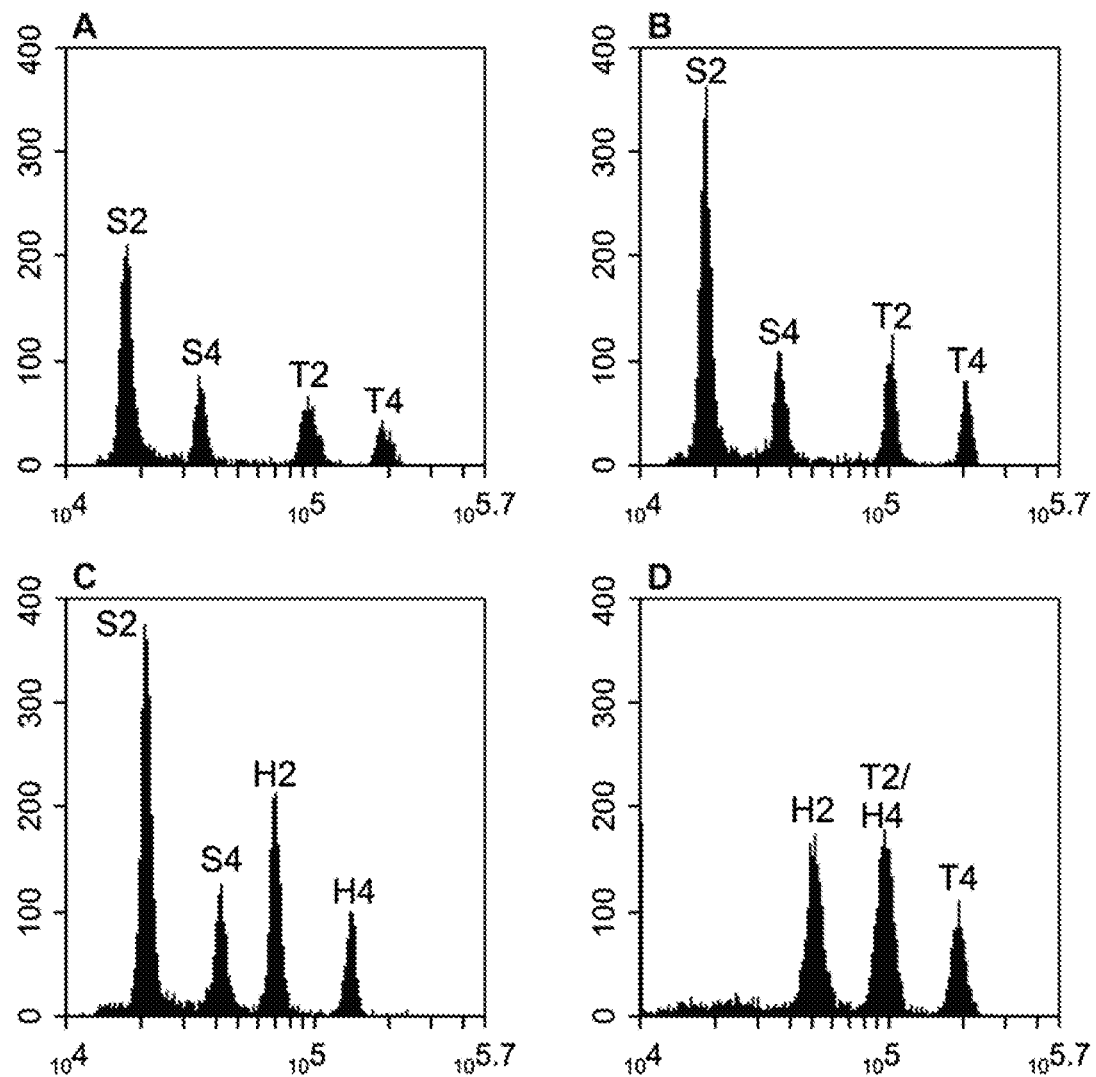

FIG. 13 depicts flow cytometry analysis to determine genome size of $T_0$ plants and offspring. Examples of genome size analysis using a BD-Accuri flow cytometer of $T_0$ plants and g3f offspring ($T_1$). FIG. 13A depicts peak analysis of *Sorghum* and $T_0$ line g11a leaf tissue. FIG. 13B depicts peak analysis of *Sorghum* and g3f offspring 108. FIG. 13C depicts peak analysis of *Sorghum* and g3f offspring 101. FIG. 13D depicts peak analysis of g3f offspring 105 and 107. S2 and S4 designate *Sorghum* 2X/2C and 2X/4C peaks, respectively. H2 and H4 designate $T_1$ diploid/dihaploid offspring (FIG. 13C, 13D) with 2C and 4C peaks, respectively. T2 and T4 designate tetraploid $T_0$ pearl millet (FIG. 13A) or tetraploid $T_1$ offspring (FIG. 13B, 13D) with 2C and 4C peaks, respectively.

Figure 14:
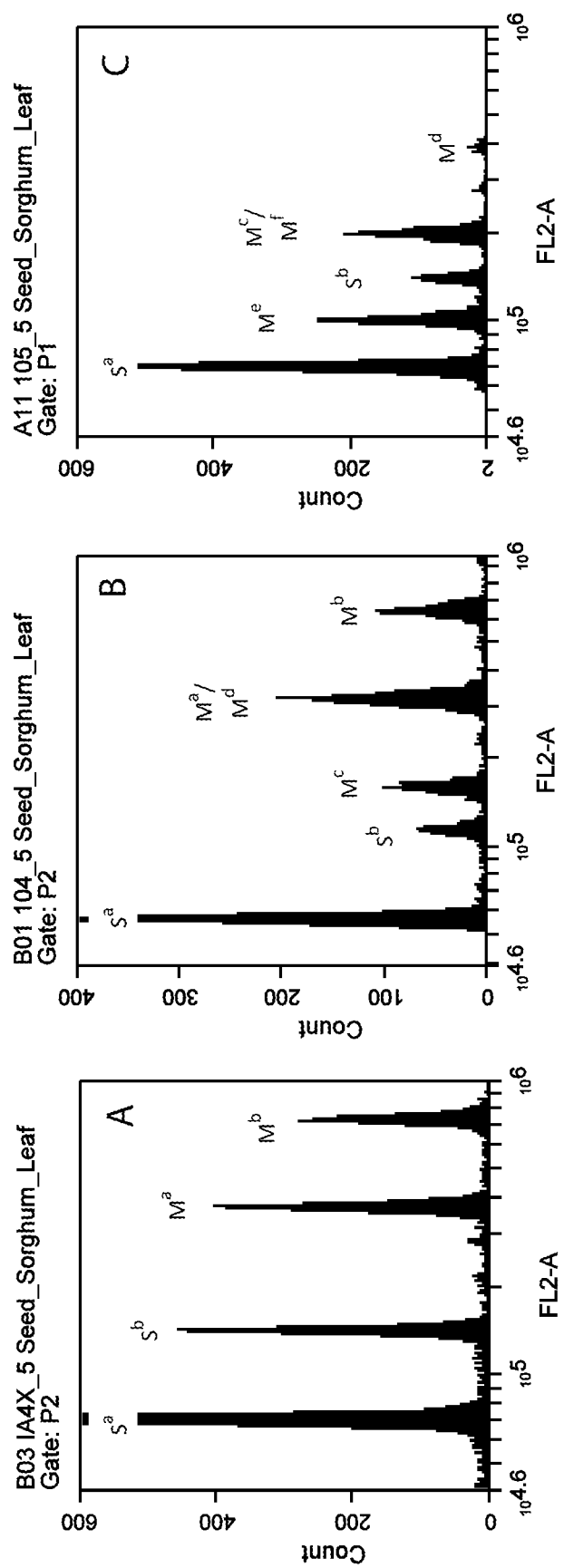

FIG. 14 depicts flow cytometry of seed, showing the production of reduced offspring. FIG. 14A shows 5 seed from an untransformed tetraploid IA4X plant with genomic peaks $M^a$ (4n/2c) and $M^b$ (4n/4c) based on comparison with *Sorghum* leaf genomic peaks $S^a$ (2n/2c) and $S^b$ (2n/4c) used for a standard. FIG. 14B shows 5 seed from g3f-offspring 104 which inherited the PsASGR-BBM transgene but remained a tetraploid plant. Seed show genomic millet peaks of $M^a$ (4n/2c) and $M^b$ (4n/4c) from fertilized embryos along with millet peaks from unfertilized reduced embryos $M^c$ (2n/2c) and $M^d$ (2n/4c) based on comparison with *Sorghum* leaf genomic peaks $S^a$ (2n/2c) and Sb (2n/4c) used for a standard. FIG. 14C shows 5 seed from g3f-offspring 105 which inherited the PsASGR-BBM transgene and showed reduction of genome size to a diploid/dihaploid. Seed show genomic millet peaks of $M^c$ (2n/2c) and $M^d$ (2n/4c) from unreduced embryos along with millet peaks from reduced embryos $M^e$ (1n/1c) and $M^f$ (1n/2c) based on comparison with *Sorghum* leaf genomic peaks $S^a$ (2n/2c) and $S^b$ (2n/4c) used for a standard.

Figure 15:
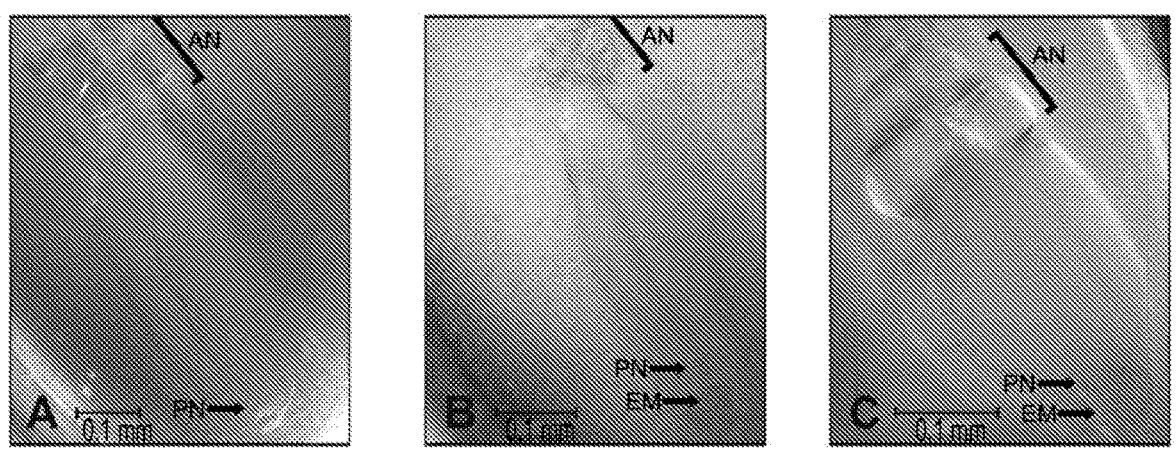

FIG. 15 depicts parthenogenetic embryo development in ovaries of sexual offspring of pearl millet $T_0$ lines g52 and g3f inheriting the gPsASGR-BBML transgene. Examples of ovaries collected and fixed 2 days after anthesis, cleared with methyl salicylate and visualized under DIC optics at 20×. FIG. 15A depicts a control ovary with a structurally mature embryo sac derived from an untransformed tissue culture line without fertilization. No embryo development is seen. Embryo development in unfertilized ovaries is clearly seen in sexual offspring 306 from transgenic line g52 (FIG. 15B) and offspring 105 from transgenic line g3f (FIG. 15C) based on the appearance of an embryo-like structure (EM) at the micropylar end of the embryo sac; polar nuclei (PN), and antipodal cells (AN).

Figure 16:
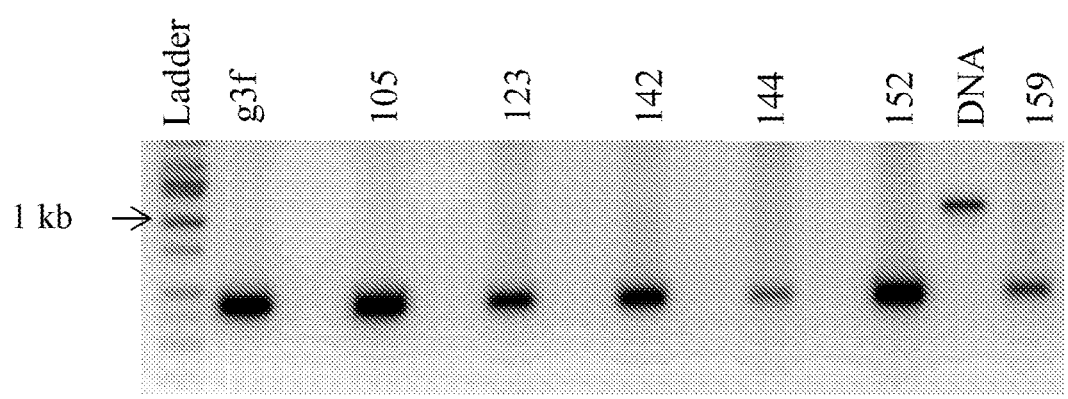

FIG. 16 depicts results from non-quantitative RT-PCR analysis of gPsASGR-BBML expression in ovaries of g3f offspring. Total RNA was isolated from ovaries at day of anthesis from g3f and g3f offspring. Three micrograms of total RNA was subjected to DNAse treatment, reverse transcribed and an aliquot of the first strand cDNA was amplified with PsASGR-BBML specific primers p779/80 (Y. Akiyama et al., *BMC Evolutionary Biology*, 11:289 (2011)). The genomic DNA sample was isolated from an apomictic $BC_8$ plant. Ladder is HI-LO DNA marker (Minnesota Molecular).

Figures 17, 18:
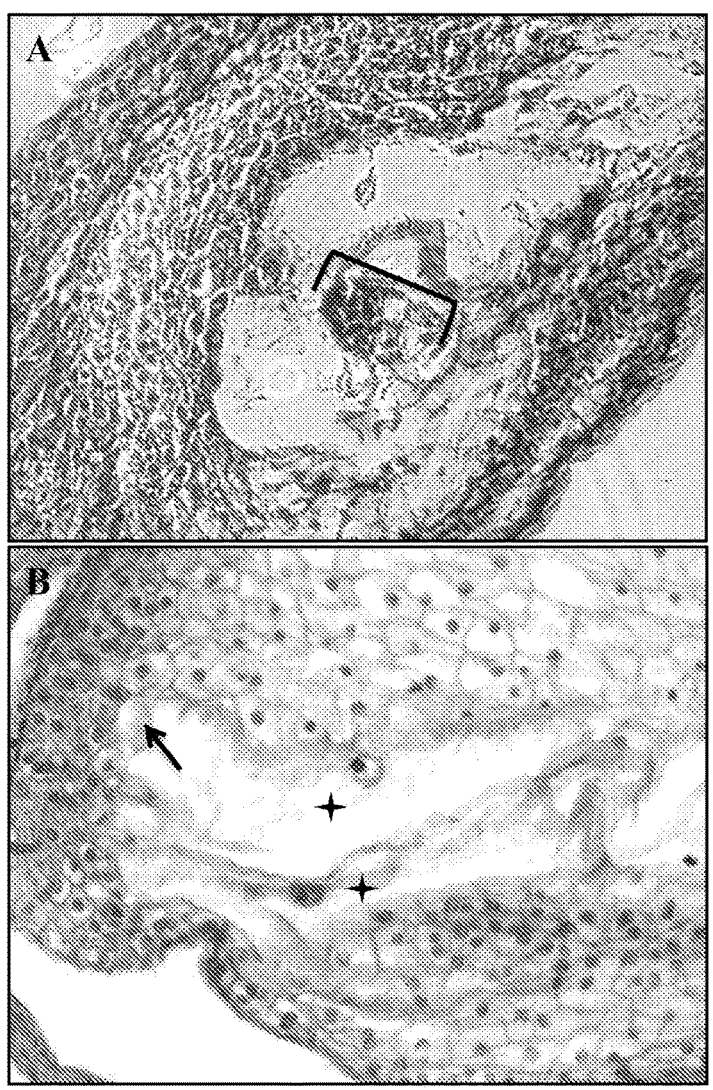

FIG. 17 depicts results from semi-quantitative RT-PCR analysis of the reduction in PsASGR-BBML expression in apomictic RNAi F1 lines. Image of signals produced after hybridization of RT-PCR products of unpollinated ovary tissue from RNAi F1 lines at day of anthesis for quantification. Signals from triplicate PCR reactions were averaged to determine the final reduction of PsASGR-BBML in ASGR positive/RNAi positive lines compared to the control plant (ASGR positive/RNAi negative). The ADF3 signal was used to normalize starting RNA amounts for each sample. Reductions were calculated using the following formula: (1−(averaged signal of ASGR-BBML RNAi line/averaged signal of ADF3)/(averaged signal of ASGR-BBML control line/averaged signal of ADF3))×100 (Table 7).

FIG. 18 depicts an example of histological observation used to determine embryo cell number in control and PsASGR-BBML RNAi lines. FIG. 18A depicts a section and embryo cell count of control plant S7-6T10. Embryo development is marked with a bracket. This embryo contains greater than 16 cells. FIG. 18B depicts a section of RNAi line S5-5T-28. No embryo development is identified in this ovary (egg cell is marked with an arrow) containing 2 aposporous embryo sacs denoted by stars.

Figure 19:
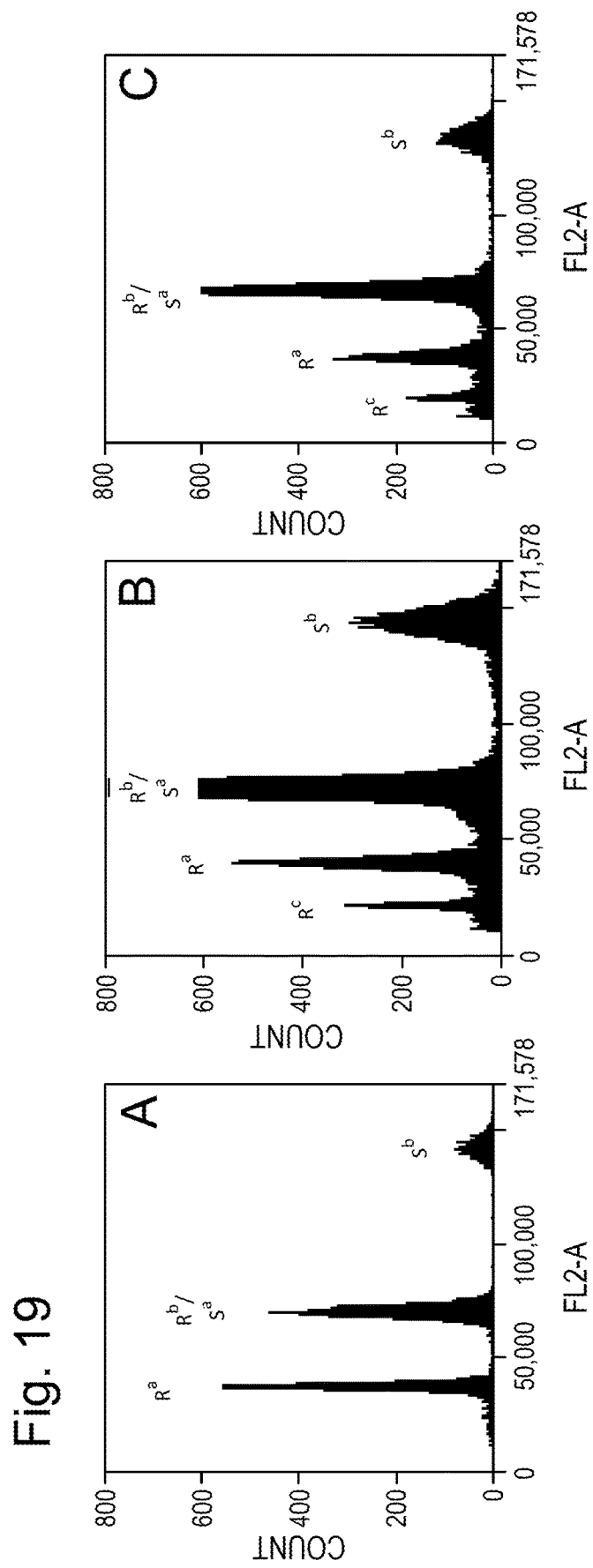

FIG. 19 depicts flow cytometry of dissected embryos, showing the production of haploid offspring in rice transgenic plants carrying the PsASGR-BBM transgene. FIG. 19A shows leaf genomic peaks of untransformed rice $R^a$ (2n/2c) and $R^b$ (2n/4C) and *Sorghum* $S^a$ (2n/2c) and $S^b$ (2n/4c). Rice peak $R^b$ and *Sorghum* peak $S^a$ overlap due to similar genome sizes. FIG. 19B shows 5 dissected embryos from T₀ rice line 26 which contains a transcriptionally active PsASGR-BBM transgene. Rice line 26 embryos show genomic rice peaks of $R^a$ (2n/2c) from fertilized embryos along with rice peaks from unfertilized reduced embryos $R^c$ (1n/1c) based on comparison with *Sorghum* leaf genomic peaks $S^a$ (2n/2c) and $S^b$ (2n/4C). FIG. 19C shows 5 dissected embryos from T₀ rice line 34 which contains a transcriptionally active PsASGR-BBM transgene. Rice line 34 embryos show genomic rice peaks of $R^a$ (2n/2c) from fertilized embryos along with rice peaks from unfertilized reduced embryos $R^c$ (1n/1c) based on comparison with *Sorghum* leaf genomic peaks $S^a$ (2n/2c) and $S^b$ (2n/4C).

DETAILED DESCRIPTION OF THE INVENTION

Unless otherwise noted, terms are to be understood according to conventional usage by those of ordinary skill in the relevant art.

As used herein, the terms "plant" and "plant part" can include inclusively, as context indicates, plant cells, plant protoplasts, plant cell tissue cultures from which plants can be regenerated, plant calli, plant clumps, and plant cells that are intact in plants or parts of plants such as embryos, pollen, ovules, seeds, flowers, kernels, ears, cobs, husks, stalks, roots, root tips, anthers, and the like.

The term polynucleotide can include the terms "nucleic acid", "nucleic acid sequence", and "oligonucleotide", as those terms are generally understood in the art. What is included in a specific instance will be appreciated by a person of skill in the art as indicated by the context, but where no particular context limits the scope, then the term will be understood to be broadly inclusive. Therefore, the term polynucleotide can also include DNAs or RNAs that contain one or more modified bases. Thus, DNAs or RNAs with backbones modified for stability or for other reasons are "polynucleotides", as that term is intended herein. Moreover, DNAs or RNAs comprising unusual bases, such as inosine, or modified bases, such as tritylated bases, to name just two examples, are polynucleotides as the term is used herein. It will be appreciated that a great variety of modifications have been made to DNA and RNA that serve many useful purposes known to those of skill in the art. The term polynucleotide as it is employed herein embraces such chemically, enzymatically or metabolically modified forms of polynucleotides, as well as the chemical forms of DNA and RNA characteristic of viruses and cells, including simple and complex cells, inter alia.

As used herein, the term "transgenic" describes a non-naturally occurring plant that contains a genome modified by man, wherein the plant includes in its genome an exogenous nucleic acid molecule, which can be derived from the same or a different species, including non-plant species. The exogenous nucleic acid molecule can be a gene regulatory element such as a promoter, enhancer, or other regulatory element, or can contain a coding sequence, which can be linked to a native or heterologous gene regulatory element. Transgenic plants that arise from sexual cross or by selfing are descendants of such a plant.

As used herein, "polymorphism" means the presence of one or more variations of a nucleic acid sequence at one or more loci in a population of one or more individuals. The variation can comprise, but is not limited to, one or more base changes, the insertion of one or more nucleotides, or the deletion of one or more nucleotides. A polymorphism includes a single nucleotide polymorphism (SNP), a simple sequence repeat (SSR), indels (insertions and deletions), a restriction fragment length polymorphism, a haplotype, and a tag SNP. In addition, a polymorphism can include a genetic marker, a gene, a DNA-derived sequence, a RNA-derived sequence, a promoter, a 5' untranslated region of a gene, a 3' untranslated region of a gene, microRNA, siRNA, a quantitative trait locus (QTL), a satellite marker, a transgene, mRNA, ds mRNA, a transcriptional profile, or a methylation pattern. A polymorphism can arise from random processes in nucleic acid replication, through mutagenesis, as a result of mobile genomic elements, from copy number variation and during the process of meiosis, such as unequal crossing over, genome duplication and chromosome breaks and fusions. The variation can be commonly found or can exist at low frequency within a population, the former having greater utility in general plant breeding and the latter can be associated with rare but important phenotypic variation.

As used herein, a "marker" can refer to a polymorphic nucleic acid sequence or nucleic acid feature. In a broader aspect, a "marker" can be a detectable characteristic that can be used to discriminate between heritable differences between organisms. Examples of such characteristics can include genetic markers, protein composition, protein levels, oil composition, oil levels, carbohydrate composition, carbohydrate levels, fatty acid composition, fatty acid levels, amino acid composition, amino acid levels, biopolymers, pharmaceuticals, starch composition, starch levels, fermentable starch, fermentation yield, fermentation efficiency, energy yield, secondary compounds, metabolites, morphological characteristics, and agronomic characteristics.

As used herein, a "genotype" can refer to the genetic component of the phenotype, and this can be indirectly characterized using markers or directly characterized by nucleic acid sequencing. Suitable markers include a phenotypic character, a metabolic profile, a genetic marker, or some other type of marker. A genotype can constitute an allele for at least one genetic marker locus or a haplotype for at least one haplotype window. In some embodiments, a genotype can represent a single locus, and in others it can represent a genome-wide set of loci. In some embodiments, the genotype can reflect the sequence of a portion of a chromosome, an entire chromosome, a portion of the genome, and the entire genome.

As used herein, a "construct" or "gene construct" can refer to a polynucleotide which codes for the particular gene of the gene construct. Such polynucleotides can be operably linked to one or more untranslated regions (UTRs), and/or one or more transcriptional initiation regulatory sequence/promoter regulatory region which is capable of directing the transcription of the polynucleotide in the intended host cell, such as tissues of a transformed plant, thereby regulating expression of a given gene. Expression of a given gene can be determined in terms of the amount of gene product or protein expressed, and a variety of methods can be used for detecting protein expression levels, including, for example, enzyme linked immunosorbent assays (ELISA), Western blots, immunoprecipitations, and immunofluorescence, and the like.

The construction of such gene constructs which can be employed in conjunction with the present invention is well known to those of skill in the art in light of the present disclosure. See, e.g., Sambrook et al.; *Molecular Cloning: A Laboratory Manual*; Cold Spring Harbor, N.Y. (1989); Gelvin et al.; *Plant Molecular Biology Manual* (1990); *Plant Biotechnology: Commercial Prospects and Problems*, eds. Prakash et al.; Oxford & IBH Publishing Co.; New Delhi, India; (1993); and Heslot et al.; *Molecular Biology and Genetic Engineering of Yeasts*; CRC Press, Inc., USA;

(1992). For example, plant expression vectors may include (1) a cloned plant gene under the transcriptional control of 5' and 3' regulatory sequences and (2) a dominant selectable marker. Such plant gene constructs may also contain, if desired, a promoter regulatory region (e.g., one conferring inducible, constitutive, environmentally- or developmentally-regulated, or cell- or tissue-specific/selective expression), a transcription initiation start site, a ribosome binding site, an RNA processing signal, a transcription termination site, and/or a polyadenylation signal. Constitutive, tissue-preferred, or inducible promoters can be employed. For example, certain promoters are known to those in the art to be capable of initiating transcription preferentially in certain tissues, such as leaves, roots, fruit, seeds, or flowers.

As used herein, a "vector" can refer to any nucleic acid construct which is able to enter a plant cell, including circular or linear nucleic acids, and/or bacterial, viral, fungal, plant and synthesized nucleic acids, as well as homologous or heterologous nucleic acid constructs.

As used herein, the terms "transform", "transformed", and "transforming" can refer to the introduction of a foreign gene into a plant. Numerous methods for introducing foreign genes into plants are known and can be used to insert nucleic acid sequences into a plant host, including biological and physical plant transformation protocols. See, for example, Miki et al. (1993) "Procedure for Introducing Foreign DNA into Plants," in *Methods in Plant Molecular Biology and Biotechnology*, ed. Glick and Thompson (CRC Press, Inc., Boca Raton), pages 67-88. The methods chosen can vary with the host plant, and many such methods are known to those in the art; these include chemical transfection methods such as calcium phosphate, microorganism-mediated gene transfer such as *Agrobacterium* (Horsch et al. (1985) *Science* 227:1229-1231), electroporation, micro-injection, and biolistic bombardment. Expression cassettes and vectors and in vitro culture methods for plant cell or tissue transformation and regeneration of plants are known and available. See, for example, Gruber et al. (1993) "Vectors for Plant Transformation," in *Methods in Plant Molecular Biology and Biotechnology*, ed. Glick and Thompson (CRC Press, Inc., Boca Raton), pages 89-119.

Once a single transformed plant has been obtained, e.g., a plant transformed with a desired gene, conventional plant breeding methods can be used to transfer the structural gene and associated regulatory sequences via crossing and backcrossing. In general, such plant breeding techniques are used to transfer a desired gene into a specific plant, e.g., a crop plant or another type of plant used for commercial purposes. Accordingly, the methods of the claimed invention can be used in, for example, plant breeding, plant improvement, propagation of unstable and/or recessive genotypes, seed production, and trait propagation, as well as other purposes involving the reproduction of plants.

As used herein, the terms "sequence identity" or "identity" in the context of two nucleic acid or polypeptide sequences includes reference to the residues in the two sequences that are the same when aligned for maximum correspondence over a specified comparison window. When percentage of sequence identity is used in reference to proteins it is recognized that residue positions that are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are often said to have "sequence similarity" or "similarity". Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

Those in the art recognize that the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

The percentage of sequence identity/similarity is an integer selected from the group consisting of from 50 to 99. Exemplary sequence identity/similarity values include 55%, 60%, 65%, 70%, 75%, 80%, 85%, 90%, and 95%. Sequence identity can be determined using, for example, the GAP, CLUSTALW, or BLAST algorithms, preferably BLAST. Substantial identity of nucleotide or amino acid sequences for these purposes normally means sequence identity of at least 60%, 70%, 80%, 90%, and 95% or higher.

Moreover, one of skill in the art will recognize that the sequence identity values can be appropriately adjusted to determine corresponding identity of proteins encoded by two nucleotide sequences by taking into account codon degeneracy, amino acid similarity, reading frame positioning, and the like. Polypeptides that are "substantially similar" share sequences as noted above except that residue positions, which are not identical, can differ by conservative amino acid changes. Another indication that nucleotide sequences are substantially identical is if two molecules hybridize to each other under stringent conditions. Generally, stringent conditions are selected to be about 5° C. to about 20° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. Typically, stringent wash conditions are those in which the salt concentration is about 0.02 molar at pH 7 and the temperature is at least about 50, 55, or 60° C. However, nucleic acids which do not hybridize to each other under stringent conditions are still substantially identical if the polypeptides that they encode are substantially identical. This may occur, e.g., when a copy of a nucleic acid is created using the maximum codon degeneracy permitted by the genetic code. One indication that two nucleic acid sequences are substantially identical is that the polypeptide encoded by the first nucleic acid is immunologically cross reactive with the polypeptide encoded by the second nucleic acid.

For a description of various libraries, vectors, nucleic acids, etc., see, for example, Stratagene Cloning Systems, Catalogs 1999 (La Jolla, Calif.); and, Amersham Life Sciences, Inc, Catalog '99 (Arlington Heights, Ill.).

The specification and claims use the singular forms "a", "an", and "the". These terms are intended to not exclude a plural interpretation, and may preferably include a plural interpretation, depending on the context. Thus, for example, reference to "a compound" may include a variety of such compounds, or several of those same compounds, unless the interpretation is contrary to the context in which it is used.

Apomixis is a naturally occurring developmental process of asexual reproduction wherein the offspring produced are genetically identical to the mother plant, thereby resulting in clonal propagation of the maternal plant through seed. Multiple forms of apomixis exist in nature. For example, gametophytic apomixis is characterized by apomeiosis, which is the formation of unreduced embryo sacs derived from nucellar cells of the ovary, as well as by parthenogenesis, which is the development of the unreduced egg into an embryo. The ability to accomplish apomixis via genetic engineering or introgression can have a major economic impact for agricultural crops, as breeding programs would have the ability to transmit apomixis through the paternal gametes, then subsequently fix hybrid genotypes/vigor through clonal propagation of the maternal seed.

Apospory is one form of apomixis, which is prevalent in the grass family. This gametophytic form of apomixis is characterized by the failure of meiosis (apomeiosis) or by the degeneration of meiotic products and the development of embryo sacs from chromosomally unreduced nucellar cells. In these embryo sacs, the unreduced egg develops parthenogenetically. Therefore, apomeiosis and parthenogenesis are two fundamental components of apomixis. The results described herein demonstrate the molecular basis for apomixis in a plant species where the reproductive process has naturally evolved. This discovery can be utilized to facilitate the propagation of superior gene combinations in crop plants. A gene that induces the apomixis trait has been highly sought after for decades. Such a gene can be of great value in plant breeding.

The present work describes apomictic species in the genera *Pennisetum* and *Cenchrus*; both genera are in the grass family, which is the single most important family of cultivated plants. One of the members of this family is pearl millet (*Pennisetum glaucum* syn. *Cenchrus americanus*), which is a sexual diploid grain crop with significant production in the semi-arid tropics. The genus *Pennisetum* also has many apomictic species, most of which have been crossed with pearl millet in an attempt to introduce gene(s) for apomixis; however, male sterility during backcrossing has heretofore limited their use for conventional transfer of the apomixis trait (Dujardin M., Hanna W., *J. Hered.* 74:277-279 (1983a); Dujardin M., Hanna W., *Crop Sci.* 23:156-160 (1983b); Dujardin M., Hanna W., *Theor. Appl. Genet.* 69:97-100 (1984); Dujardin M., Hanna W., *Crop Sci.* 25:59-62 (1985)). Some progress with conventional transfer has been achieved via the use of apomictic *P. squamulatum* (2n=8x=56) (Akiyama Y. et al., *J. Hered.* 97:521-524 (2006)) as the male parent in crosses with artificially induced tetraploid pearl millet (Dujardin M., Hanna W., *J. Genet.* Breed. 43:145-151 (1989)).

Apospory is the type of apomictic reproduction in *Pennisetum/Cenchrus* (Ozias-Akins P. et al., *Funct. Integr. Genomics* 3:94-104 (2003)), i.e., one or more somatic cells of the nucellus begins to enlarge, and the nucleus of each aposporous initial undergoes two successive mitotic divisions to produce a four-nucleate embryo sac. The four nuclei comprise the egg, two synergids, and one polar nucleus, or, alternatively, the egg, one synergid, and two polar nuclei. The uni- or bi-nucleate central cell must be fertilized in pseudogamous species in order for endosperm to develop (Kojima A., Nagato Y., *Sex. Plant Reprod.* 5:79-85 (1992); Naumova T. et al., *Acta Botanica Neerlandica* 42:299-312 (1993); Nogler G., Gametophytic apomixis, in: B. M. Johri (Ed.), *Embryology of Angiosperms*, Springer, Berlin. pp. 475-518. (1984)). Thus, there is selection pressure for normal microsporogenesis resulting in viable pollen even though female meiosis can be irregular. The unreduced egg cell begins parthenogenetic development (Vielle J. et al., Link. *Plant J.* 8:309-316 (1995)) either slightly before or soon after single fertilization of the central cell in apomictic *Cenchrus ciliaris*.

The reproductive phenotype of species and hybrids in a genus usually can be determined unambiguously based on screening of a relatively small number of cleared pistils (which have been made optically transparent through chemical treatment). Phenotype in the genus *Pennisetum* can also be established via a dominant, red marker gene (Hanna W., Burton G., *J. Heredity* 83:386-388 (1992)) that, when present in the pollen parent of a testcross, will allow the classification of red progeny as having arisen through sexual reproduction.

The *Pennisetum squamulatum* origin of apomixes has been previously described (U.S. Pat. No. 5,811,636). In addition, a nucleic acid marker has been used to identify a clone containing the gene of interest (U.S. Pat. No. 6,028, 185), and some apospory genes have been previously characterized (Huo H. "Genetic analysis of the apospory-specific genomic region (ASGR) in *Pennisetum squamulatum*: from mapping to candidate gene" (Doctoral dissertation) (2008). Retrieved from http <colon slash slash> dbs <dot> galib <dot> uga <dot> edu <slash> cgi-bin <slash> getd <dot> cgi?userid=galileo&serverno=9&instcode=ugal; Zeng Y. "Identification and characterization of apospory candidate genes in *Pennisetum* and *Cenchrus*" (Doctoral dissertation) (2008). Retrieved from http <colon slash slash> dbs <dot> galib <dot> uga <dot> edu <slash> cgi-bin <slash> getd <dot> cgi?userid=galileo&serverno=9&instcode=ugal)). Apomixis is transmitted by a physically large, non-recombining chromosomal region in *P. squamulatum*; this region is known as the apospory-specific genomic region (ASGR) (P. Ozias-Akins, D. Roche, W. W. Hanna, *Proc Natl Acad Sci USA* 95:5127-5132 (1998)), and the PsASGR-BabyBoom-Like (PsASGR-BBML) genes reside within this region (G. Gualtieri et al., *Plant Physiology* 140:963-971 (2006)).

Apomixis in *Pennisetum* has been mapped molecularly via RAPD, RFLP, AFLP, and SCAR markers conducted in backcross populations as well as through a pseudo-testcross between the heterozygous apomict *P. squamulatum* (as male parent) and sexual pearl millet (Dujardin M., Hanna W., *J. Genet. Breed.* 43:145-151 (1989); Goel S. et al., *Genetics* 163:1069-1082 (2003); Ozias-Akins P. et al., *Proc. Natl. Acad. Sci. USA* 95:5127-5132 (1998); Ozias-Akins P. et al., *Theor. Appl. Genet.* 85:632-638 (1993)). It was determined that a single linkage group from the apomictic parent was necessary and sufficient for the transmission of apomixis, and a single, intact chromosome has been transmitted to the $BC_8$ generation where it has been found to reside in a tetraploid pearl millet background (Singh et al., *Crop Sci.* 50:892-902 (2011)). Mapping in a second species, namely *C. ciliaris*, has yielded similar results (Jessup R. et al., *Crop Sci.* 42:1688-1694 (2002); Roche D. et al., *Plant J.* 19:203-208 (1999)). In both species, high-resolution mapping is prevented by a non-recombining chromosomal block, although the size of the ASGR has been reduced by recombination to ~¼ of a chromosome or ~50 Mb. A recombinant in buffelgrass was recently recovered that demonstrates separation of apomeiosis and parthenogenesis (Conner et al., *Planta* 238:51-63 (2013)). This recombinant retained the portion of the ASGR required for aposporous embryo sac formation; however, the portion of the ASGR necessary for parthenogenesis was lost. Comparison of the ASGR between buffelgrass and *P. squamulatum* shows conservation both on the macrosyntenic and microsyntenic level (Goel S. et al., *Genetics* 173:389-400 (2006); Gualtieri G. et al., *Plant Physiol* 140 963-971 (2006)).

DNA sequence analysis of bacterial artificial chromosome clones (Roche D. et al., *Theor. Appl. Genet.* 104:804-812 (2002)) mapped to the ASGR has been conducted to search for synteny between rice and the two apomictic species under study. While small regions of microsynteny were identified whereas macrosynteny was not established, 25 *C. ciliaris* and 23 *P. squamulatum* ASGR genes were identified (Conner J. et al., *Plant Physiol.* 147:1396-1411 (2008)), with the sequencing data showed that overall the ASGR is a gene-poor and transposable element rich region. The identification of a highly abundant long terminal repeat (LTR) sequence within the ASGR sequencing data has allowed for the development of sequence-specific amplified polymorphism (SSAP) markers, which have been used to efficiently target the ASGR (Huo H. et al., *Theor. Appl. Genet.* 119: 199-212 (2009)).

As described herein, in *Pennisetum squamulatum* (L.) R. Br., apomixes has been found to segregate as a single dominant locus, namely the ASGR, which contains multiple copies of the PsASGR-BBML gene. The present study investigated the function of PsASGR-BBML in sexual tetraploid pearl millet and apomictic F₁ plants. PsASGRBBML was found to be expressed in egg-cells prior to fertilization, and expression of PsASGR-BBML in sexual pearl millet was found to induce parthenogenesis and the production of haploid offspring. Reduced PsASGR-BBML expression in apomictic F₁ transgenic plants inheriting a PsASGR-BBML silencing construct was found to correspond with fewer parthenogenetic embryos and cell number in parthenogenetic embryos. These data demonstrate the key role of the PsASGR-BBML gene in parthenogenesis in the apomictic pathway.

The results described herein describe a gene found in tightly-linked ASGR bacterial artificial chromosome (BAC) vectors of both apomictic species, but lost in the recombinant *C. ciliaris* plant lacking parthenogenesis; this gene has high protein similarity to the BABY BOOM (BBM) gene of *Brassica napus*. BBM originally was coined as the gene name for a cDNA transcript that was induced in microspore cultures of *Brassica napus* (BnBBM) undergoing somatic embryogenesis (Boutilier K. et al., *Plant Cell* 14:1737-1749 (2002)). BnBBMJ and BnBBM2 predicted proteins are 98% similar to one another and are also 85% similar to their *Arabidopsis* ortholog.

These three proteins have the key feature of an AP2-domain region. AP2 domains, named for an amino acid repeat identified in the APETALA2 gene of *Arabidopsis* (Jofuku K. et al., *Plant Cell* 6:1211-1225 (1994)), a flower development gene that also was shown to be involved in regulation of other floral homeotic genes, are 60-70 amino acid DNA-binding domains (Pfam—PF00847). These AP2 domains are characteristic of a large family of transcription factor proteins that cluster due to their similarity in this conserved region, which is highly conserved among not only BBM but other related developmental genes in this class.

The APETALA 2/ETHYLENE RESPONSE FACTOR (AP2/ERF) DNA-binding domain family has been identified in a wide group of plants, such as mosses, algae, gymnosperms, and angiosperms. The AP2 gene family is divided into two groupings, namely the ERF-like (ethylene response element binding factor) and AP2-like groups (Weigel D. *Plant Cell* 7:388-389 (1995); Ohme-Takagi M. and Shinshi H. *Plant Cell* 7:173-182 (1995); Okamuro J. et al., *Proceedings of the National Academy of Sciences* 94:7076-7081 (1997)). The ERF-like group is characterized as having only a single AP2 domain; in this group, functions tend to be related to stress responses (biotic and abiotic) (Riechmann J. and Meyerowitz E., *Biol. Chem.* 379:633-646 (1998)). The AP2-like genes contain two AP2 domains (repeat 1 and 2) that have similarity to one another and a short interdomain linker region; this group can be further divided into two groups, namely eu-AP2 (which includes APETELA2) and ANT (for AINTEGUMENTA) lineages. The ANT lineage can itself be divided between basalANT and euANT lineages, which contain specific motifs euANT1 thru 4 (S. Kim, P. S. Soltis, K. Wall, D. E. Soltis, *Mol. Biol. Evol.* 23:107-120 (2006)), which contain the PLETHORA-like, AINTEGUMENTA-like, AINTEGUMENTA-like1, AINTEGUMENTA-like5 and BBM-like subgroups. Proteins within these subgroups have critical roles in meristem maintenance, cell proliferation, organ initiation and growth, embryogenesis, and root formation (A. Horstman, V. Willemsen, K Boutilier, R. Heidstra, *Trends in Plant Science* 19:146-157 (2014)). The ANT lineage is required for integument initiation and female gametophyte development in addition to early growth of other primordia, with the exception of roots (Elliott R. et al., *Plant Cell* 8:155-168 (1996); Klucher K. et al., *The Plant Cell* 8:137-153 (1996)). ANT, AtBBM, and BnBBM genes fall within the ANT clade (Kim S. et al., *Mol. Biol. Evol.* 23:107-120 (2006)).

Figure 2:
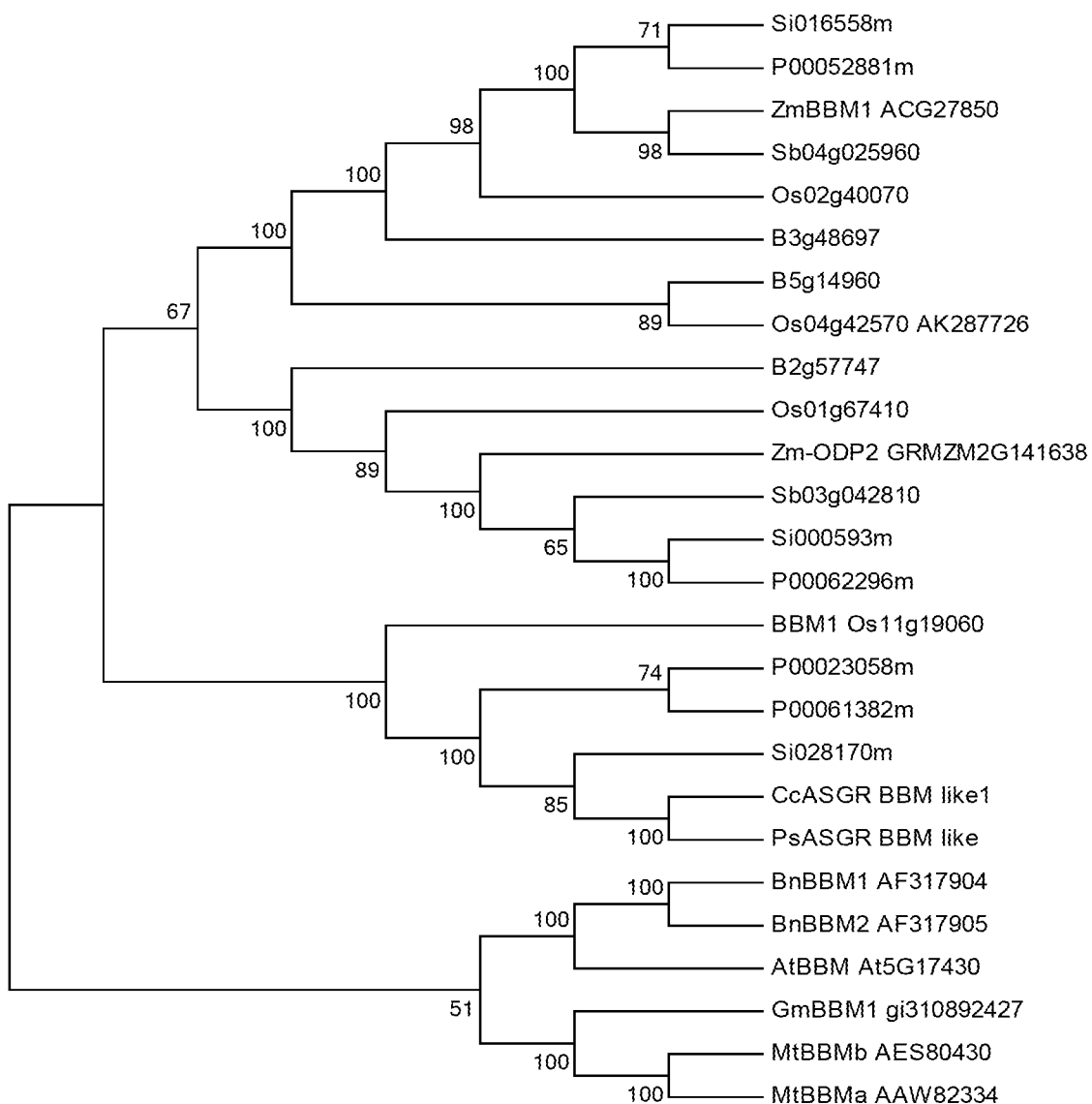
FIG. 2 depicts a phylogenetic tree of 26 BBM-like proteins. The evolutionary history was inferred using the Neighbor-Joining method (N. Saitou, M. Nei, *Molecular Biology and Evolution* 4:406-425 (1987)). The evolutionary distances were computed using the JTT matrix-based method (D. T. Jones, W. R. Taylor, J. M. Thornton, *Computer Applications in the Biosciences* 8:275-282 (1992)). The bootstrap consensus tree shown was inferred from 1000 replicates (J. Felsenstein, *Evolution* 39:783-791 (1985)). Branches corresponding to partitions reproduced in less than 50% bootstrap replicates were collapsed. The percentage of replicate trees in which the associated taxa clustered together in the bootstrap test is shown next to the branches. All ambiguous positions were removed for each sequence pair. There were a total of 1067 positions in the final dataset. Evolutionary analyses were conducted in MEGA6 (K. Tamura et al., *Molecular Biology and Evolution* 30:2725-2729 (2013)).

A BBM-like gene from *Zea mays* called ODP2 has previously been described (International Patent No. WO2005075655; U.S. Pat. No. 8,420,893). However, the apomixis-specific BBM differs substantially from the maize BBM genes outside of the AP2-domain. The BBM, BBM-like, and ASGR-BBM-like proteins share a conserved bbm-1 domain that has not been identified in other members of the euANT lineage. Deletion of the bbm-1 domain has eliminated the ability of transgenic plants to induce somatic embryogenesis on cotyledons (S. El Ouakfaoui et al., *Plant Mol Biol* 74:313-326 (2010)). A published phylogenetic study of the BBM-like proteins (S. El Ouakfaoui et al., *Plant Mol Biol* 74:313-326 (2010)) was extended to include BBM-like proteins from newly sequenced monocots. A distinct clade of proteins from *Oryza sativa*, including the ASGRBBMs, BBM1 (Os11g19060), and proteins from *Setaria italica* and *Panicum virgatum* were found to be formed in the majority of phylogenic trees constructed (FIG. 2). No functional studies on the genes within this clade, other than PsASGR-BBML, have been reported, although the UniGene database at NCBI (http <colon slash slash> www <dot> ncbi <dot> nlm <dot> nih <dot> gov <slash> unigene) and the Rice Oligonucleotide Array Database (http <colon slash slash> www <dot> ricearray <dot> org <slash> expression <slash> expression <dot> php) contains limited expression data for BBM1.

While BBM genes have been expressed from sexual species in ovules prior to fertilization, neither embryo development nor an apomixis phenotype has been observed to date. The expression of BnBBM has been observed in microspores 3-4 days post-induction (at the time they were destined to become embryogenic), persisting throughout the time frame tested (28 days post-induction) (Boutilier K. et al., *Plant Cell* 14:1737-1749 (2002); Malik M. et al., *Plant Physiology* 144:134-154 (2007)). BnBBM expression, as determined by RT-PCR, has also been observed in 3-day-old seeds/globular embryos, and expression was found to persist throughout embryo development (Malik M. et al., *Plant Physiology* 144:134-154 (2007)). BnBBM and BnLEC1 (LEAFY COTYLEDON 1), whose expression primarily occurs during microspore and zygotic embryogenesis, are considered to be markers for embryogenesis. BBM was also found to be detectable in *Arabidopsis* ovules in free-nuclear endosperm, as established by in situ hybridization (Boutilier K. et al., *Plant Cell* 14:1737-1749 (2002)). While expression was found to decline in endosperm once cellularization was initiated, to date there has been no published evidence for expression of BBM in egg or zygote cells within ovules. BnBBM was originally considered to provide a route to induction of adventitious embryony in seeds, hence maternally derived embryos as a form of apomixis (U.S. Pat. No. 7,151,170). In adventitious embryony, no alteration in embryo sac development occurs; rather, somatic cells of the ovule, usually nucellus, directly divide to form embryos. Adventitious embryony is therefore sporophytic apomixis.

Figure 1:
FIG. 1 depicts the T-Coffee alignment of a subset of BabyBoom (BBM), BabyBoom-Like (BBM-like), and apospory-specific genomic region (ASGR)-BBM-like proteins with labeled domains.
Figure 1:
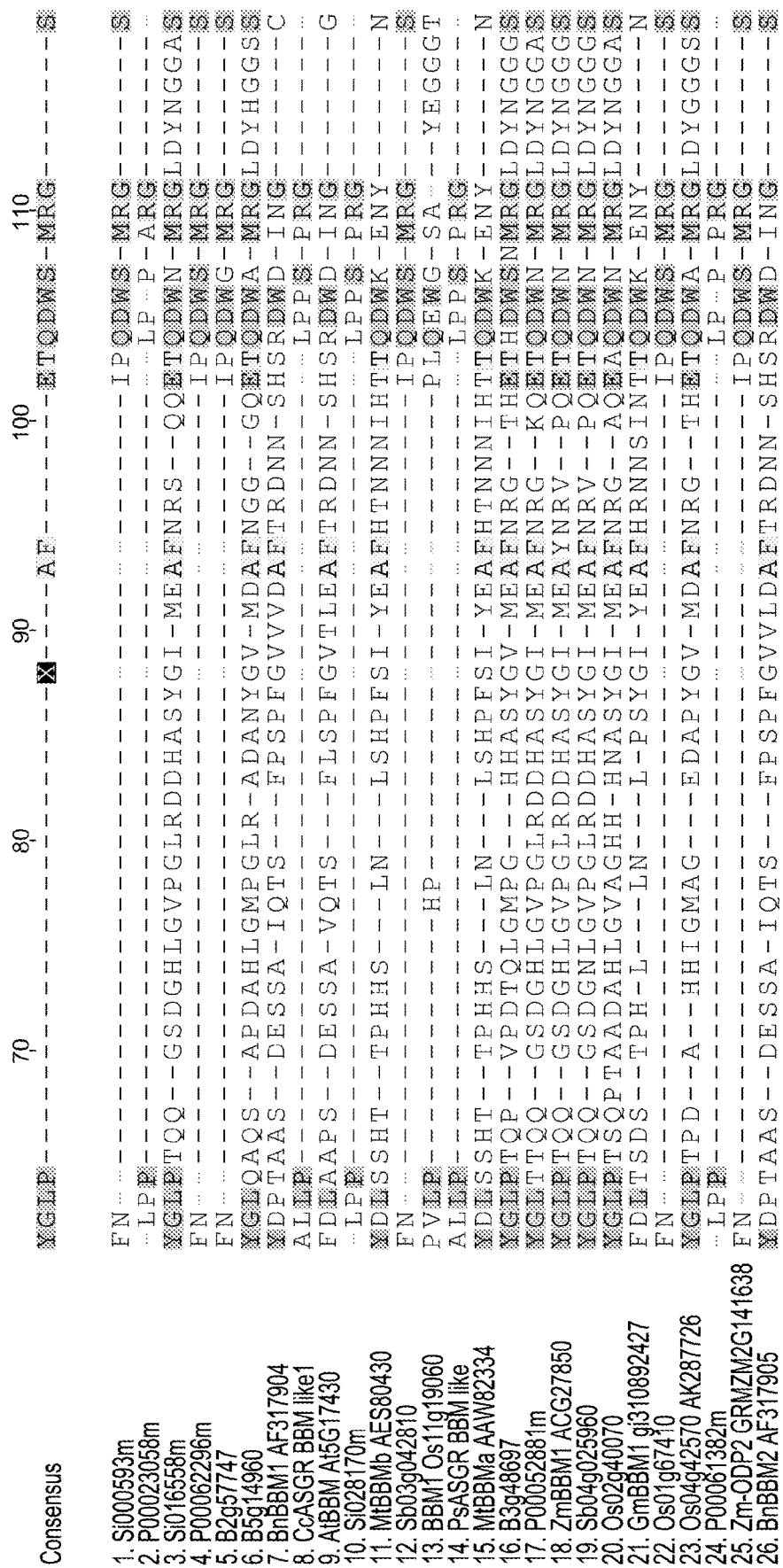
Figure 1:
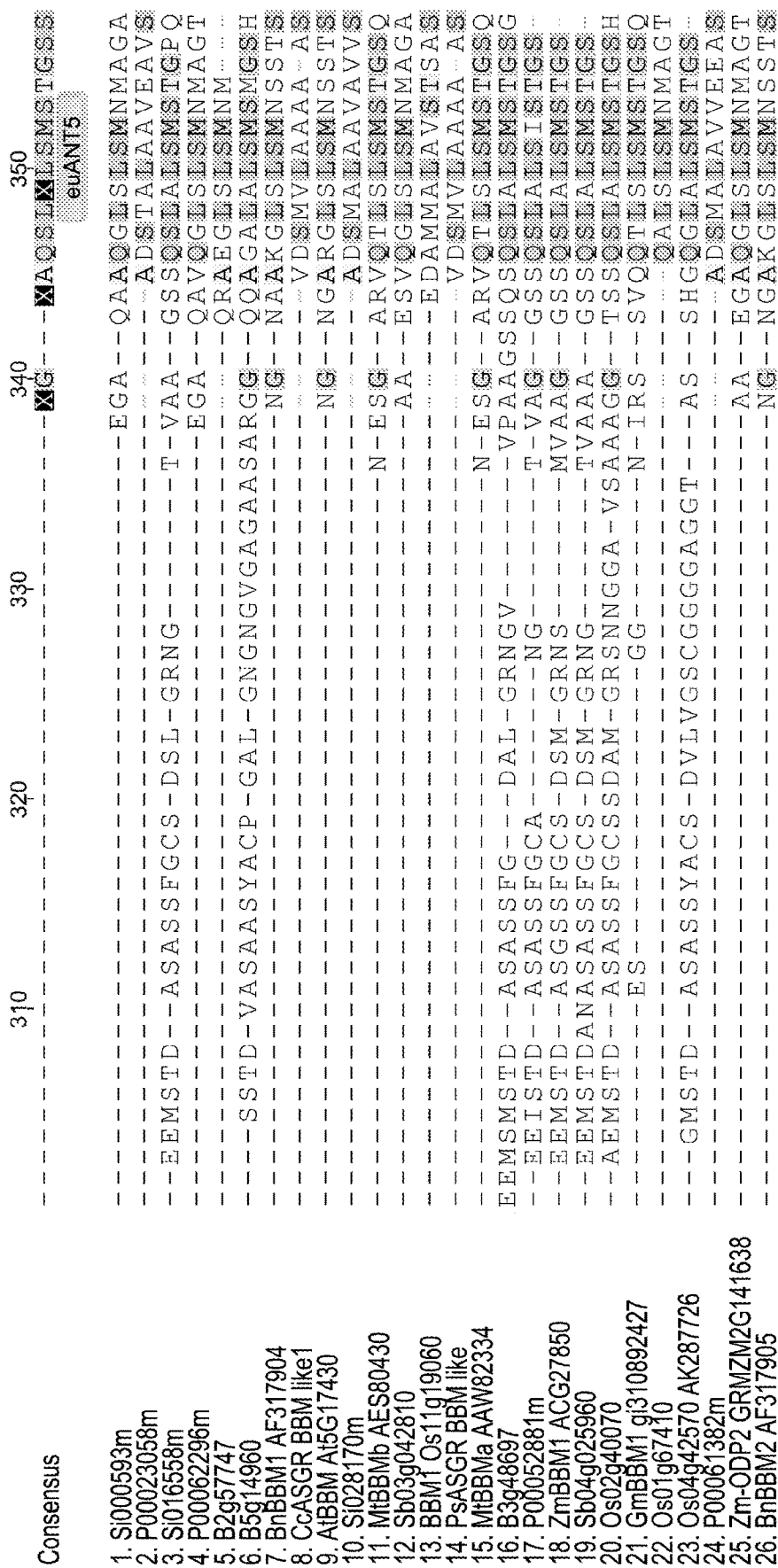
Figure 1:
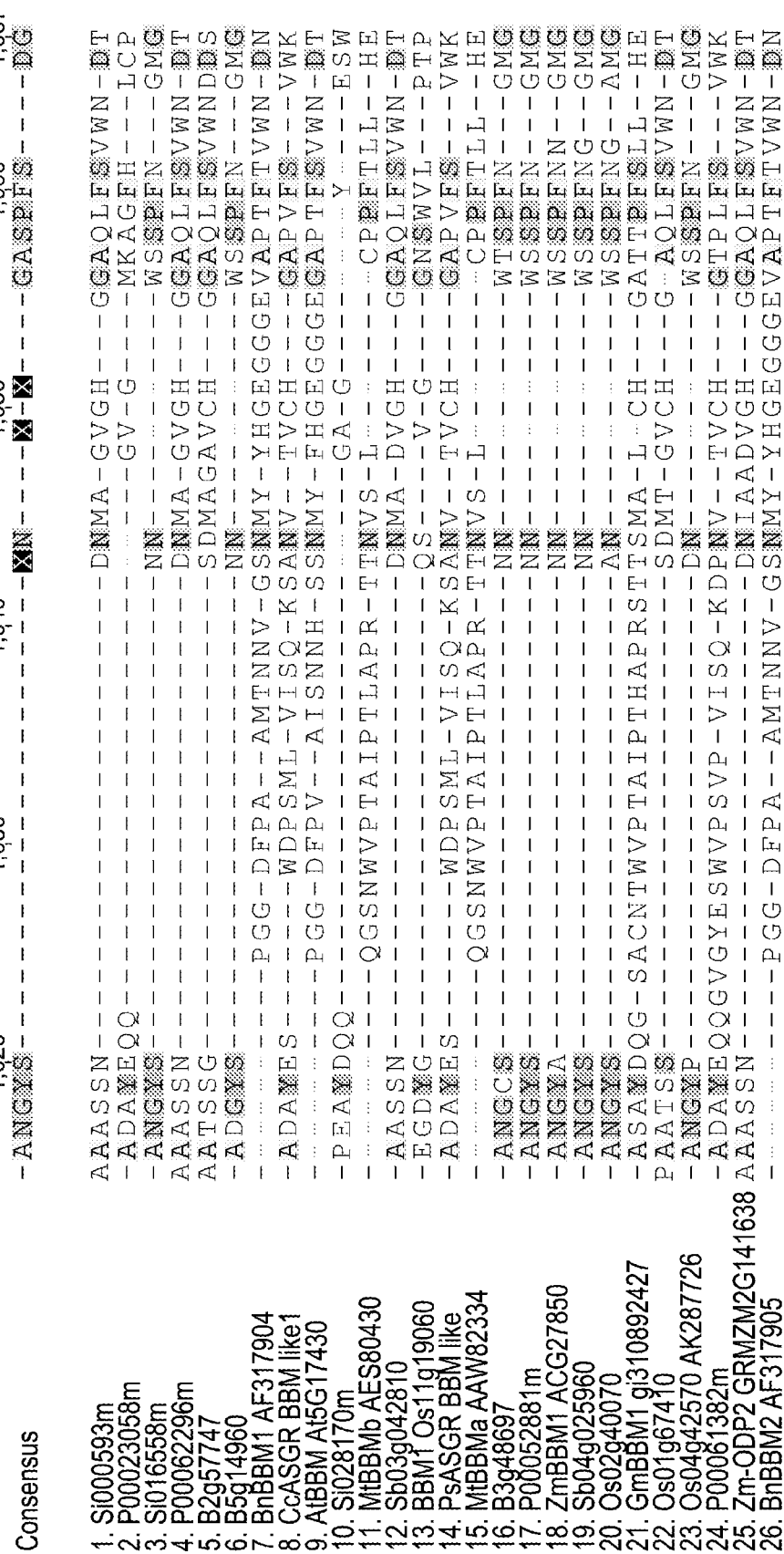

While amino acid similarity between the AP2 regions of ASGR-BBML and BnBBM is high (96%), the similarity declines significantly outside of this region (35% similarity upstream and 27% similarity downstream). Three highly conserved genomic duplications of PsASGR-BBML have been identified from ASGR-linked BACs p203, p207 (J. A. Conner et al., *Plant Physiol.* 147:1396-411 (2008)), and p208 to date. The p208 PsASGR-BBML sequence is identical to the p207 PsASGR-BBML2 sequence (EU559277.1), with the exception of the number of AT repeats (11 vs. 17) found in intron 1. The conservation of gene sequence means that it is not clear which of the PsASGR-BBML genomic regions are transcribed. The PsASGR-BBML transcript encodes a 545 amino acid protein derived from the splicing of 8 exons, a 73 bp 5' UTR, and multiple 3' UTRs, with lengths ranging from 30 to 258 bp. The PsASGR-BBML gene contains two AP2 DNA-binding domains and is therefore predicted to function as a transcription factor (FIG. 1). Two ASGR-linked copies of ASGR-BBML also have been found to be present in apomictic *Cenchrus ciliaris* (J. A. Conner et al., *Plant Physiol.* 147:1396-411 (2008)), both of which are transcribed. CcASGR-BBM-like1 contains a full open reading frame nearly identical to PsASGR-BBML whereas CcASGR-BBMlike2 contains two nonsense mutations, the first of which is located within the first AP2 domain. Two related, but ASGR-unlinked, BBML (non-ASGR-BBML) genes also have been isolated from *C. ciliaris*, and orthologs have been found to be present in *P. squamulatum*. A previous comparative study with rice showed that ASGR-BBML was most closely related to a BBM gene at rice locus Os11g19060 (Conner J. et al., *Plant Physiol.* 147:1396-1411 (2008)), for which no function has been identified to date; expression has been documented in seed (5 days after pollination) and embryo (25 days after pollination), but not pistil (see http <colon slash slash> rice <dot> plantbiology <dot> msu <dot> edu <slash> cgi-bin <slash> ORF_infopage <dot> cgi?orf=LOC_Os11g19060). Furthermore, ASGR-BBML is conserved among eight apomictic, but absent from seven sexual, *Pennisetum* species tested (Akiyama Y. et al., *BMC Evol. Biol.* 11:289 (2011)).

Due to the protein similarity of the ASGR-BBM-LIKE (ASGR-BBML) gene to BBM, it was evaluated as to its use as an "apomixis" gene. As described herein, the ASGR-BBML gene was identified, and its role in parthenogenesis was characterized. ASGR-BBML was found to have an important role as a key gene in the induction of parthenogenesis in the apomictic pathway.

These results demonstrate that ASGR-BBML can be used to achieve in parthenogenesis in plants that do not normally show this phenotype. The seed set of the transformed lines was low, and plant offsprings can be screened for ploidy level. Parthenogenetic transgenic lines can thereby produce offspring that are reduced to the diploid level (or haploid within the context of the cell cycle). As haploid induction followed by chromosome doubling is a breeding practice followed in many cereal crops to more rapidly obtain homozygous lines, these findings can be used for haploid induction in sexual plants or clonal reproduction through an apomictic pathway dependent on chromosomal non-reduction in egg cells.

Having described the invention in detail, it will be apparent that modifications, variations, and equivalent embodiments are possible without departing the scope of the invention defined in the appended claims. Furthermore, it should be appreciated that all examples in the present disclosure are provided as non-limiting examples.

EXAMPLES

The following non-limiting examples are provided to further illustrate embodiments of the invention disclosed herein. It should be appreciated by those of skill in the art that the techniques disclosed in the examples that follow represent approaches that have been found to function well in the practice of the invention, and thus can be considered to constitute examples of modes for its practice. However, those of skill in the art should, in light of the present disclosure, appreciate that many changes can be made in the specific embodiments that are disclosed and still obtain a like or similar result without departing from the spirit and scope of the invention.

Example 1

Materials and Methods

DNA Extraction

DNA extraction was accomplished using a cetyltrimethyl ammonium bromide (CTAB) protocol (J. Conner, G. Gunawan, P. Ozias-Akins, *Planta* 238:51-63 (2013)).

PCR Amplification

Different PCR conditions were required based on primer combinations and amplicon length. Primer and PCR information for all unpublished amplicons appears in Table 1. PCR reactions were performed according to manufacturer recommendations unless noted otherwise. Reactions were performed in a GeneAmp 9700 Thermocycler (Applied Biosystems, Foster City, Calif., USA).

Non-Quantitative RT-PCR Tissue Expression of ASGR-BBML

Expression of ASGR-BBML was confirmed by RT-PCR using RNA isolated from various tissues, including the following: ovaries isolated one day prior to anthesis, through seed development, and up to five days after anthesis; anthers at 1 day prior to anthesis; root tips collected from greenhouse-grown potted plants; newly emerging leaf tissue; and embryogenic callus derived from apomictic *Pennisetum* $BC_8$ lines (M. Singh et al., *Crop Science* 50:892-902 (2010)). Total RNA was extracted from the various tissues via the RNeasy plant mini kit (QIAGEN, Valencia, Calif., USA) and subjected to DNAse treatment (Invitrogen, Carlsbad, Calif., USA). Three to five micrograms of total RNA was used for first-strand cDNA synthesis via oligo-dT and SuperScriptIII (Invitrogen). Two μL of the first-strand cDNA synthesis reaction was used for PCR amplification using ASGR-BBML specific primers p779/80 (Y. Akiyama et al., *BMC Evolutionary Biology*, 11:289 (2011)) or actin depolymerizing factor 3 (ADF3) primers p1127/1128 which were used as a control. PCR products were run on a 1.25% agarose gel, stained with ethidium bromide, and imaged with the Molecular Imager Gel Doc XR System (Bio-Rad Laboratories, Hercules, Calif., USA).

Rapid Amplification of cDNA Ends (RACE) of PsASGR-BBML

RACE products for the 5' and 3' UTRs for PsASGR-BBML were generated via the GeneRacer RLM-RACE kit (Invitrogen) and total RNA extracted from spikelet tissues from apomictic BC7 Line 58 (M. Singh et al., *Crop Science* 50:892-902 (2010)). The PCR primers used are listed in Table 1. The amplified PCR products were gel purified with QIAquick gel extraction kit (QIAGEN) and cloned into either a PCR4-TOPO (Invitrogen) or a pGEM-T easy (Promega, Madison, Wis., USA) vector. Nucleotide sequencing was carried out with a CEQ 8000 Genetic Analysis System (Beckman Coulter, Fullerton, Calif., USA), and sequences were processed with Vector NTI (Invitrogen).

Sequence Analysis of PsASGR-BBML Transgene

Total RNA was extracted from ovaries at the day of anthesis for g3f offspring, namely 105, 123, 144, and 159. Three μg of RNA was subjected to DNAse treatment (Invitrogen) and used for first-strand cDNA synthesis using oligo-dT and SuperScriptIII (Invitrogen). Two μL of the first-strand cDNA synthesis reaction was used for PCR amplification via transgene specific primers p1792/p1801 and p2347/p423. Amplified PCR products were gel purified with QIAquick gel extraction kit (QIAGEN) and cloned into PCR4-TOPO (Invitrogen). Nucleotide sequencing was conducted at the Laboratory for Genomics and Bioinformatics (University of Georgia, Athens, Ga.). Vector and bad quality sequences were removed, and trimmed sequences were then assembled using Geneious Pro 5.6.6 (Biomatters Limited, Auckland, New Zealand).

Transformation Constructs

PsASGR-BBMpromoter-GUS construct. pCambia3301 was digested with BamHI/NcoI to remove the CaMV 35S promoter, which was replaced with a 2,074 bp PCR-generated BamHI/NcoI PsASGR-BBMLpromoter fragment, which was amplified from BAC p208 (D. Roche et al. *Theor Appl Genet.*, 104:804-812 (2002)) using primers p690 and p692. The BamHI site is endogenous to the promoter and is located just downstream of p690. An NcoI site was incorporated into p692. The PsASGR-BBMLpromoter-GUS-Nos polyA cassette in pCambia3301 was removed by digestion with BamHI/BseYI, blunted, and then placed into pACH20 (A. H. Christensen, P. H. Quail, *Transgenic Research*, 5:213-218 (1996)) at a blunted and dephosphorylated HindIII site to create plasmid 2BE.

gPsASGR-BBML construct. The pBluescript vector was engineered with 2,074 bp of the PsASGRBBML promoter, 3540 bp of the 8 exon, 7 intron PsASGR-BBML coding region from BAC p208 (D. Roche et al. *Theor Appl Genet.*, 104:804-812 (2002)), and 609 bp 3' of the stop codon, including the predicted poly(A) signal.

RNAi-BBM-3p construct. The binary expression vector pMCG161 (http <colon slash slash> www <dot> chromdb <dot> org) was used for RNAi vector construction. A 425 bp amplicon covering 52% of the last exon of PsASGRBBML and incorporating restriction enzymes for cloning into pMCG161 was generated via primers p966 and p967 and inserted into pMCG161 following instructions available at http <colon slash slash> www <dot> chromdb <dot> org.

Ubi-Hygro construct. pCB13 (H. Yang et al., *Plant Cell Reports*, 17:693-699 (1998)) was digested with HindII/BamHI to remove the CaMV 35S promoter and replaced with the HindIII/BamHI maize ubiquitin (Ubi-1) promoter fragment from pAHC20 (A. H. Christensen, P. H. Quail, *Transgenic Research*, 5:213-218 (1996)).

Plant Transformation

Embryogenic callus generated from 7-10 day old immature embryos of tetraploid sexual IA4X plants were bombarded, selected (25 mg/l Hygromycin B or 15 mg/l PPT) and regenerated according to a previous protocol (J. J. Goldman, W. W. Hanna, G. Fleming, P. Ozias-Akins, *Plant Cell Rep.*, 21:999-1009 (2003)). The PsASGR-BBMpromoter-GUS lines were bombarded with a mix of plasmids 2BE and p524EGFP.1 (G. H. Fleming, O. Olivares-Fuster, S. Del-Bosco, J. W. Grosser, *In Vitro Cell Dev Biol Plant* 36:450-455 (2000)), the gPsASGR-BBML lines were bombarded with a mix of plasmids gPsASGR-BBML, p524EGFP.1 and Ubi-Hygro, and the RNAi lines were bombarded with plasmid RNAi-BBM-3p.

Embryo Rescue

Media for embryo rescue were based on previous work for zygotic *Pennisetum* embryos at 5 DAP (C. Nitsch et al., "Production of haploid plants of *Zea mays* and *Pennisetum* through androgenesis." *Variability in plants regenerated from tissue culture.* Praeger, N.Y. (1982): 69-91) and used 1× Nitsch & Nitsch Basal Medium w/vitamins (PhytoTechnology Laboratories, Shawnee Mission, Kans.), 1% sucrose, gibberellic acid (1 mg/L), indoleacetic acid (0.03 mg/L), 0.75% agar, pH 5.8 with 0.2% Plant Preservative Mixture (PPM) (Plant Cell Technology, Inc., Washington, D.C.). Developing (10 to 15 days after pollination) and mature seed were sterilized according to a previous protocol (J. J. Goldman, W. W. Hanna, G. Fleming, P. Ozias-Akins, *Plant Cell Rep.*, 21:999-1009 (2003)). Embryos were surgically removed, placed scutellum side up on the media, and monitored for root and shoot elongation. Embryos were left on the GA/IAA media for up to 10 days and were then discarded if no root/shoot growth occurred. Offspring with root and shoot growth were moved to a 1× Murashige & Skoog (MS) medium w/vitamins (PhytoTechnology Laboratories) supplemented with 3% sucrose, 0.75% agar pH 5.8 with PPM until growth permitted hardening and movement into the greenhouse.

X-Gluc Staining for β-Glucuronidase Activity for PsASGR_BBMpromoter-GUS Lines

Eight independent PsASGR_BBMpromoter-GUS lines were produced which contained a full-length transgene based on overlapping PCR amplifications using transgene-specific primers, namely p2354/p2355; p2349/p2350; and p2885/p2886 (Table 1). The PsASGR_BBMpromoter-GUS $T_0$ lines were either allowed to self-pollinate or were cross-pollinated with apomictic BCs-Line 63 pollen. Seeds from 5 lines were germinated, and then genotyped for inheritance of the ASGR if crossed and the PsASGR_BBMpromoter-GUS transgene. Initially, PsASGR_BBMpromoter-GUS gene expression patterns were examined from ovaries dissected one day prior to anthesis or on the day of anthesis from heads bagged prior to stigma exsertion; stigmas were mechanically removed prior to anthesis.

New PsASGR_BBMpromoter-GUS plants were germinated and isolated to a single greenhouse in order to further control for unintended pollination. All heads were continually cut back prior to pollen shed in order to keep the greenhouse free of millet pollen. Florets were collected one day prior to anthesis, with the anthers being manually removed. The emasculated florets were then placed on 1× MS media, 0.75% agar pH 5.8 with 0.2% PPM and incubated in a growth chamber under long-day light condition at 27° C. for 24 hours. Ovaries were the dissected and incubated in an X-Gluc reaction solution (100 mM sodium phosphate/pH 7.0, 10 mM EDTA, 0.5 mM potassium ferrocyanide, 0.5 mM potassium ferricyanide, 0.1% Triton X-100, and 1 mM 5-bromo-4-chloro-3-β-D-glucuronide) at 37° C. for 48 hours. X-Gluc-stained ovaries were dehydrated in 15, 30, and 50% ethanol at room temperature for 1 hour each and were then fixed in FAA (50% ethanol, 3.7% formaldehyde, and 5% acetic acid) overnight. FAA-fixed ovaries were further dehydrated in 70, 85, 90, 100, and 100% ethanol at room temperature for 1 hour each, then the dehydrated ovaries were cleared by a series of ethanol:methyl salicylate solutions (3:1, 1:1, and 1:3 for 1 hour each). Cleared ovaries were stored in 100% methyl salicylate for 1 hour. Phase-contrast images of the ovaries acquired using an Axioskop 2 Plus microscope, AxioCam camera and Axio Vision software 4.8 (Zeiss, Thornwood, N.Y.).

Genotyping of gPsASGR_BBML/Ubi_Hygo Transgenic Lines

Nine independent lines were recovered which contained both the gPsASGR_BBML and Ubi_Hygo constructs, based on results from PCR amplification using p1800/01 and p297/298, respectively.

Flow Cytometry

Samples were processed to run on a BD Accuri C6 flow cytometer (BD Biosciences, San Jose, Calif. USA) or a Partec Ploidy analyzer (Partec, Munster, Germany). The process involved chopping young leaf tissue of *Sorghum* (control) and samples (unknown) together in 1000 µL of Tris-MgCl2 nuclei extraction buffer (0.2 M Tris-HCl, pH 7.5, 4 mM MgCl2×6H20, 0.5% Triton X-100) and passing the mixture through a 30 µm CellTrics disposable filter (Partec). 500 µL of RNAse/propidium iodide solution (BD Biosciences) was added to the filtered samples, which were then incubated on ice for 15 minutes. For the BD Accuri C6 flow cytometric analysis, gating was set by the selection of objects that exhibited a strong correlation between the FL2 and FL3 signals using a flow rate of 14 µL sample per minute. At least 3000 events were collected for each sample within the gated region. Samples were run on the Partec Ploidy analyzer until peaks could be confidently called. Ploidy level was determined based on the G1 and G2 sample peaks relative to the *Sorghum* control G1 and G2 peaks.

Root Tip Chromosomal Counts

If available, six healthy root tips were harvested from g3f offspring, cleaned of soil, placed in Eppendorf tubes with 300 µl dH20, treated with nitrous oxide for 2 to 2½ hours under 150 psi, and finally fixed in fresh ethanol:acetic acid (3:1) for a minimum of 2 days. The meristematic region of the root was incubated in 0.3% cellulase RS (Karlan Research, Torrance, Calif.), 0.3% pectolyase Y23 (Karlan Research), and 0.3% cytohelicase (Sigma-Aldrich, St. Louis) in 30 mM citrate buffer, at a pH of 4.5 at 37 C for 60-90 minutes.

After enzymatic digestion, a minimum of 3 root tips from each plant was spread individually on glass slides. Chromosomal spreads were located, digitally photographed, and chromosome number was then counted using Adobe Photoshop CS6. Ploidy level of each plant was determined using a minimum of 4 spreads originating from at least 2 slides.

RNAi Screening

Sixteen independent sexual tetraploid IA4X lines were recovered which contained the RNAi_BBM_3p construct based on PCR amplification for the BAR gene and the RNAi sense and antisense inserts using the following primers: p992/p993, p1222/p1223 and p1224/p1125, respectively. Eight lines were crossed with *P. squamulatum* pollen, thereby generating $F_1$ offspring. The $F_1$ offspring plants from each line were screened with *P. squamulatum*-specific primers p1032/1035, RNAi_BBM_3p primers p992/p993, p1222/p1223 and p1224/p1125, and ASGR-specific primers Ugt197 (P. Ozias-Akins, D. Roche, W. W. Hanna, *Proc Natl Acad Sci USA* 95:5127-5132 (1998)). ASGRpositive/RNAi-positive and ASGR-negative/RNAi-positive plants were subsequently tested for expression of the RNAi transgene using RT-PCR analysis of total RNA from leaf tissue and primers p1226/p1227 derived from the octopine synthase terminator region of the transgene. Twenty-five plants from 5 lines were chosen for further analysis; these included 14 ASGR-positive/RNAi-positive, 5 ASGRpositive/RNAi-negative and 6 ASGR-negative/RNAi-positive plants.

Semi-Quantitative Analysis of PsASGR-BBML Expression

Semi-quantitative RT-PCR quantification of PsASGR-BBML was based on a previous protocol (E. Albertini et al., *Plant Molecular Biology* 56:879-894 (2004)). ADF3 primers p1127/1128 were used as an internal control, along with PsASGR-BBML specific primers, namely p779/p780 (Y. Akiyama et al., *BMC Evolutionary Biology*, 11:289 (2011)). Each assay used 3.3 µg of total RNA extracted from ovaries at the day of anthesis via the RNeasy plant mini kit (QIAGEN), and the samples were subjected to DNAse treatment (Invitrogen, Carlsbad, Calif., USA) for first-strand cDNA synthesis using oligodT and SuperScriptIII (Invitrogen). Two µl of the cDNA synthesis reaction were used in all PCR reactions; all reactions were run in triplicate. The PCR cycle number determined empirically for ADF3 and PsASGR-BBML was found to be 26 and 40 cycles, respectively. Hybridization imaging was conducted with a Storm phosphorimager (Amersham Biosciences, Pittsburgh, Pa., USA), and bands were quantified using ImageQuant v5.0 following the manufacturer's instructions (Amersham Biosciences).

Histological Analysis of Embryo Development in RNAi Lines

Heads were bagged prior to stigma exsertion, and stigmas were removed prior to anthesis to prevent pollination. Spikelets from heads were collected 2 days after anthesis, fixed in FAA, and then subjected to a 30-min vacuum treatment at 15 mm Hg prior to a 24-hour fixation at room temperature. Dehydration was initiated with TBA1 (40% ethanol, 10% tertiary butyl alcohol (TBA), 50% distilled water) for 2 hours, then transferred through TBA2 (50% ethanol, 20% TBA, 30% distilled water) for 8 hours, TBA3 (50% ethanol, 35% TBA, 15% distilled water) for 1 hr, TBA 4 (45% ethanol, 55% TBA) for 1 hour, TBA 5 (25% ethanol, 75% TBA) for 1 hour, and TBA 6 (100% TBA) for 1 hour. Ovaries were then transferred to fresh 100% TBA for another 8 hours prior to being transferred to TBA:paraffin oil (Fisher, Pittsburgh, Pa., USA) (1:1) at 58° C. overnight. Ovaries were taken through three changes of pure Paraplast X-tra (Fisher, Pittsburgh, Pa.) for 48 hours each before embedding. Sectioning was then carried out for all samples at 9 µm. Samples were stained with safranin O/fast green using a modification to a previously described protocol (Jensen 1962) wherein embedded and sectioned samples were de-waxed in ethanol, then coated with 0.05% nitrocellulose (diluted from collodion, Fisher, Pittsburgh, Pa.) in ether-alcohol (50% diethyl ether, 50% ethanol) for 30 seconds. Rehydration of samples was accomplished by transfer through 70% ethanol, 30% ethanol, and distilled water for 5 minutes each. Staining was performed first in Safranin O solution (4 g Safranin O, 100 ml distilled water, 100 ml 95% ethanol, 4 g sodium acetate) for 5 minutes. Samples then were subjected to dehydration in the following series of solutions for 5 minutes each: two changes of distilled water, 50% ethanol, 95% ethanol, 100% ethanol. Samples subsequently were stained in fast green solution (1 g fast green, 100 ml 100% ethanol, 100 ml cellosolve and 100 ml clove oil) for 4 seconds, then immediately placed into pure clove oil for 10 seconds, prior to being quickly transferred into clearing mix (50% clove oil, 25% ethanol, 25% histoclear). Slides were finally cleared in histoclear for 5 minutes and were then mounted with permount.

Phylogenetic Analysis

The proteins identified in the BBM-like clade (S. El Ouakfaoui et al., *Plant Mol Biol* 74:313-326 (2010)) were downloaded from NCBI. Each member of the Grass clade in Phytozome was then individually searched using BLASTP and the entire PsASGR-BBML protein. All proteins with similarity to PsASGR-BBML extending past the AP2 domains were downloaded, while truncated proteins and those without a bbm-1 domain (S. El Ouakfaoui et al., *Plant Mol Biol* 74:313-326 (2010)) were removed. The phytozome target databases employed were the *Sorghum bicolor* v1.4 proteome; *Zea mays* proteome, *Setaria italica* proteome, *Panicum virgatum* v0.0 proteome, *Oryza sativa* proteome, and *Brachypodium distachyon* proteome. Proteins that were found to be identical between the BBM-like clade (S. El Ouakfaoui et al., *Plant Mol Biol* 74:313-326 (2010)) and Phytozome were removed. Twenty-six amino acid sequences were aligned using multiple web based alignment programs; the results were that both T-Coffee (http <colon slash slash> tcoffee <dot> crg <dot> cat <slash> apps <slash> tcoffee <slash> do <dot> regular) and Mafft (http <colon slash slash> mafft <dot> cbrc <dot> jp <slash> alignment <slash> server) alignments identified the most conserved domains the BBM-like clade, especially within the C terminus of the proteins without editing. The T-Coffee alignment produced a 1,067 amino acid consensus sequence length with 283 conserved positions for all proteins (FIG. 1). The Mafft alignment produced a 1,040 amino acid consensus length with 264 conserved positions for all proteins using the E-INS-I command. The T-Coffee alignment was used to create phylogenetic trees (P. Di Tommaso et al., *Nucl. Acids Res.* 39 (suppl 2):W13-W17 (2011)) via MEGA6 software (K. Tamura et al., *Molecular Biology and Evolution* 30:2725-2729 (2013)) (FIG. 2).

TABLE 1

Primers and PCR conditions.

| | Primer ID | Primer sequence 5' to 3' | DNA polymerase used | Anneal/ Extension |
|---|---|---|---|---|
| PsASGR-BBM promoter construct | P690 P692 | CCTCAGTGCATCAGCGAAGG (SEQ ID NO: 6) TGGAACCCATGGCGGAACGC (SEQ ID NO: 7) | iProof High-Fidelity | 60° C./ 1 min |
| PsASGR-RNAi construct | P966 P968 | GTACTAGTGGCGCGCCCCTCAATGCTGTCACGAACTT (SEQ ID NO: 8) GTGCGATCGCCCTAGGCAACACCTGTCATGTCCTGAA (SEQ ID NO: 9) | PrimeSTAR HS tak | 68° C./ /30 sec |
| Genomic ORF and cDNA sequencing | P1792 P1801 | TTCCACCAACAACTGGCTGCGCT (SEQ ID NO: 10) TTCTCATGGCTCCTAGACTCCCAC (SEQ ID NO: 11) | ORF: Primestar GXL rapid method cDNA: iProof High-Fidelity with DMSO | 60° C./ 40 sec 64° C./ 1 min |
| cDNA 5'UTR sequencing | p2347 p423 | CCCTAGGATCAGTGCTAGTGC (SEQ ID NO: 12) GGGCTTCATACCTTCCTGTCCAT (SEQ ID NO: 13) | Primestar GXL | 60° C./ 30 sec |
| PsASGRpromoter-GUS-1 | p2354 p2355 | GAAACGGGAAAGGAGTCAAA (SEQ ID NO: 14) CGCTAGTGCCTTGTCCAGTT (SEQ ID NO: 15) | Takara ExTaq Hot Start | 60° C./ 2 min |
| PsASGRpromoter-GUS-1 | p2349 p2350 | GCCGCGTTCCGCCATGGTA (SEQ ID NO: 16) TGACACCGCGCGCGATAATTT (SEQ ID NO: 17) | Takara ExTaq Hot Start | 60° C./ 2 min |
| PsASGRpromoter-GUS-3 | P2885 P2886 | ACGATCAACAGATGACTGCCT (SEQ ID NO: 18) TGATGTGGTGGCGATGGAAT (SEQ ID NO: 19) | Jump Start | 60° C./ 30 sec |
| 3'RACE gene-specific primer | P1021 | TGGCAAGCAAGAATAGGAAGTGTGGC (SEQ ID NO: 20) | Jump Start | RACE manual |
| 3' RACE nested gene-specific primer | P1022 | GGCACATTCAGTACCCAGGAGGA (SEQ ID NO: 21) | Jump Start | RACE manual |
| 5'RACE gene specific primer for RT | P1025 | TTCCTTGAGACGCTTTGGAGTGC (SEQ ID NO: 22) | Jump Start | 62° C./ 2 min |

TABLE 1-continued

Primers and PCR conditions.

| Primer | Primer ID | Primer sequence 5' to 3' | DNA polymerase used | Anneal/ Extension |
|---|---|---|---|---|
| 5'RACE gene specific primer | P1026 | GCTCTTGACGTCATACCGGCTCA (SEQ ID NO: 23) | Jump Start | 62° C./ 2 min |
| 5'RACE nested gene specific primer | P1028 | AAGTTCGTGACAGCATTGAGGCCTC (SEQ ID NO: 24) | Jump Start | 62° C./ 2 min |
| Screen for Ubi_Hygo construct | P296 P297 | CCCCAATGTCAAGCACTTCCG (SEQ ID NO: 25) CCGCGACGTCTGTCGAGAAG (SEQ ID NO: 26) | Jump Start | 60° C./ 30 sec |
| Initial screen of for gPsASGR-BBML construct | P1800 P1801 | TTCCTCAGGCGCCAATACTGG (SEQ ID NO: 27) TTCTCATGGCTCCTAGACTCCCAC (SEQ ID NO: 28) | Jump Start | 62° C./ 30 sec |
| BBM_RNAi_3 construct BAR | P992 P993 | CATCGTGACAAGCACGGTCAACTTC (SEQ ID NO: 29) ATATCCGAGCGCCTCGTGCATGCG (SEQ ID NO: 30) | Jump Start | 62° C./ 30 sec |
| BBM_RNAi_3 construct RNAi sense | P1222 P1223 | GTTGAGTGGCCCTGTTTCTC (SEQ ID NO: 31) CATTGATCAGCCTAACCAAACA (SEQ ID NO: 32) | Jump Start | 55° C./ 30 sec |
| BBM_RNAi_3 construct RNAi anti-sense | P1224 P1225 | GGCGGTAAGGATCTGAGCTA (SEQ ID NO: 33) CAAATTCTAATCCCCAATCCAA (SEQ ID NO: 34) | Jump Start | 55° C./ 30 sec |
| Ps-specific | P1032 P1035 | AGGCTGTCGACTGCAGCTAT (SEQ ID NO: 35) CAGAATTGTCATCATGTAAGAACCAC (SEQ ID NO: 36) | Jump Start | 59° C./ 30 sec |
| octopine synthase | P1226 P1227 | AGTGGGTCTAGAGTCCTGCTT (SEQ ID NO: 37) GGCGGTAAGGATCTGAGCTA (SEQ ID NO: 38) | Jump Start | 55° C./ 30 sec |
| ADF3 | P1127 P1128 | ACGAGGATTTCACCAACAGC (SEQ ID NO: 39) AACGCATAGACGACGCCT (SEQ ID NO: 40) | Jump Start | 55° C./ 30 sec | iProof (Bio-Rad Laboratories)
JumpStart Taq DNA Polymerase (Sigma)
Takara ExTaq Hot Start, Primestar GXL, PrimeSTAR HS DNA polymerase (Clonetech Laboratories, Inc, Mountain View, CA)

Example 2

ASGR-BBML Overexpression in *Arabidopsis*

Figure 3:
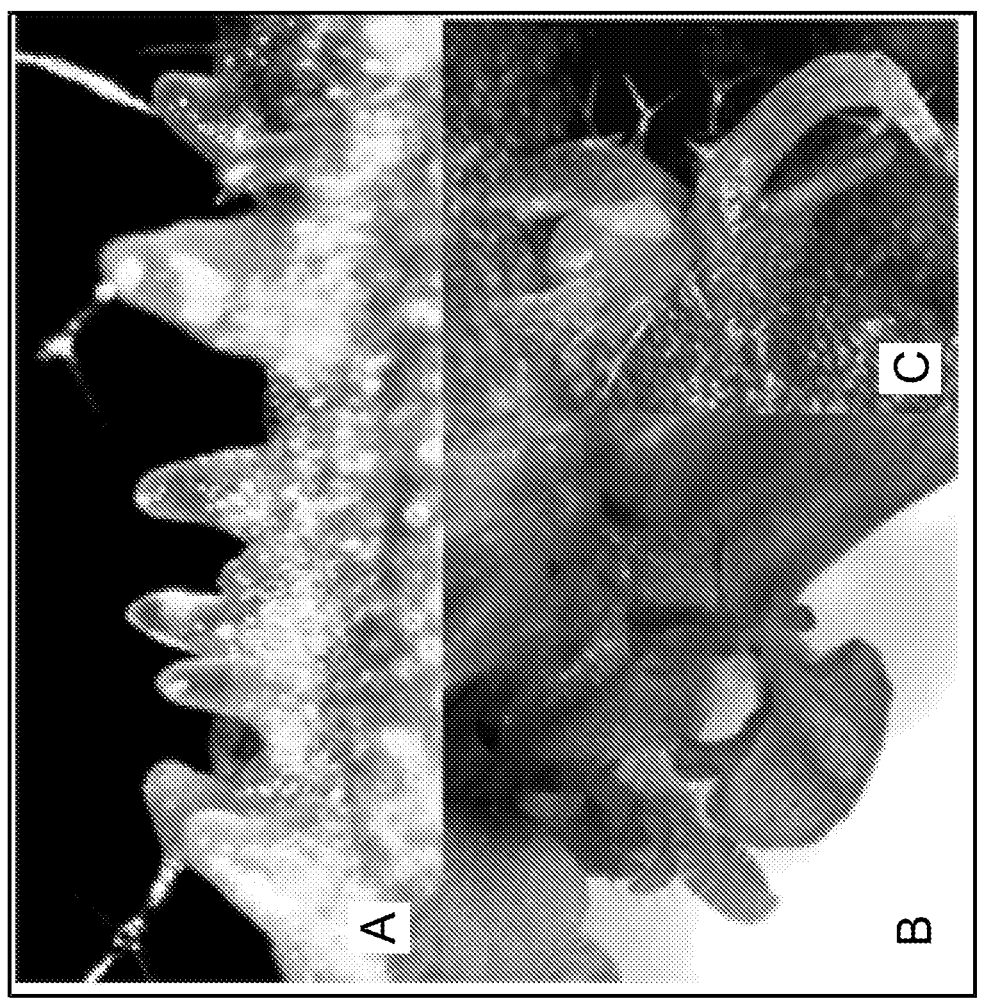
FIG. 3 depicts the results of overexpression of ASGR-BBML in *Arabidopsis*, including the formation of trichomed projections, as depicted in FIG. 3A, ectopic shoots, as depicted in FIG. 3B, and ectopic flowers, as depicted in FIG. 3C.
Figure 5:
FIG. 5 depicts the results of in situ hybridization of globular embryos, as depicted in FIG. 5A, and later stage embryos, as depicted in FIGS. 5B and 5C, using a locked nucleic acid oligonucleotide probe designed to target ASGR-BBML.

A full-length ASGR-BBML cDNA from *P. squamulatum* was identified via 5' and 3' RACE. The cDNA was found to be overexpressed in *Arabidopsis* using the CaMV35S promoter, with pleiotropic effects of overexpression such as the formation of ectopic shoots, projections with trichomes, and incomplete flowers (FIGS. 3A-C). Fertility was found to be impaired in these lines, and distorted segregation of the transgene was observed. The overexpression phenotype for ASGR-BBML is more readily interpreted when overexpression is under the control of an inducible promoter.

Example 3

ASGR-BBML Expression in *P. squamulatum*, *C. ciliaris*, and Apomictic Backcrosses Transformation of sexual tetraploid pearl millet with the genomic copy of the ASGR-BBML gene construct, including a promoter and 3'UTR, was found to induce the formation of embryos in meiotically-derived embryo sacs in the absence of corresponding endosperm fertilization. Fertilization was prevented by bagging of heads prior to stigma exsertion and subsequent removal of stigma/style prior to anther exsertion, with evidence for lack of fertilization in ovules being the persistence of two polar nuclei in the central cell and absence of endosperm formation. Expression of ASGR-BBML was previously observed by RT-PCR in two apomictic species (*P. squamulatum* and *C. ciliaris*) and in apomictic *Pennisetum* backcross 7 and 8 lines (M. Singh et al., Crop Science 50:892-902 (2010)) in ovaries starting 1-day prior to anthesis and continuing through early seed development, in anthers 1-day prior to anthesis and roots.

Figure 4:
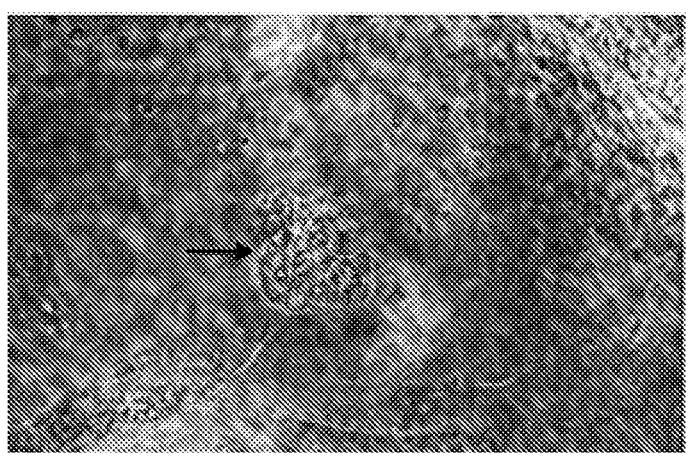
FIG. 4 depicts $BC_8$ embryo development in the absence of pollination.

PsASGR-BBML was found to be expressed in embryogenic callus derived from apomictic *Pennisetum* $BC_8$ lines. In the apomictic species and the apomictic backcrosses, embryo development in aposporous embryo sacs can initiate prior to pollen shed, continuing for several days after pollen shed when pollination is prevented and no endosperm is formed (FIG. 4). Although globular and later stage embryos showed good signal, low levels of ASGR-BBML gene expression in reproductive tissues resulted in inconclusive RNA in situ hybridization experiments for early stages of embryo development (FIGS. 5A-D). Therefore, expression was determined by RT-PCR.

Figure 6:
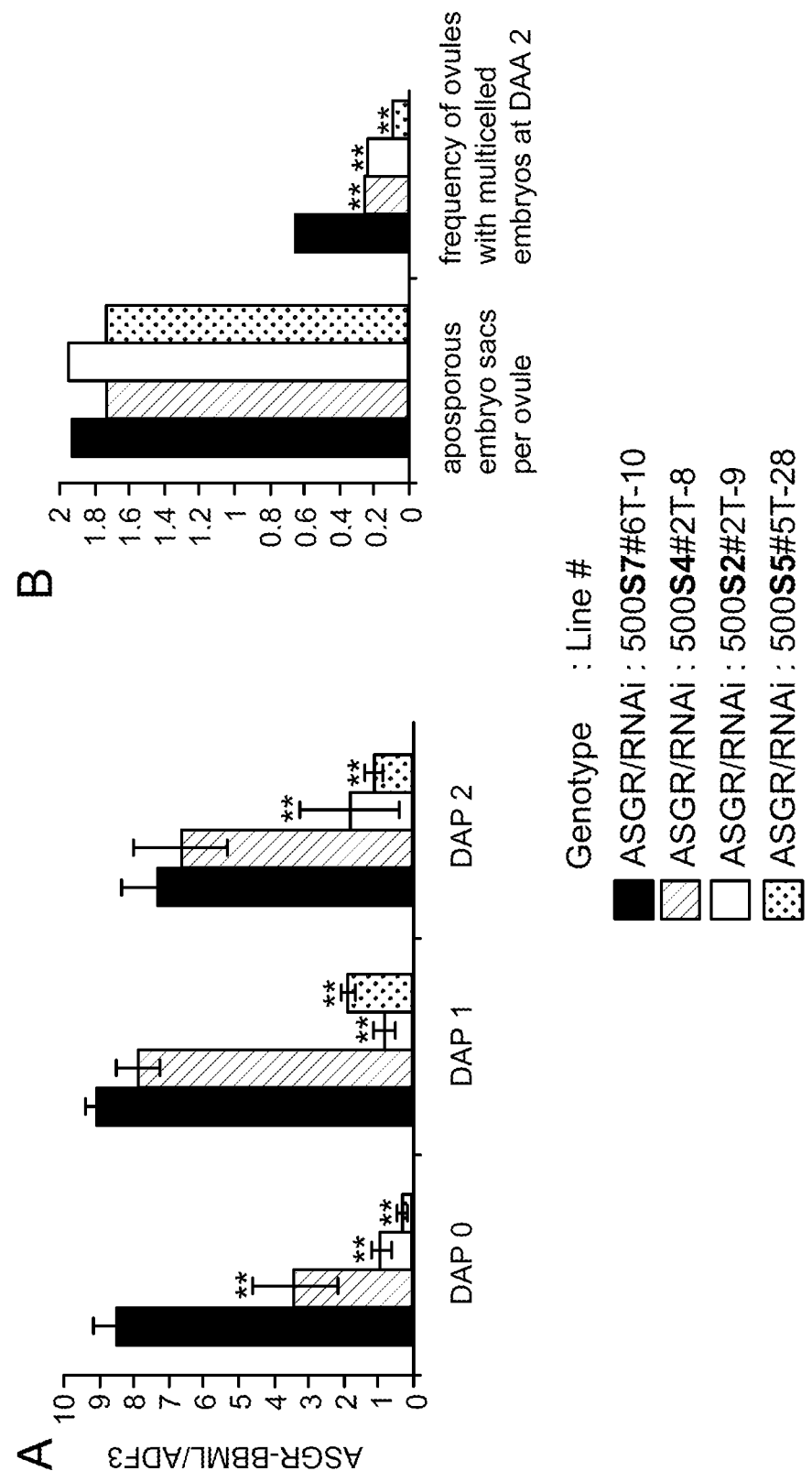
FIG. 6 depicts results from ASGR-BBML expression studies. The differences in ASGR-BBML expression among RNAi events (S7>S4>S2>S5), as shown in FIG. 6A, are correlated with the frequency of ovules with multicelled embryos but not the number of aposporous embryo sacs per ovule, as shown in FIG. 6B.

Unpollinated pistils were examined both for transcription of ASGR-BBML as well as for embryo development prior to the day of pollen shed and up to two days after pollen shed; pollination was prevented by removing the stigmas. Expression of the ASGR-BBML gene was demonstrated to correlate with parthenogenetic development of the unreduced egg in apomictic *P. squamulatum* and *C. ciliaris*; that is, expression was detected in the absence of pollination as ensured by removal of stigmas prior to anther dehiscence and pollen shed (DAP0 in FIG. 6). Anthers, pollen, and roots from *P. squamulatum* and *C. ciliaris* showed ASGR-BBML expression, but stigmas and leaf tissue did not; however, expression in the leaf was demonstrated in apomictic *Pennisetum* BC$_7$ and BC$_8$ lines. The temporal pattern of expression (by semi-quantitative RT-PCR) of a second embryo-expressed gene, namely LEC, and the non-ASGR-BBML genes identified in *C. ciliaris*, was slightly delayed as compared with ASGR-BBML. AtBBM has been shown to upregulate its own expression but not to directly regulate expression of LEC (Passarinho P. et al., *Plant Mol. Biol.* 68:225-237 (2008)). Accordingly, the non-ASGR-BBML genes can be targets of ASGR-BBML.

Example 4

Knockdown of ASGR-BBML Expression

Tetraploid pearl millet was transformed with a portion of the ASGR-BBML coding region in an inverted repeat (IR) construct via microprojectile bombardment and selection on phosphinothricin. Transcription of the IR proceeded via the CaMV 35S promoter. Homology-dependent gene silencing depends on the formation of hairpin RNA and triggering of the RNA interference where endogenous gene sense transcripts are targeted for degradation (Ossowski S. et al., *Plant Journal* 53:674-690 (2008); Eamens A. et al., *Plant Physiology* 147:456-468 (2008)). According to Southern blot hybridization, the ASGR-BBML IR did not show significant homology with pearl millet.

RNAi lines were generated by transformation of tetraploid IA4X, but no RNAi phenotype was expected until the IR was combined with the ASGR by crossing. Crosses of IA4X RNAi lines with *P. squamulatum* produced progeny that combined both genes and were then screened for transcription of the transgene, changes in transcription of ASGR-BBML, and changes in reproductive development. Transcription of ASGR-BBML as determined by semi-quantitative RT-PCR varied in the progeny of several events, as follows: a reduction in ASGR-BBML signal (FIG. 6A) correlated with reduced precocious embryo development (FIG. 6B) and event S7>S4>S2>S5. Similar observations were made while analyzing a knockdown line containing a different portion of the gene as an inverted repeat expressed under the control of the rice actin 1 promoter.

Since no complete knockdown was obtained from either of these experiments, these data did not correlate ASGR-BBML expression with the extent of embryo development vs causality (ASGR-BBML expression was responsible for embryo induction); therefore, additional experiments were undertaken to test the role of ASGR-BBML in parthenogenesis. These consisted of the following steps: 1) transformation of sexual pearl millet with beta-glucuronidase (GUS) as a reporter gene, expressed under the control of the native BBM promoter, and 2) transformation of sexual pearl millet with ASGR-BBML, either as cDNA or as genomic DNA under control of its native promoter.

Although the organ-specific expression pattern of ASGR-BBML has been extensively characterized by RT-PCR in two apomictic species (*P. squamulatum* and *C. ciliaris*) and apomictic *Pennisetum* backcrosses, this does not enable the cellular location of expression to be determined. Expression in apomicts was observed in gynoecia (pistils) up to 2 days prior to pollination; expression was also observed after pollination as embryos began to develop and continued to grow. These analyses were conducted by RT-PCR because ASGR-BBML transcripts are of low abundance in gynoecia at anthesis; therefore, transcripts were not detected by in situ hybridization.

Figure 7:
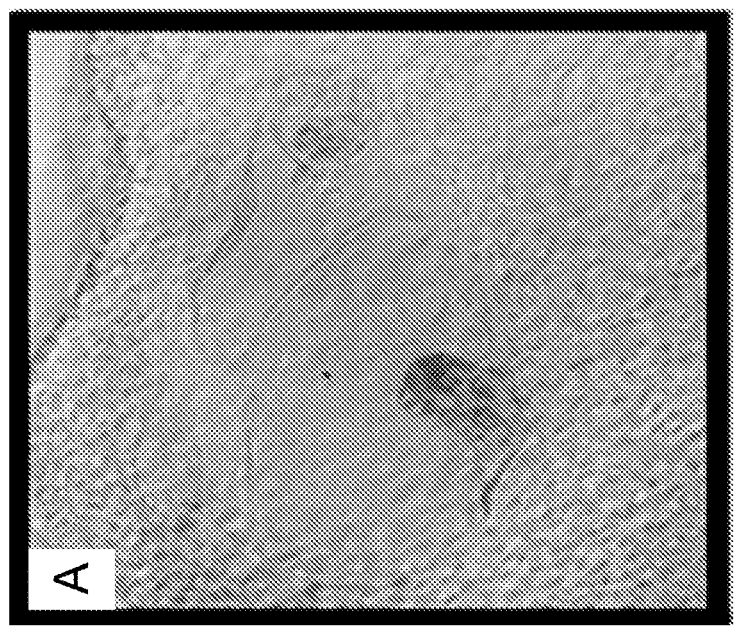
FIG. 7 depicts a cleared ovule from an apomictic plant derived from crossing $BC_8$ with the GUS-expressing transgenic pearl millet. Expression is seen in egg cells and in young embryos.
Figure 7:
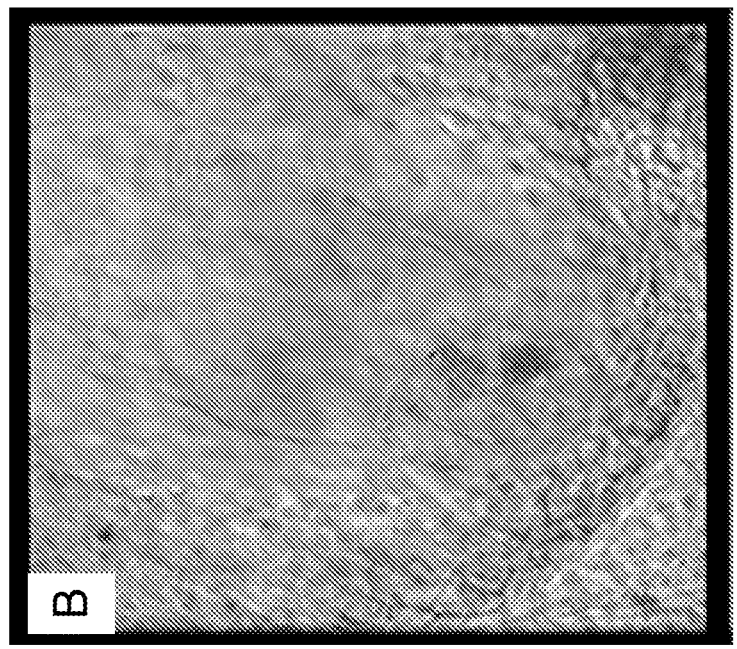
Figure 8:
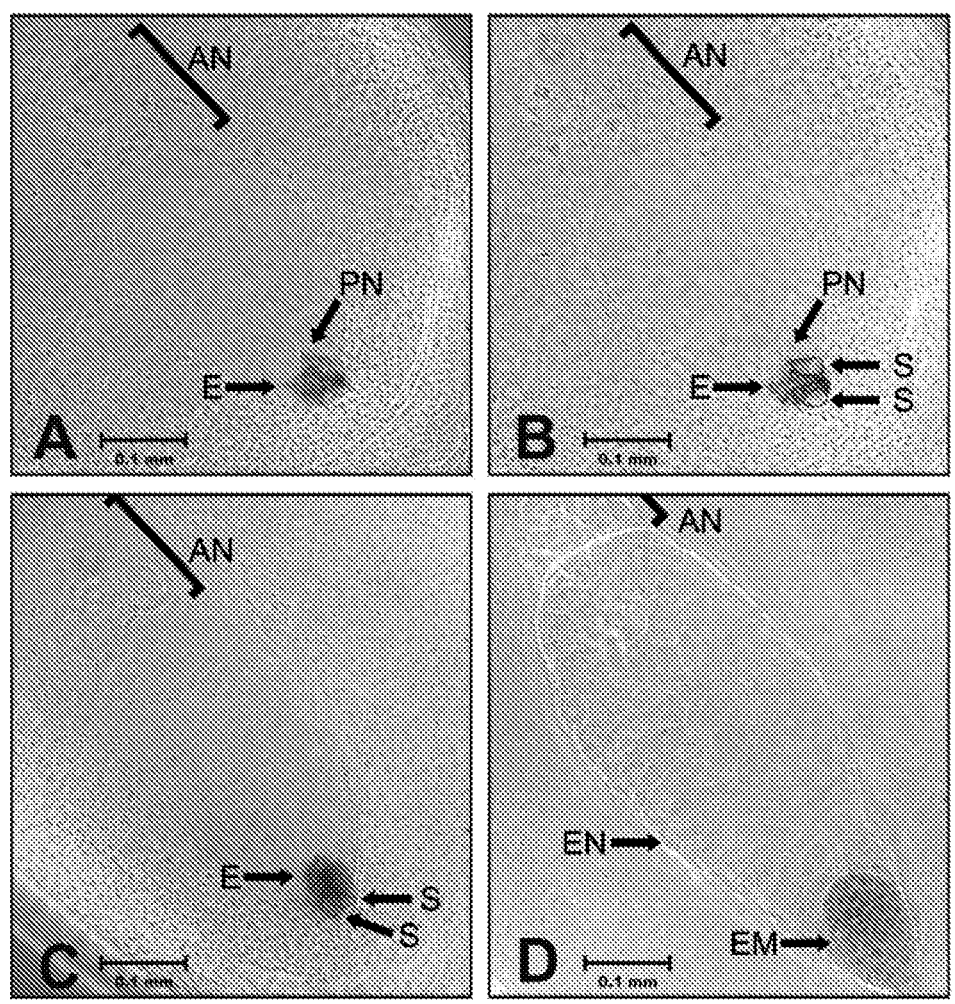
FIG. 8 depicts PsASGR-BBML expression in sexual embryo sacs. Ovaries from three sexual offspring derived from a $T_0$ PsASGR-BBMLpromoter-GUS line are shown (FIG. 8A-D).

The pattern of PsASGR-BBML expression was investigated at the cellular level in ovaries prior to fertilization via a PsASGR-BBML promoter-GUS construct. In apomictic lines recovered from crosses with transgenic pearl millet, dividing unreduced egg cells expressing GUS were identified in aposporous embryo sacs (FIG. 7). In unfertilized embryo sacs on day of anthesis, GUS signal was observed within the egg cell; a weaker GUS signal sometimes occurred in the synergids (FIG. 8A-C). The synergid signal can be attributed to lower expression of PsASGR-BBML or leakage of GUS signal from the egg cell. The presence of intact synergid cells and polar nuclei within the embryo sac demonstrate that PsASGR-BBML expression occurs prior to fertilization. No GUS staining was visualized in the central cell or antipodal cells of the sexual embryo sac or in the surrounding ovary tissues (FIG. 8A-C). GUS activity was also identified in cells of the developing embryo characterized up to 3 days after fertilization (FIG. 8D); GUS activity was not identified not in the developing endosperm.

This pattern of expression indicates that BBM is cell autonomous and expressed within a developmental time frame that is consistent a role in parthenogenesis. To obtain more definitive evidence, sexual pearl millet was transformed with ASGR-BBML either as cDNA or genomic DNA under control of its native promoter. The two versions of the construct are as described below according to the sequences provided in Table 2 below, which provides the cDNA, genomic DNA, amino acid sequence, and promoter sequence of ASGR-BBML. Genomic construct: 2074 bp ASGR-BBM promoter (p208) (containing a 6-residue GGATCC BamHI restriction site sequence) upstream of the 3,540 bp coding region (exons:introns) as well as 610 bp of the 3'UTR. cDNA construct: 2074 bp ASGR-BBM promoter (containing a 6-residue GGATCC BamHI restriction site sequence) fused to the 1,638 bp cDNA coding region as well as 610 bp of the 3' UTR region. The alignment of the cDNA to the genomic DNA is depicted in FIG. 9.

TABLE 2

ASGR-BBML cDNA, genomic DNA, amino acid sequence, and promoter sequence; the start codons are indicated by single underline, and the stop codons are indicated through double underline.

SEQ ID NO: 1. ASGR-BBM cDNA sequence with UTRs
TCTCTCTCTCTTCTCTCTCTCCATTTCTCTTCCCTAGGATCAGTGCTAGT
GCTTGCAGCGGCCGCGTTCCGAGATGGGTTCCACCAACAACTGGCTGCGC
TTCGCCTCGTTCTCCGGCGGCGGCGGCGCCAAGGATGCCGCGGCCCTGCT
CCCGCTGCCGCCCTCGCCCCGTGGCGATGTCGACGAGGCCGGCGCAGAGC
CGAAGCTCGAGGACTTCCTCGGCCTGCAGGAGCCGAGCGCCGCCGCGGTG
GGGGCTGGGCGGCCATTCGCGGTGGGTGGCGGTGCGAGCTCCATCGGGCT
GTCCATGATCAGGAACTGGCTGCGCAGCCAGCCGGCGCCGGCCGGCCCTG
CTGCCGGGGTCGATTCGATGGTGCTGGCGGCTGCGGCGGCGTCGACGGAG
GTGGCCGGCGATGGCGCGGAGGGCGGCGGCGCCGTGGCTGACGCGGTGCA
GCAGAGGAAGGCGGCGGCGGTGGACACTTTCGGGCAGCGGACCTCCATAT
ACCGCGGCGTCACAAAGCATAGATGGACAGGAAGGTATGAAGCCCATCTT TABLE 2-continued ASGR-BBML cDNA, genomic DNA, amino acid sequence, and promoter sequence; the start codons are indicated by single underline, and the stop codons are indicated through double underline.

TGGGACAATAGCTGCAGAAGAGAAGGTCAAACTCGGAAAGGTAGACAAGT
GTATCTTGGTGGATATGATAAAGAAGAAAAAGCAGCTAGAGCTTATGATT
TAGCTGCTCTCAAGTACCGGGGCACCACAACTACTACAAATTTTCCGATG
AGCAACTATGAAAAGGAGTTAGAAGAGATGAAGCATATGTCACGACAAGA
ATATGTTGCATCCCTTAGAAGGAAAAGCAGTGGTTTTTCTCGTGGTGCAT
CAATTTACCGAGGGGTTACCAGGCACCATCAGCATGGAAGGTGGCAAGCA
AGAATAGGAAGTGTGGCAGGAAACAAGGATCTTTATTTGGGCACATTCAG
TACCCAGGAGGAAGCTGCAGAGGCTTACGACATTGCTGCCATCAAATTCC
GAGGCCTCAATGCTGTCACGAACTTTGACATGAGCCGGTATGACGTCAAG
AGCATCATTGAGAGCAGCTCCCTGCCTGTTGGCGGCACTCCAAAGCGTCT
CAAGGAAGTGCCTGATCAATCAGATATGGGCATCAACATAAACGGTGACT
CTGCTGGTCATATGACTGCTATCAACCTTCTTACTGATGGCAATGAAGAG
TATGGAGCTGAGAGTTATGGTTACAGTGGTTGGTGTCCCACAGCCATGAC
GCCAATCCCCTTTCAATTCAGCAATGGCCATGACCATTCCAGGCTGTGGT
GCAAGCCAGAGCAGGACAATGCGGTTGTTGCAGCACTGCATAACCTGCAT
CACCTCCAGCACTTGCCAGCCCCAGTTGGCACCCATAATTTTTCCAGCCC
ATCGCCTGTTCAGGACATGACAGGTGTTGCCGATGCTTCATCGCCACCAG
TAGAATCTAATTCATTCTGTACAATGGGGACGTTGGTTACCATGGTGCCA
TGGGTGGCAGCTATGCCATGCCGGTTGCCACACTAGTTGAGGGCAACTCT
GCGGGCAGTGGCTATGGAGTTGAGGAAGGCACAGGGTCTGAAATCTTTGG
TGGACGGAACTTGTATTCTCTCTCCCAAGGTTCCTCAGGCGCCAATACTG
GAAAGGCAGATGCTTATGAAAGCTGGGATCCATCTATGCTGGTGATATCA
CAGAAGTCTGCCAATGTGACTGTCTGCCATGGCGCACCTGTATTTTCAGT
TTGGAAA<u>TGA</u>TGGTTAGATGAAAATATAGTAGTGATTAACTAGTTCTT
GGAGGGGAAGATTAAATTCTAGGTATACAAAAGTTTAATTTATTAGTGCT
TCAAGATCTCGTATGAAAAAAAGTTTTGCTGCTTAATCAGCTCCAGTGGG
AGTCTAGGAGCCATGAGAAATGTCGTTTTATTATTGACTAATGCTACAAT
GCTAACATGCTGACTCTTTTGAATGGCACAAGAGCTCTGGTGTTTCAATA
CATCAGCCAGTTTCATT

SEQ ID NO: 2. ASGR-BBM cDNA sequence
<u>ATG</u>GGTTCCACCAACAACTGGCTGCGCTTCGCCTCGTTCTCCGGCGGCAG
CGGCGCCAAGGATGCCGCGGCCCTGCTCCCGCTGCCGCCCTCGCCCCGTG
GCGATGTCGACGAGGCCGGCGCAGAGCCGAAGCTCGAGGACTTCCTCGGC
CTGCAGGAGCCGAGCGCCGCCGCGGTGGGGCTGGGCGGCCATTCGCGGT
GGGTGGCGGTGCGAGCTCCATCGGGCTGTCCATGATCAGGAACTGGCTGC
GCAGCCAGCCGGCGCCGGCCGGCCTGCTGCGGGGGTGCATTCGATTCGATGTG
CTGGCGGCTGCGGCGGCGTCGACGGAGGTGGCCGGCGATGGCGGAGGG
CGGCGGCGCCGTGGCTGACGCGGTGCAGCAGAGGAAGGCGGCGGCGGTGG
ACACTTTCGGGCAGCGGACCTCCATATACCGCGGCGTCACAAAGCATAGA
TGGACAGGAAGGTATGAAGCCCATCTTTGGGACAATAGCTGCAGAAGAGA
AGGTCAAACTCGGAAAGGTAGACAAGTGTATCTTGGTGGATATGATAAAG
AAGAAAAAGCAGCTAGAGCTTATGATTAGCTGCTCTCAAGTACCGGGGC
ACCACAACTACTACAAATTTTCCGATGAGCAACTATGAAAAGGAGTTAGA
AGAGATGAAGCATATGTCACGACAAGAATATGTTGCCCCTTAGAAGGAA
AAGCAGTGGTTTTTCTCGTGGTGCATCAATTTACCGAGGGGTTACCAGG
CACCATCAGCATGGAAGGTGGCAAGCAAGAATAGGAAGTGTGGCAGGAAA
CAAGGATCTTTATTTGGGCACATTCAGTACCCAGGAGGAAGCTGCAGAGG
CTTACGACATTGCTGCCATCAAATTCCGAGGCCTCAATGCTGTCACGAAC
TTTGACATGAGCCGGTATGACGTCAAGAGCATCATTGAGAGCAGCTCCCT
GCCTGTTGGCGGCACTCCAAAGCGTCTCAAGGAAGTGCCTGATCAATCAG
ATATGGGCATCAACATAAACGGTGACTCTGCTGGTCATATGACTGCTATC
AACCTTCTTACTGATGGCAATGACAGCTATGGAGCTGAGAGTTATGGTTA
CAGTGGTTGGTGTCCCACAGCCATGACGCCAATCCCCTTTCAATTCAGCA
ATGGCCATGACCATTCCAGGCTGTGGTGCAAGCCAGAGCAGGACAATGCG
GTTGTTGCAGCACTGCATAACCTGCATCACCTCCAGCACTTGCCAGCCCC
AGTTGGCACCCATAATTTTTCCAGCCATCGCCTGTTCAGGACATGACAG
GTGTTGCCGATGCTTCATCGCCACCAGTAGAATCTAATTCATTCTGTAC
AATGGGGACGTTGGTTACCATGGTGCCATGGGTGGCAGCTATGCCATGCC
GGTTGCCACACTAGTTGAGGGCAACTCTGCGGGCAGTGGCTATGGAGTTG
AGGAAGGCACAGGGTCTGAAATCTTTGGTGGACGGAACTTGTATTCTCTC
TCCCAAGGTTCCTCAGGCGCCAATACTGGAAAGGCAGATGCTTATGAAAG
CTGGGATCCATCTATGCTGGTGATATCACAGAAGTCTGCCAATGTGACTG
TCTGCCATGGCGCACCTGTATTTTCAGTTTGGAAA<u>TGA</u>

SEQ ID NO: 3. ASGR-BBM construct sequence
GGATCCAGCCATGTCTAAACGATCAACAGATGACTGCCTAATATAAGGTT
TTTGGGTTGTTGAATAATTAGGCAATATCCATATTAGATTCCGAAAGCAG
TAAAACATGACAATGATAGTAACTAGTATGCACGCATAAGACATACTAGA
CGATAGTAACAACATAACCATGAACTCAGTAAACATGACTAAAAGATTGA
TCTTAGATCCGTACCTGGCGCTCAGAGTTGCAAGCACTGCGGAGGGCGTC
GATACTTCGGGGAAGCAAGCGGCGCAGACGAAGCGACGACGGTGTTCCG
GACGGCACGTAGCAGCCGACATTGAAGGCAATGCGCCCTCTCGTCAGGAG
ACTTGCTAGGAAGACGAGCCACGATGACGACGATTGAGCAGTCACGCGGA
GCACTTCCCAAAAACCTTATTCGCCCTCTCCCGGTGCAGGATCGCAAGGA TABLE 2-continued ASGR-BBML cDNA, genomic DNA, amino acid sequence, and promoter sequence; the start codons are indicated by single underline, and the stop codons are indicated through double underline.

CGGACGGTTCCGGAGACCTGCTCTCCCAATCACCTGTGCACGCAGGTGTT
CGGGATGGAGTAGATGGCGGCGGCGGCGGCGCAGCAGCGAGCGAGAGAGG
CAAAGTCCTAACTCAGATCAGATCTATTTTAGGGATACCCTTTCATGGGG
CCTTTCCGTAGATAGTCTATTGTGCATCTCTTCTGTGAGGGGTGGTCCA
TTTTTATATGGAGGGAAACCTCCAACACCCTCGTCTATTAGCAATATGAG
ACTAATAGATGGTGTACCCCCTCATCACGCTAATGGGCCTTTGAGATTTA
TTCAGGAATTATTGGATTGGCTAATGGGCCAAGCCCAAAATTCCAACACA
ATCAAGTTTGCCTCGCATATCTCGATTCTCGAACCAACCTCCGAGCCATA
TCTGATTGTAGACAAGTAAACAAACTCGGAGGCGGAAGGGGGAACTGACC
CGTTGAACGCCGTCACTGCCGGAACCGACGTCGCCGTCACTGAAGAAGAA
GGAAGATGCTTCCGAACCACCCAATACAAAACCTCACTAATTCCTCGCTG
ACGCCAGAGCAGCACGCCGACGAAACGGGAAAGGAGTCAAAATACCTTATT
CCATCGCCACCACATCATTTGGGCGCTGCTCGCTGATACGCCGGCGGGAG
CGGTGGCAGCCAGGTGTACGCCCCCGCGGACTGCGCGCCGGCTGGCCGGC
CGGCCACCGGGGCCGGGGCCCTTCAATCTCTTAGGGCGTCCCCAACAAGG
CTGATTCAGCTAGCTATTTTGAGTGTACACATCAGCATGTATCCTACATGG
AGGAAAGAAGAGTATGCATTGAACATTGAGCCGGCTATTTGCTCGTCGCCT
ATCTAGCACATCACCCAAGGCAGCGCTGTGTCTATGGCCTGGCAGAAAAT
ATTGTTTAAATAACAAGTAGCCAGCTTTAGTAGATAGTACTTTCTCTTGC
TGGCTTTTTTTTTTTGATAACAGCTCTTGCTGGCTTTTAGCGTGCCGG
CTCCGAGCTACTCCCTCTGTCCCAGAATTTGAGTCGCCGGCCAACAGTGA
AATGAGAGAGGGGCACGGAGTCCCAACGACAGTAATATTGGGACAGGGAG
TAGCAGCTATCCAGGACTGCTGTAGACGCCCTTAGTCCTCGACTCCTCGC
AGCCTTTCGCCGTTGAAAGAATCACACCGCCCCCTGCAGTTACGTGTTAA
CCCAACCCGGGCCATTGGTCAGTCCCTAACCCGGGCGGTTGACCGCTAGA
AATTAGAATTAACCCTTGGTTAACACCGGTCAAAGCGCACATATGCGGTG
CAATCTAATCGAAGTGGCCGCGTCATAATTACACACGCCCGCTCCTACAC
GTGTGCCCCGTTCATACGCATGCTCACCTCGCGCGTTCCCATGAGGTTTC
ACACCCCTTGTGGGAATCCAAGGCGTCAGAGATTTATTGATCCCATTTCC
CTAGCCTGCCTCGCCTCTCTATCTACTTGTGTGGAGATTAGAGCACAGCA
GCGAGAAAGGGCTTGCAGTCTATAAAGGCGACAAGAGCCCACACCCTCCT
CTCTCTCTCTTCTCTCTCTCCCATTTCTCTTTCCCTAGGATCAGTGCTAG
TGCTTGCAGCGGCCGCGTTCCGAGATGGGTTCCACCAACAACTGGCTGCG
CTTCGCCTCGTTCTCCGGCGGCGCCAAGGATGCCGCGGCCCTGC
TCCCGCTGCCGCCCTCGCCCCGTGGCGATGTCGACGAGGCCGGCGCAGAG
CCGAAGCTCGAGGACTTCCTCGGCCTGCAGGAGCCGAGCGCCGCCGCGGT
GGGGGCTGGGCGGCCATTCGCGGTGGGTGGCGGTGCGAGCTCCATCGGGC
TGTCCATGATCAGGAACTGGCTGCGCAGCCAGCCGGCGCCGGCCGGCCT
GCTGCGGGGTCGATTCGATGGTGCTGGCGGCTGCGGCGGCGTCGACGGA
GGTGGCCGGCGATGGCGCGGAGGGCGGCGGCGCCGTGGCTGACGCGGTGC
AGCAGAGGAAGGCGGCGGCGGTGGACACTTTCGGGCAGCGGACCTTTCG
TACCGCGGCGTCACAAAGTAGGTTCTTGATTTTATTTTGGTTTTGGAAAA
ATTCTTCTTTGTTTTTCTGTTTTCTTCCGACTGGTATATCTTGTGTTAA
GAACTTTTTCATTAGATGCATGTCATACTGTTGCTTTTTCTTGTTGCTTTT
GAACCTTTTTGGCGTTTGCAATTGGATATACAGAACCTATATTAT
CCCCTTTAGTAACCAGTAGATTCTTTTTTTTCTTTTTTTTTTTGCTT
TCGATGTTGTTAGTGTTCTTGCATCACGCATGTTTTTCCTCTGATATTTT
AATGGACGATATCATCTCTAGTTCAAGTTTTTGCTCTTGCTCTTGTTGTA
GTGGTGCTAAGATTTTTATGACGAGTCTTTGTGCTGTTTGAAAATGTA
AGCATCTCACAGTTCTAAAATATATATATATATATATATAAGTCTCTC
ATGTTGATTTGTGGATGTACTGAAGCCCGCGCGCACACATGCACACACC
GCACGCTCACACGCCCTAAATCCCGGTGCAACACCAGGGTTGTCCCCGA
TGGGGATCGAACCCTGGCGGGTGCCTAACCACCGTCAGCTCCCACCACC
GAGCTATCAGCTCGTTTGCCCATATTTCGTGTGGTACCTCGATATTTTA
TATTTCTAGATTGCTGTATCTATCTTCTAGACTTATATAAGTGTTGCGCC
ACTCATACTTTTTACCGCCTGTAATCGAGTAGAACTGCTTCCTCTTTTGA
TTATATTGTATCAGTTAAATGATCTTGTTGTTGATGTGTTTACCACTTTA
CCATCACCATTGCATGAAATCACTTCAAGACATGTATTCATGATTTTGCT
GGCTAAATTTGCTAGTGGCACATCATGTGGTAAAAAATATTTTTAGTT
TGTGCTTGCTATTCTTTTCGGTCATCCCTTCGTGCCTGTTTATCCAGAAC
ACCCAATCTGCTTCACATAGTTTTTGAATGCTATCATCATATTTCTTTTT
TGGAGATATTGTTACTAAAAGTTTGGCTTTGTCCTCAATAGGCATAGATG
GACAGGAAGGTATGAAGCCCATCTTTGGGACAATAGCTGCAGAAGAGAAG
GTCAAACTCGGAAAGGTAGACAAGTGTAATGATTATAATAGATATTTAA
ATTTGTAATTATAAGCTGCATCATATTATTATTTATTAGATCGGCTTTAA
AATTTCACTAGCTAATTTAGTGTTTTCTTTTCTTCATCGATACTCTGAA
TCGCTTCATTCCATTGATTCAGTGTATCTTGGTAAGTAATACTTGTTTAC
AATTGCAAAATGGTATATCTTGTTGTTTCTCATGTCAAGTATATTAAA
TATGTGGTTGATGCATTGAAGGTGGATATGATAAAGAAGAAAAAGCAGCT
AGAGCTTATGATTTAGCTGCTCTCAAGTACCGGGGCACCACAACTACTAC
AAATTTTCCGGTATTACTTATTGTTAATATGTTGGTTCTCCAGAATTGAT
ATTTTACTTCTAATATATAACTGCGTATATGAATGAATGTTGTAAGATTT
TGCATTTTATGTTCAGATGAGCAACTATGAAAAGGAGTTAGAAGAGATGA
AGCATATGTCACGACAAGAATATGTTGCATCCCTTAGAAGGTACATGTGT
TGTCAAAACTTTGTACCTTCATGGAAACTGAACTTATATATTTCACAAAT

TABLE 2-continued

ASGR-BBML cDNA, genomic DNA, amino acid sequence,
and promoter sequence; the start codons are
indicated by single underline, and the stop
codons are indicated through double underline.

```
GGATTGACATAGAACATATATTTGTGATACAGGAAAAGCAGTGGTTTTTC
TCGTGGTGCATCAATTTACCGAGGGGTTACCAGGTACAAAATATTCCTTT
TCCTTATTATCTCTGGTTTTAGTTAGCAAGTGCATTGTTTCTATGGGAAT
TTGTGTTGCATGTAGATGGGAATTTGTGTTGCATGTAGATCATAAATAGT
TGCAACTATTAATCTCATCGTTCTATTGCTGAATAGTTGTGGTACTCCTT
TACCACAGTTGACTATGATATTCTATTATATTATTTTTCTTGCAAAGTTG
ATATTTAATTGCTTGTCTAGCTAACTTTCAAGCAATCATGTAAAACAGGC
ACCATCAGCATGGAAGGTGGCAAGCAAGAATAGGAAGTGTGGCAGGAAAC
AAGGATCTTTATTTGGGCACATTCAGTAAGTCACATTTTAATATTTTTAA
TGAAGCACTGATTTTTTTTTGTCAAGCAAAATGGAAGCAAGACAGAAAAA
CATAAACCTACTGGAGCACCTTTTTCATTATTTTGTCTCTTGAATATAAT
AGTATGTGGCTGACCTCTCCCTGTGTAGGTACCCAGGAGGAAGCTGCAGA
GGCTTACGACATTGCTGCCATCAAATTCCGAGGCCTCAATGCTGTCACGA
ACTTTGACATGAGCCGGTATGACGTCAAGAGCATCATTGAGAGCAGCTCC
CTGCCTGTTGGCGGCACTCCAAAGCGTCTCAAGGAAGTGCCTGATCAATC
AGATATGGGCATCAACATAAACGGTGACTCTGCTGGTCATATGACTGCTA
TCAACCTTCTTACTGATGGCAATGACAGCTATGGAGCTGAGAGTTATGGT
TACAGTGGTTGGTGTCCCACAGCCATGACGCCAATCCCCTTTCAATTCAG
CAATGGCCATGACCATTCCAGGCTGTGGTGCAAGCCAGAGCAGGACAATG
CGGTTGTTGCAGCACTGCATAACCTGCATCACCTCCAGCACTTGCCAGCC
CCAGTTGGCACCCATAATTTTTTCCAGCCATCGCCTGTTCAGGACATGAC
AGGTGTTGCCGATGCTTCATCGCCACCAGTAGAATCTAATTCATTCCTGT
ACAATGGGGACGTTGGTTACCATGGTGCCATGGGTGGCAGCTATGCCATG
CCGGTTGCCACACTAGTTGAGGGCAACTCTGCGGGCAGTGGCTATGGAGT
TGAGGAAGGCACAGGGTCTGAAATCTTTGGTGGACGGAACTTGTATTCTC
TCTCCCAAGGTTCCTCAGGCGCCAATACTGGAAAGGCAGATGCTTATGAA
AGCTGGGATCCATCTATGCTGGTGATATCACAGAAGTCTGCCAATGTGAC
TGTCTGCCATGGCGCACCTGTATTTTCAGTTTGGAAATGATGGTTAGATG
AAAATATAGTAGTGATATTAACTAGTTCTTGGAGGGGAAGATTAAATTCT
AGGTATACAAAAGTTTAATTTATTAGTGCTTCAAGATCTCGTATGAAAAA
AAGTTTTGCTGCTTAATCAGCTCCAGTGGGAGTCTAGGAGCCATGAGAAA
TGTCGTTTTATTATTGACTAATGCTACAATGCTAACATGCTGACTCTTTT
GAATGGCACAAGAGCTCTGGTGTTTCAATACATCAGCCAGTTTCATTATT
GTCCATTTGCTGTGCACATTTTCTGCGCTGGCACCTATAATAATATGATT
CTAAACTGTGAATTAGTTCAGATGTCAACTGTAAGTAACTTTATTTTAGC
TTTCTTATATACATCTCTTTTTCTTTTTGAGAAACGGGCTTTGCCCCCAG
CCTTCATAGGAGGCTGGTGCAGCGTACCGGGTCCGAACCTGGGCTGGTGA
CGTCCTCAGCATGAGCGCCCACCACCGAGCTACACGCTCGTCTGCTCTTA
TATACATCTCTTCAGTAAGGGTAATATGGTACTTCACAGTTCACAGTCCA
GTCATTCCAACCATGGATGAGCAAAATGTGCTTGTGCACATGGTGGGTC
```

SEQ ID NO: 4. ASGR-BBM amino acid sequence
MGSTNNWLRFASFSGGGGAKDAAALLPLPPSPRGDVDEAGAEPKLEDFLG
LQEPSAAAVGAGRPFAVGGGASSIGLSMIRNWLRSQPAPAGPAAGVDSMV
LAAAAASTEVAGDGAEGGGAVADAVQQRKAAAVDTFGQRTSIYRGVTKHR
WTGRYEAHLWDNSCRREGQTRKGRQVYLGGYDKEEKAARAYDLAALKYRG
TTTTTNFPMSNYEKELEEMKHMSRQEYVASLRRKSSGFSRGASIYRGVTR
HHQHGRWQARIGSVAGNKDLYLGTFSTQEEAAEAYDIAAIKFRGLNAVTN
FDMSRYDVKSIIESSSLPVGGTPKRLKEVPDQSDMGININGDSAGHMTAI
NLLTDGNDSYGAESYGYSGWCPTAMTPIPFQFSNGHDHSRLWCKPEQDNA
VVAALHNLHHLQHLPAPVGTHNFFQPSPVQDMTGVADASSPPVESNSFLY
NGDVGYHGAMGGSYAMPVATLVEGNSAGSGYGVEEGTGSEIFGGRNLYSL
SQGSSGANTGKADAYESWDPSMLVISQKSANVTVCHGAPVFSVWK*

SEQ ID NO: 5. ASGR-BBM promoter sequence
```
GGATCCAGCCATGTCTAAACGATCAACAGATGACTGCCTAATATAAGGTT
TTTGGGTTGTTGAATAATTAGGCAATATCCATATTAGATTCCGAAAGCAG
TAAAACATGACAATGATAGTAACTAGTATGCACGCATAAGACATACTAGA
CGATAGTAACAACATAACCATGAACTCAGTAAACATGACTAAAGATTGGA
TCTTAGATCCGTACCTGGCGCTCAGAGTTGCAAGCACTGCGGAGGGCGTC
GATACTTCGGGGAAGACAAGCGGCGCAGACGAAGCGACGACGGTGTTCCG
GACGGCACGTAGCAGCCGACATTGAAGGCAATGCGCCCTCTCGTCAGGAG
ACTTGCTAGGAAGACGAGCCACGATGACGACGATTGAGCAGTCACGCGGA
GCACTTCCCAAAAACCTTATTCGCCCTCTCCCGGTGCAGGATCGCAAGGA
CGGACGGTTCCGGAGACCTGCTCTCCCAATCACCTGTGCACGCAGGTGTT
CGGGATGGAGTAGATGGCGGCGGCGGCGGCGCAGCAGCGACGAGAGAGG
CAAAGTCCTAACTCAGATCAGATCTATTTTAGGGATACCCTTTCATGGGG
CCTTTCCGTAGATAGTCTATTGTGCATCTCTTCTGTGAGGGGTGGTCCA
TTTTTATATGGAGGGAAACCTCCAACACCCTCGTCTATTAGCAATATGAG
ACTAATAGATGTGTACCCCCTCATCACGCTAATGGGCCTTTGAGATTTA
TTCAGGAATTATTGGATTGGCTAATGGGCCAAGCCCAAAATTCCAACACA
ATCAAGTTTGCCTCGCATATCTCGATTCTCGAACCAACCTCCGAGCCATA
TCTGATTGTAGACAAGTAAACAAACTCGGAGGCGGAAGGGGGAACTGACC
CGTTGAACGCCGTCACTGCCGGAACCGACGTCGCCGTCACTGAAGAAGAA
GGAAGATGCTTCCGAACCACCCAATACAAAACCTCACTAATTCCTCGCTG
```

TABLE 2-continued

ASGR-BBML cDNA, genomic DNA, amino acid sequence,
and promoter sequence; the start codons are
indicated by single underline, and the stop
codons are indicated through double underline.

```
ACGCCAGAGCAGACGCCGACGAAACGGGAAAGGAGTCAAAATACCTTATT
CCATCGCCACCACATCATTTGGGCGCTGCTCGCTGATACGCCGGCGGGAG
CGGTGGCAGCCAGGTGTACGCCCCCGCGGACTGCGCGCCGGCTGGCCGGC
CGGCCACCGGGGCCGGGGCCCTTCAATCTCTTAGGGCGTCCCCAACAAGG
CTGATTCAGCTAGCTATTTGAGTGTACACATCAGCATGTATCCTACATGG
AGGAAAGAGAGTATGCATTGAACATTGAGCCGGCTATTTGCTCGTCGCCT
ATCTAGCACATCACCCAAGGCAGCGCTGTGTCTATGGCCTGGCAGAAAAT
ATTGTTTAAATAACAAGTAGCCAGCTTTAGTAGATAGTACTTTCTCTTGC
TGGCTTTTTTTTTTTTGATAACAGCTCTTGCTGGCTTTTAGCGTGCCGG
CTCCGAGCTACTCCCTCTGTCCCAGAATTTGAGTCGCCGGCCAACAGTGA
AATGAGAGAGGGGCACGGAGTCCCAACGACAGTAATATTGGGACAGGGAG
TAGCAGCTATCCAGGACTGCTGTAGACGCCCTTAGTCCTCGACTCCTCGC
AGCCTTTCGCCGTTGAAAGAATCACACCGCCCCCTGCAGTTACGTGTTAA
CCCAACCCGGGCCATTGGTCAGTCCCTAACCCGGGCGGTTGACCGCTAGA
AATTAGAATTAACCCTTGGTTAACACCGGTCAAAGCGCACATATGCGGTG
CAATCTAATCGAAGTGGCCGCGTCATAATTACACACGCCCGCTCCTATAC
GTGTGCCCCGTTCATACGCATGCTCACCTCGCGCGTTCCCATGAGGTTTC
ACACCCCTTGTGGGAATCCAAGGCGTCAGAGATTTATTGATCCCATTTCC
CTAGCCTGCCTCGCCTCTCTATCTACTTGTGTGGAGATTAGAGCACAGCA
GCGAGAAAGGGCTTGCAGTCTATAAAGGCGACAAGAGCCCACACCCTCCT
CTCTCTCTCTTCTCTCTCCATTTCTCTTCCCTAGGATCAGTGCTAG
TGCTTGCAGCGGCCGCGTTCCGAG
```

Example 5 gPsASGR-BBML-Containing Transgenic Pearl Millet Lines

Transgenic lines were regenerated from these experiments, and two plates of pearl millet embryogenic tissues were bombarded for each construct. For these constructs, the marker gene selected was for hygromycin resistance rather than phosphinothricin resistance. Of 5 cDNA construct lines, consisting of 13 plants total, that were regenerated and screened by ovule clearing, 3 plants showed a low frequency of small groups of densely cytoplasmic dividing cells in the nucellus; however, none of these was clearly interpreted as representing an organized embryo structure beyond the globular stage.

Of the nine independent transgenic lines (18 plants) containing the transgene, gPsASGR-BBML, generated from sexual tetraploid pearl millet, four lines, consisting of six plants, were not analyzed as a result of lack of flowering or demise of the plant. Four plants within 3 lines showed evidence of embryo formation from egg cells in the absence of fertilization, and 3 plants died prior to ovary analysis. Evidence for lack of fertilization was the persistence of polar nuclei in the central cell of the embryo sac. Parthenogenesis was assayed two days after anthesis for the remaining transgenic plants using a cleared-pistil technique (B. A. Young, R. T. Sherwood, E. C. Bashaw, Can. J. Bot. 57:1668-1672 (1979)), and observation was conducted via differential interference contrast (DIC) or phase contrast optics. Fertilization was prevented by bagging heads prior to stigma exsertion and removing stigmas/styles prior to anthesis (since the plants are protygynous, meaning that stigmas exsert prior to anthers).

As shown in Table 3, the presence of embryos developing in the same embryo sac where polar nuclei persist (embryo+ PN) provides evidence that the embryo sac was not fertilized and that the egg is developing parthenogenetically. Examples of embryo formation in embryo sacs with polar nuclei are shown in FIG. 10. Since this would be indicative parthenogenesis in a sexual plant where meiosis occurs, the parthenogenetically-derived, haploid embryos are expected to have half the chromosome number and DNA content (FIG. 10) of the mother plant. Offspring #105 (FIG. 10D) and #106 (FIG. 10C) are examples of haploid (1n=2x) individuals with half the expected DNA content of progeny from a sexual diploid (2n=4x) plant (e.g. #100 (FIG. 10B), #107 (FIG. 10D) and #108 (FIGS. 10A, 10C)). While not all embryos developed parthenogenetically in these lines (embryo sac+PN), this was likely due to incomplete penetrance of the phenotype as well as segregation of the transgene. While not all embryo sacs developed normally (no embryo sac/abnormal sac structure) in these lines, this was likely due to variation induced by tissue culture, poor health of plants, and/or a pleiotropic effect of the transgene. Further information regarding these alternatives can be gleaned via genetic analysis. Stigma removal was not 100%, resulting in occasional pollination (last column).

TABLE 3

| Line | Embryo + PN | Embryo Sac + PN | No Embryo Sac | Abnormal embryo sac structure | Pollination occurred - clear endosperm development |
|---|---|---|---|---|---|
| G3f#35_1st | 24 | 24 | 12 | 5 | 4 |
| G3f#35_A | 4 | 14 | 17 | 5 | 10 |
| G3f#35_B | 11 | 19 | 20 | 5 | 8 |
| G11a#37_1st | 3 | 7 | 3 | 2 | 3 |
| G11a#37_2nd | 8 | 14 | 12 | 5 | 11 |
| G52#72 1st | 11 | 16 | 1 | 5 | 22 |
| G52#72 2nd | 6 | 13 | 11 | 1 | 24 |

All lines contained structurally mature embryo sacs (FIG. 11A), of which three independent lines (g3f, g11a, and g52) showed parthenogenesis (FIGS. 11B, 11C) based on the persistence of polar nuclei in the central cell and an absence of endosperm development, as endosperm can be readily visualized in fertilized embryo sacs of the same developmental stage. When pollination was not prevented, all three lines demonstrated endosperm formation at day 2 (FIG. 11D). A minimum of 3 heads and 150 ovaries were analyzed for each of the 3 lines, wherein the percentage of structurally mature sexual embryo sacs (FIG. 11A) on each head and the percentage of those containing parthenogenetic embryos at 2 days after anthesis were 66, 79, 71, and 35, 36, 35 for lines g11a, g52 and g3f, respectively. gPsASGR-BBML transgene expression was verified by RT-PCR with RNA extracted from open-pollinated ovaries 2 days after anthesis for lines g52 and g3f (FIG. 12). To rule out potential ploidy changes induced by tissue culture selection and regeneration, the three $T_0$ gPsASGR-BBML lines were analyzed via flow cytometry (FIG. 13A). All three lines were shown to maintain a tetraploid ploidy level.

As a result of low germination rates and low seed set for lines g11a and g52, embryo rescue was employed on developing seed 10 to 15 days after pollination and on non-germinating mature seed in order to recover offspring from the 3 lines. Seed analyzed via flow cytometry demonstrated the production of reduced offspring (FIG. 14).

Pollination with Red IA4X plants, which are sexual tetraploid lines containing a dominant Rp1 allele which confers a dark red pigmentation in the midrib and sheath of leaves (W. W. Hanna, G. W. Burton, *J Hered.* 83:386-388 (1992)), over multiple heads and days was used to compensate in part for potential pollen sterility of the transgenic lines. Plant g11a set a total of nine seed, two offspring of which survived to greenhouse planting. Plant g52 set 97 seed 31 offspring of which survived to greenhouse planting. Plant g3f set hundreds of seed of which 194 were randomly selected, with 107 surviving to greenhouse planting.

All offspring were analyzed for the inheritance of a 3,694 bp amplicon covering the gPsASGR-BBML open reading frame starting five base pairs downstream from the start codon and amplifying into the 3' UTR (ORF amplicon). The two g11a offspring showed no inheritance of the transgene. All offspring from g52 showed red pigmentation of the midrib; these were derived from the fertilization of g52 sexual embryo sacs with Red IA4X pollen. Nine of the offspring plants carried at least one copy of the ORF amplicon. The g3f offspring plants had a mix of both green and red pigmentation of the midrib. Twenty-six g3f offspring plants carried at least one copy of the ORF amplicon.

All offspring plants from line g52 were assayed for parthenogenesis (Table 4, FIG. 15B), which demonstrated that only offspring inheriting the ORF amplicon showed parthenogenesis 2 days after anthesis. No embryo formation was identified in 791 structurally mature sexual embryo sacs from 21 g52 offspring which did not inherit the ORF amplicon. Ninety sexual embryo sacs displayed embryo development as well as polar nuclei from the nine g52 offspring inheriting the ORF amplicon. The percentage of ovules showing embryo development ranged from 12% to 53% in the various g52 offspring.

A subset of offspring plants generated from the g3f line was assayed for parthenogenesis (Table 5, FIG. 15C). No embryo formation was identified in a total of 951 structurally mature sexual embryo sacs from 28 g3f offspring which did not inherit the ORF amplicon. Three of the 26 offspring inheriting the ORF amplicon were unavailable for parthenogenesis assay because they did not flower. Of the remaining 23 offspring inheriting the ORF ampicon, 19 displayed parthenogenesis, and four did not. The percentage of structurally mature embryo sacs in which embryo development was observed ranged from 1% to 52% from the various g3f offspring displaying parthenogenesis. Of the four offspring carrying the transgene but not showing parthenogenesis, plants 123, 144, and 159 were assayed for transgene expression via RT-PCR analysis (FIG. 16). In all three offspring, gPsASGR-BBML expression was detected in unpollinated ovaries at the day of anthesis. Two transgene-specific amplicons covering the gPsASGR-BBML cDNA transgene from the 5' UTR through the 3' UTR were sequenced from plants 123, 144, and 159, along with plant 105 which also displayed parthenogenesis. All sequences were found to be identical to the PsASGR-BBM cDNA sequences derived from the BC7 and BC8 apomictic plants.

Because g3f offspring were a mix of both red and green pigmentation of the midrib, determination of ploidy level of the green phenotypes was required (Table 6). Six offspring were diploid/dihaploid in genome size as analyzed via flow cytometry using *Sorghum* as the genome size reference (FIG. 13B-C). The diploid/dihaploid offspring were further confirmed by mixing predicted diploid/dihaploid and tetraploid offspring together in order to generate 3 peaks (FIG. 13D). All six haploid offspring carry the ORF amplicon; of the four that flowered, all displayed parthenogenesis (FIG. 15C). The role of PsASGR-BBML in apomictic development was evaluated in apomictic $F_1$ transgenic lines using an RNAi knock-down strategy with a RNAi-BBM-3p construct. As direct transformation and regeneration of apomictic *P. squamulatum* was not possible, an alternative strategy and screening protocol for generating apomictic $F_1$ plants with reduced expression of PsASGR-BBML was employed. After screening, three plants, each of which was derived from a different line, with a genotype of ASGR-positive/RNAi-positive showed reduced PsASGR-BBML gene expression based on semi-quantitative analysis of PsASGR-BBML expression at the day of pollination (Table 7, FIG. 17), as compared against the ASGR-positive/RNAi-negative control genotype. The three PsASGR-BBML reduced-expression $F_1$ plants were found to contain the same percentage of ovules with aposporous embryo sac formation as the control plant (Table 7). The plants were then pollinated with Red IA4X pollen, and offspring were found to be derived through apomixis based on the lack of red pigmentation of the midrib and uniform phenotypes. However, histological observation showed that the number of ovaries showing parthenogenetic embryo development and the number of cells in those embryos 2 days after anthesis was significantly reduced in the PsASGRBBML reduced-expression lines (Table 7, FIG. 18).

Analysis of sexual transgenic lines which carry the gPsASGR-BBML transgene and produce fertilization-independent embryo formation and diploid/dihaploid offspring, albeit at somewhat low penetrance, demonstrates that the PsASGR-BBML gene alone can promote parthenogenesis in sexual tetraploid pearl millet, which are plants which do not normally show this trait. None of the $T_0$ lines or offspring from the $T_0$ lines showed complete penetrance of the trait; this incomplete penetrance within the original $T_0$ lines and offspring of lines g3f and g52 is likely due to transgene segregation, transgene expression levels, and/or unknown genetic factors interacting with PsASGRBBML. Although transcription of the transgene was identified in offspring that did not demonstrate parthenogenesis, quantifying levels of transgene expression is difficult due to variation in percentage of structurally mature sexual embryo sacs and the inability to verify that RNA is being extracted from ovaries that are at the same developmental stage. Generation of inbred lines containing a single copy of the gPsASGR-BBML transgene or the expression of the gPsASGRBBML transgene using egg-specific promoters with different expression levels would be advantageous to confirm these issues.

Ploidy level was not found to be critical for PsASGR-BBML transgene-induced parthenogenesis, as the four chromosomally reduced diploid/dihaploid offspring generated from g3f showed a similar range of parthenogenesis levels as the unreduced tetraploid offspring. While most natural apomicts are polyploid, natural populations and experimentally recovered apomictic diploids/dihaploids from several species have been identified. For example, polyploid apomictic plants can produce diploids/dihaploids offspring either through the genetic separation of the apomeiosis and parthenogenesis loci (R. D. Noyes, J. D. Wagner, *American Journal of Botany* 101:1-10 (2014)) or through the parthenogenetic development of a reduced egg carrying an apomixis locus (M. Dujardin, W. W. Hanna, *Theor Appl Genet* 72:33-36 (1986)).

The lack of an $F_1$ aposporous transgenic line showing complete knock-down of PsASGRBBML precludes a determination of whether PsASGR-BBML is the sole gene required to induce parthenogenesis in plants programmed for the apomixis pathway through the inheritance of the ASGR. However, given that the number of ovaries showing parthenogenetic embryo development and that the number of cells in those embryos at 2 days after anthesis were significantly reduced in the $F_1$ PsASGR-BBML-reduced-expression lines, PsASGRBBML clearly has an important role in parthenogenesis in the apomictic reproductive pathway.

While members of the BBM-like clade of AP2 transcription factors have noted roles in somatic embryogenesis and cell proliferation, these results have uncovered for the first time the role for PsASGRBBML in parthenogenesis. It is worth noting that neither maize nor *Sorghum* have a PsASGR-BBML protein more related to PsASGR-BBML than does the more distantly related species rice. Therefore, this newly discovered role can have a major impact on the ability to genetically engineer apomixis into crop species This technique therefore can also be used as an alternative method for haploid induction in order to rapidly obtain homozygous lines for breeding.

TABLE 4

Visual determination of parthenogenesis in cleared ovaries 2 days after anthesis in offspring from g52.

| Offspring Designation: | Genotype-ORF amplicon: | Number of identified developing embryos with polar nuclei in structurally mature sexual embryo sacs | Number of identified developing embryos without distinct polar nuclei but also without endosperm development | Number of structurally mature sexual embryo sacs without embryo development | Number of ovaries with no structurally mature sexual embryo sacs | Percentage of structurally mature sexual embryo sacs | Percentage of parthenogenesis in structurally mature sexual embryo sacs |
|---|---|---|---|---|---|---|---|
| 300 | − | 0 | 0 | 25 | 4 | 86 | 0 |
| 301 | − | 0 | 0 | 22 | 22 | 50 | 0 |
| 302 | − | 0 | 0 | 37 | 10 | 79 | 0 |
| 305 | − | 0 | 0 | 40 | 13 | 75 | 0 |
| 307 | − | 0 | 0 | 46 | 6 | 88 | 0 |
| 309 | − | 0 | 0 | 34 | 12 | 74 | 0 |
| 310 | − | 0 | 0 | 30 | 19 | 61 | 0 |
| 311 | − | 0 | 0 | 45 | 5 | 90 | 0 |
| 312 | − | 0 | 0 | 39 | 6 | 87 | 0 |
| 313 | − | 0 | 0 | 44 | 7 | 86 | 0 |
| 314 | − | 0 | 0 | 48 | 3 | 94 | 0 |
| 315 | − | 0 | 0 | 40 | 14 | 74 | 0 |
| 317 | − | 0 | 0 | 41 | 12 | 77 | 0 |
| 319 | − | 0 | 0 | 32 | 14 | 70 | 0 |
| 320 | − | 0 | 0 | 49 | 0 | 100 | 0 |
| 321 | − | 0 | 0 | 26 | 21 | 55 | 0 |
| 322 | − | 0 | 0 | 41 | 5 | 89 | 0 |
| 323 | − | 0 | 0 | 31 | 20 | 61 | 0 |

TABLE 4-continued

Visual determination of parthenogenesis in cleared ovaries 2 days after anthesis in offspring from g52.

| Offspring Designation: | Genotype-ORF amplicon: | Number of identified developing embryos with polar nuclei in structurally mature sexual embryo sacs | Number of identified developing embryos without distinct polar nuclei but also without endosperm development | Number of structurally mature sexual embryo sacs without embryo development | Number of ovaries with no structurally mature sexual embryo sacs | Percentage of structurally mature sexual embryo sacs | Percentage of parthenogenesis in structurally mature sexual embryo sacs |
|---|---|---|---|---|---|---|---|
| 326 | − | 0 | 0 | 48 | 8 | 86 | 0 |
| 329 | − | 0 | 0 | 29 | 17 | 63 | 0 |
| 330 | − | 0 | 0 | 44 | 11 | 80 | 0 |
| Total numbers analyzed without the gPsASGR-BBM ORF | | 21 | 0 | 0 | 791 | 229 | 78 | 0 |
| 303 | + | 7 | 0 | 25 | 16 | 67 | 22 |
| 306 | + | 10 | 0 | 45 | 13 | 81 | 18 |
| 308 | + | 7 | 4 | 24 | 8 | 81 | 31 |
| 316 | + | 11 | 1 | 29 | 11 | 79 | 29 |
| 318 | + | 6 | 0 | 33 | 8 | 83 | 15 |
| 324 | + | 8 | 3 | 21 | 14 | 70 | 34 |
| 325* | + | 31 | 6 | 33 | 12 | 85 | 53 |
| 327 | + | 6 | 1 | 28 | 12 | 74 | 20 |
| 328 | + | 4 | 0 | 30 | 15 | 69 | 12 |
| Total numbers analyzed with the gPsASGR-BBM ORF | | 9 | 90 | 15 | 268 | 109 | 77 | 28 |

*data combined from 2 heads collected on different days for analysis

TABLE 5

Visual determination of parthenogenesis in cleared ovaries 2 days after anthesis in offspring from g3f.

| Offspring Designation: | Genotype-ORF amplicon: | Number of identified developing embryos with polar nuclei in structurally mature sexual embryo sacs | Number of identified developing embryos without distinct polar nuclei but also without endosperm development | Number of structurally mature sexual embryo sacs without embryo development | Number of ovaries with no structurally mature sexual embryo sacs | Percentage of structurally mature sexual embryo sacs | Percentage of parthenogenesis in structurally mature sexual embryo sacs |
|---|---|---|---|---|---|---|---|
| 111 | − | 0 | 0 | 34 | 15 | 69 | 0 |
| 112 | − | 0 | 0 | 37 | 12 | 76 | 0 |
| 113 | − | 0 | 0 | 37 | 18 | 67 | 0 |
| 114 | − | 0 | 0 | 29 | 17 | 63 | 0 |
| 115 | − | 0 | 0 | 30 | 21 | 59 | 0 |
| 116 | − | 0 | 0 | 42 | 5 | 89 | 0 |
| 119 | − | 0 | 0 | 39 | 10 | 80 | 0 |
| 120 | − | 0 | 0 | 38 | 16 | 70 | 0 |
| 124 | − | 0 | 0 | 42 | 6 | 88 | 0 |
| 126 | − | 0 | 0 | 36 | 11 | 77 | 0 |
| 128 | − | 0 | 0 | 30 | 17 | 64 | 0 |
| 129 | − | 0 | 0 | 29 | 12 | 71 | 0 |
| 130 | − | 0 | 0 | 29 | 17 | 63 | 0 |
| 132 | − | 0 | 0 | 27 | 20 | 57 | 0 |
| 133 | − | 0 | 0 | 28 | 21 | 57 | 0 |
| 137 | − | 0 | 0 | 43 | 8 | 84 | 0 |
| 138 | − | 0 | 0 | 42 | 10 | 81 | 0 |
| 140 | − | 0 | 0 | 33 | 14 | 70 | 0 |
| 145 | − | 0 | 0 | 48 | 19 | 72 | 0 |
| 151 | − | 0 | 0 | 33 | 11 | 75 | 0 |
| 153 | − | 0 | 0 | 32 | 18 | 64 | 0 |

TABLE 5-continued

Visual determination of parthenogenesis in cleared ovaries 2 days after anthesis in offspring from g3f.

| Offspring Designation: | Genotype-ORF amplicon: | Number of identified developing embryos with polar nuclei in structurally mature sexual embryo sacs | Number of identified developing embryos without distinct polar nuclei but also without endosperm development | Number of structurally mature sexual embryo sacs without embryo development | Number of ovaries with no structurally mature sexual embryo sacs | Percentage of structurally mature sexual embryo sacs | Percentage of parthenogenesis in structurally mature sexual embryo sacs |
|---|---|---|---|---|---|---|---|
| 154 | − | 0 | 0 | 27 | 15 | 64 | 0 |
| 161 | − | 0 | 0 | 30 | 16 | 65 | 0 |
| 163 | − | 0 | 0 | 25 | 17 | 60 | 0 |
| 167 | − | 0 | 0 | 27 | 18 | 60 | 0 |
| 168 | − | 0 | 0 | 25 | 17 | 60 | 0 |
| 178 | − | 0 | 0 | 38 | 6 | 86 | 0 |
| 188 | − | 0 | 0 | 41 | 5 | 89 | 0 |
| Total numbers analyzed without the gPsASGR-BBM ORF | | 28 | 0 | 0 | 951 | 392 | 71 | 0 |
| 100† | + | 5 | 2 | 28 | 22 | 61 | 20 |
| 101† | + | 5 | 4 | 8 | 24 | 41 | 53 |
| 104 | + | 16 | 0 | 22 | 15 | 72 | 42 |
| 105*† | + | 20 | 0 | 30 | 23 | 68 | 40 |
| 106† | + | 6 | 1 | 16 | 23 | 50 | 30 |
| 108 | + | 6 | 0 | 28 | 12 | 74 | 18 |
| 117 | + | 4 | 0 | 29 | 18 | 65 | 12 |
| 122 | + | 9 | 2 | 26 | 13 | 74 | 30 |
| 131 | + | 8 | 0 | 20 | 16 | 64 | 29 |
| 142 | + | 5 | 0 | 23 | 29 | 49 | 18 |
| 146 | + | 11 | 2 | 18 | 14 | 69 | 42 |
| 147 | + | 8 | 2 | 21 | 17 | 65 | 32 |
| 152 | + | 6 | 3 | 27 | 14 | 72 | 25 |
| 158* | + | 1 | 0 | 84 | 67 | 56 | 1 |
| 160 | + | 7 | 0 | 24 | 16 | 66 | 23 |
| 189 | + | 3 | 0 | 31 | 15 | 69 | 9 |
| 196 | + | 7 | 2 | 23 | 14 | 70 | 28 |
| 197 | + | 9 | 7 | 15 | 21 | 60 | 52 |
| 208* | + | 5 | 1 | 74 | 23 | 78 | 8 |
| 123*, 0 | + | 0 | 0 | 79 | 30 | 72 | 0 |
| 144*, 0 | + | 0 | 0 | 118 | 29 | 80 | 0 |
| 159*, 0 | + | 0 | 0 | 82 | 53 | 61 | 0 |
| 183*, 0 | + | 0 | 0 | 77 | 22 | 78 | 0 |
| 102 | + | N/A | N/A | N/A | N/A | N/A | N/A |
| 103 | + | N/A | N/A | N/A | N/A | N/A | N/A |
| 191 | + | N/A | N/A | N/A | N/A | N/A | N/A |
| Total numbers analyzed with the gPsASGR-BBM ORF | | 26 | 122 | 26 | 903 | 530 | 66 | 14 |

N/A = plant did not flower or ovaries collected did not contain >15 structurally mature sexual embryo sacs out of ~50 processed.
*data combined from two independently collected heads.
0plants with the gASGR-BBM transgene not showing expected parthenogenesis.
†plants with 2× ploidy level.

TABLE 6

Ploidy level of g3f offspring with green pigmentation of the midrib determined either by flow cytometry or chromosomal counts from root tips.

| Offspring designation | Ploidy level | transgene | Offspring designation | Ploidy level | transgene | Offspring designation | Ploidy level | transgene | Offspring designation | Ploidy level | transgene |
|---|---|---|---|---|---|---|---|---|---|---|---|
| 100 | 2x | + | 115 | 4x* | − | 102 | 2x | + | 127 | 4x | − |
| 101 | 2x | + | 118 | 4x* | − | 103 | 2x | + | 128 | 4x* | − |

TABLE 6-continued

Ploidy level of g3f offspring with green pigmentation of the midrib determined either by flow cytometry or chromosomal counts from root tips.

| Offspring designation | Ploidy level | transgene | Offspring designation | Ploidy level | transgene |
|---|---|---|---|---|---|
| 105 | 2x | + | 133 | 4x* | − |
| 106 | 2x | + | 139 | 4x* | − |
| 108 | 4x | + | 140 | 4x* | − |
| 117 | 4x* | + | 143 | 4x* | − |
| 122 | 4x* | + | 145 | 4x* | − |
| 142 | 4x* | + | 151 | N/A | − |
| 146 | 4x* | + | 153 | 4x | − |
| 147 | 4x* | + | 154 | 4x | − |
| 158 | 4x* | + | 161 | 4x | − |
| 159 | 4x | + | 167 | 4x | − |
| 160 | 4x | + | 178 | 4x | − |
| 183 | 4x* | + | 193 | 4x | − |
| 191 | 4x* | + | 198 | 4x* | − |
| 196 | 4x* | + | 201 | 4x* | − |
| 197 | 4x* | + | | | |

*Ploidy level determined by chromosomal root-tip counts.

TABLE 7

Analysis of PsASGR-BBML expression and embryo development from selected $F_1$ RNAi plants.

| Plant designation | Plant genotype | % of ovaries containing aposporous embryo sacs | % reduction of PsASGR-BBML at DOP based on control plant on day of anthesis | % of ovules producing parthenogenetic embryos at +2 DOP | % of embryos greater than 16 cells at +2 DOP from ovaries showing parthenogenesis |
|---|---|---|---|---|---|
| S7-6T-10 (control) | ASGR+ RNAi− | 97.1 | 0 | 64.4 | 38 |
| S4-2T-8 | ASGR+ RNAi+ | 96.4 | 59.87 | 24.6 | 5.6 |
| S2-2T-9 | ASGR+ RNAi+ | 96.3 | 88.84 | 23.7 | 0 |
| S5-5T-28 | ASGR+ RNAi+ | 97.0 | 95.90 | 8.5 | 0 |

Example 6 gPsASGR-BBML-Containing Transgenic Rice Lines

The genomic PsASGR-BBM construct used in pearl millet transformation, which included A 2074 bp ASGR-BBM promoter (p208) (containing a 6-residue GGATCC BamHI restriction site sequence) upstream of the 3,540 bp coding region (exon:introns) plus 610 bp of the 3'UTR and residing in a blue script plasmid, was transferred using enzymes at the multiple cloning site to pCambia1300 for transformation of rice (Oryza sativa Japonica cv. Nipponbare). Sixteen different rice lines were found to contain the complete coding region of the PsASGR-BBM construct based on PCR analysis. RNA was isolated from four different lines of developing rice seed, and expression of the PsASGR-BBM transgene was assayed by non-quantitative RT-PCR. All four lines showed PsASGR-BBM transgene expression. Flow cytometry using ~5 dissected developing rice embryos was used to determine whether haploid (1n/1c) offspring were generated from rice transgenic lines carrying the PsASGR-BBM transgene (FIG. 19). Sorghum was used as a control for samples. Eight lines showed production of haploid offspring based on this analysis.

Example 7

Haploid Induction in Maize and Other Crops

The present invention can be used as an alternative method for haploid induction in maize and other cereals. Specific lines of maize have been identified that, when used as pollinators, result in a low (2-8%) frequency recovery of haploid offspring from seed of the maternal parent (Chang M. and Coe E. H., "Doubled haploids," pp 127-142, in *Molecular Genetic Approaches to Maize Improvement*, Kritz A. L. and Larkins B, Eds, Springer). These lines are extensively used in commercial maize breeding programs in North America and Europe.

The advantage of haploid induction in breeding is that different gene combinations can be fixed in each line once the chromosome number is doubled from haploid to diploid. This rapid recovery of homozygous inbred lines allows selection of inbred parents that can generate high-yielding, high-quality hybrids. Multiple inducer lines of maize have been identified, and the mechanism of haploid induction reported for at least one of them is chromosome elimination (Zhang Z. et al., *Plant Cell Reports* 27:1851-1860 (2008)). Chromosome elimination post-fertilization is more likely to result in male contribution to haploid offspring than the invention described herein, where fertilization of the egg is avoided.

Haploid induction using the present invention can be of use in crops other than maize where inducer lines are not known. Any heterozygous individual will generate unique gene combinations in each egg if eggs are being formed from meiotically-derived products and are haploid. Each unique haploid individual will become homozygous and fertile once chromosomes are artificially doubled by chemical treatment. Homozygous lines can be more quickly generated by the method described herein for testing in the field.

Example 8

Expression of ASGR-BBML to Induce Egg Division in Absence of Fertilization

A further use of this invention is as a component of apomixis. Both apomeiosis and parthenogenesis are required for functional gametophytic apomixis. Apomeiosis can be achieved by a combination of mutations affecting meiosis (Crismani W. et al., *J. Exp. Bot.* 64:55-65 (2013)), with the outcome of chromosomal non-reduction in megaspores, i.e., mitosis rather than meiosis. Somatic cells that assume a gametophytic fate through epigenetic alterations (Grimanelli D., *Curr. Opin. Plant Biol.* 15:57-62 (2012)) also result in unreduced spore-like cells that potentially can give rise to unreduced gametes (eggs). By whatever means unreduced eggs are formed, proper temporal and spatial expression of ASGR-BBML can induce the egg cells to behave as zygotes and divide in the absence of fertilization. The division of an unreduced egg to form the embryo component of a seed satisfies the conditions for apomixis provided that the endosperm of the seed can also complete development to yield a viable propagule.

Example 9

Use of Apomixis for Efficient Seed Production

Apomixis results in genetic identity of the offspring of a mother plant. The mother plant can be highly heterozygous, but since apomixis bypasses meiosis, there is no segregation of traits among seed-derived progeny. Apomixis can be used for more efficient hybrid seed production in hybrid crops, such as maize and the like, eliminating the need to use separate male and female parents grown in isolation to generate hybrid seed. Apomixis can also be used for seed propagation of heterozygous crops, such as potato and the like, that typically are vegetatively propagated through tubers, organs that can harbor and transmit diseases across generations. Apomixis can also promote the development of hybrids in crops where hybrids currently are not available due to the lack of parental lines that can be easily crossed on a commercial scale. Apomixis can be used as a breeding tool to increase and test large numbers of novel hybrids generated by sexual reproduction, but increased through apomictic reproduction. The present invention, egg development into an embryo without fertilization, is an essential component of apomixis or clonal reproduction through seeds.

The various methods and techniques described above provide a number of ways to carry out the application. Of course, it is to be understood that not necessarily all objectives or advantages described can be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as taught or suggested herein. A variety of alternatives are mentioned herein. It is to be understood that some preferred embodiments specifically include one, another, or several features, while others specifically exclude one, another, or several features, while still others mitigate a particular feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be employed in various combinations by one of ordinary skill in this art to perform methods in accordance with the principles described herein. Among the various elements, features, and steps some will be specifically included and others specifically excluded in diverse embodiments.

Although the application has been disclosed in the context of certain embodiments and examples, it will be understood by those skilled in the art that the embodiments of the application extend beyond the specifically disclosed embodiments to other alternative embodiments and/or uses and modifications and equivalents thereof.

In some embodiments, the numbers expressing quantities of ingredients, properties such as molecular weight, reaction conditions, and so forth, used to describe and claim certain embodiments of the application are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

In some embodiments, the terms "a" and "an" and "the" and similar references used in the context of describing a particular embodiment of the application (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (for example, "such as") provided with respect to certain embodiments herein is intended merely to better illuminate the application and does not pose a limitation on the scope of the application otherwise claimed. No language in the specification should be construed as indicating any non-claimed element essential to the practice of the application.

Preferred embodiments of this application are described herein, including the best mode known to the inventors for carrying out the application. Variations on those preferred embodiments will become apparent to those of ordinary skill in the art upon reading the foregoing description. It is contemplated that skilled artisans can employ such variations as appropriate, and the application can be practiced otherwise than specifically described herein. Accordingly, many embodiments of this application include all modifications and equivalents of the subject matter recited in the claims appended hereto as permitted by applicable law. Moreover, any combination of the above-described elements in all possible variations thereof is encompassed by the application unless otherwise indicated herein or otherwise clearly contradicted by context.

All patents, patent applications, publications of patent applications, and other material, such as articles, books, specifications, publications, documents, things, and/or the like, referenced herein are hereby incorporated herein by this reference in their entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that can be employed can be within the scope of the application. Thus, by way of example, but not of limitation, alternative configurations of the embodiments of the application can be utilized in accordance with the teachings herein. Accordingly, embodiments of the present application are not limited to that precisely as shown and described.

What is claimed is:

1. A method of propagating from one or more gametophytic or sporophytic cells in an ovule of a plant in the absence of egg cell fertilization, the method comprising:

transforming a plant with an ASGR-BBML gene construct comprising a nucleic acid encoding a polypeptide having at least 95% sequence identity to the polypeptide of SEQ ID NO: 4, wherein the nucleic acid is operably linked to a promoter; and growing and selecting a progeny plant from the one or more gametophytic or sporophytic cells, wherein the progeny plant contains one or more sets of chromosomes from the transformed plant, and wherein propagation of the plant occurs in the absence of egg cell fertilization.

2. The method of claim 1, wherein the embryo is formed from an unreduced egg.

3. The method of claim 1, wherein the embryo is formed from a reduced egg.

4. The method of claim 1, wherein the embryo is formed from a somatic cell.

5. The method of claim 1 in which a polyploid plant is transformed to produce a diploid or dihaploid progeny plant.

6. The method of claim 1, in which a diploid plant is transformed to produce a haploid progeny plant.

7. The method of claim 6, in which the haploid progeny plant is treated to achieve chromosome doubling and production of a homozygous plant.

8. The method of claim 1, wherein the progeny plant is obtained via culturing.

9. The method of claim 1, wherein the plant is a monocot.

10. The method of claim 1, wherein the plant is a dicot.

11. The method of claim 1, wherein the plant comprises a grass or a leguminous plant.

12. The method of claim 11, wherein the grass is a species of millet, rice, maize, wheat, sorghum, or switchgrass.

13. The method of claim 1, wherein the plant is heterozygous and is transformed to produce a haploid offspring.

14. The method of claim 1, wherein the method is used to propagate one or more heritable traits in the plant.

15. A plant or plant part produced by the method of claim 1, wherein the plant or plant part comprises said gene construct.

16. A method of producing seed of a plant in the absence of egg cell fertilization, the method comprising:

transforming a plant with an ASGR-BBML gene construct comprising a nucleic acid encoding a polypeptide having at least 95% sequence identity to the polypeptide of SEQ ID NO:4 wherein the nucleic acid is operably linked to a promoter; and growing the transformed plant so as to produce seed and selecting seed from said plant that comprise the gene construct, wherein said seed is produced in the absence of egg cell fertilization and, wherein the seed contains one or more sets of chromosomes from the transformed plant.

17. A seed produced by the method of claim 16, wherein the seed comprises said gene construct.

* * * * *

SEQUENCE LISTING

```
<160> NUMBER OF SEQ ID NOS: 69

<210> SEQ ID NO 1
<211> LENGTH: 1968
<212> TYPE: DNA
<213> ORGANISM: Pennisetum squamulatum

<400> SEQUENCE: 1
tctctctctc ttctctctct ccatttctct tccctaggat cagtgctagt gcttgcagcg      60
gccgcgttcc gagatgggtt ccaccaacaa ctggctgcgc ttcgcctcgt tctccggcgg     120
cggcggcgcc aaggatgccg cggccctgct cccgctgccg ccctcgcccc gtggcgatgt     180
cgacgaggcc ggcgcagagc cgaagctcga ggacttcctc ggcctgcagg agccgagcgc     240
cgccgcggtg ggggctgggc ggccattcgc ggtgggtggc ggtgcgagct ccatcgggct     300
gtccatgatc aggaactggc tgcgcagcca gccggcgccg gccgggcctg ctgcgggggt     360
cgattcgatg gtgctggcgg ctgcggcggc gtcgacggag gtggccggcg atggcgcgga     420
gggcggcggc gccgtggctg acgcggtgca gcagaggaag gcggcggcgg tggacacttt     480
cgggcagcgg acctccatat accgcggcgt cacaaagcat agatggacag gaaggtatga     540
agcccatctt tgggacaata gctgcagaag agaaggtcaa actcggaaag gtagacaagt     600
gtatcttggt ggatatgata aagaagaaaa agcagctaga gcttatgatt tagctgctct     660
caagtaccgg ggcaccacaa ctactacaaa ttttccgatg agcaactatg aaaaggagtt     720
agaagagatg aagcatatgt cacgacaaga atatgttgca tcccttagaa ggaaaagcag     780
tggtttttct cgtggtgcat caatttaccg aggggttacc aggcaccatc agcatggaag     840
gtggcaagca agaataggaa gtgtggcagg aaacaaggat ctttatttgg gcacattcag     900
tacccaggag gaagctgcag aggcttacga cattgctgcc atcaaattcc gaggcctcaa     960
tgctgtcacg aactttgaca tgagccggta tgacgtcaag agcatcattg agagcagctc    1020
cctgcctgtt ggcggcactc caaagcgtct caaggaagtg cctgatcaat cagatatggg    1080
catcaacata aacggtgact ctgctggtca tatgactgct atcaaccttc ttactgatgg    1140
caatgacagc tatggagctg agagttatgg ttacagtggt tggtgtccca cagccatgac    1200
gccaatcccc tttcaattca gcaatggcca tgaccattcc aggctgtggt gcaagccaga    1260
gcaggacaat gcggttgttg cagcactgca taacctgcat cacctccagc acttgccagc    1320
cccagttggc acccataatt ttttccagcc atcgcctgtt caggacatga caggtgttgc    1380
cgatgcttca tcgccaccag tagaatctaa ttcattcctg tacaatgggg acgttggtta    1440
ccatggtgcc atgggtggca gctatgccat gccggttgcc acactagttg agggcaactc    1500
tgcgggcagt ggctatggag ttgaggaagg cacagggtct gaaatctttg gtggacgaa     1560 cttgtattct ctctcccaag gttcctcagg cgccaatact ggaaaggcag atgcttatga    1620
```

```
aagctgggat ccatctatgc tggtgatatc acagaagtct gccaatgtga ctgtctgcca   1680
tggcgcacct gtattttcag tttggaaatg atggttagat gaaaatatag tagtgatatt   1740
aactagttct tggaggggaa gattaaattc taggtataca aaagtttaat ttattagtgc   1800
ttcaagatct cgtatgaaaa aaagttttgc tgcttaatca gctccagtgg gagtctagga   1860
gccatgagaa atgtcgtttt attattgact aatgctacaa tgctaacatg ctgactcttt   1920
tgaatggcac aagagctctg gtgtttcaat acatcagcca gtttcatt                1968

<210> SEQ ID NO 2
<211> LENGTH: 1638
<212> TYPE: DNA
<213> ORGANISM: Pennisetum squamulatum

<400> SEQUENCE: 2
atgggttcca ccaacaactg ctgcgcttc gcctcgttct ccggcggcgg cggcgccaag      60
gatgccgcgg ccctgctccc gctgccgccc tcgccccgtg cgatgtcga cgaggccggc    120 gcagagccga agctcgagga cttcctcggc ctgcaggagc cgagcgccgc cgcggtgggg    180
gctgggcggc cattcgcggt gggtggcggt gcgagctcca tcgggctgtc catgatcagg    240
aactggctgc gcagccagcc ggcgccggcc gggcctgctg cggggtcga ttcgatggtg     300 ctggcggctg cggcggcgtc gacggaggtg gccggcgatg gcgcggaggg cggcggcgcc    360
gtggctgacg cggtgcagca gaggaaggcg gcggcggtgg acactttcgg gcagcggacc    420
tccatatacc gcggcgtcac aaagcataga tggacaggaa ggtatgaagc ccatctttgg    480
gacaatagct gcagaagaga aggtcaaact cggaaaggta gacaagtgta tcttggtgga    540
tatgataaag aagaaaaagc agctagagct tatgatttag ctgctctcaa gtaccggggc    600
accacaacta ctacaaattt tccgatgagc aactatgaaa aggagttaga agagatgaag    660
catatgtcac gacaagaata tgttgcatcc cttagaagga aaagcagtgg ttttttctcgt   720 ggtgcatcaa tttaccgagg ggttaccagg caccatcagc atggaaggtg gcaagcaaga    780
ataggaagtg tggcaggaaa caaggatctt tatttgggca cattcagtac ccaggaggaa    840
gctgcagagg cttacgacat tgctgccatc aaattccgag gcctcaatgc tgtcacgaac    900
tttgacatga gccggtatga cgtcaagagc atcattgaga gcagctccct gcctgttggc    960
ggcactccaa agcgtctcaa ggaagtgcct gatcaatcag atatgggcat caacataaac   1020
ggtgactctg ctggtcatat gactgctatc aaccttctta ctgatggcaa tgacagctat   1080
ggagctgaga gttatggtta cagtggttgg tgtcccacag ccatgacgcc aatccccttt   1140
caattcagca atggccatga ccattccagg ctgtggtgca agccagagca ggacaatgcg   1200
gttgttgcag cactgcataa cctgcatcac ctccagcact tgccagcccc agttggcacc   1260
cataattttt tccagccatc gcctgttcag gacatgacag gtgttgccga tgcttcatcg   1320
ccaccagtag aatctaattc attcctgtac aatgggacg ttggttacca tggtgccatg     1380
ggtggcagct atgccatgcc ggttgccaca ctagttgagg gcaactctgc gggcagtggc    1440
tatggagttg aggaaggcac agggtctgaa atctttggtg gacggaactt gtattctctc    1500
tcccaaggtt cctcaggcgc caatactgga aaggcagatg cttatgaaag ctgggatcca    1560
tctatgctgg tgatatcaca gaagtctgcc aatgtgactg tctgccatgg cgcacctgta   1620
ttttcagttt ggaaatga                                                 1638

<210> SEQ ID NO 3
```

<211> LENGTH: 6210
<212> TYPE: DNA
<213> ORGANISM: Pennisetum squamulatum

<400> SEQUENCE: 3

| | | | | | |
|---|---|---|---|---|---|
| ggatccagcc | atgtctaaac | gatcaacaga | tgactgccta | atataaggtt | tttgggttgt | 60 |
| tgaataatta | ggcaatatcc | atattagatt | ccgaaagcag | taaaacatga | caatgatagt | 120 |
| aactagtatg | cacgcataag | acatactaga | cgatagtaac | aacataacca | tgaactcagt | 180 |
| aaacatgact | aaagattgga | tcttagatcc | gtacctggcg | ctcagagttg | caagcactgc | 240 |
| ggagggcgtc | gatacttcgg | ggaagacaag | cggcgcagac | gaagcgacga | cggtgttccg | 300 |
| gacggcacgt | agcagccgac | attgaaggca | atgcgccctc | tcgtcaggag | acttgctagg | 360 |
| aagacgagcc | acgatgacga | cgattgagca | gtcacgcgga | gcacttccca | aaaaccttat | 420 |
| tcgccctctc | ccggtgcagg | atcgcaagga | cggacggttc | cggagacctg | ctctcccaat | 480 |
| cacctgtgca | cgcaggtgtt | cgggatggag | tagatggcgg | cggcggcggc | gcagcagcga | 540 |
| gcgagagagg | caaagtccta | actcagatca | gatctatttt | agggataccc | tttcatgggg | 600 |
| cctttccgta | gatagtctat | tgtgcatctc | ttctgtgagg | gggtggtcca | tttttatatg | 660 |
| gagggaaacc | tccaacaccc | tcgtctatta | gcaaatatga | actaatagat | ggtgtacccc | 720 |
| ctcatcacgc | taatgggcct | ttgagattta | ttcaggaatt | attggattgg | ctaatgggcc | 780 |
| aagcccaaaa | ttccaacaca | atcaagtttg | cctcgcatat | ctcgattctc | gaaccaacct | 840 |
| ccgagccata | tctgattgta | gacaagtaaa | caaactcgga | ggcggaaggg | ggaactgacc | 900 |
| cgttgaacgc | cgtcactgcc | ggaaccgacg | tcgccgtcac | tgaagaagaa | ggaagatgct | 960 |
| tccgaaccac | ccaatacaaa | acctcactaa | ttcctcgctg | acgccagagc | agacgccgac | 1020 |
| gaaacgggaa | aggagtcaaa | ataccttatt | ccatcgccac | cacatcattt | gggcgctgct | 1080 |
| cgctgatacg | ccggcgggag | cggtggcagc | caggtgtacg | ccccgcgga | ctgcgcgccg | 1140 |
| gctggccggc | cggccaccgg | ggccggggcc | cttcaatctc | ttagggcgtc | cccaacaagg | 1200 |
| ctgattcagc | tagctatttg | agtgtacaca | tcagcatgta | tcctacatgg | aggaaagaga | 1260 |
| gtatgcattg | aacattgagc | cggctatttg | ctcgtcgcct | atctagcaca | tcacccaagg | 1320 |
| cagcgctgtg | tctatggcct | ggcagaaaat | attgtttaaa | taacaagtag | ccagctttag | 1380 |
| tagatagtac | tttctcttgc | tggctttttt | tttttttgat | aacagctctt | gctggctttt | 1440 |
| agcgtgccgg | ctccgagcta | ctccctctgt | cccagaattt | gagtcgccgg | ccaacagtga | 1500 |
| aatgagagag | gggcacggag | tcccaacgac | agtaatattg | ggacagggag | tagcagctat | 1560 |
| ccaggactgc | tgtagacgcc | cttagtcctc | gactcctcgc | agcctttcgc | cgttgaaaga | 1620 |
| atcacaccgc | cccctgcagt | tacgtgttaa | cccaacccgg | gccattggtc | agtccctaac | 1680 |
| ccgggcggtt | gaccgctaga | aattagaatt | aacccttggt | taacaccggt | caaagcgcac | 1740 |
| atatgcggtg | caatctaatc | gaagtggccg | cgtcataatt | acacacgccc | gctcctatac | 1800 |
| gtgtgccccg | ttcatacgca | tgctcacctc | gcgcgttccc | atgaggtttc | acacccttg | 1860 |
| tgggaatcca | aggcgtcaga | gatttattga | tcccatttcc | ctagcctgcc | tcgcctctct | 1920 |
| atctacttgt | gtggagatta | gagcacagca | gcgagaaagg | gcttcagtc | tataaaggcg | 1980 |
| acaagagccc | acaccctcct | ctctctctct | cttctctctc | tccatttctc | ttccctagga | 2040 |
| tcagtgctag | tgcttgcagc | ggccgcgttc | cgagatgggt | tccaccaaca | actggctgcg | 2100 |
| cttcgcctcg | ttctccggcg | gcggcggcgc | caaggatgcc | gcggccctgc | tcccgctgcc | 2160 |
| gccctcgccc | cgtggcgatg | tcgacgaggc | cggcgcagag | ccgaagctcg | aggacttcct | 2220 |

```
cggcctgcag gagccgagcg ccgccgcggt gggggctggg cggccattcg cggtgggtgg    2280
cggtgcgagc tccatcgggc tgtccatgat caggaactgg ctgcgcagcc agccggcgcc    2340
ggccgggcct gctgcggggg tcgattcgat ggtgctggcg gctgcggcgg cgtcgacgga    2400
ggtggccggc gatggcgcgg agggcggcgg cgccgtggct gacgcggtgc agcagaggaa    2460
ggcggcggcg gtggacactt tcgggcagcg gacctccata taccgcggcg tcacaaagta    2520
ggttcttgat tttattttgg ttttggaaaa attcttcttt gttttttctg ttttcttccg    2580
actggtatat cttgtgttaa gaactttttc attagatgca tgtcatactg ttgcttttc     2640 ttgttgcttt gaacctttg gcgtttgcag cttcgtttgg atatacagaa cctatattat     2700
cccctttagt aaccagtaga ttcttttttt ttctttttt tttttgctt tcgatgttgt      2760 tagtgttctt gcatcacgca tgttttcct ctgatatttt aatggacgat atcatctcta     2820
gttcaagttt ttgctcttgc tcttgttgta gtggtgctaa gattttaaa aaaaaaatt     2880 atgagcagtt cttgtgctgt ttgaaaatgt aagcatctca cagttctaaa atatatatat    2940
atatatatat ataagtctct catgttgatt tgtggatgta ctgaagcccc gcgcgcacac    3000
atgcacacac cgcacgctca cacgccctaa atccccggtg caacaccagg gttgtccccg    3060
atggggatcg aaccctggcg ggtggcctaa ccaccgtcag ctcccaccac cgagctatca    3120
gctcgtttgc ccatatttcg tgtggtacct cgatatttt atatttctag attgctgtat    3180
ctatcttcta gacttatata agtgttgcgc cactcatact ttttaccgcc tgtaatcgag    3240
tagaactgct tcctcttttg attatattgt atcagttaaa tgatcttgtt gttgatgtgt    3300
ttaccacttt accatcacca ttgcatgaaa tcacttcaag acatgtattc atgatttggc    3360
tggctaaatt tgctagtggc acatacatgt ggtaaaaaa tatttttagt ttgtgcttgc    3420 tattctttc ggtcatccct tcgtgcctgt ttatccagaa cacccaatct gcttcacata    3480
gtttttgaat gctatcatca tatttctttt ttggagatat tgttactaaa agtttggctt    3540
tgtcctcaat aggcatagat ggacaggaag gtatgaagcc catctttggg acaatagctg    3600
cagaagagaa ggtcaaactc ggaaaggtag acaaggtaat gattataata tagatattta    3660
aatttgtaat tataagctgc atcatattat tatttattag atcggcttta aaatttcact    3720
agctaattta gtgttttct tttcttcatc gatacctgca atcgcttcat tccattgatt     3780
cagtgtatct tggtaagtaa tacttgttta caattgcaaa atggtatatc tcttgttgtt    3840
tctcatgtca agtatattaa atatgtggtt gatgcattga aggtggatat gataaagaag    3900
aaaaagcagc tagagcttat gatttagctg ctctcaagta ccggggcacc acaactacta    3960
caaattttcc ggtattactt attgttaata tgttggttct ccagaattga tattttactt    4020
ctaatatata actgcgtata tgaatgaatg ttgtaagatt ttgcattta tgttcagatg     4080 agcaactatg aaaaggagtt agaagagatg aagcatatgt cacgacaaga atatgttgca    4140
tcccttagaa ggtacatgtg ttgtcaaaac tttgtacctt catggaaact gaacttatat    4200
atttcacaaa tggattgaca tagaacatat atttgtgata caggaaaagc agtggttttt    4260
ctcgtggtgc atcaatttac cgagggggtta ccaggtacaa aatattcctt ttccttatta   4320
tctctggttt tagttagcaa gtgcattgtt tctatgggaa tttgtgttgc atgtagatgg    4380
gaatttgtgt tgcatgtaga tcataaatag ttgcaactat taatctcatc gttctattgc    4440
tgaatagttg tggtactcct ttaccacagt tgactatgat attctattat attatttttc    4500
ttgcaaagtt gatatttaat tgcttgtcta gctaactttc aagcaatcat gtaaaacagg    4560
```

| | |
|---|---|
| caccatcagc atggaaggtg gcaagcaaga ataggaagtg tggcaggaaa caaggatctt | 4620 |
| tatttgggca cattcagtaa gtcacatttt aatatttta atgaagcact gattttttt | 4680 |
| tgtcaagcaa aatggaagca agacagaaaa acataaacct actggagcac cttttttcatt | 4740 |
| attttgtctc ttgaatataa tagtatgtgg ctgacctctc cctgtgtagg tacccaggag | 4800 |
| gaagctgcag aggcttacga cattgctgcc atcaaattcc gaggcctcaa tgctgtcacg | 4860 |
| aactttgaca tgagccggta tgacgtcaag agcatcattg agagcagctc cctgcctgtt | 4920 |
| ggcggcactc caaagcgtct caaggaagtg cctgatcaat cagatatggg catcaacata | 4980 |
| aacggtgact ctgctggtca tatgactgct atcaaccttc ttactgatgg caatgacagc | 5040 |
| tatggagctg agagttatgg ttacagtggt tggtgtccca cagccatgac gccaatcccc | 5100 |
| tttcaattca gcaatggcca tgaccattcc aggctgtggt gcaagccaga gcaggacaat | 5160 |
| gcggttgttg cagcactgca taacctgcat cacctccagc acttgccagc cccagttggc | 5220 |
| acccataatt ttttccagcc atcgcctgtt caggacatga caggtgttgc cgatgcttca | 5280 |
| tcgccaccag tagaatctaa ttcattcctg tacaatgggg acgttggtta ccatggtgcc | 5340 |
| atgggtggca gctatgccat gccggttgcc acactagttg agggcaactc tgcgggcagt | 5400 |
| ggctatggag ttgaggaagg cacagggtct gaaatctttg gtggacggaa cttgtattct | 5460 |
| ctctcccaag gttcctcagg cgccaatact ggaaaggcag atgcttatga agctgggat | 5520 |
| ccatctatgc tggtgatatc acagaagtct gccaatgtga ctgtctgcca tggcgcacct | 5580 |
| gtattttcag tttggaaatg atggttagat gaaaatatag tagtgatatt aactagttct | 5640 |
| tggagggga gattaaattc taggtataca aagtttaat ttattagtgc ttcaagatct | 5700 |
| cgtatgaaaa aagttttgc tgcttaatca gctccagtgg gagtctagga gccatgagaa | 5760 |
| atgtcgtttt attattgact aatgctacaa tgctaacatg ctgactcttt tgaatggcac | 5820 |
| aagagctctg gtgtttcaat acatcagcca gtttcattat tgtccatttg ctgtgcacat | 5880 |
| tttctgcgct ggcacctata ataatatgat tctaaactgt gaattagttc agatgtcaac | 5940 |
| tgtaagtaac tttatttag ctttcttata tacatctctt tttctttttg agaaacgggc | 6000 |
| tttgcccca gccttcatag gaggctggtg cagcgtaccg ggtccgaacc tgggctggtg | 6060 |
| acgtcctcag catgagcgcc caccaccgag ctacacgctc gtctgctctt atatacatct | 6120 |
| cttcagtaag ggtaatatgg tacttcacag ttcacagtcc agtcattcca accatggatg | 6180 |
| agcaaaatgt gcttgtgcac atggtgggtc | 6210 |

<210> SEQ ID NO 4
<211> LENGTH: 545
<212> TYPE: PRT
<213> ORGANISM: Pennisetum squamulatum

<400> SEQUENCE: 4

Met Gly Ser Thr Asn Asn Trp Leu Arg Phe Ala Ser Phe Ser Gly Gly
1               5                   10                  15

Gly Gly Ala Lys Asp Ala Ala Ala Leu Leu Pro Leu Pro Pro Ser Pro
            20                  25                  30

Arg Gly Asp Val Asp Glu Ala Gly Ala Glu Pro Lys Leu Glu Asp Phe
        35                  40                  45

Leu Gly Leu Gln Glu Pro Ser Ala Ala Val Gly Ala Gly Arg Pro
    50                  55                  60

Phe Ala Val Gly Gly Gly Ala Ser Ser Ile Gly Leu Ser Met Ile Arg
65                  70                  75                  80

```
Asn Trp Leu Arg Ser Gln Pro Ala Pro Ala Gly Pro Ala Ala Gly Val
                85                  90                  95

Asp Ser Met Val Leu Ala Ala Ala Ala Ser Thr Glu Val Ala Gly
            100                 105                 110

Asp Gly Ala Glu Gly Gly Ala Val Ala Asp Ala Val Gln Gln Arg
            115                 120                 125

Lys Ala Ala Ala Val Asp Thr Phe Gly Gln Arg Thr Ser Ile Tyr Arg
130                 135                 140

Gly Val Thr Lys His Arg Trp Thr Gly Arg Tyr Glu Ala His Leu Trp
145                 150                 155                 160

Asp Asn Ser Cys Arg Arg Glu Gly Gln Thr Arg Lys Gly Arg Gln Val
                165                 170                 175

Tyr Leu Gly Gly Tyr Asp Lys Glu Glu Lys Ala Ala Arg Ala Tyr Asp
            180                 185                 190

Leu Ala Ala Leu Lys Tyr Arg Gly Thr Thr Thr Thr Asn Phe Pro
            195                 200                 205

Met Ser Asn Tyr Glu Lys Glu Leu Glu Glu Met Lys His Met Ser Arg
210                 215                 220

Gln Glu Tyr Val Ala Ser Leu Arg Arg Lys Ser Ser Gly Phe Ser Arg
225                 230                 235                 240

Gly Ala Ser Ile Tyr Arg Gly Val Thr Arg His His Gln His Gly Arg
                245                 250                 255

Trp Gln Ala Arg Ile Gly Ser Val Ala Gly Asn Lys Asp Leu Tyr Leu
                260                 265                 270

Gly Thr Phe Ser Thr Gln Glu Glu Ala Ala Glu Ala Tyr Asp Ile Ala
            275                 280                 285

Ala Ile Lys Phe Arg Gly Leu Asn Ala Val Thr Asn Phe Asp Met Ser
290                 295                 300

Arg Tyr Asp Val Lys Ser Ile Ile Glu Ser Ser Ser Leu Pro Val Gly
305                 310                 315                 320

Gly Thr Pro Lys Arg Leu Lys Glu Val Pro Asp Gln Ser Asp Met Gly
                325                 330                 335

Ile Asn Ile Asn Gly Asp Ser Ala Gly His Met Thr Ala Ile Asn Leu
                340                 345                 350

Leu Thr Asp Gly Asn Asp Ser Tyr Gly Ala Glu Ser Tyr Gly Tyr Ser
            355                 360                 365

Gly Trp Cys Pro Thr Ala Met Thr Pro Ile Pro Phe Gln Phe Ser Asn
            370                 375                 380

Gly His Asp His Ser Arg Leu Trp Cys Lys Pro Glu Gln Asp Asn Ala
385                 390                 395                 400

Val Val Ala Ala Leu His Asn Leu His His Leu Gln His Leu Pro Ala
                405                 410                 415

Pro Val Gly Thr His Asn Phe Phe Gln Pro Ser Pro Val Gln Asp Met
            420                 425                 430

Thr Gly Val Ala Asp Ala Ser Ser Pro Pro Val Glu Ser Asn Ser Phe
            435                 440                 445

Leu Tyr Asn Gly Asp Val Gly Tyr His Gly Ala Met Gly Gly Ser Tyr
450                 455                 460

Ala Met Pro Val Ala Thr Leu Val Glu Gly Asn Ser Ala Gly Ser Gly
465                 470                 475                 480

Tyr Gly Val Glu Glu Gly Thr Gly Ser Glu Ile Phe Gly Gly Arg Asn
                485                 490                 495

Leu Tyr Ser Leu Ser Gln Gly Ser Ser Gly Ala Asn Thr Gly Lys Ala
```

|     |     |     | 500 |     |     |     | 505 |     |     |     | 510 |     |     |
|-----|-----|-----|-----|-----|-----|-----|-----|-----|-----|-----|-----|-----|-----|
| Asp | Ala | Tyr | Glu | Ser | Trp | Asp | Pro | Ser | Met | Leu | Val | Ile | Ser | Gln | Lys |
|     |     |     | 515 |     |     |     | 520 |     |     |     | 525 |     |     |

| Ser | Ala | Asn | Val | Thr | Val | Cys | His | Gly | Ala | Pro | Val | Phe | Ser | Val | Trp |
|-----|-----|-----|-----|-----|-----|-----|-----|-----|-----|-----|-----|-----|-----|-----|-----|
|     |     | 530 |     |     |     | 535 |     |     |     | 540 |     |     |     |     |     |

Lys
545

<210> SEQ ID NO 5
<211> LENGTH: 2074
<212> TYPE: DNA
<213> ORGANISM: Pennisetum squamulatum

<400> SEQUENCE: 5

```
ggatccagcc atgtctaaac gatcaacaga tgactgccta atataaggtt tttgggttgt      60
tgaataatta ggcaatatcc atattagatt ccgaaagcag taaaacatga caatgatagt     120
aactagtatg cacgcataag acatactaga cgatagtaac aacataacca tgaactcagt     180
aaacatgact aaagattgga tcttagatcc gtacctggcg ctcagagttg caagcactgc     240
ggagggcgtc gatacttcgg ggaagacaag cggcgcagac gaagcgacga cggtgttccg     300
gacggcacgt agcagccgac attgaaggca atgcgccctc tcgtcaggag acttgctagg     360
aagacgagcc acgatgacga cgattgagca gtcacgcgga gcacttccca aaaaccttat     420
tcgccctctc ccggtgcagg atcgcaagga cggacggttc cggagacctg ctctcccaat     480
cacctgtgca cgcaggtgtt cgggatggag tagatggcgg cggcggcggc gcagcagcga     540
gcgagagagg caaagtccta actcagatca gatctatttt agggataccc tttcatgggg     600
cctttccgta gatagtctat tgtgcatctc ttctgtgagg gggtggtcca tttttatatg     660
gagggaaacc tccaacaccc tcgtctatta gcaatatgag actaatagat ggtgtacccc     720
ctcatcacgc taatgggcct ttgagattta ttcaggaatt attggattgg ctaatgggcc     780
aagcccaaaa ttccaacaca atcaagtttg cctcgcatat ctcgattctc gaaccaacct     840
ccgagccata tctgattgta gacaagtaaa caaactcgga ggcggaaggg ggaactgacc     900
cgttgaacgc cgtcactgcc ggaaccgacg tcgccgtcac tgaagaagaa ggaagatgct     960
tccgaaccac ccaatacaaa acctcactaa ttcctcgctg acgccagagc agacgccgac    1020
gaaacgggaa aggagtcaaa ataccttatt ccatcgccac cacatcattt gggcgctgct    1080
cgctgatacg ccggcgggag cggtggcagc caggtgtacg ccccgcgga ctgcgcgccg    1140
gctggcggc cggccaccgg ggccggggcc cttcaatctc ttagggcgtc cccaacaagg    1200
ctgattcagc tagctatttg agtgtacaca tcagcatgta tcctacatgg aggaaagaga    1260
gtatgcattg aacattgagc cggctatttg ctcgtcgcct atctagcaca tcacccaagg    1320
cagcgctgtg tctatggcct ggcagaaaat attgtttaaa taacaagtag ccagctttag    1380
tagatagtac tttctcttgc tggctttttt ttttttgat aacagctctt gctggctttt    1440
agcgtgccgg ctccgagcta ctccctctgt cccagaattt gagtcgccgg ccaacagtga    1500
aatgagagag gggcacggag tcccaacgac agtaatattg ggacagggag tagcagctat    1560
ccaggactgc tgtagacgcc cttagtcctc gactcctcgc agcctttcgc cgttgaaaga    1620
atcacaccgc ccctgcagt tacgtgttaa cccaacccgg gccattggtc agtccctaac    1680
ccgggcggtt gaccgctaga aattagaatt aacccttggt taacaccggt caaagcgcac    1740
atatgcggtg caatctaatc gaagtggccg cgtcataatt acacacgccc gctcctatac    1800
```

```
gtgtgccccg ttcatacgca tgctcacctc gcgcgttccc atgaggtttc acacccttg      1860 tgggaatcca aggcgtcaga gatttattga tcccatttcc ctagcctgcc tcgcctctct      1920
atctacttgt gtggagatta gagcacagca gcgagaaagg gcttgcagtc tataaaggcg      1980
acaagagccc acaccctcct ctctctctct cttctctctc tccatttctc ttccctagga      2040
tcagtgctag tgcttgcagc ggccgcgttc cgag                                  2074

<210> SEQ ID NO 6
<211> LENGTH: 20
<212> TYPE: DNA
<213> ORGANISM: Pennisetum squamulatum

<400> SEQUENCE: 6
cctcagtgca tcagcgaagg                                                    20

<210> SEQ ID NO 7
<211> LENGTH: 20
<212> TYPE: DNA
<213> ORGANISM: Pennisetum squamulatum

<400> SEQUENCE: 7
tggaacccat ggcggaacgc                                                    20

<210> SEQ ID NO 8
<211> LENGTH: 37
<212> TYPE: DNA
<213> ORGANISM: Artificial Sequence
<220> FEATURE:
<223> OTHER INFORMATION: synthetic construct

<400> SEQUENCE: 8
gtactagtgg cgcgcccctc aatgctgtca cgaactt                                 37

<210> SEQ ID NO 9
<211> LENGTH: 37
<212> TYPE: DNA
<213> ORGANISM: Artificial Sequence
<220> FEATURE:
<223> OTHER INFORMATION: synthetic construct

<400> SEQUENCE: 9
gtgcgatcgc cctaggcaac acctgtcatg tcctgaa                                 37

<210> SEQ ID NO 10
<211> LENGTH: 23
<212> TYPE: DNA
<213> ORGANISM: Pennisetum squamulatum

<400> SEQUENCE: 10
ttccaccaac aactggctgc gct                                                23

<210> SEQ ID NO 11
<211> LENGTH: 24
<212> TYPE: DNA
<213> ORGANISM: Pennisetum squamulatum

<400> SEQUENCE: 11
ttctcatggc tcctagactc ccac                                               24

<210> SEQ ID NO 12
<211> LENGTH: 21
<212> TYPE: DNA
<213> ORGANISM: Pennisetum squamulatum
```

```
<400> SEQUENCE: 12
ccctaggatc agtgctagtg c                                              21

<210> SEQ ID NO 13
<211> LENGTH: 23
<212> TYPE: DNA
<213> ORGANISM: Pennisetum squamulatum

<400> SEQUENCE: 13
gggcttcata ccttcctgtc cat                                            23

<210> SEQ ID NO 14
<211> LENGTH: 20
<212> TYPE: DNA
<213> ORGANISM: Pennisetum squamulatum

<400> SEQUENCE: 14
gaaacgggaa aggagtcaaa                                                20

<210> SEQ ID NO 15
<211> LENGTH: 20
<212> TYPE: DNA
<213> ORGANISM: Escherichia coli

<400> SEQUENCE: 15
cgctagtgcc ttgtccagtt                                                20

<210> SEQ ID NO 16
<211> LENGTH: 19
<212> TYPE: DNA
<213> ORGANISM: Artificial Sequence
<220> FEATURE:
<223> OTHER INFORMATION: synthetic construct

<400> SEQUENCE: 16
gccgcgttcc gccatggta                                                 19

<210> SEQ ID NO 17
<211> LENGTH: 21
<212> TYPE: DNA
<213> ORGANISM: Agrobacterium tumefaciens

<400> SEQUENCE: 17
tgacaccgcg cgcgataatt t                                              21

<210> SEQ ID NO 18
<211> LENGTH: 21
<212> TYPE: DNA
<213> ORGANISM: Pennisetum squamulatum

<400> SEQUENCE: 18
acgatcaaca gatgactgcc t                                              21

<210> SEQ ID NO 19
<211> LENGTH: 20
<212> TYPE: DNA
<213> ORGANISM: Pennisetum squamulatum

<400> SEQUENCE: 19
tgatgtggtg gcgatggaat                                                20

<210> SEQ ID NO 20
```

```
<211> LENGTH: 26
<212> TYPE: DNA
<213> ORGANISM: Pennisetum squamulatum

<400> SEQUENCE: 20
tggcaagcaa gataggaag tgtggc                                           26

<210> SEQ ID NO 21
<211> LENGTH: 23
<212> TYPE: DNA
<213> ORGANISM: Pennisetum squamulatum

<400> SEQUENCE: 21
ggcacattca gtacccagga gga                                             23

<210> SEQ ID NO 22
<211> LENGTH: 23
<212> TYPE: DNA
<213> ORGANISM: Pennisetum squamulatum

<400> SEQUENCE: 22
ttccttgaga cgctttggag tgc                                             23

<210> SEQ ID NO 23
<211> LENGTH: 23
<212> TYPE: DNA
<213> ORGANISM: Pennisetum squamulatum

<400> SEQUENCE: 23
gctcttgacg tcataccggc tca                                             23

<210> SEQ ID NO 24
<211> LENGTH: 25
<212> TYPE: DNA
<213> ORGANISM: Pennisetum squamulatum

<400> SEQUENCE: 24
aagttcgtga cagcattgag gcctc                                           25

<210> SEQ ID NO 25
<211> LENGTH: 21
<212> TYPE: DNA
<213> ORGANISM: Streptomyces hygroscopicus

<400> SEQUENCE: 25
ccccaatgtc aagcacttcc g                                               21

<210> SEQ ID NO 26
<211> LENGTH: 20
<212> TYPE: DNA
<213> ORGANISM: Streptomyces hygroscopicus

<400> SEQUENCE: 26
ccgcgacgtc tgtcgagaag                                                 20

<210> SEQ ID NO 27
<211> LENGTH: 21
<212> TYPE: DNA
<213> ORGANISM: Pennisetum squamulatum

<400> SEQUENCE: 27
ttcctcaggc gccaatactg g                                               21
```

```
<210> SEQ ID NO 28
<211> LENGTH: 24
<212> TYPE: DNA
<213> ORGANISM: Pennisetum squamulatum

<400> SEQUENCE: 28
ttctcatggc tcctagactc ccac                                              24

<210> SEQ ID NO 29
<211> LENGTH: 25
<212> TYPE: DNA
<213> ORGANISM: Streptomyces hygroscopicus

<400> SEQUENCE: 29
catcgtgaca agcacggtca acttc                                             25

<210> SEQ ID NO 30
<211> LENGTH: 24
<212> TYPE: DNA
<213> ORGANISM: Streptomyces hygroscopicus

<400> SEQUENCE: 30
atatccgagc gcctcgtgca tgcg                                              24

<210> SEQ ID NO 31
<211> LENGTH: 20
<212> TYPE: DNA
<213> ORGANISM: Zea mays

<400> SEQUENCE: 31
gttgagtggc cctgtttctc                                                   20

<210> SEQ ID NO 32
<211> LENGTH: 22
<212> TYPE: DNA
<213> ORGANISM: Oryza sativa

<400> SEQUENCE: 32
cattgatcag cctaaccaaa ca                                                22

<210> SEQ ID NO 33
<211> LENGTH: 20
<212> TYPE: DNA
<213> ORGANISM: Oryza sativa

<400> SEQUENCE: 33
ggcggtaagg atctgagcta                                                   20

<210> SEQ ID NO 34
<211> LENGTH: 22
<212> TYPE: DNA
<213> ORGANISM: Agrobacterium tumefaciens

<400> SEQUENCE: 34
caaattctaa tccccaatcc aa                                                22

<210> SEQ ID NO 35
<211> LENGTH: 20
<212> TYPE: DNA
<213> ORGANISM: Pennisetum squamulatum

<400> SEQUENCE: 35
aggctgtcga ctgcagctat                                                   20
```

<210> SEQ ID NO 36
<211> LENGTH: 26
<212> TYPE: DNA
<213> ORGANISM: Pennisetum squamulatum

<400> SEQUENCE: 36
cagaattgtc atcatgtaag aaccac                                          26

<210> SEQ ID NO 37
<211> LENGTH: 21
<212> TYPE: DNA
<213> ORGANISM: Artificial Sequence
<220> FEATURE:
<223> OTHER INFORMATION: synthetic construct

<400> SEQUENCE: 37
agtgggtcta gagtcctgct t                                               21

<210> SEQ ID NO 38
<211> LENGTH: 20
<212> TYPE: DNA
<213> ORGANISM: Agrobacterium tumefaciens

<400> SEQUENCE: 38
ggcggtaagg atctgagcta                                                 20

<210> SEQ ID NO 39
<211> LENGTH: 20
<212> TYPE: DNA
<213> ORGANISM: Pennisetum glaucum

<400> SEQUENCE: 39
acgaggattt caccaacagc                                                 20

<210> SEQ ID NO 40
<211> LENGTH: 18
<212> TYPE: DNA
<213> ORGANISM: Pennisetum glaucum

<400> SEQUENCE: 40
aacgcataga cgacgcct                                                   18

<210> SEQ ID NO 41
<211> LENGTH: 660
<212> TYPE: PRT
<213> ORGANISM: Setaria italica

<400> SEQUENCE: 41

Met Ala Thr Val Asn Asn Trp Leu Ala Phe Ser Leu Ser Pro Gln Asp
1               5                   10                  15

Leu Pro Pro Ser Gln Thr Asp Ser Thr Leu Ile Ser Ala Thr Ala Thr
            20                  25                  30

Asp Glu Val Ser Gly Asp Val Cys Phe Asn Ile Pro Gln Asp Trp Ser
        35                  40                  45

Met Arg Gly Ser Glu Leu Ser Ala Leu Val Ala Glu Pro Lys Leu Glu
    50                  55                  60

Asp Phe Leu Gly Gly Ile Asn Phe Ser Glu Gln His His Lys Ala Asn
65                  70                  75                  80

Leu Asn Val Ile Pro Ser Ser Asn Ala Cys Tyr Ala Ser Ser Gly
                85                  90                  95

Ala Ser Thr Gly Tyr His Gln Leu Tyr His His Gln Ser Ser Ala Leu

```
            100                 105                 110
His Phe Ala Asp Ser Val Met Val Ala Ser Ala Gly Val His Asp
            115                 120                 125
Gly Gly Ala Ser Met Leu Ser Ala Ala Thr Val Asn Gly Gly Ala
        130                 135                 140
Gly Ala Ala Ser Ala Asn Gly Gly Ser Ile Gly Leu Ser Met Ile Lys
145                 150                 155                 160
Asn Trp Leu Arg Ser Gln Pro Ala Pro Leu Pro Gln Pro Arg Val
                165                 170                 175
Val Ala Ala Ala Glu Gly Ala Gln Ala Ala Gln Gly Leu Ser Leu Ser
                180                 185                 190
Met Asn Met Ala Gly Ala Gln Gly Ala Gly Met Pro Leu Leu Ala Gly
            195                 200                 205
Glu Arg Gly Arg Ala Pro Glu Ser Val Ser Thr Ser Ala Gln Gly Gly
        210                 215                 220
Ala Val Ala Ala Arg Lys Glu Asp Ser Gly Ser Ser Gly Gly Ala Gly
225                 230                 235                 240
Ala Leu Leu Ala Val Ser Thr Asp Thr Gly Ser Gly Thr Val Ala
                245                 250                 255
Glu Thr Ala Ala Arg Lys Thr Val Asp Thr Phe Gly Gln Arg Thr Ser
                260                 265                 270
Ile Tyr Arg Gly Val Thr Arg His Arg Trp Thr Gly Arg Tyr Glu Ala
                275                 280                 285
His Leu Trp Asp Asn Ser Cys Arg Arg Glu Gly Gln Thr Arg Lys Gly
            290                 295                 300
Arg Gln Gly Gly Tyr Asp Lys Glu Glu Lys Ala Ala Arg Ala Tyr Asp
305                 310                 315                 320
Leu Ala Ala Leu Lys Tyr Trp Gly Pro Thr Thr Thr Thr Asn Phe Pro
                325                 330                 335
Val Ser Asn Tyr Glu Lys Glu Leu Glu Glu Met Lys His Met Thr Arg
            340                 345                 350
Gln Glu Phe Val Ala Ser Leu Arg Arg Lys Ser Ser Gly Phe Ser Arg
        355                 360                 365
Gly Thr Gln Glu Glu Ala Ala Glu Ala Tyr Asp Ile Ala Ala Ile Lys
    370                 375                 380
Phe Arg Gly Leu Asn Ala Val Thr Asn Phe Asp Met Ser Arg Tyr Asp
385                 390                 395                 400
Val Lys Ser Ile Leu Asp Ser Ser Ala Leu Pro Ile Gly Ser Ala Ala
                405                 410                 415
Lys Arg Leu Lys Glu Ala Glu Ala Ala Ser Ala Gln His Ala Gly
            420                 425                 430
Val Val Ser Tyr Asp Val Gly Arg Ile Ala Ser His Leu Gly Asp Gly
            435                 440                 445
Gly Ala Leu Ala Ala Tyr Gly Thr His Tyr His Ala Ala Ala Ala
        450                 455                 460
Trp Pro Thr Ile Ala Phe Gln Pro Ser Ala Ala Ala Gly Leu Tyr
465                 470                 475                 480
His Pro Tyr Ala Gln Pro Met Arg Gly Trp Cys Lys Gln Glu Gln Asp
                485                 490                 495
His Ala Val Ile Ala Ala His Ser Leu His Glu Leu Asn His Leu
                500                 505                 510
Asn Leu Gly Ala Gly Gly Gly Ala His Asp Phe Phe Ser Ala Gly Gln
            515                 520                 525
```

Ala Ala Met His Gly Leu Gly Ser Ile Asp Asn Ala Ser Leu Glu His
        530                 535                 540

Ser Thr Gly Ser Asn Ser Val Val Tyr Asn Gly Val Gly Asp Ser Asn
545                 550                 555                 560

Gly Gly Ala Val Gly Gly Tyr Met Met Pro Met Ser Ala Ala Thr
                565                 570                 575

Ala Thr Thr Thr Ala Met Val Ser His Glu Gln Val His Ala Arg Ser
                580                 585                 590

His Gln Gly Glu His Asp Glu Ala Thr Lys Gln Ala Ala Gln Met Gly
            595                 600                 605

Tyr Glu Ser Tyr Leu Val Asn Ala Glu Ala Tyr Gly Gly Arg
        610                 615                 620

Met Pro Ser Trp Thr Pro Ala Ser Ala Pro Ala Ala Ala Ser Ser Asn
625                 630                 635                 640

Asp Asn Met Ala Gly Val Gly His Gly Gly Ala Gln Leu Phe Ser Val
                645                 650                 655

Trp Asn Asp Thr
            660

<210> SEQ ID NO 42
<211> LENGTH: 481
<212> TYPE: PRT
<213> ORGANISM: Panicum virgatum

<400> SEQUENCE: 42

Met Gly Ser Thr Asn Asn Trp Leu Gly Phe Ala Ser Phe Ser Gly Ala
1               5                   10                  15

Ala Ala Ala Asp Asp Val Leu Pro Leu Pro Pro Ala Arg Gly Asp
            20                  25                  30

Glu Ala Gly Ala Glu Pro Lys Leu Glu Asp Phe Leu Gly Leu His Glu
        35                  40                  45

Pro Ala Ala Ala Val Ala Gly Arg Pro Phe Ala Gly Ser Gly Gly Gly
    50                  55                  60

Ala Ser Ser Ile Gly Leu Ser Met Ile Lys Asn Trp Leu Arg Ser Gln
65                  70                  75                  80

Pro Ala Pro Gly Pro Ala Gly Ala Asp Ser Thr Ala Leu Ala Ala Val
                85                  90                  95

Glu Ala Val Ser Thr Asp Gly Ser Arg Lys Val Thr Asp Ser Ala Glu
            100                 105                 110

Ser Val Ala Ala Val Val Asp Thr Ala Gln Gln Arg Lys Ala Val Ala
        115                 120                 125

Ala Val Asp Thr Phe Gly Gln Arg Thr Ser Ile Tyr Arg Gly Val Thr
    130                 135                 140

Lys His Arg Trp Thr Gly Arg Tyr Glu Ala His Leu Trp Asp Asn Ser
145                 150                 155                 160

Cys Arg Arg Glu Gly Gln Thr Arg Lys Gly Arg Gln Met Tyr Leu Gly
                165                 170                 175

Gly Tyr Asp Lys Glu Glu Lys Ala Ala Arg Ala Tyr Asp Leu Ala Ala
            180                 185                 190

Leu Lys Tyr Trp Gly Thr Thr Thr Thr Asn Phe Pro Met Ser Asn
        195                 200                 205

Tyr Glu Lys Glu Leu Glu Glu Met Lys His Met Ser Arg Gln Glu Tyr
    210                 215                 220

Val Ala Ser Leu Arg Arg His Asn Ile Ser Cys Gly Ile Gly Lys Ala

```
            225                 230                 235                 240
    Val Asp Phe Leu Val Arg Arg Phe Asn Tyr Arg Gly Val Thr Arg
                        245                 250                 255

His His Gln His Gly Arg Trp Gln Ala Arg Ile Gly Arg Val Ala Gly
                        260                 265                 270

Asn Lys Asp Leu Tyr Leu Gly Thr Phe Ser Thr Gln Glu Glu Ala Ala
                        275                 280                 285

Glu Ala Tyr Asp Ile Ala Ala Ile Lys Phe Arg Gly Leu Asn Ala Val
                290                 295                 300

Thr Asn Phe Asp Met Ser Arg Tyr Asp Val Lys Ser Ile Met Glu Ser
    305                 310                 315                 320

Ser Ala Leu Pro Val Gly Gly Thr Thr Lys Cys Leu Arg Asp Val Pro
                        325                 330                 335

Asp Gln Phe Gly Lys Gly Met Asn Ser Asn Gly Ala Asp Ser Ala Ser
                        340                 345                 350

His Met Thr Ala Thr Lys Leu Asn Phe Leu Leu Met Ala Leu Ala Ala
                        355                 360                 365

Val Pro Met Arg Ile Met Val Thr Val Ala Ala Leu Thr Ala Gln Gly
                370                 375                 380

Gly Thr His Asn Phe Phe His Pro Ser Pro Ser Val Asp Pro Asn Ser
    385                 390                 395                 400

Phe Leu Tyr Asn Gly Gly Val Gly Tyr His Ala Ile Gly Gly Gly Tyr
                        405                 410                 415

Pro Met Pro Val Ala Thr Leu Val Asp Gly Asn Tyr Val Pro Ser Gly
                        420                 425                 430

Tyr Gly Val Glu Glu Ala Ser Ser Asp Ile Tyr Ser Gly Arg Asn Leu
                        435                 440                 445

Tyr Tyr Leu Ser Gln Ala Ser Pro Ser Asp Ser Thr Gly Lys Ala Asp
                450                 455                 460

Ala Tyr Glu Gln Gln Gly Val Gly Met Lys Ala Gly Phe His Leu Cys
    465                 470                 475                 480

Pro

<210> SEQ ID NO 43
<211> LENGTH: 674
<212> TYPE: PRT
<213> ORGANISM: Setaria italica

<400> SEQUENCE: 43

Met Ala Ser Ala Asn Asn Trp Leu Gly Phe Ser Leu Ser Gly Gln Asp
    1               5                   10                  15

Asn Pro Gln Ala Asn Gln Asp Ser Ser Pro Ala Ala Gly Ile Asp
                    20                  25                  30

Ile Ser Gly Ala Thr Asp Phe Tyr Gly Leu Pro Thr Gln Gln Gly Ser
                35                  40                  45

Asp Gly His Leu Gly Val Pro Gly Leu Arg Asp His Ala Ser Tyr
            50                  55                  60

Gly Ile Met Glu Ala Phe Asn Arg Ser Gln Gln Glu Thr Gln Asp Trp
    65                  70                  75                  80

Asn Met Arg Gly Leu Asp Tyr Asn Gly Gly Ala Ser Glu Leu Ser Met
                    85                  90                  95

Leu Val Gly Ser Ser Gly Gly Lys Arg Ala Val Glu Asp Gly Glu Pro
                    100                 105                 110

Lys Leu Glu Asp Phe Leu Gly Gly Asn Ser Phe Val Ser Glu Gln Asp
```

```
            115                 120                 125
Gln Ser Gly Gly Tyr Leu Phe Ser Gly Val Pro Met Ala Ser Ser Thr
    130                 135                 140

Asn Ser Asn Ser Gly Ser Asn Thr Met Glu Leu Ser Met Ile Lys Thr
145                 150                 155                 160

Trp Leu Arg Asn Asn Gln Val Pro Gln Pro Gln Pro Ala Pro His
                165                 170                 175

Gln Ala Ala Pro Gln Pro Glu Glu Met Ser Thr Asp Ala Ser Ala Ser
            180                 185                 190

Ser Phe Gly Cys Ser Asp Ser Leu Gly Arg Asn Gly Thr Val Ala Ala
        195                 200                 205

Gly Ser Ser Gln Ser Leu Ala Leu Ser Met Ser Thr Gly Pro Gln His
    210                 215                 220

Leu Pro Met Val Val Ala Gly Gly Gly Gly Ala Ser Gly Ala Ala
225                 230                 235                 240

Ala Ser Glu Ser Thr Ser Ser Glu Asn Lys Arg Ala Ser Gly Ala Met
                245                 250                 255

Asp Ser Pro Ser Ser Gly Ala Ile Glu Ala Val Pro Arg Lys Ser Ile
            260                 265                 270

Asp Thr Phe Gly Gln Arg Thr Ser Ile Tyr Arg Gly Val Thr Arg His
        275                 280                 285

Arg Trp Thr Gly Arg Tyr Glu Ala His Leu Trp Asp Asn Ser Cys Arg
    290                 295                 300

Arg Glu Gly Gln Ser Arg Lys Gly Arg Gln Gly Gly Tyr Asp Lys Glu
305                 310                 315                 320

Asp Lys Ala Ala Arg Ala Tyr Asp Leu Ala Ala Leu Lys Tyr Trp Gly
                325                 330                 335

Thr Thr Thr Thr Thr Asn Phe Pro Ile Ser Asn Tyr Glu Lys Glu Leu
            340                 345                 350

Glu Glu Met Lys His Met Thr Arg Gln Glu Tyr Ile Ala Tyr Leu Arg
        355                 360                 365

Arg Asn Ser Ser Gly Phe Ser Arg Gly Ala Ser Lys Tyr Arg Gly Val
    370                 375                 380

Thr Arg His His Gln His Gly Arg Trp Gln Ala Arg Ile Gly Arg Val
385                 390                 395                 400

Ala Gly Asn Lys Asp Leu Tyr Leu Gly Thr Phe Ser Thr Glu Glu Glu
                405                 410                 415

Ala Ala Glu Ala Tyr Asp Ile Ala Ala Ile Lys Phe Arg Gly Leu Asn
            420                 425                 430

Ala Val Thr Asn Phe Asp Met Ser Arg Tyr Asp Val Lys Ser Ile Leu
        435                 440                 445

Glu Ser Ser Thr Leu Pro Val Gly Gly Ala Ala Arg Arg Leu Lys Asp
    450                 455                 460

Ala Val Asp His Val Glu Ala Gly Ala Thr Ile Trp Arg Ala Asp Met
465                 470                 475                 480

Asp Ala Gly Val Ile Ser Gln Leu Ala Asp Ala Gly Met Gly Ala Tyr
                485                 490                 495

Ala Ser Tyr Gly His His Gly Trp Pro Thr Ile Ala Phe Gln Gln Pro
            500                 505                 510

Ser Pro Leu Thr Val His Tyr Pro Tyr Gly Gln Pro Ser Arg Gly Trp
        515                 520                 525

Cys Lys Pro Glu Gln Asp Ala Ala Val Ala Ala Ala His Ser Leu
    530                 535                 540
```

```
Gln Asp Leu Gln Gln Leu His Leu Gly Ser Ala Ala His Asn Phe Phe
545                 550                 555                 560

Gln Ala Ser Ser Ser Thr Val Tyr Asn Gly Gly Ala Ser Ala
            565                 570                 575

Ala Gly Tyr Gln Gly Leu Gly Gly Gly Gly Ser Phe Leu Met
            580                 585                 590

Pro Ser Ser Thr Val Val Ala Asp Gln Gly His Ser Ser Thr Ala Asn
            595                 600                 605

Gln Gly Ser Thr Cys Ser Tyr Gly Asp Asp Gln Asp Gly Lys Leu Ile
            610                 615                 620

Gly Tyr Asp Ala Met Ala Ala Ala Gly Gly Asp Pro Tyr Ala Ala
625                 630                 635                 640

Arg Ser Gly Tyr Gln Phe Ser Gln Gly Ser Gly Ser Thr Val Ser Ile
                    645                 650                 655

Ala Arg Ala Asn Gly Tyr Ser Asn Asn Trp Ser Ser Pro Phe Asn Gly
                660                 665                 670

Met Gly

<210> SEQ ID NO 44
<211> LENGTH: 658
<212> TYPE: PRT
<213> ORGANISM: Panicum virgatum

<400> SEQUENCE: 44

Met Ala Thr Val Asn Asn Trp Leu Ala Phe Ser Leu Ser Gln Gln Asp
1               5                   10                  15

Leu Pro Pro Ser Gln Thr Asp Ser Thr Leu Ile Ser Ala Ala Ala Thr
                20                  25                  30

Asp Glu Val Ser Gly Asp Val Cys Phe Asn Ile Pro Gln Asp Trp Ser
            35                  40                  45

Met Arg Gly Ser Glu Leu Ser Ala Leu Val Ala Glu Pro Lys Leu Glu
        50                  55                  60

Asp Phe Leu Gly Gly Ile Asn Phe Ser Glu Gln His His Lys Ala Asn
65                  70                  75                  80

Leu Asn Val Ile Pro Ser Ser Ser Thr Cys Tyr Ala Ser Ser Gly
                85                  90                  95

Ala Ser Thr Gly Tyr His Gln Leu Tyr His His Pro Ser Ser Ala Leu
            100                 105                 110

His Phe Ala Asp Ser Val Met Val Ala Ser Ser Ala Gly Val His Asp
        115                 120                 125

Gly Gly Ala Met Leu Ser Ala Ala Thr Ala His Gly Gly Ala Gly Ala
    130                 135                 140

Ala Gly Ala Asn Gly Gly Ser Ile Gly Leu Ser Met Ile Lys Asn Trp
145                 150                 155                 160

Leu Arg Ser Gln Pro Ala Pro Pro Gln Pro Arg Val Ala Val Pro
                165                 170                 175

Glu Gly Ala Gln Ala Val Gln Gly Leu Ser Leu Ser Met Asn Met Ala
            180                 185                 190

Gly Thr Gln Gly Ala Gly Met Pro Phe Leu Ala Gly Asp Arg Gly Arg
        195                 200                 205

Ala Pro Glu Ser Val Ser Thr Ser Ala Gln Gly Gly Ala Val Ala Ala
    210                 215                 220

Arg Lys Glu Asp Ser Gly Gly Ser Gly Gly Ala Gly Ala Leu Val Val
225                 230                 235                 240
```

-continued

```
Ala Val Ser Thr Asp Thr Gly Ser Gly Ser Gly Ala Ser Ala
                245             250             255

Glu Thr Ala Ala Arg Lys Thr Val Asp Thr Phe Gly Gln Arg Thr Ser
                260             265             270

Ile Tyr Arg Gly Val Thr Arg His Arg Trp Thr Gly Arg Tyr Glu Ala
            275             280             285

His Leu Trp Asp Asn Ser Cys Arg Arg Glu Gly Gln Thr Arg Lys Gly
        290             295             300

Arg Gln Gly Gly Tyr Asp Lys Glu Lys Ala Ala Arg Ala Tyr Asp
305             310             315             320

Leu Ala Ala Leu Lys Tyr Trp Gly Pro Thr Thr Thr Thr Asn Phe Pro
                325             330             335

Val Ser Asn Tyr Glu Lys Glu Leu Glu Glu Met Lys His Met Thr Arg
                340             345             350

Gln Glu Phe Val Ala Ser Leu Arg Arg Lys Ser Ser Gly Phe Ser Arg
            355             360             365

Gly Thr Gln Glu Glu Ala Ala Glu Ala Tyr Asp Ile Ala Ala Ile Lys
        370             375             380

Phe Arg Gly Leu Asn Ala Val Thr Asn Phe Asp Met Ser Arg Tyr Asp
385             390             395             400

Val Lys Ser Ile Leu Asp Ser Ser Ala Leu Pro Ile Gly Ser Ala Ala
                405             410             415

Lys Arg Leu Lys Glu Ala Glu Ala Ala Ser Ala Gln His His Ala
            420             425             430

Gly Val Val Ser Tyr Asp Val Gly Arg Ile Ala Ser Gln Leu Gly Asp
        435             440             445

Gly Gly Ala Leu Ala Ala Tyr Gly Ala His Tyr His Ala Ala Ala Ala
        450             455             460

Ala Ala Trp Pro Thr Ile Ala Phe Gln Pro Gly Ala Ala Gly Gly
465             470             475             480

Leu Tyr His Pro Tyr Ala Gln Pro Leu Arg Gly Trp Cys Lys Gln Glu
                485             490             495

Gln Asp His Ala Val Ile Ala Ala His Ser Leu Gln Glu Leu Asn
            500             505             510

His Leu Asn Leu Gly Ala Gly Ala His Asp Phe Phe Ser Ala Gly Gln
        515             520             525

Ala Ala Met His Gly Leu Gly Ser Ile Asp Asn Ser Ser Leu Glu His
        530             535             540

Ser Thr Gly Ser Asn Ser Val Val Tyr Asn Gly Val Gly Asp Ser Asn
545             550             555             560

Gly Gly Gly Gly Tyr Met Met Pro Met Asn Ala Ala Ala Thr Thr
                565             570             575

Thr Ala Met Val Asn His Glu Gln Val His Ala Arg Ala His Gly Asp
            580             585             590

His Asp Glu Ala Ser Lys Gln Val Met Gly Tyr Glu Ser Tyr Leu Val
        595             600             605

Asn Ala Glu Ala Ala Tyr Gly Gly Gly Arg Met Pro Ser Trp Thr Thr
610             615             620

Ala Ser Ala Ser Pro Val Ala Ala Ala Ala Ser Ser Asn Asp Asn
625             630             635             640

Met Ala Gly Val Gly His Gly Gly Ala Gln Leu Phe Ser Val Trp Asn
                645             650             655
```

Asp Thr

<210> SEQ ID NO 45
<211> LENGTH: 627
<212> TYPE: PRT
<213> ORGANISM: Brachypodium distachyon

<400> SEQUENCE: 45

Met Ala Thr Val Asn Asn Trp Leu Gly Phe Ser Leu Ser Pro Gln Glu
1               5                   10                  15

Leu Pro Ser Ala Ala Ala Ala Gly Asp Val Ser Gly Ala Asp
            20                  25                  30

Val Cys Phe Asn Ile Pro Gln Asp Trp Gly Met Arg Gly Ser Glu Leu
                35                  40                  45

Ser Ala Leu Val Ala Glu Pro Lys Leu Glu Asp Phe Leu Gly Gly Ile
        50                  55                  60

Ser Ser Tyr Ser Asp His His Lys Ala Ala Arg Ser Asn Asn Met Asn
65                  70                  75                  80

Ile Asn Gly Ala Ala Ala Cys Tyr Ala Ser Gly Ser Ser Gly Tyr
                85                  90                  95

Gln Leu Tyr His Asp His Pro Asn Ser Leu Gln Phe Ala Asp Ser Val
            100                 105                 110

Met Val Ala Ser Ser Ala Gly Gly Val His Asn Glu His Gly Ile Met
            115                 120                 125

Ala Ser Thr Thr Ala Asn Gly Ala Gly Thr Asn Gly Gly Ile Gly Leu
        130                 135                 140

Ser Met Ile Lys Ser Trp Leu Arg Ser Gln Pro Ala Pro Ala Gln Gln
145                 150                 155                 160

Glu Gln Gln Arg Ala Glu Gly Leu Ser Leu Ser Met Asn Met Pro Leu
                165                 170                 175

Leu Gln Ala Ala Ala Ala Glu Thr Ser Leu Ser Thr His Arg Trp Thr
            180                 185                 190

Gly Arg Tyr Glu Ala His Leu Trp Asp Asn Ser Cys Arg Arg Glu Gly
            195                 200                 205

Gln Thr Arg Lys Gly Arg Gln Val Tyr Leu Gly Gly Tyr Asp Lys Glu
        210                 215                 220

Glu Lys Ala Ala Arg Ala Tyr Asp Leu Ala Ala Leu Lys Tyr Trp Gly
225                 230                 235                 240

Pro Thr Thr Thr Thr Asn Phe Pro Val Asp Asn Tyr Glu Lys Glu Leu
                245                 250                 255

Glu Glu Met Lys His Met Thr Arg Gln Glu Phe Val Ala Ser Leu Arg
            260                 265                 270

Arg Lys Ser Ser Gly Phe Ser Arg Gly Ala Ser Ile Tyr Arg Gly Val
        275                 280                 285

Thr Arg His His Gln His Gly Arg Trp Gln Ala Arg Ile Gly Arg Val
    290                 295                 300

Ala Gly Asn Lys Asp Leu Tyr Leu Gly Thr Phe Ser Thr Gln Glu Glu
305                 310                 315                 320

Ala Ala Glu Ala Tyr Asp Ile Ala Ala Ile Lys Phe Arg Gly Leu Asn
                325                 330                 335

Ala Val Thr Asn Phe Asp Met Ser Arg Tyr Asp Val Lys Ser Ile Leu
            340                 345                 350

Asp Ser Thr Ala Ala Leu Pro Val Gly Gly Thr Lys Arg Leu Arg Asp
        355                 360                 365

-continued

```
Ala Ala Ala Asp Gln His Tyr Gln Gln Arg Ala Gly Gly Val Val
370                 375                 380

Ser Tyr Ala Ala Pro Gln Leu Gly Gly Val Asn Glu Thr Ala Leu Ala
385                 390                 395                 400

Tyr Gly Ala Pro Tyr Tyr His His Gln Thr Ser Ala Ala Ala Trp Pro
            405                 410                 415

Thr Ile Ala Phe Gln Ala Ala Pro Gln Ala Ser Ser Gly His Gly His
            420                 425                 430

Met Leu Tyr His Pro Tyr Gly Gln Pro Leu Met Arg Gly Trp Cys Lys
            435                 440                 445

Gln Glu Gln Glu Gln Gly Gln Gly Gln Gln Glu Pro Asp His Ala Val
450                 455                 460

Ile Ala Ala His Ser Leu Gln Asp Leu His His Leu Asn Leu Gly
465                 470                 475                 480

Ala Gly Ala His Asp Phe Phe Ser Gln His Ala His Ala Met His Gln
                485                 490                 495

Gln Gln Gln Gln His Gly Gly Leu Gly Ser Val Asp Asn Asn Gly Ala
                500                 505                 510

Ala Ser Leu Glu His Ser Thr Gly Ser Asn Ser Val Val Tyr Asn Gly
                515                 520                 525

Ala Ala Ala Ala Gly Asp Thr Asn Asn Ser Tyr Met Leu Pro Pro Met
530                 535                 540

Ser Ala Ala Ala Ala Gly Phe Gly Leu Arg Asp Gln Gln Asp Glu
545                 550                 555                 560

Gly Gly Lys Met Ala Tyr Glu Asn Phe Leu Leu Gly Ala Ala Thr Asp
                565                 570                 575

Gly Tyr Cys Gly Pro Gly Arg Met Ala Ala Thr Trp Thr Pro Val Ser
            580                 585                 590

Val Ser Ala Ala Gln Pro Val Ala Thr Ser Ser Gly Ser Asp Met
                595                 600                 605

Ala Gly Ala Val Cys His Gly Gly Ala Gln Leu Phe Ser Val Trp Asn
            610                 615                 620

Asp Asp Ser
625

<210> SEQ ID NO 46
<211> LENGTH: 686
<212> TYPE: PRT
<213> ORGANISM: Brachypodium distachyon

<400> SEQUENCE: 46

Met Ala Ser Ala Asn Asn Trp Leu Gly Phe Ser Leu Ser Gly Gln Gly
1               5                   10                  15

Asn Ser Gln Ala Pro Pro Ala Ala Ala Ile Asp Val Ser Gly Ala
            20                  25                  30

Gly Asp Phe Tyr Gly Leu Gln Ala Gln Ser Ala Pro Asp Ala His Leu
            35                  40                  45

Gly Met Pro Gly Leu Arg Ala Asp Ala Asn Tyr Gly Val Met Asp Ala
50                  55                  60

Phe Asn Gly Gly Gly Gln Glu Thr Gln Asp Trp Ala Met Arg Gly Leu
65                  70                  75                  80

Asp Tyr His Gly Gly Ser Ser Glu Leu Ser Met Leu Val Gly Ser Ser
                85                  90                  95

Ser Gly Arg Met Thr Val Asp Asp Gly Gly Ala Pro Lys Leu Glu Asp
                100                 105                 110
```

```
Phe Leu Gly Gly Gly Asn Ser Phe Ser Asp Val Gln Asp Gln Thr Gly
            115                 120                 125

Gly Tyr Leu Phe Ser Gly Ala Gly Ala Thr Met Gly Ser Gly Ala Asp
        130                 135                 140

Gln Ala Ala Ala His Ser Val Asp Gly Arg Gly Gly Ser Thr Ile
145                 150                 155                 160

Glu Leu Ser Met Ile Lys Ser Trp Leu Arg Asn Asp Asn Gln Ala His
                165                 170                 175

Ala Gln Pro Asp Gln Glu Met Ser Ser Thr Asp Val Ala Ser Ala Ala
                180                 185                 190

Ser Tyr Ala Cys Pro Gly Ala Leu Gly Asn Gly Asn Val Gly Ala
                195                 200                 205

Gly Ala Ala Ser Ala Arg Gly Gly Gln Gln Ala Gly Ala Leu Ala Leu
        210                 215                 220

Ser Met Ser Met Gly Ser His His Ala His Ser Gln Leu Ser Val Val
225                 230                 235                 240

Ala Ala Ala Ala Gly Gly Gly Gly Ala Ala Glu Ser Thr Ser Ser
                245                 250                 255

Asp Asn Lys Arg Val Asp Ser Pro Ser Ala Gly Ala Ala Asp Ala Gly
                260                 265                 270

Gln Arg Lys Ser Ile Asp Thr Phe Gly Gln Arg Thr Ser Ile Tyr Arg
                275                 280                 285

Gly Val Thr Arg His Arg Trp Thr Gly Arg Tyr Glu Ala His Leu Trp
        290                 295                 300

Asp Asn Ser Cys Arg Arg Glu Gly Gln Thr Arg Lys Gly Lys Gln Gly
305                 310                 315                 320

Gly Tyr Asp Lys Glu Asp Lys Ala Ala Arg Ala Tyr Asp Leu Ala Ala
                325                 330                 335

Leu Lys Tyr Trp Gly Thr Thr Thr Thr Thr Asn Ile Pro Ile Ser Thr
                340                 345                 350

Tyr Glu Lys Glu Ile Glu Glu Met Lys His Met Thr Arg Gln Glu Tyr
        355                 360                 365

Ile Ala Tyr Leu Arg Arg Asn Ser Ser Gly Phe Ser Arg Gly Ala Ser
        370                 375                 380

Lys Tyr Arg Gly Val Thr Arg His His Gln Gln Gly Arg Trp Gln Ala
385                 390                 395                 400

Arg Ile Gly Arg Val Ala Gly Asn Lys Asp Leu Tyr Leu Gly Thr Phe
                405                 410                 415

Thr Thr Glu Glu Glu Ala Ala Glu Ala Tyr Asp Ile Ala Ala Ile Lys
        420                 425                 430

Phe Arg Gly Leu Asn Ala Val Thr Asn Phe Glu Met Ser Arg Tyr Asp
        435                 440                 445

Val Lys Ser Ile Leu Glu Gly Ser Thr Leu Pro Val Gly Gly Ala Ala
        450                 455                 460

Arg Arg Leu Lys Glu Ala Ala Glu Leu Ala Glu Ala Gly Val Trp Arg
465                 470                 475                 480

Ala Glu Asp Gly Ser Ile Val Ser His Leu Thr His Ala Asp Gly Gly
                485                 490                 495

Ile Gly Ile Gly Met Gly Gly Thr Pro Tyr His Gly Trp Pro Thr Ser
                500                 505                 510

Ile Ala Phe Gly Gly His Gly Gln Leu Met His Ala Ser Pro Ala Ala
                515                 520                 525
```

```
Gln Ala Leu Ala Val His Tyr Pro Pro Tyr Gly Ala Gly Trp Cys Lys
            530                 535                 540

Pro Glu Gln Asp Ala Val Ile Ala Ala Ala Gly His Gly Val His Asp
545                 550                 555                 560

Ser Ser Gln Gly Gln Gly Gln Glu Leu His Leu Gly Thr His Asn Phe
                565                 570                 575

Phe His Pro Ala Ala Arg Ser Ser Tyr Ser Asn Gly Thr Gly Gly Gly
            580                 585                 590

Trp Tyr Gln Gly Val Asn Gly Asn Gly Tyr Leu Met Pro Gln Val Gly
                595                 600                 605

Thr Val Val Asp Ala Asp Asn Val Gln Gly His Ser Gly Ser Thr Ala
610                 615                 620

Thr Thr Asn Glu Glu Gly Arg Leu Met Ala Ala Gly Tyr Gly Asp
625                 630                 635                 640

Gly Gly Gly Gly Val Asp Pro Tyr Ala Ala Met Arg Arg Ala Tyr Glu
                645                 650                 655

Leu Ser Gln Gly Ser Ser Ser Val Ser Val Ala Lys Val Ala Asp
                660                 665                 670

Gly Tyr Ser Asn Asn Trp Ser Ser Pro Phe Asn Gly Met Gly
            675                 680                 685

<210> SEQ ID NO 47
<211> LENGTH: 579
<212> TYPE: PRT
<213> ORGANISM: Brassica napus

<400> SEQUENCE: 47

Met Asn Asn Asn Trp Leu Gly Phe Ser Leu Ser Pro Tyr Glu Gln Asn
1                   5                   10                  15

His His Arg Lys Asp Val Tyr Ser Ser Thr Thr Thr Val Val Asp
                20                  25                  30

Val Ala Gly Glu Tyr Cys Tyr Asp Pro Thr Ala Ala Ser Asp Glu Ser
            35                  40                  45

Ser Ala Ile Gln Thr Ser Phe Pro Ser Pro Phe Gly Val Val Asp
        50                  55                  60

Ala Phe Thr Arg Asp Asn Asn Ser His Ser Arg Asp Trp Asp Ile Asn
65                  70                  75                  80

Gly Cys Ala Cys Asn Asn Ile His Asn Asp Glu Gln Asp Gly Pro Lys
                85                  90                  95

Leu Glu Asn Phe Leu Gly Arg Thr Thr Thr Ile Tyr Asn Thr Asn Glu
            100                 105                 110

Asn Val Gly Asp Gly Ser Gly Ser Gly Cys Tyr Gly Gly Gly Asp Gly
        115                 120                 125

Gly Gly Gly Ser Leu Gly Leu Ser Met Ile Lys Thr Trp Leu Arg Asn
    130                 135                 140

Gln Pro Val Asp Asn Val Asp Asn Gln Glu Asn Gly Asn Ala Ala Lys
145                 150                 155                 160

Gly Leu Ser Leu Ser Met Asn Ser Ser Thr Ser Cys Asp Asn Asn
                165                 170                 175

Asp Ser Asn Asn Asn Val Val Ala Gln Gly Lys Thr Ile Asp Asp Ser
            180                 185                 190

Val Glu Ala Thr Pro Lys Lys Thr Ile Glu Ser Phe Gly Gln Arg Thr
        195                 200                 205

Ser Ile Tyr Arg Gly Val Thr Arg His Arg Trp Thr Gly Arg Tyr Glu
    210                 215                 220
```

Ala His Leu Trp Asp Asn Ser Cys Lys Arg Glu Gly Gln Thr Arg Lys
225                 230                 235                 240

Gly Arg Gln Val Tyr Leu Gly Gly Tyr Asp Lys Glu Lys Ala Ala
            245                 250                 255

Arg Ala Tyr Asp Leu Ala Ala Leu Lys Tyr Trp Gly Thr Thr Thr
            260                 265                 270

Thr Asn Phe Pro Met Ser Glu Tyr Glu Lys Glu Val Glu Glu Met Lys
            275                 280                 285

His Met Thr Arg Gln Glu Tyr Val Ala Ser Leu Arg Arg Lys Ser Ser
290                 295                 300

Gly Phe Ser Arg Gly Ala Ser Ile Tyr Arg Gly Val Thr Arg His His
305                 310                 315                 320

Gln His Gly Arg Trp Gln Ala Arg Ile Gly Arg Val Ala Gly Asn Lys
            325                 330                 335

Asp Leu Tyr Leu Gly Thr Phe Gly Thr Gln Glu Glu Ala Ala Glu Ala
            340                 345                 350

Tyr Asp Ile Ala Ala Ile Lys Phe Arg Gly Leu Thr Ala Val Thr Asn
            355                 360                 365

Phe Asp Met Asn Arg Tyr Asn Val Lys Ala Ile Leu Glu Ser Pro Ser
370                 375                 380

Leu Pro Ile Gly Ser Ala Ala Lys Arg Leu Lys Glu Ala Asn Arg Pro
385                 390                 395                 400

Val Pro Ser Met Met Met Ile Ser Asn Asn Val Ser Glu Ser Glu Asn
            405                 410                 415

Ser Ala Ser Gly Trp Gln Asn Ala Ala Val Gln His His Gln Gly Val
            420                 425                 430

Asp Leu Ser Leu Leu His Gln His Gln Glu Arg Tyr Asn Gly Tyr Tyr
            435                 440                 445

Tyr Asn Gly Gly Asn Leu Ser Ser Glu Ser Ala Arg Ala Cys Phe Lys
450                 455                 460

Gln Glu Asp Asp Gln His His Phe Leu Ser Asn Thr Gln Ser Leu Met
465                 470                 475                 480

Thr Asn Ile Asp His Gln Ser Ser Val Ser Asp Ser Val Thr Val
            485                 490                 495

Cys Gly Asn Val Val Gly Tyr Gly Gly Tyr Gln Gly Phe Ala Ala Pro
            500                 505                 510

Val Asn Cys Asp Ala Tyr Ala Ala Ser Glu Phe Asp Tyr Asn Ala Arg
            515                 520                 525

Asn His Tyr Tyr Phe Ala Gln Gln Gln Thr Gln Gln Ser Pro Gly
            530                 535                 540

Gly Asp Phe Pro Ala Ala Met Thr Asn Asn Val Gly Ser Asn Met Tyr
545                 550                 555                 560

Tyr His Gly Glu Gly Gly Gly Glu Val Ala Pro Thr Phe Thr Val Trp
            565                 570                 575

Asn Asp Asn

<210> SEQ ID NO 48
<211> LENGTH: 545
<212> TYPE: PRT
<213> ORGANISM: Cenchrus ciliaris

<400> SEQUENCE: 48

Met Gly Ser Thr Asn Asn Trp Leu Arg Phe Val Ser Phe Ser Gly Gly
1               5                   10                  15

-continued

Gly Gly Ala Lys Asp Ala Ala Leu Leu Pro Leu Pro Pro Ser Pro
        20              25              30

Arg Gly Asp Val Asp Glu Ala Gly Ala Glu Pro Lys Leu Glu Asp Phe
        35              40              45

Leu Gly Leu Gln Glu Pro Ser Ala Ala Val Gly Ala Gly Arg Pro
50              55              60

Phe Ala Val Gly Gly Gly Ala Ser Ser Ile Gly Leu Ser Met Ile Lys
65              70              75              80

Asn Trp Leu Arg Ser Gln Pro Ala Pro Ala Gly Pro Ala Ala Gly Val
                85              90              95

Asp Ser Met Val Leu Ala Ala Ala Ala Ser Thr Glu Val Ala Gly
                100             105             110

Asp Gly Ala Glu Gly Gly Ala Val Ala Asp Ala Val Gln Gln Arg
        115             120             125

Lys Ala Ala Val Asp Thr Phe Gly Gln Arg Thr Ser Ile Tyr Arg
130             135             140

Gly Val Thr Lys His Arg Trp Thr Gly Arg Tyr Glu Ala His Leu Trp
145             150             155             160

Asp Asn Ser Cys Arg Arg Glu Gly Gln Thr Arg Lys Gly Arg Gln Val
                165             170             175

Tyr Leu Gly Gly Tyr Asp Lys Glu Glu Lys Ala Ala Arg Ala Tyr Asp
        180             185             190

Leu Ala Ala Leu Lys Tyr Arg Gly Thr Thr Thr Thr Thr Asn Phe Pro
        195             200             205

Met Ser Asn Tyr Glu Lys Glu Leu Glu Glu Met Lys His Met Ser Arg
210             215             220

Gln Glu Tyr Val Ala Ser Leu Arg Arg Lys Ser Ser Gly Phe Ser Arg
225             230             235             240

Gly Ala Ser Ile Tyr Arg Gly Val Thr Arg His His Gln His Gly Arg
            245             250             255

Trp Gln Ala Arg Ile Gly Ser Val Ala Gly Asn Lys Asp Leu Tyr Leu
        260             265             270

Gly Thr Phe Ser Thr Gln Glu Glu Ala Ala Glu Ala Tyr Asp Ile Ala
        275             280             285

Ala Ile Lys Phe Arg Gly Leu Asn Ala Val Thr Asn Phe Asp Met Ser
290             295             300

Arg Tyr Asp Val Lys Ser Ile Glu Ser Ser Ser Leu Pro Val Gly
305             310             315             320

Gly Ala Pro Lys Arg Leu Lys Glu Val Pro Asp Gln Ser Asp Met Gly
                325             330             335

Ile Asn Ile Asn Gly Asp Ser Ala Gly His Met Thr Ala Ile Asn Leu
            340             345             350

Leu Thr Asp Gly Asn Asp Ser Tyr Gly Ala Glu Ser Tyr Gly Tyr Ser
        355             360             365

Gly Trp Cys Pro Thr Ala Met Thr Pro Ile Pro Phe Gln Phe Ser Ile
        370             375             380

Gly His Asp His Ser Arg Leu Trp Cys Lys Pro Glu Gln Asp Asn Ala
385             390             395             400

Val Val Ala Ala Leu His Asn Leu His His Leu Gln His Leu Pro Ala
                405             410             415

Pro Val Gly Thr His Asn Phe Phe Gln Pro Ser Pro Val Gln Asp Met
            420             425             430

```
Thr Gly Val Ala Asp Ala Ser Ser Pro Pro Val Glu Ser Asn Ser Phe
            435                 440                 445

Leu Tyr Asn Gly Asp Val Gly Tyr His Gly Ala Met Gly Gly Ser Tyr
450                 455                 460

Ala Met Pro Val Ala Thr Leu Val Glu Gly Asn Ser Ala Gly Ser Gly
465                 470                 475                 480

Tyr Gly Val Glu Glu Gly Thr Gly Ser Glu Ile Phe Gly Gly Arg Asn
                485                 490                 495

Leu Tyr Ser Leu Ser Gln Gly Ser Ser Gly Ala Asn Thr Gly Lys Ala
            500                 505                 510

Asp Ala Tyr Glu Ser Trp Asp Pro Ser Met Leu Val Ile Ser Gln Lys
        515                 520                 525

Ser Ala Asn Val Thr Val Cys His Gly Ala Pro Val Phe Ser Val Trp
    530                 535                 540

Lys
545

<210> SEQ ID NO 49
<211> LENGTH: 584
<212> TYPE: PRT
<213> ORGANISM: Arabidopsis thaliana

<400> SEQUENCE: 49

Met Asn Ser Met Asn Asn Trp Leu Gly Phe Ser Leu Ser Pro His Asp
1               5                   10                  15

Gln Asn His His Arg Thr Asp Val Asp Ser Ser Thr Thr Arg Thr Ala
            20                  25                  30

Val Asp Val Ala Gly Gly Tyr Cys Phe Asp Leu Ala Ala Pro Ser Asp
        35                  40                  45

Glu Ser Ser Ala Val Gln Thr Ser Phe Leu Ser Pro Phe Gly Val Thr
    50                  55                  60

Leu Glu Ala Phe Thr Arg Asp Asn Asn Ser His Ser Arg Asp Trp Asp
65                  70                  75                  80

Ile Asn Gly Gly Ala Cys Asn Asn Ile Asn Asn Glu Gln Asn Gly
                85                  90                  95

Pro Lys Leu Glu Asn Phe Leu Gly Arg Thr Thr Ile Tyr Asn Thr
            100                 105                 110

Asn Glu Thr Val Val Asp Gly Asn Gly Asp Cys Gly Gly Gly Asp Gly
        115                 120                 125

Gly Gly Gly Gly Ser Leu Gly Leu Ser Met Ile Lys Thr Trp Leu Ser
    130                 135                 140

Asn His Ser Val Ala Asn Ala Asn His Gln Asp Asn Gly Asn Gly Ala
145                 150                 155                 160

Arg Gly Leu Ser Leu Ser Met Asn Ser Ser Thr Ser Asp Ser Asn Asn
                165                 170                 175

Tyr Asn Asn Asn Asp Asp Val Val Gln Glu Lys Thr Ile Val Asp Val
            180                 185                 190

Val Glu Thr Thr Pro Lys Lys Thr Ile Glu Ser Phe Gly Gln Arg Thr
        195                 200                 205

Ser Ile Tyr Arg Gly Val Thr Arg His Arg Trp Thr Gly Arg Tyr Glu
    210                 215                 220

Ala His Leu Trp Asp Asn Ser Cys Lys Arg Glu Gly Gln Thr Arg Lys
225                 230                 235                 240

Gly Arg Gln Val Tyr Leu Gly Gly Tyr Asp Lys Glu Glu Lys Ala Ala
                245                 250                 255
```

Arg Ala Tyr Asp Leu Ala Ala Leu Lys Tyr Trp Gly Thr Thr Thr Thr
                260                 265                 270

Thr Asn Phe Pro Leu Ser Glu Tyr Glu Lys Glu Val Glu Glu Met Lys
                275                 280                 285

His Met Thr Arg Gln Glu Tyr Val Ala Ser Leu Arg Arg Lys Ser Ser
            290                 295                 300

Gly Phe Ser Arg Gly Ala Ser Ile Tyr Arg Gly Val Thr Arg His His
305                 310                 315                 320

Gln His Gly Arg Trp Gln Ala Arg Ile Gly Arg Val Ala Gly Asn Lys
                325                 330                 335

Asp Leu Tyr Leu Gly Thr Phe Gly Thr Gln Glu Glu Ala Ala Glu Ala
            340                 345                 350

Tyr Asp Ile Ala Ala Ile Lys Phe Arg Gly Leu Ser Ala Val Thr Asn
            355                 360                 365

Phe Asp Met Asn Arg Tyr Asn Val Lys Ala Ile Leu Glu Ser Pro Ser
370                 375                 380

Leu Pro Ile Gly Ser Ser Ala Lys Arg Leu Lys Asp Val Asn Asn Pro
385                 390                 395                 400

Val Pro Ala Met Met Ile Ser Asn Asn Val Ser Glu Ser Ala Asn Asn
                405                 410                 415

Val Ser Gly Trp Gln Asn Thr Ala Phe Gln His His Gln Gly Met Asp
                420                 425                 430

Leu Ser Leu Leu Gln Gln Gln Glu Arg Tyr Val Gly Tyr Tyr Asn
            435                 440                 445

Gly Gly Asn Leu Ser Thr Glu Ser Thr Arg Val Cys Phe Lys Gln Glu
            450                 455                 460

Glu Glu Gln Gln His Phe Leu Arg Asn Ser Pro Ser His Met Thr Asn
465                 470                 475                 480

Val Asp His His Ser Ser Thr Ser Asp Asp Ser Val Thr Val Cys Gly
                485                 490                 495

Asn Val Val Ser Tyr Gly Gly Tyr Gln Gly Phe Ala Ile Pro Val Gly
                500                 505                 510

Thr Ser Val Asn Tyr Asp Pro Phe Thr Ala Ala Glu Ile Ala Tyr Asn
            515                 520                 525

Ala Arg Asn His Tyr Tyr Ala Gln His Gln Gln Gln Gln Ile
            530                 535                 540

Gln Gln Ser Pro Gly Gly Asp Phe Pro Val Ala Ile Ser Asn Asn His
545                 550                 555                 560

Ser Ser Asn Met Tyr Phe His Gly Glu Gly Gly Glu Gly Ala Pro
                565                 570                 575

Thr Phe Ser Val Trp Asn Asp Thr
            580

<210> SEQ ID NO 50
<211> LENGTH: 527
<212> TYPE: PRT
<213> ORGANISM: Setaria italica

<400> SEQUENCE: 50

Met Gly Ser Thr Asn Asn Trp Leu Gly Phe Ala Ser Phe Ser Gly Ala
1               5                   10                  15

Ala Asp Asp Ala Ala Ile Leu Pro Pro Leu Pro Pro Ser Pro Arg Gly
            20                  25                  30

Asp Gly Ala Gly Ala Glu Pro Lys Leu Glu Asp Phe Leu Gly Leu Gln

```
            35                  40                  45
Glu Pro Ala Ala Thr Val Ala Ala Gly Arg Pro Phe Val Gly Thr Gly
 50                  55                  60

Gly Ala Ser Ser Ile Gly Leu Ser Met Ile Lys Asn Trp Leu Arg Ser
 65                  70                  75                  80

Gln Pro Ala Pro Glu Pro Ala Val Ala Ala Asp Ser Met Ala Leu Ala
                 85                  90                  95

Ala Val Ala Val Val Ser Pro Glu Gly Ser Gly Lys Val Thr Asp Asp
            100                 105                 110

Gly Ala Glu Ser Gly Gly Gly Ala Val Val Ala Ala Gln Gln Arg
        115                 120                 125

Lys Ala Ala Val Asp Thr Phe Gly Gln Arg Thr Ser Ile Tyr Arg
130                 135                 140

Gly Val Thr Lys His Arg Trp Thr Gly Arg Tyr Glu Ala His Leu Trp
145                 150                 155                 160

Asp Asn Ser Cys Arg Arg Glu Gly Gln Thr Arg Lys Gly Arg Gln Val
                165                 170                 175

Tyr Leu Gly Gly Tyr Asp Lys Glu Lys Ala Ala Arg Ala Tyr Asp
            180                 185                 190

Leu Ala Ala Leu Lys Tyr Trp Gly Thr Thr Thr Thr Asn Phe Gln
        195                 200                 205

Ile Ser Asn Tyr Glu Lys Glu Leu Glu Glu Met Lys His Met Ser Arg
210                 215                 220

Gln Glu Tyr Val Ala Ser Leu Arg Arg His Val Lys Ser Ser Gly Phe
225                 230                 235                 240

Ser Arg Gly Ala Ser Ile Tyr Arg Gly Val Thr Arg His His Gln His
                245                 250                 255

Gly Arg Trp Gln Ala Arg Ile Gly Arg Val Ala Gly Asn Lys Asp Leu
            260                 265                 270

Tyr Leu Gly Thr Phe Ser Thr Gln Glu Glu Ala Ala Glu Ala Tyr Asp
        275                 280                 285

Ile Ala Ala Ile Lys Phe Arg Gly Leu Asn Ala Val Thr Asn Phe Asp
290                 295                 300

Met Ser Arg Tyr Asp Val Lys Ser Ile Ile Glu Ser Ser Ser Leu Pro
305                 310                 315                 320

Val Gly Gly Thr Thr Lys Arg Leu Lys Asp Val Pro Asp Gln Ser Asp
                325                 330                 335

Met Gly Arg Asn Gly His Ser Ala Asp Ser Val Gly His Met Thr Ala
            340                 345                 350

Thr Asn Leu Leu Thr Asp Gly Ile Gly Ser Tyr Gly Pro Glu Asn Tyr
        355                 360                 365

Gly Tyr Ser Gly Trp Ser Pro Ala Ala Met Thr Ser Ile Pro Leu Gln
370                 375                 380

Phe Ser Asn Gly His Asp Gln Ser Arg Leu Trp Cys Lys Pro Glu Gln
385                 390                 395                 400

Asp Ser Ala Val Val Ala Ala His Asn Leu His Leu Gln His
                405                 410                 415

Phe Pro Ala Pro Gly Gly Thr His Asn Phe Gln Pro Ser Pro Ile
            420                 425                 430

Gln Asp Met Thr Gly Val Ala Asp Val Ser Pro Ser Val Asp Ser
        435                 440                 445

Asn Ser Phe Ser Tyr Asn Gly Ser Val Gly Tyr His Gly Ala Met Gly
450                 455                 460
```

```
Gly Gly Tyr Ala Met Pro Val Thr Thr Leu Val Glu Gly Asn Pro Ala
465                 470                 475                 480

Ala Ser Gly Tyr Gly Val Glu Glu Gly Thr Thr Asp Val Tyr Asp Cys
                485                 490                 495

Arg Asn Ile Tyr Tyr Leu Ser Gln Gly Ser Pro Gly Ala Asn Thr Gly
            500                 505                 510

Lys Pro Glu Ala Tyr Asp Gln Gln Gly Ala Gly Tyr Glu Ser Trp
        515                 520                 525

<210> SEQ ID NO 51
<211> LENGTH: 689
<212> TYPE: PRT
<213> ORGANISM: Medicago truncatula

<400> SEQUENCE: 51

Met Ala Ser Met Asn Leu Leu Gly Phe Ser Leu Ser Pro Gln Glu Gln
1               5                   10                  15

His Pro Ser Thr Gln Asp Gln Thr Val Ala Ser Arg Phe Gly Phe Asn
            20                  25                  30

Pro Asn Glu Ile Ser Gly Ser Asp Val Gln Gly Asp His Cys Tyr Asp
        35                  40                  45

Leu Ser Ser His Thr Thr Pro His His Ser Leu Asn Leu Ser His Pro
50                  55                  60

Phe Ser Ile Tyr Glu Ala Phe His Thr Asn Asn Ile His Thr Thr
65                  70                  75                  80

Gln Asp Trp Lys Glu Asn Tyr Asn Asn Gln Asn Leu Leu Leu Gly Thr
                85                  90                  95

Ser Cys Met Asn Gln Asn Val Asn Asn Asn Gln Gln Ala Gln Pro
            100                 105                 110

Lys Leu Glu Asn Phe Leu Gly Gly His Ser Phe Thr Asp His Gln Glu
        115                 120                 125

Tyr Gly Gly Ser Asn Ser Tyr Ser Ser Leu His Leu Pro Pro His Gln
    130                 135                 140

Pro Glu Ala Ser Cys Gly Gly Asp Gly Ser Thr Ser Asn Asn Asn
145                 150                 155                 160

Ser Ile Gly Leu Ser Met Ile Lys Thr Trp Leu Arg Asn Gln Pro Pro
                165                 170                 175

Pro Pro Glu Asn Asn Asn Asn Asn Asn Glu Ser Gly Ala Arg Val
            180                 185                 190

Gln Thr Leu Ser Leu Ser Met Ser Thr Gly Ser Gln Ser Ser Ser
        195                 200                 205

Val Pro Leu Leu Asn Ala Asn Val Met Ser Gly Glu Ile Ser Ser Ser
    210                 215                 220

Glu Asn Lys Gln Pro Pro Thr Thr Ala Val Val Leu Asp Ser Asn Gln
225                 230                 235                 240

Thr Ser Val Val Glu Ser Ala Val Pro Arg Lys Ser Val Asp Thr Phe
                245                 250                 255

Gly Gln Arg Thr Ser Ile Tyr Arg Gly Val Thr Arg His Arg Trp Thr
            260                 265                 270

Gly Arg Tyr Glu Ala His Leu Trp Asp Asn Ser Cys Arg Arg Glu Gly
        275                 280                 285

Gln Thr Arg Lys Gly Arg Gln Val Tyr Leu Gly Gly Tyr Asp Lys Glu
    290                 295                 300

Glu Lys Ala Ala Arg Ala Tyr Asp Leu Ala Ala Leu Lys Tyr Trp Gly
```

```
            305                 310                 315                 320
        Thr Thr Thr Thr Thr Asn Phe Pro Ile Ser His Tyr Glu Lys Glu Val
                        325                 330                 335
        Glu Glu Met Lys His Met Thr Arg Gln Glu Tyr Val Ala Ser Leu Arg
                    340                 345                 350
        Arg Lys Ser Ser Gly Phe Ser Arg Gly Ala Ser Ile Tyr Arg Gly Val
                355                 360                 365
        Thr Arg His His Gln His Gly Arg Trp Gln Ala Arg Ile Gly Arg Val
            370                 375                 380
        Ala Gly Asn Lys Asp Leu Tyr Leu Gly Thr Phe Ser Thr Gln Glu Glu
        385                 390                 395                 400
        Ala Ala Glu Ala Tyr Asp Val Ala Ala Ile Lys Phe Arg Gly Leu Ser
                        405                 410                 415
        Ala Val Thr Asn Phe Asp Met Ser Arg Tyr Asp Val Lys Thr Ile Leu
                    420                 425                 430
        Glu Ser Ser Thr Leu Pro Ile Gly Gly Ala Ala Lys Arg Leu Lys Asp
                435                 440                 445
        Met Glu Gln Val Glu Leu Asn His Val Asn Val Asp Ile Ser His Arg
            450                 455                 460
        Thr Glu Gln Asp His Ser Ile Ile Asn Asn Thr Ser His Leu Thr Glu
        465                 470                 475                 480
        Gln Ala Ile Tyr Ala Ala Thr Asn Ala Ser Asn Trp His Ala Leu Ser
                        485                 490                 495
        Phe Gln His Gln Gln Pro His His Tyr Asn Ala Asn Asn Met Gln
                    500                 505                 510
        Leu Gln Asn Tyr Pro Tyr Gly Thr Gln Thr Gln Lys Leu Trp Cys Lys
                515                 520                 525
        Gln Glu Gln Asp Ser Asp His Ser Thr Tyr Thr Thr Ala Thr Asp
            530                 535                 540
        Ile His Gln Leu Gln Leu Gly Asn Asn Asn Asn Thr His Asn Phe
        545                 550                 555                 560
        Phe Gly Leu Gln Asn Ile Met Ser Met Asp Ser Ala Ser Met Asp Asn
                        565                 570                 575
        Ser Ser Gly Ser Asn Ser Val Val Tyr Gly Gly Asp His Gly Gly
                    580                 585                 590
        Tyr Gly Asn Gly Gly Tyr Met Ile Pro Met Ala Ile Ala Asn Asp
                595                 600                 605
        Gly Asn Gln Asn Pro Arg Ser Asn Asn Asn Phe Gly Glu Ser Glu Ile
            610                 615                 620
        Lys Gly Phe Gly Tyr Glu Asn Val Phe Gly Thr Thr Thr Asp Pro Tyr
        625                 630                 635                 640
        His Ala Gln Ala Ala Arg Asn Leu Tyr Tyr Gln Pro Gln Gln Leu Ser
                        645                 650                 655
        Val Asp Gln Gly Ser Asn Trp Val Pro Thr Ala Ile Pro Thr Leu Ala
                    660                 665                 670
        Pro Arg Thr Thr Asn Val Ser Leu Cys Pro Pro Phe Thr Leu Leu His
                675                 680                 685
        Glu

<210> SEQ ID NO 52
<211> LENGTH: 700
<212> TYPE: PRT
<213> ORGANISM: Sorghum bicolor
```

```
<400> SEQUENCE: 52

Met Ala Thr Val Asn Asn Trp Leu Ala Phe Ser Leu Ser Pro Gln Glu
1               5                   10                  15

Leu Pro Pro Thr Gln Thr Asp Ser Thr Leu Ile Ser Ala Ala Thr Thr
            20                  25                  30

Asp Val Ser Gly Asp Val Cys Phe Asn Ile Pro Gln Asp Trp Ser
        35                  40                  45

Met Arg Gly Ser Glu Leu Ser Ala Leu Val Ala Glu Pro Lys Leu Glu
        50                  55                  60

Asp Phe Leu Gly Gly Ile Ser Phe Ser Glu Gln His His Lys Ala Asn
65                      70                  75                  80

Cys Asn Met Ile Pro Ser Thr Ser Ser Thr Ala Cys Tyr Ala Ser Ser
                85                  90                  95

Gly Ala Thr Ala Gly Tyr His His Gln Leu Tyr His Gln Pro Thr Ser
                100                 105                 110

Ser Ala Leu His Phe Ala Asp Ser Val Met Val Ala Ser Ser Ala Gly
            115                 120                 125

Gly Val His Asp Gly Gly Ala Met Leu Ser Ala Ala Ser Ala Asn Gly
        130                 135                 140

Ser Ala Gly Ala Gly Ala Ala Ser Ala Asn Gly Ser Gly Ser Ile Gly
145                 150                 155                 160

Leu Ser Met Ile Lys Asn Trp Leu Arg Ser Gln Pro Ala Pro Met Gln
                165                 170                 175

Pro Arg Val Ala Ala Ala Glu Ser Val Gln Gly Leu Ser Leu Ser Met
            180                 185                 190

Asn Met Ala Gly Ala Thr Gln Gly Ala Ala Gly Met Pro Leu Leu Ala
        195                 200                 205

Gly Glu Arg Gly Arg Ala Pro Glu Ser Val Ser Thr Ser Ala Gln Gly
210                 215                 220

Gly Ala Val Val Thr Ala Pro Lys Glu Asp Ser Gly Gly Ser Gly Val
225                 230                 235                 240

Ala Ala Thr Gly Ala Leu Val Ala Val Ser Thr Asp Thr Gly Gly Ser
                245                 250                 255

Gly Ala Ser Ala Asp Asn Thr Ala Arg Lys Thr Val Asp Thr Phe Gly
            260                 265                 270

Gln Arg Thr Ser Ile Tyr Arg Gly Val Thr Arg His Arg Trp Thr Gly
        275                 280                 285

Arg Tyr Glu Ala His Leu Trp Asp Asn Ser Cys Arg Arg Glu Gly Gln
290                 295                 300

Thr Arg Lys Gly Arg Gln Gly Gly Tyr Asp Lys Glu Glu Lys Ala Ala
305                 310                 315                 320

Arg Ala Tyr Asp Leu Ala Ala Leu Lys Tyr Trp Gly Pro Thr Thr Thr
                325                 330                 335

Thr Asn Phe Pro Val Asn Asn Tyr Glu Lys Glu Leu Glu Asp Met Lys
            340                 345                 350

His Met Thr Arg Gln Glu Phe Val Ala Ser Leu Arg Arg Lys Ser Ser
        355                 360                 365

Gly Phe Ser Arg Gly Ala Ser Ile Tyr Arg Gly Val Thr Arg His His
370                 375                 380

Gln His Gly Arg Trp Gln Ala Arg Ile Gly Arg Val Ala Gly Asn Lys
385                 390                 395                 400

Asp Leu Tyr Leu Gly Thr Phe Ser Thr Gln Glu Glu Ala Ala Glu Ala
                405                 410                 415
```

-continued

```
Tyr Asp Ile Ala Ala Ile Lys Phe Arg Gly Leu Asn Ala Val Thr Asn
            420                 425                 430

Phe Asp Met Ser Arg Tyr Asp Val Lys Ser Ile Leu Asp Ser Ser Ala
            435                 440                 445

Leu Pro Ile Gly Ser Ala Ala Lys Arg Leu Lys Glu Ala Glu Ala Ala
450                 455                 460

Ala Ser Ala Gln His His Ala Gly Val Val Ser Tyr Asp Val Gly Arg
465                 470                 475                 480

Ile Ala Ser Gln Leu Gly Asp Gly Ala Leu Ala Ala Ala Tyr Gly
            485                 490                 495

Ala His Tyr His Gly Ala Trp Pro Thr Ile Ala Phe Gln Pro Ser Ala
            500                 505                 510

Ala Thr Gly Leu Tyr His Pro Tyr Ala Gln Pro Met Arg Gly Trp Cys
            515                 520                 525

Lys Gln Glu Gln Asp His Ala Val Ile Ala Ala His Ser Leu Gln
            530                 535                 540

Glu Leu His His Leu Asn Leu Gly Ala Ala Ala Gly Ala His Asp Phe
545                 550                 555                 560

Phe Ser Ala Gly Gln Gln Ala Ala Met His Gly Leu Gly Ser Met Asp
            565                 570                 575

Asn Ala Ser Leu Glu His Ser Thr Gly Ser Asn Ser Val Val Tyr Asn
            580                 585                 590

Gly Val Gly Asp Ser Asn Gly Ser Thr Val Val Gly Ser Gly Gly Tyr
            595                 600                 605

Met Met Pro Met Ser Ala Ala Thr Ala Thr Ala Thr Ala Met Val
            610                 615                 620

Ser His Glu Gln Val His Ala Arg Ala Gln Gly Asp His His Asp Glu
625                 630                 635                 640

Ala Lys Gln Ala Ala Gln Met Gly Tyr Glu Ser Tyr Leu Val Asn Ala
            645                 650                 655

Glu Asn Tyr Gly Gly Gly Arg Met Ser Ala Ala Trp Ala Thr Val Ser
            660                 665                 670

Ala Pro Pro Ala Ala Ser Ser Asn Asp Asn Met Ala Asp Val Gly His
            675                 680                 685

Gly Gly Ala Gln Leu Phe Ser Val Trp Asn Asp Thr
690                 695                 700

<210> SEQ ID NO 53
<211> LENGTH: 559
<212> TYPE: PRT
<213> ORGANISM: Oryza sativa

<400> SEQUENCE: 53

Met Ala Ser Ile Thr Asn Trp Leu Gly Phe Ser Ser Ser Phe Ser
1               5                   10                  15

Gly Ala Gly Ala Asp Pro Val Leu Pro His Pro Leu Gln Glu Trp
            20                  25                  30

Gly Ser Ala Tyr Glu Gly Gly Thr Val Ala Ala Ala Gly Gly Glu
        35                  40                  45

Glu Thr Ala Ala Pro Lys Leu Glu Asp Phe Leu Gly Met Gln Val Gln
            50                  55                  60

Gln Glu Thr Ala Ala Ala Ala Gly His Gly Arg Gly Gly Ser Ser
65                  70                  75                  80

Ser Val Val Gly Leu Ser Met Ile Lys Asn Trp Leu Arg Ser Gln Pro
```

-continued

```
                85                  90                  95
Pro Pro Ala Val Val Gly Gly Glu Asp Ala Met Met Ala Leu Ala Val
            100                 105                 110
Ser Thr Ser Ala Ser Pro Val Asp Ala Thr Val Pro Ala Cys Ile
            115                 120                 125
Ser Pro Asp Gly Met Gly Ser Lys Ala Ala Asp Gly Gly Ala Ala
130                 135                 140
Glu Ala Ala Ala Ala Ala Ala Gln Arg Met Lys Ala Ala Met Asp
145                 150                 155                 160
Thr Phe Gly Gln Arg Thr Ser Ile Tyr Arg Gly Val Thr Lys His Arg
                165                 170                 175
Trp Thr Gly Arg Tyr Glu Ala His Leu Trp Asp Asn Ser Cys Arg Arg
                180                 185                 190
Glu Gly Gln Thr Arg Lys Gly Arg Gln Val Asn Ala Gly Gly Tyr Asp
                195                 200                 205
Lys Glu Glu Lys Ala Ala Arg Ala Tyr Asp Leu Ala Ala Leu Lys Tyr
210                 215                 220
Trp Gly Thr Thr Thr Thr Thr Asn Phe Pro Val Ser Asn Tyr Glu Lys
225                 230                 235                 240
Glu Leu Asp Glu Met Lys His Met Asn Arg Gln Glu Phe Val Ala Ser
                245                 250                 255
Leu Arg Arg Lys Ser Ser Gly Phe Ser Arg Gly Ala Ser Ile Tyr Arg
                260                 265                 270
Gly Val Thr Arg His His Gln His Gly Arg Trp Gln Ala Arg Ile Gly
                275                 280                 285
Arg Val Ala Gly Asn Lys Asp Leu Tyr Leu Gly Thr Phe Gly Thr Gln
                290                 295                 300
Glu Glu Ala Ala Glu Ala Tyr Asp Ile Ala Ala Ile Lys Phe Arg Gly
305                 310                 315                 320
Leu Asn Ala Val Thr Asn Phe Asp Met Ser Arg Tyr Asp Val Lys Ser
                325                 330                 335
Ile Ile Glu Ser Ser Asn Leu Pro Ile Gly Thr Gly Thr Thr Arg Arg
                340                 345                 350
Leu Lys Asp Ser Ser Asp His Thr Asp Asn Val Met Asp Ile Asn Val
                355                 360                 365
Asn Thr Glu Pro Asn Asn Val Val Ser Ser His Phe Thr Asn Gly Val
                370                 375                 380
Gly Asn Tyr Gly Ser Gln His Tyr Gly Tyr Asn Gly Trp Ser Pro Ile
385                 390                 395                 400
Ser Met Gln Pro Ile Pro Ser Gln Tyr Ala Asn Gly Gln Pro Arg Ala
                405                 410                 415
Trp Leu Lys Gln Glu Gln Asp Ser Ser Val Val Thr Ala Ala Gln Asn
                420                 425                 430
Leu His Asn Leu His His Phe Ser Ser Leu Gly Tyr Thr His Asn Phe
                435                 440                 445
Phe Gln Gln Ser Asp Val Pro Asp Val Thr Gly Phe Val Asp Ala Pro
            450                 455                 460
Ser Arg Ser Ser Asp Ser Tyr Ser Phe Arg Tyr Asn Gly Thr Asn Gly
465                 470                 475                 480
Phe His Gly Leu Pro Gly Gly Ile Ser Tyr Ala Met Pro Val Ala Thr
                485                 490                 495
Ala Val Asp Gln Gly Gln Gly Ile His Gly Tyr Gly Glu Asp Gly Val
                500                 505                 510
```

Ala Gly Ile Asp Thr Thr His Asp Leu Tyr Gly Ser Arg Asn Val Tyr
        515                 520                 525

Tyr Leu Ser Glu Gly Ser Leu Leu Ala Asp Val Glu Lys Glu Gly Asp
    530                 535                 540

Tyr Gly Gln Ser Val Gly Gly Asn Ser Trp Val Leu Pro Thr Pro
545                 550                 555

<210> SEQ ID NO 54
<211> LENGTH: 545
<212> TYPE: PRT
<213> ORGANISM: Pennisetum squamulatum

<400> SEQUENCE: 54

Met Gly Ser Thr Asn Asn Trp Leu Arg Phe Ala Ser Phe Ser Gly Gly
1               5                   10                  15

Gly Gly Ala Lys Asp Ala Ala Leu Leu Pro Leu Pro Pro Ser Pro
            20                  25                  30

Arg Gly Asp Val Asp Glu Ala Gly Ala Glu Pro Lys Leu Glu Asp Phe
        35                  40                  45

Leu Gly Leu Gln Glu Pro Ser Ala Ala Val Gly Ala Gly Arg Pro
    50                  55                  60

Phe Ala Val Gly Gly Gly Ala Ser Ser Ile Gly Leu Ser Met Ile Arg
65                  70                  75                  80

Asn Trp Leu Arg Ser Gln Pro Ala Pro Ala Gly Pro Ala Ala Gly Val
                85                  90                  95

Asp Ser Met Val Leu Ala Ala Ala Ala Ser Thr Glu Val Ala Gly
            100                 105                 110

Asp Gly Ala Glu Gly Gly Ala Val Ala Asp Ala Val Gln Gln Arg
        115                 120                 125

Lys Ala Ala Val Asp Thr Phe Gly Gln Arg Thr Ser Ile Tyr Arg
    130                 135                 140

Gly Val Thr Lys His Arg Trp Thr Gly Arg Tyr Glu Ala His Leu Trp
145                 150                 155                 160

Asp Asn Ser Cys Arg Arg Glu Gly Gln Thr Arg Lys Gly Arg Gln Val
                165                 170                 175

Tyr Leu Gly Gly Tyr Asp Lys Glu Glu Lys Ala Ala Arg Ala Tyr Asp
            180                 185                 190

Leu Ala Ala Leu Lys Tyr Arg Gly Thr Thr Thr Thr Asn Phe Pro
        195                 200                 205

Met Ser Asn Tyr Glu Lys Glu Leu Glu Met Lys His Met Ser Arg
    210                 215                 220

Gln Glu Tyr Val Ala Ser Leu Arg Arg Lys Ser Ser Gly Phe Ser Arg
225                 230                 235                 240

Gly Ala Ser Ile Tyr Arg Gly Val Thr Arg His His Gln His Gly Arg
                245                 250                 255

Trp Gln Ala Arg Ile Gly Ser Val Ala Gly Asn Lys Asp Leu Tyr Leu
            260                 265                 270

Gly Thr Phe Ser Thr Gln Glu Glu Ala Ala Glu Ala Tyr Asp Ile Ala
        275                 280                 285

Ala Ile Lys Phe Arg Gly Leu Asn Ala Val Thr Asn Phe Asp Met Ser
    290                 295                 300

Arg Tyr Asp Val Lys Ser Ile Ile Glu Ser Ser Ser Leu Pro Val Gly
305                 310                 315                 320

Gly Thr Pro Lys Arg Leu Lys Glu Val Pro Asp Gln Ser Asp Met Gly

```
                    325                 330                 335
Ile Asn Ile Asn Gly Asp Ser Ala Gly His Met Thr Ala Ile Asn Leu
            340                 345                 350
Leu Thr Asp Gly Asn Asp Ser Tyr Gly Ala Glu Ser Tyr Gly Tyr Ser
            355                 360                 365
Gly Trp Cys Pro Thr Ala Met Thr Pro Ile Pro Phe Gln Phe Ser Asn
            370                 375                 380
Gly His Asp His Ser Arg Leu Trp Cys Lys Pro Glu Gln Asp Asn Ala
385                 390                 395                 400
Val Val Ala Ala Leu His Asn Leu His His Leu Gln His Leu Pro Ala
                405                 410                 415
Pro Val Gly Thr His Asn Phe Phe Gln Pro Ser Pro Val Gln Asp Met
                420                 425                 430
Thr Gly Val Ala Asp Ala Ser Ser Pro Pro Val Glu Ser Asn Ser Phe
            435                 440                 445
Leu Tyr Asn Gly Asp Val Gly Tyr His Gly Ala Met Gly Gly Ser Tyr
450                 455                 460
Ala Met Pro Val Ala Thr Leu Val Glu Gly Asn Ser Ala Gly Ser Gly
465                 470                 475                 480
Tyr Gly Val Glu Glu Gly Thr Gly Ser Glu Ile Phe Gly Gly Arg Asn
                485                 490                 495
Leu Tyr Ser Leu Ser Gln Gly Ser Ser Gly Ala Asn Thr Gly Lys Ala
            500                 505                 510
Asp Ala Tyr Glu Ser Trp Asp Pro Ser Met Leu Val Ile Ser Gln Lys
            515                 520                 525
Ser Ala Asn Val Thr Val Cys His Gly Ala Pro Val Phe Ser Val Trp
        530                 535                 540
Lys
545

<210> SEQ ID NO 55
<211> LENGTH: 686
<212> TYPE: PRT
<213> ORGANISM: Medicago truncatula

<400> SEQUENCE: 55

Met Asn Leu Leu Gly Phe Ser Leu Ser Pro Gln Glu Gln His Pro Ser
1               5                   10                  15
Thr Gln Asp Gln Thr Val Ala Ser Arg Phe Gly Phe Asn Pro Asn Glu
                20                  25                  30
Ile Ser Gly Ser Asp Val Gln Gly Asp His Cys Tyr Asp Leu Ser Ser
            35                  40                  45
His Thr Thr Pro His His Ser Leu Asn Leu Ser His Pro Phe Ser Ile
        50                  55                  60
Tyr Glu Ala Phe His Thr Asn Asn Ile His Thr Thr Gln Asp Trp
65                  70                  75                  80
Lys Glu Asn Tyr Asn Asn Gln Asn Leu Leu Gly Thr Ser Cys Met
                85                  90                  95
Asn Gln Asn Val Asn Asn Asn Gln Gln Ala Gln Pro Lys Leu Glu
            100                 105                 110
Asn Phe Leu Gly Gly His Ser Phe Thr Asp His Gln Glu Tyr Gly Gly
        115                 120                 125
Ser Asn Ser Tyr Ser Ser Leu His Leu Pro Pro His Gln Pro Glu Ala
    130                 135                 140
```

```
Ser Cys Gly Gly Gly Asp Gly Ser Thr Ser Asn Asn Ser Ile Gly
145                 150                 155                 160

Leu Ser Met Ile Lys Thr Trp Leu Arg Asn Gln Pro Pro Pro Glu
            165                 170                 175

Asn Asn Asn Asn Asn Asn Glu Ser Gly Ala Arg Val Gln Thr Leu
        180                 185                 190

Ser Leu Ser Met Ser Thr Gly Ser Gln Ser Ser Ser Val Pro Leu
    195                 200                 205

Leu Asn Ala Asn Val Met Ser Gly Glu Ile Ser Ser Ser Glu Asn Lys
    210                 215                 220

Gln Pro Pro Thr Thr Ala Val Val Leu Asp Ser Asn Gln Thr Ser Val
225                 230                 235                 240

Val Glu Ser Ala Val Pro Arg Lys Ser Val Asp Thr Phe Gly Gln Arg
                245                 250                 255

Thr Ser Ile Tyr Arg Gly Val Thr Arg His Arg Trp Thr Gly Arg Tyr
            260                 265                 270

Glu Ala His Leu Trp Asp Asn Ser Cys Arg Arg Glu Gly Gln Thr Arg
        275                 280                 285

Lys Gly Arg Gln Val Tyr Leu Gly Gly Tyr Asp Lys Glu Glu Lys Ala
    290                 295                 300

Ala Arg Ala Tyr Asp Leu Ala Ala Leu Lys Tyr Trp Gly Thr Thr Thr
305                 310                 315                 320

Thr Thr Asn Phe Pro Ile Ser His Tyr Glu Lys Glu Val Glu Glu Met
                325                 330                 335

Lys His Met Thr Arg Gln Glu Tyr Val Ala Ser Leu Arg Arg Lys Ser
            340                 345                 350

Ser Gly Phe Ser Arg Gly Ala Ser Ile Tyr Arg Gly Val Thr Arg His
        355                 360                 365

His Gln His Gly Arg Trp Gln Ala Arg Ile Gly Arg Val Ala Gly Asn
    370                 375                 380

Lys Asp Leu Tyr Leu Gly Thr Phe Ser Thr Gln Glu Glu Ala Ala Glu
385                 390                 395                 400

Ala Tyr Asp Val Ala Ala Ile Lys Phe Arg Gly Leu Ser Ala Val Thr
                405                 410                 415

Asn Phe Asp Met Ser Arg Tyr Asp Val Lys Thr Ile Leu Glu Ser Ser
            420                 425                 430

Thr Leu Pro Ile Gly Gly Ala Ala Lys Arg Leu Lys Asp Met Glu Gln
        435                 440                 445

Val Glu Leu Asn His Val Asn Val Asp Ile Ser His Arg Thr Glu Gln
    450                 455                 460

Asp His Ser Ile Ile Asn Asn Thr Ser His Leu Thr Glu Gln Ala Ile
465                 470                 475                 480

Tyr Ala Ala Thr Asn Ala Ser Asn Trp His Ala Leu Ser Phe Gln His
                485                 490                 495

Gln Gln Pro His His Tyr Asn Ala Asn Asn Met Gln Leu Gln Asn
            500                 505                 510

Tyr Pro Tyr Gly Thr Gln Thr Gln Lys Leu Trp Cys Lys Gln Glu Gln
        515                 520                 525

Asp Ser Asp His Ser Thr Tyr Thr Thr Ala Thr Asp Ile His Gln
    530                 535                 540

Leu Gln Leu Gly Asn Asn Asn Asn Thr His Asn Phe Phe Gly Leu
545                 550                 555                 560

Gln Asn Ile Met Ser Met Asp Ser Ala Ser Met Asp Asn Ser Ser Gly
```

```
                  565                 570                 575
Ser Asn Ser Val Val Tyr Gly Gly Asp His Gly Tyr Gly Gly
                580                 585                 590

Asn Gly Gly Tyr Met Ile Pro Met Ala Ile Ala Asn Asp Gly Asn Gln
                595                 600                 605

Asn Pro Arg Ser Asn Asn Phe Gly Glu Ser Glu Ile Lys Gly Phe
        610                 615                 620

Gly Tyr Glu Asn Val Phe Gly Thr Thr Thr Asp Pro Tyr His Ala Gln
625                 630                 635                 640

Ala Ala Arg Asn Leu Tyr Tyr Gln Pro Gln Gln Leu Ser Val Asp Gln
                645                 650                 655

Gly Ser Asn Trp Val Pro Thr Ala Ile Pro Thr Leu Ala Pro Arg Thr
                660                 665                 670

Thr Asn Val Ser Leu Cys Pro Pro Phe Thr Leu Leu His Glu
                675                 680                 685

<210> SEQ ID NO 56
<211> LENGTH: 689
<212> TYPE: PRT
<213> ORGANISM: Brachypodium distachyon

<400> SEQUENCE: 56

Met Ala Ser Gly Asn Asn Trp Leu Glu Phe Ser Leu Ser Gly Gln Glu
1               5                   10                  15

Asn Pro Gln Pro His Arg Asp Ser Ser Pro Val Ala Ala Ile Asp Ile
                20                  25                  30

Ser Gly Ser Gly Asp Phe Tyr Gly Leu Pro Thr Gln Pro Val Pro Asp
            35                  40                  45

Thr Gln Leu Gly Met Pro Gly His His Ala Ser Tyr Gly Val Met Glu
        50                  55                  60

Ala Phe Asn Arg Gly Thr His Glu Thr His Asp Trp Ser Asn Met Arg
65                  70                  75                  80

Gly Leu Asp Tyr Asn Gly Gly Ser Glu Leu Ser Met Leu Val Gly
                85                  90                  95

Ser Ser Ala Val Gly Gly Lys Ile Arg Gly Ala Val Glu Glu Ile Thr
                100                 105                 110

Glu Pro Lys Leu Glu Asp Phe Leu Gly Gly Asn Ser Phe Val Asp Ser
            115                 120                 125

Glu Gln Asp Gln Ala Gly Ala Gly Gly Phe Leu Phe Ser Gly Val Pro
        130                 135                 140

Met Ala Pro Met Ala Gly Ser Asn Ser Gly Ser Asn Thr Met Glu Leu
145                 150                 155                 160

Ser Met Ile Lys Thr Trp Leu Arg Asn Asn Gln Asn His Val Ser Gln
                165                 170                 175

Pro His Pro Gln Gln His Gln Pro Gln Pro His Glu Glu Met Ser Met
            180                 185                 190

Ser Thr Asp Ala Ser Ala Ser Ser Phe Gly Asp Ala Leu Gly Arg Asn
        195                 200                 205

Gly Val Val Pro Ala Ala Gly Ser Ser Gln Ser Gln Ser Leu Ala Leu
    210                 215                 220

Ser Met Ser Thr Gly Ser Gly Ser Ser His Leu Pro Met Val Val Ala
225                 230                 235                 240

Gly Gly Ser Ala Ala Val Val Gly Ala Ala Asp Gln Pro Glu Ser Ser
                245                 250                 255
```

```
Ser Ser Glu Asn Lys Arg Ala Ser Gly Ala Met Asp Ser Pro Gly Gly
            260                 265                 270

Ala Val Glu Ala Val Ala Arg Lys Ser Ile Asp Thr Phe Gly Gln Arg
        275                 280                 285

Thr Ser Ile Tyr Arg Gly Val Thr Arg His Arg Trp Thr Gly Arg Tyr
    290                 295                 300

Glu Ala His Leu Trp Asp Asn Ser Cys Arg Arg Glu Gly Gln Ser Arg
305                 310                 315                 320

Lys Gly Arg Gln Gly Gly Tyr Asp Lys Glu Asp Lys Ala Ala Arg Ala
                325                 330                 335

Tyr Asp Leu Ala Ala Leu Lys Tyr Trp Gly Thr Thr Thr Thr Thr Asn
            340                 345                 350

Phe Pro Ile Asn Thr Tyr Glu Lys Glu Val Asp Glu Met Lys His Met
        355                 360                 365

Thr Arg Gln Glu Tyr Ile Ala Tyr Leu Arg Arg Asn Ser Ser Gly Phe
    370                 375                 380

Ser Arg Gly Ala Ser Lys Tyr Arg Gly Val Thr Arg His His Gln His
385                 390                 395                 400

Gly Arg Trp Gln Ala Arg Ile Gly Arg Val Ala Gly Asn Lys Asp Leu
                405                 410                 415

Tyr Leu Gly Thr Phe Ser Thr Glu Glu Glu Ala Ala Glu Ala Tyr Asp
            420                 425                 430

Ile Ala Ala Ile Lys Phe Arg Gly Leu Asn Ala Val Thr Asn Phe Asp
        435                 440                 445

Met Asn Arg Tyr Asp Val Lys Ser Ile Leu Glu Ser Ser Thr Leu Pro
    450                 455                 460

Val Gly Gly Ala Ala Arg Arg Leu Lys Asp Ala Pro Glu Ala Thr Ile
465                 470                 475                 480

Trp Arg Ala Gly Asp Met Asp Ala Gly Gly Ser Ser Ile Ser His Gln
                485                 490                 495

Leu Thr Asn Asn Val Gly Met Gly Gly Met Gly Pro Tyr Ala Gly Ser
            500                 505                 510

Tyr His Gln Gly His Gly Trp Pro Ser Thr Ile Val Phe Gln His Gln
        515                 520                 525

Pro Ser Pro Leu Ser Val His Tyr Pro Tyr Ala Leu His Gln Pro Pro
    530                 535                 540

Arg Gly Trp Cys Lys Pro Glu Gln Asp Val Val Ala Ala Ser His
545                 550                 555                 560

Ser Leu Gln Glu Leu Gln Gln Leu His Leu Gly Thr Ala His Asn Phe
            565                 570                 575

Phe Gln Gln Ala Ser Ala Gly Ser Thr Val Tyr Asn Gly Gly Ile Asn
        580                 585                 590

Gly Ala Gly Phe Leu Met Pro Ala Pro Ala Ser Thr Val Val Ala Glu
    595                 600                 605

Gln Gly His Ser Ser Thr Ala Thr Asn Gln Gly Ser Ile Cys Ser Tyr
610                 615                 620

Gly Asp Asp Glu Glu Gly Lys Leu Ile Gly Ile Gly Tyr Asp Ala Met
625                 630                 635                 640

Thr Met Ala Ser Thr Gly Asp Pro Tyr Ala Ala Arg Ala Ala Gly
                645                 650                 655

Gly Tyr Gly Gln Leu Pro Gln Gly Ser Ala Ser Thr Val Ser Ile Ala
            660                 665                 670

Arg Ala Asn Gly Cys Ser Asn Asn Trp Thr Ser Pro Phe Asn Gly Met
```

Gly

<210> SEQ ID NO 57
<211> LENGTH: 675
<212> TYPE: PRT
<213> ORGANISM: Panicum virgatum

<400> SEQUENCE: 57

```
Met Ala Ser Ala Asn Asn Trp Leu Gly Phe Ser Leu Ser Gly Gln Glu
1               5                   10                  15

Asn Pro Gln Pro Asn Gln Asp Ser Ser Pro Ala Ala Gly Ile Asp Ile
            20                  25                  30

Ser Gly Ala Ser Asp Phe Tyr Gly Leu Thr Thr Gln Gln Gly Ser Asp
        35                  40                  45

Gly His Leu Gly Val Pro Gly Leu Arg Asp Asp His Ala Ser Tyr Gly
    50                  55                  60

Ile Met Glu Ala Phe Asn Arg Gly Lys Gln Glu Thr Gln Asp Trp Asn
65                  70                  75                  80

Met Arg Gly Leu Asp Tyr Asn Gly Gly Ala Ser Glu Leu Ser Met Leu
                85                  90                  95

Val Gly Ser Ser Gly Gly Ser Gly Lys Arg Ala Val Gly Asp Ser
            100                 105                 110

Glu Pro Lys Leu Glu Asp Phe Leu Gly Gly Asn Ser Phe Val Ser Glu
            115                 120                 125

Gln Asp Gln Ser Gly Gly Tyr Leu Phe Ser Gly Val Pro Met Ala Ser
    130                 135                 140

Ser Thr Asn Ser Asn Ser Gly Ser Asn Thr Met Glu Ile Ser Met Ile
145                 150                 155                 160

Lys Thr Trp Leu Arg Asn Asn Asn Gln Leu Pro Gln Pro Gln Pro Pro
                165                 170                 175

Ala Thr Thr His Gln Pro Gln Pro Glu Glu Ile Ser Thr Asp Ala Ser
            180                 185                 190

Ala Ser Ser Phe Gly Cys Ala Asn Gly Thr Val Ala Gly Gly Ser Ser
        195                 200                 205

Gln Ser Leu Ala Leu Ser Ile Ser Thr Gly Ser His Leu Pro Met Val
    210                 215                 220

Val Ala Gly Gly Gly Ala Ser Gly Ala Ala Ala Ser Asp Ser Thr
225                 230                 235                 240

Ser Ser Glu Asn Lys Arg Ala Asn Gly Ala Met Asp Ser Pro Ser Ser
                245                 250                 255

Ala Ile Glu Ala Val Pro Arg Lys Ser Ile Asp Thr Phe Gly Gln Arg
            260                 265                 270

Thr Ser Ile Tyr Arg Gly Val Thr Arg His Arg Trp Thr Gly Arg Tyr
        275                 280                 285

Glu Ala His Leu Trp Asp Asn Ser Cys Arg Arg Glu Gly Gln Ser Arg
    290                 295                 300

Lys Gly Arg Gln Gly Gly Tyr Asp Lys Glu Asp Lys Ala Ala Arg Ala
305                 310                 315                 320

Tyr Asp Leu Ala Ala Leu Lys Tyr Trp Gly Thr Thr Thr Thr Asn
                325                 330                 335

Phe Pro Ile Ser Asn Tyr Glu Lys Glu Leu Glu Glu Met Lys His Met
            340                 345                 350

Thr Arg Gln Glu Tyr Ile Ala Tyr Leu Arg Arg Asn Ser Ser Gly Phe
```

355                 360                 365
Ser Arg Gly Ala Ser Lys Tyr Arg Gly Val Thr Arg His His Gln His
            370                 375                 380

Gly Arg Trp Gln Ala Arg Ile Gly Arg Val Ala Gly Asn Lys Asp Leu
385                 390                 395                 400

Tyr Leu Gly Thr Phe Ser Thr Glu Glu Ala Glu Ala Tyr Asp
                405                 410                 415

Ile Ala Ala Ile Lys Phe Arg Gly Leu Asn Ala Val Thr Asn Phe Asp
            420                 425                 430

Met Ser Arg Tyr Asp Val Lys Ser Ile Leu Glu Ser Thr Leu Pro
            435                 440                 445

Val Gly Gly Ala Ala Arg Arg Leu Lys Asp Ala Val Asp His Val Glu
            450                 455                 460

Ala Gly Gly Ala Thr Ile Trp Arg Ala Asp Met Asp Gly Ala Val Ile
465                 470                 475                 480

Ser Gln Leu Ala Asp Ala Gly Ile Gly Ala Tyr Ala Ser Tyr Gly Ala
                485                 490                 495

His His Ala Trp Pro Thr Ile Ala Phe Gln Gln Pro Ser Pro Leu Thr
            500                 505                 510

Val His Tyr Pro Tyr Gly His Ala Pro Pro Arg Gly Trp Cys Lys Pro
            515                 520                 525

Glu Gln Asp Ala Ala Ala Ala Ala Ala His Ser Leu Gln Asp
            530                 535                 540

Leu Gln Gln Leu His Leu Gly Ser Ala Ala His His Asn Phe Phe Gln
545                 550                 555                 560

Ala Ser Ser Ser Thr Val Tyr Asn Gly Ala Ala Gly Tyr His
                565                 570                 575

Gln Ala Gly Leu Gly Gly Gly Gly Gly Ser Phe Leu Met Pro Ser
            580                 585                 590

Ser Thr Val Val Ala Asp Gln Gly His Ser Ser Thr Ala Asn Gln Gly
            595                 600                 605

Ser Thr Cys Ser Tyr Gly Asp Asp Gln Glu Gly Lys Leu Val Gly Tyr
            610                 615                 620

Asp Ala Met Val Ala Thr Thr Thr Ala Gly Gly Asp Pro Tyr Ala Ala
625                 630                 635                 640

Ala Arg Ser Gly Tyr Gln Phe Ser Gln Gly Ser Gly Thr Val Ser
                645                 650                 655

Ile Ala Arg Ala Asn Gly Tyr Ser Asn Asn Trp Ser Ser Pro Phe Asn
            660                 665                 670

Gly Met Gly
            675

<210> SEQ ID NO 58
<211> LENGTH: 679
<212> TYPE: PRT
<213> ORGANISM: Zea mays

<400> SEQUENCE: 58

Met Ala Ser Ala Asn Asn Trp Leu Gly Phe Ser Leu Ser Gly Gln Asp
1               5                   10                  15

Asn Pro Gln Pro Asn Gln Asp Ser Ser Pro Ala Ala Gly Ile Asp Ile
            20                  25                  30

Ser Gly Ala Ser Asp Phe Tyr Gly Leu Pro Thr Gln Gln Gly Ser Asp
            35                  40                  45

-continued

```
Gly His Leu Gly Val Pro Gly Leu Arg Asp Asp His Ala Ser Tyr Gly
     50                  55                  60
Ile Met Glu Ala Tyr Asn Arg Val Pro Gln Glu Thr Gln Asp Trp Asn
 65                  70                  75                  80
Met Arg Gly Leu Asp Tyr Asn Gly Gly Ser Glu Leu Ser Met Leu
                 85                  90                  95
Val Gly Ser Ser Gly Gly Gly Gly Asn Gly Lys Arg Ala Val Glu
                100                 105                 110
Asp Ser Glu Pro Lys Leu Glu Asp Phe Leu Gly Gly Asn Ser Phe Val
                115                 120                 125
Ser Asp Gln Asp Gln Ser Gly Gly Tyr Leu Phe Ser Gly Val Pro Ile
    130                 135                 140
Ala Ser Ser Ala Asn Ser Asn Ser Gly Ser Asn Thr Met Glu Leu Ser
145                 150                 155                 160
Met Ile Lys Thr Trp Leu Arg Asn Asn Gln Val Ala Gln Pro Gln Pro
                165                 170                 175
Pro Ala Pro His Gln Pro Gln Pro Glu Glu Met Ser Thr Asp Ala Ser
                180                 185                 190
Gly Ser Ser Phe Gly Cys Ser Asp Ser Met Gly Arg Asn Ser Met Val
                195                 200                 205
Ala Ala Gly Gly Ser Ser Gln Ser Leu Ala Leu Ser Met Ser Thr Gly
    210                 215                 220
Ser His Leu Pro Met Val Pro Ser Gly Ala Ala Ser Gly Ala Ala
225                 230                 235                 240
Ser Glu Ser Thr Ser Ser Glu Asn Lys Arg Ala Ser Gly Ala Met Asp
                245                 250                 255
Ser Pro Gly Ser Ala Val Glu Ala Val Pro Arg Lys Ser Ile Asp Thr
                260                 265                 270
Phe Gly Gln Arg Thr Ser Ile Tyr Arg Gly Val Thr Arg His Arg Trp
                275                 280                 285
Thr Gly Arg Tyr Glu Ala His Leu Trp Asp Asn Ser Cys Arg Arg Glu
    290                 295                 300
Gly Gln Ser Arg Lys Gly Arg Gln Val Tyr Leu Gly Gly Tyr Asp Lys
305                 310                 315                 320
Glu Asp Lys Ala Ala Arg Ala Tyr Asp Leu Ala Ala Leu Lys Tyr Trp
                325                 330                 335
Gly Thr Thr Thr Thr Asn Phe Pro Ile Ser Asn Tyr Glu Lys Glu
                340                 345                 350
Leu Glu Glu Met Lys His Met Thr Arg Gln Glu Tyr Ile Ala Tyr Leu
    355                 360                 365
Arg Arg Asn Ser Ser Gly Phe Ser Arg Gly Ala Ser Lys Tyr Arg Gly
370                 375                 380
Val Thr Arg His His Gln His Gly Arg Trp Gln Ala Arg Ile Gly Arg
385                 390                 395                 400
Val Ala Gly Asn Lys Asp Leu Tyr Leu Gly Thr Phe Ser Thr Glu Glu
                405                 410                 415
Glu Ala Ala Glu Ala Tyr Asp Ile Ala Ala Ile Lys Phe Arg Gly Leu
                420                 425                 430
Asn Ala Val Thr Asn Phe Asp Met Ser Arg Tyr Asp Val Lys Ser Ile
                435                 440                 445
Leu Glu Ser Ser Thr Leu Pro Val Gly Ala Ala Arg Arg Leu Lys
    450                 455                 460
Asp Ala Val Asp His Val Glu Ala Gly Ala Thr Ile Trp Arg Ala Asp
```

```
            465                 470                 475                 480
        Met Asp Gly Ala Val Ile Ser Gln Leu Ala Glu Ala Gly Met Gly Gly
                        485                 490                 495

Tyr Ala Ser Tyr Gly His His Gly Trp Pro Thr Ile Ala Phe Gln Gln
                    500                 505                 510

Pro Ser Pro Leu Ser Val His Tyr Pro Tyr Gly Gln Pro Ser Arg Gly
                    515                 520                 525

Trp Cys Lys Pro Glu Gln Asp Ala Ala Ala Ala Ala His Ser Leu
                530                 535                 540

Gln Asp Leu Gln Gln Leu His Leu Gly Ser Ala Ala His Asn Phe Phe
        545                 550                 555                 560

Gln Ala Ser Ser Ser Thr Val Tyr Asn Gly Gly Ala Gly Ala Ser
                        565                 570                 575

Gly Gly Tyr Gln Gly Leu Gly Gly Gly Ser Ser Phe Leu Met Pro Ser
                    580                 585                 590

Ser Thr Val Val Ala Ala Ala Asp Gln Gly His Ser Ser Thr Ala Asn
                    595                 600                 605

Gln Gly Ser Thr Cys Ser Tyr Gly Asp Asp His Gln Glu Gly Lys Leu
                    610                 615                 620

Ile Gly Tyr Asp Ala Ala Met Val Ala Thr Ala Ala Gly Gly Asp Pro
        625                 630                 635                 640

Tyr Ala Ala Ala Arg Asn Gly Tyr Gln Phe Ser Gln Gly Ser Gly Ser
                        645                 650                 655

Thr Val Ser Ile Ala Arg Ala Asn Gly Tyr Ala Asn Asn Trp Ser Ser
                    660                 665                 670

Pro Phe Asn Asn Gly Met Gly
                    675

<210> SEQ ID NO 59
<211> LENGTH: 693
<212> TYPE: PRT
<213> ORGANISM: Sorghum bicolor

<400> SEQUENCE: 59

Met Ala Ser Thr Asn Asn His Trp Leu Gly Phe Ser Leu Ser Gly Gln
        1               5                   10                  15

Asp Asn Pro Gln Pro Asn His Gln Asp Ser Ser Pro Ala Ala Ala Gly
                        20                  25                  30

Ile Asp Ile Ser Gly Ala Ser Asp Phe Tyr Gly Leu Pro Thr Gln Gln
                    35                  40                  45

Gly Ser Asp Gly Asn Leu Gly Val Pro Gly Leu Arg Asp Asp His Ala
                50                  55                  60

Ser Tyr Gly Ile Met Glu Ala Phe Asn Arg Val Pro Gln Glu Thr Gln
        65                  70                  75                  80

Asp Trp Asn Met Arg Gly Leu Asp Tyr Asn Gly Gly Gly Ser Glu Leu
                        85                  90                  95

Ser Met Leu Val Gly Ser Ser Gly Gly Gly Gly Gly Gly Lys Arg
                    100                 105                 110

Ala Val Glu Asp Ser Glu Pro Lys Leu Glu Asp Phe Leu Gly Gly Asn
                    115                 120                 125

Ser Phe Val Ser Glu His Asp Gln Ser Gly Gly Tyr Leu Phe Ser Gly
                    130                 135                 140

Val Pro Met Ala Ser Ser Thr Asn Ser Asn Ser Gly Ser Asn Thr Met
        145                 150                 155                 160
```

-continued

Glu Leu Ser Met Ile Lys Thr Trp Leu Arg Asn Asn Gln Val Pro Gln
                165                 170                 175

Pro Gln Pro Ala Ala Pro His Gln Ala Pro Gln Thr Glu Glu Met
        180                 185                 190

Ser Thr Asp Ala Asn Ala Ser Ala Ser Ser Phe Gly Cys Ser Asp Ser
            195                 200                 205

Met Gly Arg Asn Gly Thr Val Ala Ala Gly Ser Ser Gln Ser Leu
        210                 215                 220

Ala Leu Ser Met Ser Thr Gly Ser His Leu Pro Met Val Val Ala Gly
225                 230                 235                 240

Gly Gly Ala Ser Gly Ala Ala Ser Glu Ser Thr Ser Ser Glu Asn Lys
                245                 250                 255

Arg Ala Ser Gly Ala Met Asp Ser Pro Gly Ser Ala Val Glu Ala Val
            260                 265                 270

Pro Arg Lys Ser Ile Asp Thr Phe Gly Gln Arg Thr Ser Ile Tyr Arg
        275                 280                 285

Gly Val Thr Arg His Arg Trp Thr Gly Arg Tyr Glu Ala His Leu Trp
        290                 295                 300

Asp Asn Ser Cys Arg Arg Glu Gly Gln Ser Arg Lys Gly Arg Gln Val
305                 310                 315                 320

Tyr Leu Gly Gly Tyr Asp Lys Glu Asp Lys Ala Ala Arg Ala Tyr Asp
                325                 330                 335

Leu Ala Ala Leu Lys Tyr Trp Gly Thr Thr Thr Thr Asn Phe Pro
        340                 345                 350

Ile Ser Asn Tyr Glu Lys Glu Leu Glu Glu Met Lys His Met Thr Arg
        355                 360                 365

Gln Glu Tyr Ile Ala Tyr Leu Arg Arg Asn Ser Ser Gly Phe Ser Arg
        370                 375                 380

Gly Ala Ser Lys Tyr Arg Gly Val Thr Arg His His Gln His Gly Arg
385                 390                 395                 400

Trp Gln Ala Arg Ile Gly Arg Val Ala Gly Asn Lys Asp Leu Tyr Leu
                405                 410                 415

Gly Thr Phe Ser Thr Glu Glu Glu Ala Ala Glu Ala Tyr Asp Ile Ala
            420                 425                 430

Ala Ile Lys Phe Arg Gly Leu Asn Ala Val Thr Asn Phe Asp Met Ser
        435                 440                 445

Arg Tyr Asp Val Lys Ser Ile Leu Glu Ser Ser Thr Leu Pro Val Gly
        450                 455                 460

Gly Ala Ala Arg Arg Leu Lys Asp Ala Val Asp His Val Glu Ala Gly
465                 470                 475                 480

Ala Thr Ile Trp Arg Ala Asp Met Asp Gly Gly Val Ile Ser Gln Leu
                485                 490                 495

Ala Glu Ala Gly Met Gly Gly Tyr Ala Ser Tyr Gly His His Ala Trp
            500                 505                 510

Pro Thr Ile Ala Phe Gln Gln Pro Ser Pro Leu Ser Val His Tyr Pro
        515                 520                 525

Tyr Gly Gln Pro Pro Ser Arg Gly Trp Cys Lys Pro Glu Gln Asp Ala
        530                 535                 540

Ala Val Ala Ala Ala Ala His Ser Leu Gln Asp Leu Gln Gln Leu His
545                 550                 555                 560

Leu Gly Ser Ala Ala His Asn Phe Phe Gln Ala Ser Ser Ser Ser Ala
                565                 570                 575

Val Tyr Asn Ser Gly Gly Gly Gly Ala Ser Gly Gly Tyr His Gln Gly

```
                    580                 585                 590
Leu Gly Gly Gly Ser Ser Phe Leu Met Pro Ser Ser Thr Val Val
                595                 600                 605

Ala Gly Ala Asp Gln Gly His Ser Ser Thr Ala Asn Gln Gly Ser
            610                 615                 620

Thr Cys Ser Tyr Gly Asp Asp His Gln Glu Gly Lys Leu Ile Gly Tyr
625                 630                 635                 640

Asp Ala Met Val Ala Ala Thr Ala Ala Gly Gly Asp Pro Tyr Ala Ala
                645                 650                 655

Ala Arg Ser Gly Tyr Gln Phe Ser Ser Gln Gly Ser Gly Ser Thr Val
                660                 665                 670

Ser Ile Ala Arg Ala Asn Gly Tyr Ser Asn Asn Trp Ser Ser Pro Phe
                675                 680                 685

Asn Gly Gly Met Gly
                690

<210> SEQ ID NO 60
<211> LENGTH: 700
<212> TYPE: PRT
<213> ORGANISM: Oryza sativa

<400> SEQUENCE: 60

Met Ala Ser Ala Asn Asn Trp Leu Gly Phe Ser Leu Ser Gly Gln Glu
1               5                   10                  15

Asn Pro Gln Pro His Gln Asp Ser Ser Pro Ala Ala Ile Asp Val
            20                  25                  30

Ser Gly Ala Gly Asp Phe Tyr Gly Leu Pro Thr Ser Gln Pro Thr Ala
            35                  40                  45

Ala Asp Ala His Leu Gly Val Ala Gly His His His Asn Ala Ser Tyr
        50                  55                  60

Gly Ile Met Glu Ala Phe Asn Arg Gly Ala Gln Glu Ala Gln Asp Trp
65                  70                  75                  80

Asn Met Arg Gly Leu Asp Tyr Asn Gly Ala Ser Glu Leu Ser Met
                85                  90                  95

Leu Val Gly Ser Ser Gly Gly Lys Arg Ala Ala Ala Val Glu Glu Thr
            100                 105                 110

Glu Pro Lys Leu Glu Asp Phe Leu Gly Gly Asn Ser Phe Val Ser Glu
            115                 120                 125

Gln Asp His His Ala Ala Gly Gly Phe Leu Phe Ser Gly Val Pro Met
130                 135                 140

Ala Ser Ser Thr Asn Ser Asn Ser Gly Ser Asn Thr Met Glu Leu Ser
145                 150                 155                 160

Met Ile Lys Thr Trp Leu Arg Asn Asn Gly Gln Val Pro Ala Gly His
                165                 170                 175

Gln Pro Gln Gln Gln Pro Ala Ala Ala Ala Ala Ala Gln Gln
            180                 185                 190

Gln Ala His Glu Ala Ala Glu Met Ser Thr Asp Ala Ser Ala Ser Ser
            195                 200                 205

Phe Gly Cys Ser Ser Asp Ala Met Gly Arg Ser Asn Asn Gly Ala
        210                 215                 220

Val Ser Ala Ala Ala Gly Gly Thr Ser Ser Gln Ser Leu Ala Leu Ser
225                 230                 235                 240

Met Ser Thr Gly Ser His Ser His Leu Pro Ile Val Val Ala Gly Gly
                245                 250                 255
```

```
Gly Asn Ala Ser Gly Gly Ala Ala Glu Ser Thr Ser Ser Glu Asn Lys
            260                 265                 270

Arg Ala Ser Gly Ala Met Asp Ser Pro Gly Gly Ala Ile Glu Ala
        275                 280                 285

Val Pro Arg Lys Ser Ile Asp Thr Phe Gly Gln Arg Thr Ser Ile Tyr
    290                 295                 300

Arg Gly Val Thr Arg His Arg Trp Thr Gly Arg Tyr Glu Ala His Leu
305                 310                 315                 320

Trp Asp Asn Ser Cys Arg Arg Glu Gly Gln Ser Arg Lys Gly Arg Gln
                325                 330                 335

Gly Gly Tyr Asp Lys Glu Asp Lys Ala Ala Arg Ala Tyr Asp Leu Ala
            340                 345                 350

Ala Leu Lys Tyr Trp Gly Thr Thr Thr Thr Thr Asn Phe Pro Ile Ser
        355                 360                 365

Asn Tyr Glu Lys Glu Leu Asp Glu Met Lys His Met Thr Arg Gln Glu
    370                 375                 380

Tyr Ile Ala Tyr Leu Arg Arg Asn Ser Ser Gly Phe Ser Arg Gly Ala
385                 390                 395                 400

Ser Lys Tyr Arg Gly Val Thr Arg His His Gln His Gly Arg Trp Gln
                405                 410                 415

Ala Arg Ile Gly Arg Val Ala Gly Asn Lys Asp Leu Tyr Leu Gly Thr
            420                 425                 430

Phe Ser Thr Glu Glu Glu Ala Ala Glu Ala Tyr Asp Ile Ala Ala Ile
        435                 440                 445

Lys Phe Arg Gly Leu Asn Ala Val Thr Asn Phe Asp Met Ser Arg Tyr
    450                 455                 460

Asp Val Lys Ser Ile Leu Glu Ser Ser Thr Leu Pro Val Gly Gly Ala
465                 470                 475                 480

Ala Arg Arg Leu Lys Glu Ala Ala Asp His Ala Glu Ala Ala Gly Ala
                485                 490                 495

Thr Ile Trp Arg Ala Ala Asp Met Asp Gly Ala Gly Val Ile Ser Gly
            500                 505                 510

Leu Ala Asp Val Gly Met Gly Ala Tyr Ala Ala Ser Tyr His His His
        515                 520                 525

His His His Gly Trp Pro Thr Ile Ala Phe Gln Gln Pro Pro Leu
    530                 535                 540

Ala Val His Tyr Pro Tyr Gly Gln Ala Pro Ala Ala Pro Ser Arg Gly
545                 550                 555                 560

Trp Cys Lys Pro Glu Gln Asp Ala Ala Val Ala Ala Ala His Ser
                565                 570                 575

Leu Gln Asp Leu Gln Gln Leu His Leu Gly Ser Ala Ala Ala His Asn
            580                 585                 590

Phe Phe Gln Ala Ser Ser Ser Ser Thr Val Tyr Asn Gly Gly Gly Gly
        595                 600                 605

Gly Tyr Gln Gly Leu Gly Gly Asn Ala Phe Leu Met Pro Ala Ser Thr
    610                 615                 620

Val Val Ala Asp Gln Gly His Ser Ser Thr Ala Thr Asn His Gly Asn
625                 630                 635                 640

Thr Cys Ser Tyr Gly Asn Glu Glu Gln Gly Lys Leu Ile Gly Tyr Asp
                645                 650                 655

Ala Met Ala Met Ala Ser Gly Ala Ala Gly Gly Gly Tyr Gln Leu Ser
            660                 665                 670

Gln Gly Ser Ala Ser Thr Val Ser Ile Ala Arg Ala Asn Gly Tyr Ser
```

```
                    675                 680                 685
Ala Asn Trp Ser Ser Pro Phe Asn Gly Ala Met Gly
    690                 695                 700

<210> SEQ ID NO 61
<211> LENGTH: 707
<212> TYPE: PRT
<213> ORGANISM: Glycine max

<400> SEQUENCE: 61

Met Gly Ser Met Asn Leu Leu Gly Phe Ser Leu Ser Pro His Glu Glu
1               5                   10                  15

His Pro Ser Ser Gln Asp His Ser Gln Thr Thr Pro Ser Arg Phe Ser
            20                  25                  30

Phe Asn Pro Asp Gly Ser Ile Ser Ser Thr Asp Val Ala Gly Gly Cys
        35                  40                  45

Phe Asp Leu Thr Ser Asp Ser Thr Pro His Leu Leu Asn Leu Pro Ser
    50                  55                  60

Tyr Gly Ile Tyr Glu Ala Phe His Arg Asn Asn Ser Ile Asn Thr Thr
65                  70                  75                  80

Gln Asp Trp Lys Glu Asn Tyr Asn Ser Gln Asn Leu Leu Leu Gly Thr
                85                  90                  95

Ser Cys Asn Lys Gln Asn Met Asn Gln Asn Gln Gln Gln Pro Lys
            100                 105                 110

Leu Glu Asn Phe Leu Gly Gly His Ser Phe Gly Glu His Glu Gln Thr
        115                 120                 125

Tyr Gly Gly Asn Ser Ala Ser Thr Asp Tyr Met Phe Pro Ala Gln Pro
    130                 135                 140

Val Ser Ala Gly Gly Gly Gly Ser Gly Gly Gly Ser Asn Asn Asn Asn
145                 150                 155                 160

Asn Ser Asn Ser Ile Gly Leu Ser Met Ile Lys Thr Trp Leu Arg Asn
                165                 170                 175

Gln Pro Pro Asn Ser Glu Asn Ile Asn Asn Asn Asn Glu Ser Gly Gly
            180                 185                 190

Asn Ile Arg Ser Ser Val Gln Gln Thr Leu Ser Leu Ser Met Ser Thr
        195                 200                 205

Gly Ser Gln Ser Ser Thr Ser Leu Pro Leu Leu Thr Ala Ser Val Asp
    210                 215                 220

Asn Gly Glu Ser Pro Ser Asp Asn Lys Gln Pro Asn Thr Ser Ala Ala
225                 230                 235                 240

Leu Asp Ser Thr Gln Thr Gly Ala Ile Glu Thr Ala Pro Arg Lys Ser
                245                 250                 255

Ile Asp Thr Phe Gly Gln Arg Thr Ser Ile Tyr Arg Gly Val Thr Arg
            260                 265                 270

His Arg Trp Thr Gly Arg Tyr Glu Ala His Leu Trp Asp Asn Ser Cys
        275                 280                 285

Arg Arg Glu Gly Gln Thr Arg Lys Gly Arg Gln Val Tyr Leu Gly Gly
    290                 295                 300

Tyr Asp Lys Glu Glu Lys Ala Ala Arg Ala Tyr Asp Leu Ala Ala Leu
305                 310                 315                 320

Lys Tyr Trp Gly Thr Thr Thr Thr Asn Phe Pro Ile Ser His Tyr
                325                 330                 335

Glu Lys Glu Leu Glu Glu Met Lys His Met Thr Arg Gln Glu Tyr Val
            340                 345                 350
```

```
Ala Ser Leu Arg Arg Lys Ser Gly Phe Ser Arg Gly Ala Ser Ile
            355                 360                 365

Tyr Arg Gly Val Thr Arg His His Gln His Gly Arg Trp Gln Ala Arg
370                 375                 380

Ile Gly Arg Val Ala Gly Asn Lys Asp Leu Tyr Leu Gly Thr Phe Ser
385                 390                 395                 400

Thr Gln Glu Glu Ala Glu Ala Tyr Asp Val Ala Ala Ile Lys Phe
                405                 410                 415

Arg Gly Leu Ser Ala Val Thr Asn Phe Asp Met Ser Arg Tyr Asp Val
                420                 425                 430

Lys Ser Ile Leu Glu Ser Thr Thr Leu Pro Ile Gly Gly Ala Ala Lys
            435                 440                 445

Arg Leu Lys Asp Met Glu Gln Val Glu Leu Ser Val Asp Asn Gly His
        450                 455                 460

Arg Ala Asp Gln Val Asp His Ser Ile Ile Met Ser Ser His Leu Thr
465                 470                 475                 480

Gln Gly Ile Asn Asn Asn Tyr Ala Gly Gly Thr Ala Thr His His
                485                 490                 495

Asn Trp His Asn Ala His Ala Phe His Gln Pro Gln Pro Cys Thr Thr
            500                 505                 510

Met His Tyr Pro Tyr Gly Gln Arg Ile Asn Trp Cys Lys Gln Glu Gln
        515                 520                 525

Gln Asp Asn Ser Asp Ala Pro His Ser Leu Ser Tyr Ser Asp Ile His
        530                 535                 540

Gln Leu Gln Leu Gly Asn Asn Gly Thr His Asn Phe Phe His Thr Asn
545                 550                 555                 560

Ser Gly Leu His Pro Met Leu Ser Met Asp Ser Ala Ser Ile Asp Asn
                565                 570                 575

Ser Ser Ser Ser Asn Ser Val Val Tyr Asp Gly Tyr Gly Gly Gly Gly
            580                 585                 590

Gly Tyr Asn Val Met Pro Met Gly Thr Thr Thr Ala Val Val Ala Ser
        595                 600                 605

Asp Gly Asp Gln Asn Pro Arg Ser Asn His Gly Phe Gly Asp Asn Glu
610                 615                 620

Ile Lys Ala Leu Gly Tyr Glu Ser Val Tyr Gly Ser Ala Thr Asp Ser
625                 630                 635                 640

Tyr His Ala His Ala Arg Asn Leu Tyr Tyr Leu Thr Gln Gln Gln Ser
                645                 650                 655

Ser Ser Val Asp Thr Val Lys Ala Ser Ala Tyr Asp Gln Gly Ser Ala
            660                 665                 670

Cys Asn Thr Trp Val Pro Thr Ala Ile Pro Thr His Ala Pro Arg Ser
        675                 680                 685

Thr Thr Ser Met Ala Leu Cys His Gly Ala Thr Thr Pro Phe Ser Leu
690                 695                 700

Leu His Glu
705

<210> SEQ ID NO 62
<211> LENGTH: 695
<212> TYPE: PRT
<213> ORGANISM: Oryza sativa

<400> SEQUENCE: 62

Met Ala Thr Met Asn Asn Trp Leu Ala Phe Ser Leu Ser Pro Gln Asp
1               5                   10                  15
```

```
Gln Leu Pro Pro Ser Gln Thr Asn Ser Thr Leu Ile Ser Ala Ala Ala
             20                  25                  30

Thr Thr Thr Thr Ala Gly Asp Ser Thr Gly Asp Val Cys Phe Asn
         35                  40                  45

Ile Pro Gln Asp Trp Ser Met Arg Gly Ser Glu Leu Ser Ala Leu Val
 50                  55                  60

Ala Glu Pro Lys Leu Glu Asp Phe Leu Gly Ile Ser Phe Ser Glu
 65              70                  75                  80

Gln Gln His His His Gly Gly Lys Gly Gly Val Ile Pro Ser Ser Ala
                 85                  90                  95

Ala Ala Cys Tyr Ala Ser Ser Gly Ser Ser Val Gly Tyr Leu Tyr Pro
             100                 105                 110

Pro Pro Ser Ser Ser Ser Leu Gln Phe Ala Asp Ser Val Met Val Ala
             115                 120                 125

Thr Ser Ser Pro Val Val Ala His Asp Gly Val Ser Gly Gly Gly Met
 130                 135                 140

Val Ser Ala Ala Ala Ala Ala Ala Ser Gly Asn Gly Gly Ile Gly
145                 150                 155                 160

Leu Ser Met Ile Lys Asn Trp Leu Arg Ser Gln Pro Ala Pro Gln Pro
                 165                 170                 175

Ala Gln Ala Leu Ser Leu Ser Met Asn Met Ala Gly Thr Thr Thr Ala
             180                 185                 190

Gln Gly Gly Gly Ala Met Ala Leu Leu Ala Gly Ala Gly Glu Arg Gly
             195                 200                 205

Arg Thr Thr Pro Ala Ser Glu Ser Leu Ser Thr Ser Ala His Gly Ala
210                 215                 220

Thr Thr Ala Thr Met Ala Gly Gly Arg Lys Glu Ile Asn Glu Glu Gly
225                 230                 235                 240

Ser Gly Ser Ala Gly Ala Val Val Ala Val Gly Ser Glu Ser Gly Gly
             245                 250                 255

Ser Gly Ala Val Val Glu Ala Gly Ala Ala Ala Ala Ala Arg Lys
             260                 265                 270

Ser Val Asp Thr Phe Gly Gln Arg Thr Ser Ile Tyr Arg Gly Val Thr
             275                 280                 285

Arg His Arg Trp Thr Gly Arg Tyr Glu Ala His Leu Trp Asp Asn Ser
             290                 295                 300

Cys Arg Arg Glu Gly Gln Thr Arg Lys Gly Arg Gln Val Leu Ile Gly
305                 310                 315                 320

Gly Tyr Asp Lys Glu Glu Lys Ala Ala Arg Ala Tyr Asp Leu Ala Ala
                 325                 330                 335

Leu Lys Tyr Trp Gly Pro Thr Thr Thr Asn Phe Pro Val Asn Asn
             340                 345                 350

Tyr Glu Lys Glu Leu Glu Glu Met Lys His Met Thr Arg Gln Glu Phe
             355                 360                 365

Val Ala Ser Leu Arg Arg Lys Ser Ser Gly Phe Ser Arg Gly Ala Ser
             370                 375                 380

Ile Tyr Arg Gly Val Thr Arg His His Gln His Gly Arg Trp Gln Ala
385                 390                 395                 400

Arg Ile Gly Arg Val Ala Gly Asn Lys Asp Leu Tyr Leu Gly Thr Phe
                 405                 410                 415

Ser Thr Gln Glu Glu Ala Ala Glu Ala Tyr Asp Ile Ala Ala Ile Lys
             420                 425                 430
```

```
Phe Arg Gly Leu Asn Ala Val Thr Asn Phe Asp Met Ser Arg Tyr Asp
            435                 440                 445

Val Lys Ser Ile Leu Asp Ser Ala Ala Leu Pro Val Gly Thr Ala Ala
450                 455                 460

Lys Arg Leu Lys Asp Ala Glu Ala Ala Ala Tyr Asp Val Gly Arg
465                 470                 475                 480

Ile Ala Ser His Leu Gly Gly Asp Gly Ala Tyr Ala Ala His Tyr Gly
                485                 490                 495

His His His His Ser Ala Ala Ala Trp Pro Thr Ile Ala Phe Gln
                500                 505                 510

Ala Ala Ala Ala Pro Pro His Ala Ala Gly Leu Tyr His Pro Tyr
            515                 520                 525

Ala Gln Pro Leu Arg Gly Trp Cys Lys Gln Glu Gln Asp His Ala Val
            530                 535                 540

Ile Ala Ala His Ser Leu Gln Asp Leu His His Leu Asn Leu Gly
545                 550                 555                 560

Ala Ala Ala Ala His Asp Phe Phe Ser Gln Ala Met Gln Gln Gln
                565                 570                 575

His Gly Leu Gly Ser Ile Asp Asn Ala Ser Leu Glu His Ser Thr Gly
            580                 585                 590

Ser Asn Ser Val Val Tyr Asn Gly Asp Asn Gly Gly Gly Gly Gly
            595                 600                 605

Tyr Ile Met Ala Pro Met Ser Ala Val Ser Ala Thr Ala Thr Ala Val
            610                 615                 620

Ala Ser Ser His Asp His Gly Gly Asp Gly Gly Lys Gln Val Gln Met
625                 630                 635                 640

Gly Tyr Asp Ser Tyr Leu Val Gly Ala Asp Ala Tyr Gly Gly Gly Gly
                645                 650                 655

Ala Gly Arg Met Pro Ser Trp Ala Met Thr Pro Ala Ser Ala Pro Ala
            660                 665                 670

Ala Thr Ser Ser Ser Asp Met Thr Gly Val Cys His Gly Ala Gln Leu
            675                 680                 685

Phe Ser Val Trp Asn Asp Thr
            690                 695

<210> SEQ ID NO 63
<211> LENGTH: 658
<212> TYPE: PRT
<213> ORGANISM: Oryza sativa

<400> SEQUENCE: 63

Met Ala Ser Ala Asp Asn Trp Leu Gly Phe Ser Leu Ser Gly Gln Gly
1               5                   10                  15

Asn Pro Gln His His Gln Asn Gly Ser Pro Ser Ala Ala Gly Asp Ala
                20                  25                  30

Ala Ile Asp Ile Ser Gly Ser Gly Asp Phe Tyr Gly Leu Pro Thr Pro
            35                  40                  45

Asp Ala His His Ile Gly Met Ala Gly Glu Asp Ala Pro Tyr Gly Val
        50                  55                  60

Met Asp Ala Phe Asn Arg Gly Thr His Glu Thr Gln Asp Trp Ala Met
65                  70                  75                  80

Arg Gly Leu Asp Tyr Gly Gly Ser Ser Asp Leu Ser Met Leu Val
                85                  90                  95

Gly Ser Ser Gly Gly Gly Arg Arg Thr Val Ala Gly Asp Gly Val Gly
                100                 105                 110
```

```
Glu Ala Pro Lys Leu Glu Asn Phe Leu Asp Gly Asn Ser Phe Ser Asp
            115                 120                 125

Val His Gly Gln Ala Ala Gly Gly Tyr Leu Tyr Ser Gly Ser Ala Val
130                 135                 140

Gly Gly Ala Gly Gly Tyr Ser Asn Gly Gly Cys Gly Gly Gly Thr Ile
145                 150                 155                 160

Glu Leu Ser Met Ile Lys Thr Trp Leu Arg Ser Asn Gln Ser Gln Gln
                165                 170                 175

Gln Pro Ser Pro Pro Gln His Ala Asp Gln Gly Met Ser Thr Asp Ala
            180                 185                 190

Ser Ala Ser Ser Tyr Ala Cys Ser Asp Val Leu Val Gly Ser Cys Gly
            195                 200                 205

Gly Gly Gly Ala Gly Thr Ala Ser Ser His Gly Gln Gly Leu Ala
210                 215                 220

Leu Ser Met Ser Thr Gly Ser Val Ala Ala Gly Gly Gly Ala
225                 230                 235                 240

Val Val Ala Ala Glu Ser Ser Ser Glu Asn Lys Arg Val Asp Ser
                245                 250                 255

Pro Gly Gly Ala Val Asp Gly Ala Val Pro Arg Lys Ser Ile Asp Thr
            260                 265                 270

Phe Gly Gln Arg Thr Ser Ile Tyr Arg Gly Val Thr Arg His Arg Trp
            275                 280                 285

Thr Gly Arg Tyr Glu Ala His Leu Trp Asp Asn Ser Cys Arg Arg Glu
290                 295                 300

Gly Gln Ser Arg Lys Gly Arg Gln Val Cys Val Gly Tyr Asp Lys
305                 310                 315                 320

Glu Asp Lys Ala Ala Arg Ala Tyr Asp Leu Ala Ala Leu Lys Tyr Trp
            325                 330                 335

Gly Thr Thr Thr Thr Asn Phe Pro Met Ser Asn Tyr Glu Lys Glu
            340                 345                 350

Leu Glu Glu Met Lys His Met Thr Arg Gln Glu Tyr Ile Ala His Leu
            355                 360                 365

Arg Arg Asn Ser Ser Gly Phe Ser Arg Gly Ala Ser Lys Tyr Arg Gly
370                 375                 380

Val Thr Arg His His Gln His Gly Arg Trp Gln Ala Arg Ile Gly Arg
385                 390                 395                 400

Val Ala Gly Asn Lys Asp Ile Tyr Leu Gly Thr Phe Ser Thr Glu Glu
                405                 410                 415

Glu Ala Ala Glu Ala Tyr Asp Ile Ala Ala Ile Lys Phe Arg Gly Leu
            420                 425                 430

Asn Ala Val Thr Asn Phe Asp Met Ser Arg Tyr Asp Val Lys Ser Ile
            435                 440                 445

Leu Asp Ser Ser Thr Leu Pro Val Gly Gly Ala Ala Arg Arg Leu Lys
450                 455                 460

Glu Ala Glu Val Ala Ala Ala Ala Gly Gly Val Ile Val Ser
465                 470                 475                 480

His Leu Ala Asp Gly Gly Val Gly Gly Tyr Tyr Tyr Gly Cys Gly Pro
            485                 490                 495

Thr Ile Ala Phe Gly Gly Gly Gln Gln Pro Ala Pro Leu Ala Val
            500                 505                 510

His Tyr Pro Ser Tyr Gly Gln Ala Ser Gly Trp Cys Lys Pro Glu Gln
            515                 520                 525
```

```
Asp Ala Val Ile Ala Ala Gly His Cys Ala Thr Asp Leu Gln His Leu
            530                 535                 540

His Leu Gly Ser Gly Gly Ala Ala Thr His Asn Phe Phe Gln Gln
545                 550                 555                 560

Pro Ala Ser Ser Ala Val Tyr Gly Asn Gly Gly Gly Gly Gly
                565                 570                 575

Asn Ala Phe Met Met Pro Met Gly Ala Val Ala Ala Ala Asp His
                580                 585                 590

Gly Gly Gln Ser Ser Ala Tyr Gly Gly Asp Glu Ser Gly Arg Leu
            595                 600                 605

Val Val Gly Tyr Asp Gly Val Val Asp Pro Tyr Ala Ala Met Arg Ser
610                 615                 620

Ala Tyr Glu Leu Ser Gln Gly Ser Ser Ser Ser Val Ser Val Ala
625                 630                 635                 640

Lys Ala Ala Asn Gly Tyr Pro Asp Asn Trp Ser Ser Pro Phe Asn Gly
                645                 650                 655

Met Gly

<210> SEQ ID NO 64
<211> LENGTH: 550
<212> TYPE: PRT
<213> ORGANISM: Panicum virgatum

<400> SEQUENCE: 64

Met Gly Ser Thr Asn Asn Trp Leu Gly Phe Ala Ser Phe Ser Gly Ala
1               5                   10                  15

Ala Ala Ala Asp Asp Ile Leu Pro Pro Leu Pro Pro Arg Gly Asp
            20                  25                  30

Glu Ala Ala Ala Glu Pro Lys Leu Glu Asp Phe Leu Gly Leu Gln Glu
            35                  40                  45

Pro Ala Ala Gly Val Ala Gly Arg Ala Pro Phe Ala Gly Ser Gly Gly
    50                  55                  60

Gly Ala Ser Ser Ile Gly Leu Ser Met Ile Lys Asn Trp Leu Arg Ser
65                  70                  75                  80

Gln Pro Ala Pro Gly Pro Ala Gly Ala Asp Ser Met Ala Leu Ala Val
                85                  90                  95

Val Glu Glu Ala Ser Thr Asp Val Arg Lys Val Thr Asp Asp Arg
            100                 105                 110

Gly Ala Glu Ser Val Ala Ala Val Asp Ala Ala Gln Gln Arg Lys
            115                 120                 125

Ala Val Ala Val Asp Thr Phe Gly Gln Arg Thr Ser Ile Tyr Arg
            130                 135                 140

Gly Val Thr Lys His Arg Trp Thr Gly Arg Tyr Glu Ala His Leu Trp
145                 150                 155                 160

Asp Asn Ser Cys Arg Arg Glu Gly Gln Thr Arg Lys Gly Arg Gln Gly
                165                 170                 175

Gly Tyr Asp Lys Glu Glu Lys Ala Ala Arg Ala Tyr Asp Leu Ala Ala
            180                 185                 190

Leu Lys Tyr Trp Gly Thr Thr Thr Thr Thr Asn Phe Pro Met Ser Asn
        195                 200                 205

Tyr Glu Lys Glu Leu Glu Glu Met Lys His Met Ser Arg Gln Glu Tyr
        210                 215                 220

Val Ala Ser Leu Arg Arg Lys Ser Ser Gly Phe Ser Arg Gly Ala Ser
225                 230                 235                 240
```

Ile Tyr Arg Gly Val Thr Arg His His Gln His Gly Arg Trp Gln Ala
            245                 250                 255

Arg Ile Gly Arg Val Ala Gly Asn Lys Asp Leu Tyr Leu Gly Thr Phe
        260                 265                 270

Ser Thr Gln Glu Glu Ala Ala Glu Ala Tyr Asp Ile Ala Ala Ile Lys
    275                 280                 285

Phe Arg Gly Leu Asn Ala Val Thr Asn Phe Asp Met Ser Arg Tyr Asp
290                 295                 300

Val Lys Ser Ile Met Glu Ser Ser Ala Leu Pro Val Gly Gly Thr Thr
305                 310                 315                 320

Lys Cys Leu Lys Asp Val His Asp Gln Ser Asp Met Gly Met Asn Ser
                325                 330                 335

Ser Gly Ala Asp Ser Ala Ser His Met Thr Ala Thr Thr Lys Leu Leu
            340                 345                 350

Thr Asp Gly Ile Gly Ser Tyr Gly Asn Glu Asn Tyr Gly Tyr Ser Gly
        355                 360                 365

Trp Ser Pro Ser Ala Met Met Arg Ile Pro Leu Gln Phe Ser Asn Gly
    370                 375                 380

Gln Glu His Ser Arg Leu Trp Cys Lys Pro Glu Gln Asp Ser Ala Val
385                 390                 395                 400

Val Ala Ala Ala His Asn Leu Gln His Leu Gln His Phe Pro Ser Pro
                405                 410                 415

Gly Gly Thr His Asp Phe Phe His Pro Ser His Val Gln Asp Val Thr
            420                 425                 430

Gly Val Ala Asp Val Ser Ser Pro Ser Val Asp Pro Asn Ser Phe Leu
        435                 440                 445

Tyr Asn Gly Val Val Gly Tyr His Gly Ser Met Gly Gly Gly Tyr Ala
    450                 455                 460

Met Pro Val Ala Thr Leu Val Asp Ser Asn His Ala Thr Ser Ser Tyr
465                 470                 475                 480

Gly Val Glu Glu Gly Thr Ser Glu Leu Tyr Ser Gly Gln Asn Leu Tyr
                485                 490                 495

Tyr Leu Ser Gln Ala Ser Pro Gly Ala Asn Thr Gly Lys Ala Asp Ala
            500                 505                 510

Tyr Glu Gln Gln Gly Val Gly Tyr Glu Ser Trp Val Pro Ser Val Pro
        515                 520                 525

Val Ile Ser Gln Lys Asp Pro Asn Val Thr Val Cys His Gly Thr Pro
    530                 535                 540

Leu Phe Ser Val Trp Lys
545                 550

<210> SEQ ID NO 65
<211> LENGTH: 706
<212> TYPE: PRT
<213> ORGANISM: Zea mays

<400> SEQUENCE: 65

Met Ala Thr Val Asn Asn Trp Leu Ala Phe Ser Leu Ser Pro Gln Glu
1               5                   10                  15

Leu Pro Pro Ser Gln Thr Thr Asp Ser Thr Leu Ile Ser Ala Ala Thr
            20                  25                  30

Ala Asp His Val Ser Gly Asp Val Cys Phe Asn Ile Pro Gln Asp Trp
        35                  40                  45

Ser Met Arg Gly Ser Glu Leu Ser Ala Leu Val Ala Glu Pro Lys Leu
    50                  55                  60

```
Glu Asp Phe Leu Gly Gly Ile Ser Phe Ser Glu Gln His His Lys Ser
 65                  70                  75                  80

Asn Cys Asn Leu Ile Pro Ser Thr Ser Ser Thr Val Cys Tyr Ala Ser
                 85                  90                  95

Ser Ala Ala Ser Thr Gly Tyr His His Gln Leu Tyr Gln Pro Thr Ser
            100                 105                 110

Ser Ala Leu His Phe Ala Asp Ser Val Met Val Ala Ser Ser Ala Gly
            115                 120                 125

Val His Asp Gly Gly Ser Met Leu Ser Ala Ala Ala Asn Gly Val
        130                 135                 140

Ala Gly Ala Ala Ser Ala Asn Gly Gly Ile Gly Leu Ser Met Ile
145                 150                 155                 160

Lys Asn Trp Leu Arg Ser Gln Pro Ala Pro Met Gln Pro Arg Ala Ala
                165                 170                 175

Ala Ala Glu Gly Ala Gln Gly Leu Ser Leu Ser Met Asn Met Ala Gly
            180                 185                 190

Thr Thr Gln Gly Ala Ala Gly Met Pro Leu Leu Ala Gly Glu Arg Ala
            195                 200                 205

Arg Ala Pro Glu Ser Val Ser Thr Ser Ala Gln Gly Gly Ala Val Val
210                 215                 220

Val Thr Ala Pro Lys Glu Asp Ser Gly Gly Ser Gly Val Ala Gly Ala
225                 230                 235                 240

Leu Val Ala Val Ser Thr Asp Thr Gly Gly Ser Gly Gly Ala Ser Ala
                245                 250                 255

Asp Asn Thr Ala Arg Lys Thr Val Asp Thr Phe Gly Gln Arg Thr Ser
            260                 265                 270

Ile Tyr Arg Gly Val Thr Arg His Arg Trp Thr Gly Arg Tyr Glu Ala
            275                 280                 285

His Leu Trp Asp Asn Ser Cys Arg Arg Glu Gly Gln Thr Arg Lys Gly
            290                 295                 300

Arg Gln Gly Gly Tyr Asp Lys Glu Glu Lys Ala Ala Arg Ala Tyr Asp
305                 310                 315                 320

Leu Ala Ala Leu Lys Tyr Trp Gly Ala Thr Thr Thr Thr Asn Phe Pro
                325                 330                 335

Val Ser Asn Tyr Glu Lys Glu Leu Glu Asp Met Lys His Met Thr Arg
            340                 345                 350

Gln Glu Phe Val Ala Ser Leu Arg Arg Lys Ser Ser Gly Phe Ser Arg
            355                 360                 365

Gly Ala Ser Ile Tyr Arg Gly Val Thr Arg His His Gln His Gly Arg
            370                 375                 380

Trp Gln Ala Arg Ile Gly Arg Val Ala Gly Asn Lys Asp Leu Tyr Leu
385                 390                 395                 400

Gly Thr Phe Ser Thr Gln Glu Glu Ala Ala Glu Ala Tyr Asp Ile Ala
                405                 410                 415

Ala Ile Lys Phe Arg Gly Leu Asn Ala Val Thr Asn Phe Asp Met Ser
            420                 425                 430

Arg Tyr Asp Val Lys Ser Ile Leu Asp Ser Ser Ala Leu Pro Ile Gly
            435                 440                 445

Ser Ala Ala Lys Arg Leu Lys Glu Ala Glu Ala Ala Ala Ser Ala Gln
            450                 455                 460

His His His Ala Gly Val Val Ser Tyr Asp Val Gly Arg Ile Ala Ser
465                 470                 475                 480
```

```
Gln Leu Gly Asp Gly Gly Ala Leu Ala Ala Ala Tyr Gly Ala His Tyr
            485                 490                 495

His Gly Ala Ala Trp Pro Thr Ile Ala Phe Gln Pro Gly Ala Ala Thr
            500                 505                 510

Thr Gly Leu Tyr His Pro Tyr Ala Gln Gln Pro Met Arg Gly Gly Gly
            515                 520                 525

Trp Cys Lys Gln Glu Gln Asp His Ala Val Ile Ala Ala Ala His Ser
530                 535                 540

Leu Gln Asp Leu His His Leu Asn Leu Gly Ala Gly Ala His Asp
545                 550                 555                 560

Phe Phe Ser Ala Gly Gln Gln Ala Ala Ala Ala Ala Met His Gly
            565                 570                 575

Leu Ala Ser Ile Asp Ser Ala Ser Leu Glu His Ser Thr Gly Ser Asn
            580                 585                 590

Ser Val Val Tyr Asn Gly Gly Val Gly Asp Ser Asn Gly Ala Ser Ala
            595                 600                 605

Val Gly Ser Gly Gly Gly Tyr Met Met Pro Met Ser Ala Ala Gly Ala
            610                 615                 620

Thr Thr Thr Ser Ala Met Val Ser His Glu Gln Met His Ala Arg Ala
625                 630                 635                 640

Tyr Asp Glu Ala Lys Gln Ala Ala Gln Met Gly Tyr Glu Ser Tyr Leu
                    645                 650                 655

Val Asn Ala Glu Asn Asn Gly Gly Arg Met Ser Ala Trp Gly Thr
                660                 665                 670

Val Val Ser Ala Ala Ala Ala Ala Ala Ser Ser Asn Asp Asn Ile
            675                 680                 685

Ala Ala Asp Val Gly His Gly Gly Ala Gln Leu Phe Ser Val Trp Asn
690                 695                 700

Asp Thr
705

<210> SEQ ID NO 66
<211> LENGTH: 579
<212> TYPE: PRT
<213> ORGANISM: Brassica napus

<400> SEQUENCE: 66

Met Asn Asn Asn Trp Leu Gly Phe Ser Leu Ser Pro Tyr Glu Gln Asn
1               5                   10                  15

His His Arg Lys Asp Val Cys Ser Ser Thr Thr Thr Ala Val Asp
            20                  25                  30

Val Ala Gly Glu Tyr Cys Tyr Asp Pro Thr Ala Ala Ser Asp Glu Ser
            35                  40                  45

Ser Ala Ile Gln Thr Ser Phe Pro Ser Pro Phe Gly Val Val Leu Asp
        50                  55                  60

Ala Phe Thr Arg Asp Asn Asn Ser His Ser Arg Asp Trp Asp Ile Asn
65                  70                  75                  80

Gly Ser Ala Cys Asn Asn Ile His Asn Asp Glu Gln Asp Gly Pro Lys
                85                  90                  95

Leu Glu Asn Phe Leu Gly Arg Thr Thr Thr Ile Tyr Asn Thr Asn Glu
            100                 105                 110

Asn Val Gly Asp Ile Asp Gly Ser Gly Cys Tyr Gly Gly Gly Asp Gly
            115                 120                 125

Gly Gly Gly Ser Leu Gly Leu Ser Met Ile Lys Thr Trp Leu Arg Asn
        130                 135                 140
```

```
Gln Pro Val Asp Asn Val Asp Asn Gln Glu Asn Gly Asn Gly Ala Lys
145                 150                 155                 160

Gly Leu Ser Leu Ser Met Asn Ser Ser Thr Ser Cys Asp Asn Asn Asn
                165                 170                 175

Tyr Ser Ser Asn Asn Leu Val Ala Gln Gly Lys Thr Ile Asp Asp Ser
            180                 185                 190

Val Glu Ala Thr Pro Lys Lys Thr Ile Glu Ser Phe Gly Gln Arg Thr
        195                 200                 205

Ser Ile Tyr Arg Gly Val Thr Arg His Arg Trp Thr Gly Arg Tyr Glu
    210                 215                 220

Ala His Leu Trp Asp Asn Ser Cys Lys Arg Glu Gly Gln Thr Arg Lys
225                 230                 235                 240

Gly Arg Gln Val Tyr Leu Gly Gly Tyr Asp Lys Glu Glu Lys Ala Ala
                245                 250                 255

Arg Ala Tyr Asp Leu Ala Ala Leu Lys Tyr Trp Gly Thr Thr Thr Thr
            260                 265                 270

Thr Asn Phe Pro Met Ser Glu Tyr Glu Lys Glu Ile Glu Glu Met Lys
        275                 280                 285

His Met Thr Arg Gln Glu Tyr Val Ala Ser Leu Arg Arg Lys Ser Ser
    290                 295                 300

Gly Phe Ser Arg Gly Ala Ser Ile Tyr Arg Gly Val Thr Arg His His
305                 310                 315                 320

Gln His Gly Arg Trp Gln Ala Arg Ile Gly Arg Val Ala Gly Asn Lys
                325                 330                 335

Asp Leu Tyr Leu Gly Thr Phe Gly Thr Gln Glu Glu Ala Ala Glu Ala
            340                 345                 350

Tyr Asp Ile Ala Ala Ile Lys Phe Arg Gly Leu Thr Ala Val Thr Asn
        355                 360                 365

Phe Asp Met Asn Arg Tyr Asn Val Lys Ala Ile Leu Glu Ser Pro Ser
    370                 375                 380

Leu Pro Ile Gly Ser Ala Ala Lys Arg Leu Lys Glu Ala Asn Arg Pro
385                 390                 395                 400

Val Pro Ser Met Met Met Ile Ser Asn Asn Val Ser Glu Ser Glu Asn
                405                 410                 415

Asn Ala Ser Gly Trp Gln Asn Ala Ala Val Gln His His Gln Gly Val
            420                 425                 430

Asp Leu Ser Leu Leu Gln Gln His Gln Glu Arg Tyr Asn Gly Tyr Tyr
        435                 440                 445

Tyr Asn Gly Gly Asn Leu Ser Ser Glu Ser Ala Arg Ala Cys Phe Lys
    450                 455                 460

Gln Glu Asp Asp Gln His His Phe Leu Ser Asn Thr Gln Ser Leu Met
465                 470                 475                 480

Thr Asn Ile Asp His Gln Ser Ser Val Ser Asp Ser Val Thr Val
                485                 490                 495

Cys Gly Asn Val Val Gly Tyr Gly Gly Tyr Gln Gly Phe Ala Ala Pro
            500                 505                 510

Val Asn Cys Asp Ala Tyr Ala Ala Ser Glu Phe Asp Tyr Asn Ala Arg
        515                 520                 525

Asn His Tyr Tyr Phe Ala Gln Gln Gln Thr Gln His Ser Pro Gly
    530                 535                 540

Gly Asp Phe Pro Ala Ala Met Thr Asn Asn Val Gly Ser Asn Met Tyr
545                 550                 555                 560
```

```
Tyr His Gly Glu Gly Gly Gly Glu Val Ala Pro Thr Phe Thr Val Trp
            565                 570                 575

Asn Asp Asn

<210> SEQ ID NO 67
<211> LENGTH: 3527
<212> TYPE: DNA
<213> ORGANISM: Pennisetum squamulatum

<400> SEQUENCE: 67
atgggttcca ccaacaactg gctgcgcttc gcctcgttct ccggcggcgg cggcgccaag     60
gatgccgcgg ccctgctccc gctgccgccc tcgccccgtg gcgatgtcga cgaggccggc    120
gcagagccga agctcgagga cttcctcggc ctgcaggagc cgagcgccgc cgcggtgggg    180
gctgggcggc cattcgcggt gggtggcggt gcgagctcca tcgggctgtc catgatcagg    240
aactggctgc gcagccagcc ggcgccggcc gggcctgctg cggggggtcga ttcgatggtg    300 ctggcggctg cggcggcgtc gacggaggtg gccggcgatg gcgcggaggg cggcggcgcc    360
gtggctgacg cggtgcagca gaggaaggcg gcggcggtgg acactttcgg gcagcggacc    420
tccatatacc gcggcgtcac aaagtaggtt cttgatttta ttttggtttt ggaaaaattc    480
ttctttgttt tttctgtttt cttccgactg gtatatcttg tgttaagaac ttttcatta    540 gatgcatgtc atactgttgc ttttcttgt tgctttgaac cttttggcgt ttgcagcttc    600
gtttggatat acagaaccta tattatcccc tttagtaacc agtagattct ttttttttct    660 ttttttttt ttgctttcga tgttgttagt gttcttgcat cacgcatgtt tttcctctga    720
tattttaatg gacgatatca tctctagttc aagttttgc tcttgctctt gttgtagtgg    780
tgctaagatt tttaaaaaaa aaattatga gcagttcttg gctgtttga aaatgtaagc    840 atctcacagt tctaaaatat atatatatat atatataa gtctctcatg ttgatttgtg    900
gatgtactga gccccgcgc gcacacatgc acacaccgca cgctcacacg ccctaaatcc    960
ccggtgcaac accagggttg tccccgatgg ggatcgaacc ctggcgggtg gcctaaccac   1020
cgtcagctcc caccaccgag ctatcagctc gtttgcccat atttcgtgtg gtacctcgat   1080
atttttatat ttctagattg ctgtatctat cttctagact tatataagtg ttgcgccact   1140
catacttttt accgcctgta atcgagtaga actgcttcct cttttgatta tattgtatca   1200
gttaaatgat cttgttgttg atgtgtttac cactttacca tcaccattgc atgaaatcac   1260
ttcaagacat gtattcatga tttggctggc taaatttgct agtggcacat acatgtggta   1320
aaaaaatatt tttagttgt gcttgctatt cttttcggtc atcccttcgt gcctgtttat   1380
ccagaacacc caatctgctt cacatagttt ttgaatgcta tcatcatatt tcttttttgg   1440
agatattgtt actaaaagtt tggctttgtc ctcaataggc atagatggac aggaaggtat   1500
gaagcccatc tttgggacaa tagctgcaga agagaaggtc aaactcggaa aggtagacaa   1560
ggtaatgatt ataatataga tatttaaatt tgtaattata agctgcatca tattattatt   1620
tattagatcg gctttaaaat ttcactagct aatttagtgt tttctttc ttcatcgata    1680 cctgcaatcg cttcattcca ttgattcagt gtatcttggt aagtaatact tgtttacaat   1740
tgcaaaatgg tatatctctt gttgtttctc atgtcaagta tattaaatat gtggttgatg   1800
cattgaaggt ggatatgata aagaagaaaa agcagctaga gcttatgatt tagctgctct   1860
caagtaccgg ggcaccacaa ctactacaaa ttttccggta ttacttattg ttaatatgtt   1920
ggttctccag aattgatatt ttacttctaa tatataactg cgtatatgaa tgaatgttgt   1980
```

```
aagattttgc attttatgtt cagatgagca actatgaaaa ggagttagaa gagatgaagc    2040
atatgtcacg acaagaatat gttgcatccc ttagaaggta catgtgttgt caaaactttg    2100
taccttcatg gaaactgaac ttatatattt cacaaatgga ttgacataga acatatattt    2160
gtgatacagg aaaagcagtg gttttctcg tggtgcatca atttaccgag gggttaccag     2220
gtacaaaata ttccttttcc ttattatctc tggttttagt tagcaagtgc attgtttcta    2280
tgggaatttg tgttgcatgt agatgggaat ttgtgttgca tgtagatcat aaatagttgc    2340
aactattaat ctcatcgttc tattgctgaa tagttgtggt actcctttac cacagttgac    2400
tatgatattc tattatatta tttttcttgc aaagttgata tttaattgct tgtctagcta    2460
actttcaagc aatcatgtaa aacaggcacc atcagcatgg aaggtggcaa gcaagaatag    2520
gaagtgtggc aggaaacaag gatctttatt tgggcacatt cagtaagtca cattttaata    2580
tttttaatga agcactgatt ttttttgtc aagcaaaatg gaagcaagac agaaaaacat     2640
aaacctactg gagcaccttt ttcattattt tgtctcttga atataatagt atgtggctga    2700
cctctccctg tgtaggtacc caggaggaag ctgcagagc ttacgacatt gctgccatca     2760
aattccgagg cctcaatgct gtcacgaact ttgacatgag ccggtatgac gtcaagagca    2820
tcattgagag cagctcccctg cctgttggcg gcactccaaa gcgtctcaag gaagtgcctg   2880
atcaatcaga tatgggcatc aacataaacg gtgactctgc tggtcatatg actgctatca    2940
accttcttac tgatggcaat gacagctatg gagctgagag ttatggttac agtggttggt    3000
gtcccacagc catgacgcca atccccttc aattcagcaa tggccatgac cattccaggc     3060
tgtggtgcaa gccagagcag gacaatgcgg ttgttgcagc actgcataac ctgcatcacc    3120
tccagcactt gccagcccca gttggcaccc ataattttt ccagccatcg cctgttcagg     3180
acatgacagg tgttgccgat gcttcatcgc caccagtaga atctaattca ttcctgtaca    3240
atggggacgt tggttaccat ggtgccatgg gtggcagcta tgccatgccg gttgccacac    3300
tagttgaggg caactctgcg ggcagtggct atggagttga ggaaggcaca gggtctgaaa    3360
tctttggtgg acggaacttg tattctctct cccaaggttc ctcaggcgcc aatactggaa    3420
aggcagatgc ttatgaaagc tgggatccat ctatgctggt gatatcacag aagtctgcca    3480
atgtgactgt ctgccatggc gcacctgtat tttcagtttg gaaatga                  3527
```

<210> SEQ ID NO 68
<211> LENGTH: 1638
<212> TYPE: DNA
<213> ORGANISM: Pennisetum squamulatum

<400> SEQUENCE: 68

```
atgggttcca ccaacaactg gctgcgcttc gcctcgttct ccggcggcgg cggcgccaag     60
gatgccgcgg ccctgctccc gctgccgccc tcgcccgtg gcgatgtcga cgaggccggc     120
gcagagccga agctcgagga cttcctcggc ctgcaggagc cgagcgccgc cgcggtgggg    180
gctgggcggc cattcgcggt gggtggcggt gcgagctcca tcgggctgtc catgatcagg    240
aactggctgc gcagccagcc ggcgccggcc gggcctgctg cgggggtcga ttcgatggtg    300
ctggcggctg cggcggcgtc gacggaggtg ccggcgatg gcgcggaggg cggcggcgcc    360
gtggctgacg cggtgcagca gaggaaggcg gcggcggtgg acactttcgg gcagcggacc    420
tccatatacc gcggcgtcac aaaagcataga tggacaggaa ggtatgaagc ccatctttgg    480
gacaatagct gcagaagaga aggtcaaact cggaaaggta gacaagtgta tcttggtgga    540
tatgataaag aagaaaaagc agctagagct tatgatttag ctgctctcaa gtaccggggc    600
```

```
accacaacta ctacaaattt tccgatgagc aactatgaaa aggagttaga agagatgaag      660
catatgtcac gacaagaata tgttgcatcc cttagaagga aaagcagtgg ttttctcgt       720 ggtgcatcaa tttaccgagg ggttaccagg caccatcagc atggaaggtg gcaagcaaga      780
ataggaagtg tggcaggaaa caaggatctt tatttgggca cattcagtac ccaggaggaa      840
gctgcagagg cttacgacat tgctgccatc aaattccgag gcctcaatgc tgtcacgaac      900
tttgacatga gccggtatga cgtcaagagc atcattgaga gcagctccct gcctgttggc      960
ggcactccaa agcgtctcaa ggaagtgcct gatcaatcag atatgggcat caacataaac     1020
ggtgactctg ctggtcatat gactgctatc aaccttctta ctgatggcaa tgacagctat     1080
ggagctgaga gttatggtta cagtggttgg tgtcccacag ccatgacgcc aatccccttt     1140
caattcagca atggccatga ccattccagg ctgtggtgca agccagagca ggacaatgcg     1200
gttgttgcag cactgcataa cctgcatcac ctccagcact tgccagcccc agttggcacc     1260
cataattttt tccagccatc gcctgttcag gacatgacag tgttgccga tgcttcatcg     1320 ccaccagtag aatctaattc attcctgtac aatggggacg ttggttacca tggtgccatg     1380
ggtggcagct atgccatgcc ggttgccaca ctagttgagg gcaactctgc gggcagtggc     1440
tatggagttg aggaaggcac agggtctgaa atctttggtg gacggaactt gtattctctc     1500
tcccaaggtt cctcaggcgc caatactgga aaggcagatg cttatgaaag ctgggatcca     1560
tctatgctgg tgatatcaca gaagtctgcc aatgtgactg tctgccatgg cgcacctgta     1620
ttttcagttt ggaaatga                                                    1638
```

```
<210> SEQ ID NO 69
<211> LENGTH: 554
<212> TYPE: PRT
<213> ORGANISM: Artificial Sequence
<220> FEATURE:
<223> OTHER INFORMATION: Consensus Sequence
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (19)..(19)
<223> OTHER INFORMATION: Xaa can be any naturally occurring amino acid
<220> FEATURE:
<221> NAME/KEY: misc_feature
<222> LOCATION: (24)..(24)
<223> OTHER INFORMATION: Xaa can be any naturally occurring amino acid
<220> FEATURE:
<221> NAME/KEY: misc_feature
<222> LOCATION: (28)..(28)
<223> OTHER INFORMATION: Xaa can be any naturally occurring amino acid
<220> FEATURE:
<221> NAME/KEY: misc_feature
<222> LOCATION: (41)..(41)
<223> OTHER INFORMATION: Xaa can be any naturally occurring amino acid
<220> FEATURE:
<221> NAME/KEY: misc_feature
<222> LOCATION: (59)..(59)
<223> OTHER INFORMATION: Xaa can be any naturally occurring amino acid
<220> FEATURE:
<221> NAME/KEY: misc_feature
<222> LOCATION: (61)..(61)
<223> OTHER INFORMATION: Xaa can be any naturally occurring amino acid
<220> FEATURE:
<221> NAME/KEY: misc_feature
<222> LOCATION: (78)..(78)
<223> OTHER INFORMATION: Xaa can be any naturally occurring amino acid
<220> FEATURE:
<221> NAME/KEY: misc_feature
<222> LOCATION: (91)..(92)
```

-continued

```
<223> OTHER INFORMATION: Xaa can be any naturally occurring amino acid
<220> FEATURE:
<221> NAME/KEY: misc_feature
<222> LOCATION: (113)..(113)
<223> OTHER INFORMATION: Xaa can be any naturally occurring amino acid
<220> FEATURE:
<221> NAME/KEY: misc_feature
<222> LOCATION: (118)..(118)
<223> OTHER INFORMATION: Xaa can be any naturally occurring amino acid
<220> FEATURE:
<221> NAME/KEY: misc_feature
<222> LOCATION: (121)..(121)
<223> OTHER INFORMATION: Xaa can be any naturally occurring amino acid
<220> FEATURE:
<221> NAME/KEY: misc_feature
<222> LOCATION: (123)..(123)
<223> OTHER INFORMATION: Xaa can be any naturally occurring amino acid
<220> FEATURE:
<221> NAME/KEY: misc_feature
<222> LOCATION: (125)..(125)
<223> OTHER INFORMATION: Xaa can be any naturally occurring amino acid
<220> FEATURE:
<221> NAME/KEY: misc_feature
<222> LOCATION: (130)..(130)
<223> OTHER INFORMATION: Xaa can be any naturally occurring amino acid
<220> FEATURE:
<221> NAME/KEY: misc_feature
<222> LOCATION: (152)..(152)
<223> OTHER INFORMATION: Xaa can be any naturally occurring amino acid
<220> FEATURE:
<221> NAME/KEY: misc_feature
<222> LOCATION: (158)..(158)
<223> OTHER INFORMATION: Xaa can be any naturally occurring amino acid
<220> FEATURE:
<221> NAME/KEY: misc_feature
<222> LOCATION: (167)..(167)
<223> OTHER INFORMATION: Xaa can be any naturally occurring amino acid
<220> FEATURE:
<221> NAME/KEY: misc_feature
<222> LOCATION: (369)..(369)
<223> OTHER INFORMATION: Xaa can be any naturally occurring amino acid
<220> FEATURE:
<221> NAME/KEY: misc_feature
<222> LOCATION: (372)..(372)
<223> OTHER INFORMATION: Xaa can be any naturally occurring amino acid
<220> FEATURE:
<221> NAME/KEY: misc_feature
<222> LOCATION: (379)..(379)
<223> OTHER INFORMATION: Xaa can be any naturally occurring amino acid
<220> FEATURE:
<221> NAME/KEY: misc_feature
<222> LOCATION: (382)..(382)
<223> OTHER INFORMATION: Xaa can be any naturally occurring amino acid
<220> FEATURE:
<221> NAME/KEY: misc_feature
<222> LOCATION: (386)..(386)
<223> OTHER INFORMATION: Xaa can be any naturally occurring amino acid
<220> FEATURE:
<221> NAME/KEY: misc_feature
<222> LOCATION: (388)..(388)
<223> OTHER INFORMATION: Xaa can be any naturally occurring amino acid
<220> FEATURE:
<221> NAME/KEY: misc_feature
<222> LOCATION: (392)..(392)
<223> OTHER INFORMATION: Xaa can be any naturally occurring amino acid
<220> FEATURE:
<221> NAME/KEY: misc_feature
<222> LOCATION: (413)..(414)
<223> OTHER INFORMATION: Xaa can be any naturally occurring amino acid
<220> FEATURE:
<221> NAME/KEY: misc_feature
<222> LOCATION: (451)..(451)
<223> OTHER INFORMATION: Xaa can be any naturally occurring amino acid
<220> FEATURE:
<221> NAME/KEY: misc_feature
<222> LOCATION: (453)..(453)
<223> OTHER INFORMATION: Xaa can be any naturally occurring amino acid
<220> FEATURE:
<221> NAME/KEY: misc_feature
```

```
<222> LOCATION: (462)..(464)
<223> OTHER INFORMATION: Xaa can be any naturally occurring amino acid
<220> FEATURE:
<221> NAME/KEY: misc_feature
<222> LOCATION: (480)..(480)
<223> OTHER INFORMATION: Xaa can be any naturally occurring amino acid
<220> FEATURE:
<221> NAME/KEY: misc_feature
<222> LOCATION: (487)..(487)
<223> OTHER INFORMATION: Xaa can be any naturally occurring amino acid
<220> FEATURE:
<221> NAME/KEY: misc_feature
<222> LOCATION: (490)..(490)
<223> OTHER INFORMATION: Xaa can be any naturally occurring amino acid
<220> FEATURE:
<221> NAME/KEY: misc_feature
<222> LOCATION: (493)..(493)
<223> OTHER INFORMATION: Xaa can be any naturally occurring amino acid
<220> FEATURE:
<221> NAME/KEY: misc_feature
<222> LOCATION: (496)..(497)
<223> OTHER INFORMATION: Xaa can be any naturally occurring amino acid
<220> FEATURE:
<221> NAME/KEY: misc_feature
<222> LOCATION: (499)..(500)
<223> OTHER INFORMATION: Xaa can be any naturally occurring amino acid
<220> FEATURE:
<221> NAME/KEY: misc_feature
<222> LOCATION: (505)..(505)
<223> OTHER INFORMATION: Xaa can be any naturally occurring amino acid
<220> FEATURE:
<221> NAME/KEY: misc_feature
<222> LOCATION: (508)..(508)
<223> OTHER INFORMATION: Xaa can be any naturally occurring amino acid
<220> FEATURE:
<221> NAME/KEY: misc_feature
<222> LOCATION: (514)..(514)
<223> OTHER INFORMATION: Xaa can be any naturally occurring amino acid
<220> FEATURE:
<221> NAME/KEY: misc_feature
<222> LOCATION: (535)..(535)
<223> OTHER INFORMATION: Xaa can be any naturally occurring amino acid
<220> FEATURE:
<221> NAME/KEY: misc_feature
<222> LOCATION: (543)..(543)
<223> OTHER INFORMATION: Xaa can be any naturally occurring amino acid
<220> FEATURE:
<221> NAME/KEY: misc_feature
<222> LOCATION: (545)..(546)
<223> OTHER INFORMATION: Xaa can be any naturally occurring amino acid

<400> SEQUENCE: 69

Met Ala Ser Xaa Asn Asn Trp Leu Gly Phe Ser Leu Ser Gly Gln Glu
1               5                   10                  15

Asn Pro Xaa Ser Gln Asp Ser Xaa Pro Ala Ala Xaa Ile Asp Val Ser
            20                  25                  30

Gly Asp Asp Cys Tyr Gly Leu Pro Xaa Ala Phe Glu Thr Gln Asp Trp
        35                  40                  45

Ser Met Arg Gly Ser Glu Leu Ser Met Leu Xaa Glu Xaa Ala Glu Pro
    50                  55                  60

Lys Leu Glu Asp Phe Leu Gly Asn Ser Phe Ser Glu Xaa Gln Asp
65                  70                  75                  80

Gln Gly Gly Tyr Leu Ala Ser Gly Val Pro Xaa Xaa Ala Gly Ser Gly
                85                  90                  95

Gly Gly Ser Gly Ser Ile Gly Leu Ser Met Ile Lys Thr Trp Leu Arg
            100                 105                 110

Xaa Gln Pro Ala Pro Xaa Pro Gln Xaa Ala Xaa Gly Xaa Ala Gln Ser
        115                 120                 125

Leu Xaa Leu Ser Met Ser Thr Gly Ser Ser Leu Pro Leu Val Ala Gly
    130                 135                 140
```

```
Glu Ser Ser Glu Asn Lys Arg Xaa Asp Ser Gly Gly Ala Xaa Val Glu
145                 150                 155                 160

Ala Val Pro Arg Lys Ser Xaa Asp Glu Thr Phe Gly Gln Arg Thr Ser
            165                 170                 175

Ile Tyr Arg Gly Val Thr Arg His Arg Trp Thr Gly Arg Tyr Glu Ala
        180                 185                 190

His Leu Trp Asp Asn Ser Cys Arg Arg Glu Gly Gln Thr Arg Lys Gly
    195                 200                 205

Arg Gln Val Tyr Leu Gly Gly Tyr Asp Lys Glu Glu Lys Ala Ala Arg
210                 215                 220

Ala Tyr Asp Leu Ala Ala Leu Lys Tyr Trp Gly Thr Thr Thr Thr Thr
225                 230                 235                 240

Asn Phe Pro Ile Ser Asn Tyr Glu Lys Glu Leu Glu Glu Met Lys His
                245                 250                 255

Met Thr Arg Gln Glu Tyr Val Ala Ser Leu Arg Arg Lys Ser Ser Gly
            260                 265                 270

Phe Ser Arg Gly Ala Ser Thr Tyr Arg Gly Val Thr Arg His His Gln
        275                 280                 285

His Gly Arg Trp Gln Ala Arg Ile Gly Arg Val Ala Gly Asn Lys Asp
    290                 295                 300

Leu Tyr Leu Gly Thr Phe Ser Thr Gln Glu Glu Ala Ala Glu Ala Tyr
305                 310                 315                 320

Asp Ile Ala Ala Ile Lys Phe Arg Gly Leu Asn Ala Val Thr Asn Phe
                325                 330                 335

Asp Met Ser Arg Tyr Asp Val Lys Ser Ile Leu Glu Ser Ser Thr Leu
            340                 345                 350

Pro Val Gly Gly Ala Ala Lys Arg Leu Lys Asp Ala Glu Asp Ala Ala
        355                 360                 365

Xaa Ala Gly Xaa Asn Ile Asn Arg Ala Asp Xaa Asp Gly Xaa Ile Ala
370                 375                 380

Ser Xaa Leu Xaa Asp Gly Gly Xaa Gly Ala Tyr Gly Tyr Gly Ala Ser
385                 390                 395                 400

Gly Trp Pro Thr Ile Ala Phe Gln Pro Gln Pro Leu Xaa Xaa His Tyr
                405                 410                 415

Pro Tyr Gly Gln Pro Ser Arg Gly Trp Cys Lys Gln Glu Gln Asp Ala
            420                 425                 430

Ala Val Ala Ala Ala His Ser Leu Gln Asp Leu Gln His Leu His
        435                 440                 445

Leu Gly Xaa Gly Xaa His Asn Phe Phe Gln Ala Ser Gly Xaa Xaa Xaa
450                 455                 460

Ser Gly Ser Asn Ser Val Val Tyr Asn Gly Gly Val Gly Tyr Gly Xaa
465                 470                 475                 480

Gly Gly Gly Gly Gly Tyr Xaa Met Pro Xaa Ser Thr Xaa Val Ala Xaa
            485                 490                 495

Xaa Gly Xaa Xaa Ser Tyr Gly Asp Xaa Glu Gly Xaa Gly Tyr Asp Ala
        500                 505                 510

Gly Xaa Asp Pro Tyr Ala Ala Arg Asn Gly Tyr Tyr Leu Ser Gln Gly
    515                 520                 525

Ser Ser Ser Ala Val Ser Xaa Ala Lys Ala Asn Gly Tyr Ser Xaa Asn
530                 535                 540

Xaa Xaa Gly Ala Ser Pro Phe Ser Asp Gly
545                 550
```